United States Patent
Valentin et al.

(10) Patent No.: US 7,238,855 B2
(45) Date of Patent: Jul. 3, 2007

(54) TYRA GENES AND USES THEREOF

(75) Inventors: Henry E. Valentin, Wildwood, MO (US); Timothy A. Mitsky, Maryland Heights, MO (US); Ming Hao, Wildwood, MO (US); Balasulojini Karunanandaa, Creve Coeur, MO (US); Qungang Qi, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 551 days.

(21) Appl. No.: 10/137,310

(22) Filed: May 3, 2002

(65) Prior Publication Data

US 2003/0176675 A1 Sep. 18, 2003

Related U.S. Application Data

(60) Provisional application No. 60/289,527, filed on May 9, 2001.

(51) Int. Cl.
*C12N 15/82* (2006.01)
*A01H 5/00* (2006.01)

(52) U.S. Cl. ................ 800/281; 800/288; 800/298; 435/320.1; 435/252.3; 435/257.1

(58) Field of Classification Search ........... 800/295, 800/281, 288, 298; 536/23.1, 23.2; 435/320.1
See application file for complete search history.

(56) References Cited

U.S. PATENT DOCUMENTS

| | | | |
|---|---|---|---|
| 4,727,219 A | 2/1988 | Brar et al. | |
| 5,304,478 A | 4/1994 | Bird et al. | |
| 5,429,939 A | 7/1995 | Misawa et al. | |
| 5,432,069 A | 7/1995 | Grüninger et al. | |
| 5,545,816 A | 8/1996 | Ausich et al. | |
| 5,618,988 A | 4/1997 | Hauptmann et al. | |
| 5,684,238 A | 11/1997 | Ausich et al. | |
| 5,693,507 A | 12/1997 | Daniell et al. | |
| 5,750,865 A | 5/1998 | Bird et al. | |
| 5,792,903 A | 8/1998 | Hirschberg et al. | |
| 5,876,964 A | 3/1999 | Croteau et al. | |
| 5,908,940 A | 6/1999 | Lane et al. | |
| 6,281,017 B1 | 8/2001 | Croteau et al. | |
| 6,303,365 B1 | 10/2001 | Martin et al. | |
| 6,541,259 B1* | 4/2003 | Lassner et al. | 435/468 |
| 6,653,530 B1* | 11/2003 | Shewmaker et al. | 800/282 |
| 2002/0069426 A1 | 6/2002 | Boronat et al. | |
| 2002/0108148 A1 | 8/2002 | Boronat et al. | |
| 2003/0148300 A1 | 8/2003 | Valentin et al. | 435/6 |
| 2003/0150015 A1 | 8/2003 | Norris et al. | |
| 2003/0154513 A1 | 8/2003 | van Eenennaam et al. | |
| 2003/0166205 A1 | 9/2003 | van Eenennaam et al. | |
| 2003/0170833 A1 | 9/2003 | Lassner et al. | |
| 2003/0176675 A1 | 9/2003 | Valentin et al. | |
| 2003/0213017 A1 | 11/2003 | Valentin et al. | |
| 2004/0018602 A1 | 1/2004 | Lassner et al. | |
| 2004/0045051 A1 | 3/2004 | Norris et al. | |

FOREIGN PATENT DOCUMENTS

| | | |
|---|---|---|
| CA | 2339519 | 2/2000 |
| CA | 2343919 | 3/2000 |
| CA | 2372332 | 11/2000 |
| DE | 198 35 219 A1 | 8/1998 |
| EP | 0 531 639 A2 | 3/1993 |
| EP | 0 531 639 A3 | 3/1993 |
| EP | 0 674 000 A2 | 9/1995 |
| EP | 0 723 017 A2 | 7/1996 |
| EP | 0 763 542 A2 | 3/1997 |
| EP | 1 033 405 A2 | 9/2000 |
| EP | 1 063 297 A1 | 12/2000 |
| FR | 2 778 527 | 11/1999 |
| GB | 560529 | 4/1944 |
| WO | WO 91/02059 | 2/1991 |
| WO | WO 91/09128 | 6/1991 |
| WO | WO 91/13078 | 9/1991 |
| WO | WO 93/18158 | 9/1993 |
| WO | WO 94/11516 | 5/1994 |
| WO | WO 94/12014 | 6/1994 |
| WO | WO 94/18337 | 8/1994 |
| WO | WO 95/08914 | 4/1995 |
| WO | WO 95/18220 | 7/1995 |
| WO | WO 95/23863 | 9/1995 |

(Continued)

OTHER PUBLICATIONS

Hudson et al. 1984. J Mol Biol. vol. 180, pp. 1023-1051.*
Xia et al. J Gen Microbiol. 1992, vol. 138, pp. 1309-1316.*
Doerks et al. 1998. Trends Genet. vol. 14(6), pp. 248-250.*
DellaPenna D. Progress in the dissection and manipulation of vitamin E synthesis. Trends Plant Sci. Dec. 2005; 10(12):574-9. Review.*
Valentin H.E. et al. Biotechnological production and-application of vitamin E: current state and prospects. Appl Microbiol Biotechnol. Sep. 2005;68(4):436-44. Epub Oct. 26, 2005. Review.*

(Continued)

*Primary Examiner*—Cynthia Collins
(74) *Attorney, Agent, or Firm*—Fulbright & Jaworski L.L.P.

(57) ABSTRACT

The present invention is in the field of plant genetics and biochemistry. More specifically, the invention relates to genes associated with the tocopherol biosynthesis pathway. The present invention provides and includes nucleic acid molecules, proteins, and antibodies associated with the genes of the tocopherol biosynthesis pathway. The present invention also provides methods for utilizing such agents, for example in gene isolation, gene analysis and the production of transgenic plants. Moreover, the present invention includes transgenic plants modified to express proteins associated with the tocopherol pathway. In addition, the present invention includes methods for the production of products from the tocopherol biosynthesis pathway.

40 Claims, 81 Drawing Sheets

FOREIGN PATENT DOCUMENTS

| | | |
|---|---|---|
| WO | WO 95/34668 | 12/1995 |
| WO | WO 96/02650 | 2/1996 |
| WO | WO 96/06172 | 2/1996 |
| WO | WO 96/13149 | 5/1996 |
| WO | WO 96/13159 | 5/1996 |
| WO | WO 96/36717 A2 | 11/1996 |
| WO | WO 96/36717 A3 | 11/1996 |
| WO | WO 96/38567 | 12/1996 |
| WO | WO 97/17447 | 5/1997 |
| WO | WO 97/27285 | 7/1997 |
| WO | WO 97/49816 | 12/1997 |
| WO | 98/06862 A1 | 2/1998 |
| WO | WO 98/04685 | 2/1998 |
| WO | WO 98/18910 | 5/1998 |
| WO | WO 99/04021 | 1/1999 |
| WO | WO 99/04622 | 2/1999 |
| WO | WO 99/06580 | 2/1999 |
| WO | WO 99/07867 | 2/1999 |
| WO | WO 99/11757 | 3/1999 |
| WO | WO 99/19460 | 4/1999 |
| WO | WO 99/55889 | 11/1999 |
| WO | WO 99/58649 | 11/1999 |
| WO | WO 00/01650 | 1/2000 |
| WO | WO 00/08169 | 2/2000 |
| WO | WO 00/08187 | 2/2000 |
| WO | 00/10380 | 3/2000 |
| WO | WO 00/11165 | 3/2000 |
| WO | WO 00/14207 | 3/2000 |
| WO | WO 00/17233 | 3/2000 |
| WO | WO 00/22150 A3 | 4/2000 |
| WO | WO 00/28005 | 5/2000 |
| WO | WO 00/32757 A2 | 6/2000 |
| WO | WO 00/32757 A3 | 6/2000 |
| WO | WO 00/34448 | 6/2000 |
| WO | WO 00/42205 A2 | 7/2000 |
| WO | WO 00/42205 A3 | 7/2000 |
| WO | 00/32757 A2 | 8/2000 |
| WO | 00/32757 A3 | 8/2000 |
| WO | WO 00/46346 | 8/2000 |
| WO | WO 00/61771 | 10/2000 |
| WO | WO 00/63389 | 10/2000 |
| WO | WO 00/63391 | 10/2000 |
| WO | WO 00/65036 A2 | 11/2000 |
| WO | WO 00/65036 A3 | 11/2000 |
| WO | WO 00/68393 | 11/2000 |
| WO | WO 01/04330 | 1/2001 |
| WO | WO 01/09341 | 2/2001 |
| WO | WO 01/12827 | 2/2001 |
| WO | WO 01/21650 | 3/2001 |
| WO | WO 01/44276 | 6/2001 |
| WO | WO 01/62781 | 8/2001 |
| WO | WO 01/79472 | 10/2001 |
| WO | WO 01/88169 A2 | 11/2001 |
| WO | WO 01/88169 A3 | 11/2001 |
| WO | 02/00901 A1 | 1/2002 |
| WO | WO 02/00901 | 1/2002 |
| WO | WO 02/12478 | 2/2002 |
| WO | 02/31173 A2 | 4/2002 |
| WO | WO 02/26933 | 4/2002 |
| WO | WO 02/29022 | 4/2002 |
| WO | WO 02/33060 | 4/2002 |
| WO | WO 02/46441 | 6/2002 |
| WO | WO 02/072848 | 9/2002 |
| WO | WO 02/089561 | 11/2002 |
| WO | WO 03/034812 | 5/2003 |
| WO | WO 03/047547 | 6/2003 |

OTHER PUBLICATIONS

Xia T. et al. GenBank Accession No. M74135, Apr. 12, 2000.*
Xia T. et al. GenBank Accession No. Q02287, Apr. 1, 1993.*
International Search Report, PCT/US02/13898, Sep. 13, 2002 (7 pages).
Collakova et al., "Isolation and Functional Analysis of Homogentisate Phytyltransferase from *Synechocystis* sp. PCC 6803 and Arabidopsis", *Plant Physiology*, vol. 127, pp. 1113-1124 (2001).
Norris et al., "Genetic Dissection of Carotenoid Synthesis in Arabidopsis Defines Plastoquinone as an Essential Component of Phytoene Desaturation", *The Plant Cell*, vol. 7, pp. 2139-2149 (1995).
Shintani et al., "Elevating the Vitamin E Content of Plants Through Metabolic Engineering", *SCIENCE*, vol. 282, pp. 2098-2100 (1998).
Xia et al., "The pheA/tyrAroF region from *Erwinia herbicola*: an emerging comparative basis for analysis of gene organization and regulation in enteric bacteria", Database GENBANK on STN, GenBank ACC. No. (GBN): M74133, *J. Mol. Evol.*, vol. 36, No. 2, pp. 107-120, Abstract (1993).
Bowie et al., "Deciphering the Message in Protein Sequences: Tolerance to Amino Acid Substitutions", Science, 247:1306-1310 (1990).
McConnell et al., "Role of *Phabulosa* and *Phavoluta* in determining radial patterning in shoots", Nature, 411(6838): 709-713 (2001).
Baker et al., NCBI Accession No. X64451 (Dec. 1993).
Tsegaye et al., "the Role of two dioxygenases in regulating vitamin e biosynthesis," *Plant Biology*, 1999:100-101, 1999 (Abstract).
Arigoni et al., "Terpenoid biosynthesis from 1-deoxy-D-xylulose in higher plants by intramolecular skeletal rearrangement", *Proc. Natl. Acad. Sci. USA*, 94:10600-10605 (1997).
Bouvier et al., "Dedicated Roles of Plastid Transketolases during the Early Onset of Isoprenoid Biogenesis in Pepper Fruits", *Plant Physiol.*, 117:1423-1431 (1998).
Eisenreich et al., "The deoxyxylulose phosphate pathway of terpenoid biosynthesis in plants and microorganisms", *Chemistry & Biology*, 5(9):R221-R233 (1998).
Fiedler et al., "The formation of homogentisate in the biosynthesis of tocopherol and plastoquinone in spinach chloroplasts", *Planta*, 155:511-515 (1982).
Herz et al., "Biosynthesis of terpenoids: YgbB protein converts 4-diphosphocytidyl-2C-methyl-D-erythritol 2-phosphate to 2C-methyl-D-erythritol 2,4-cyclodiphosphate", *Proc. Natl. Acad. Sci. U.S.A.*, 97(6):2486-2490 (2000).
Kaneko et al., "Complete Genomic Sequence of the Filamentous Nitrogen-fixing Cyanobacterium *Anabaena* sp. Strain PCC 7120", *DNA Research*, 8(5): 205-213 (2001).
Keegstra, K., "Transport and Routing of Proteins into Chloroplasts", *Cell*, 56(2):247-53 (1989).
Keller et al., "Metabolic compartmentation of plastid prenyllip biosynthesis Evidence for the involvement of a multifunctional geranylgeranyl reductase" *Eur. J. Biochem.*, 251:413-417 (1998).
Lange et al., "A family of transketolases that directs isoprenoid biosynthesis via a mevalonate-independent pathway", *Proc. Natl. Acad. Sci. USA*, 95:2100-2104 (1998).
Lois et al., "Cloning and characterization of a gene from *Escherichia coli* encoding a transketolase-like enzyme that catalyzes the synthesis of D-1-deoxyxylulose 5-phosphate, a common precursor for isoprenoid, thiamin, and pyridoxol biosynthesis", *Proc. Natl. Acad. Sci. USA*, 95(5):2105-2110 (1998).
Marshall et al., "Biosynthesis of tocopherols: a re-examination of the biosynthesis and metabolism of 2-methyl-6-phytyl-1,4-benzoquinol", *Phytochemistry*, 24(8):1705-1711 (1985).
Nawrath et al., "Targeting of the polyhydroxybutyrate biosynthetic pathway to the plastids of *Arabidopsis thaliana* results in high levels of polymer accumulation", *Proc. Natl. Acad. Sci. U.S.A.*, 91:12760-12764 (1994).
NCBI General Identifier No. 1653572, Accession No. BAA18485.
Norris et al., "Complementation of the Arabidopsis *pds 1* Mutation with the Gene Encoding Hydroxyphenylpyruvate Dioxygenase", *Plant Physiology*, 117:1317-1323 (1998).
Okada et al., "Five Geranylgeranyl Diphosphate Synthases Expressed in Different Organs Are Localized into Three Subcellular Compartments in Arabidopsis", *Plant Physiology*, 122:1045-1056 (2000).

Rohdich et al., "Cytidine 5'-triphosphate-dependent biosynthesis of isoprenoids: YgbP protein of *Escherichia coli* catalyzes the formation of 4-diphosphocytidyl-2-C-methylerythritol", *Proc. Natl. Acad. Sci. USA*, 96(21):11758-11763 (1999).

Rohmer et al., "Glyceraldehyde 3-Phosphate and Pyruvate as Precursors of Isoprenic Units in an Alternative Non-mevalonate Pathway for Terpenoid Biosynthesis", *J. Am. Chem. Soc.*, 118:2564-2566 (1996).

Rohmer et al., "Isoprenoid biosynthesis in bacteria: a novel pathway for the early steps leading to isopentenyl diphosphate", *Biochem. J.*, 295:517-524 (1993).

Rohmer, M., "Isoprenoid biosynthesis via the mevalonate-independent route, a novel target for antibacterial drugs?", *Progress in Drug Research*, 50:136-154 (1998).

Rohmer, M., "A Mevalonate-independent Route to Isopentenyl Diphosphate", *Comprehensive Natural Products Chemistry*, 2:45-67 (1999).

Saint-Guily et al., "Complementary DNA Sequence of an Adenylate Translocator from *Arabidopsis thaliana*", *Plant Physiology*, 100(2):1069-1071 (1992).

Sato et al., "Structural Analysis of *Arabidopsis thaliana* Chromosome 5. X. Sequence Features of the Regions of 3,076,755 bp Covered by Sixty P1 and TAC Clones", *DNA Research*, 7(1):31-63 (2000).

Scolnik and Bartley, "Nucleotide Sequence of an *Arabidopsis* cDNA for Geranylgeranyl Pyrophosphate Synthase", *Plant Physiology*, 104(4):1469-1470 (1994).

Smith et al., "The cloning of two *Arabidopsis* genes belonging to a phosphate transporter family", *Plant Journal*, 11(1):83-92 (1997).

Soll et al., "Tocopherol and Plastoquinone Synthesis in Spinach Chloroplasts Subfractions", *Arch. Biochem. Biophys.* 204(2):544-550 (1980).

Sprenger et al., "Identification of thiamin-dependent synthase in *Escherichia coli* required for the formation of the 1-deoxy-D-xylulose 5-phosphate precursor to isoprenoids, thiamin, and pyridoxol", *Proc. Natl. Acad. Sci. USA*, 94:12857-12862 (1997).

Takahashi et al., "A 1-deoxy-D-xylulose 5-phosphate reductoisomerase catalyzing the formation of 2-C-methyl-D-erythritol 4-phosphate in an alternative nonmevalonate pathway for terpenoid biosynthesis", *Proc. Natl. Acad. Sci. U.S.A.*, 95(17), 9879-9884 (1998).

Xia et al., "A monofunctional prephenate dehydrogenase created by cleavage of the 5' 109 bp fo the *tyrA* gene from *Erwinia herbicola*", *J Gen. Microbiol.* 138(7):1309-1316 (1992).

Addlesee et al., "Cloning, sequencing and functional assignment of the chlorophyll biosyntheses gene, *chlP*, of *Synechocystis* sp. PCC 6803", FEBS Letters 389 (1996) 126-130.

Arango et al., "Tocopherol synthesis from homogentisate in *Capsicum anuum* L. (yellow pepper) chromoplast membranes: evidence for tocopherol cyclase", Biochem J., 336:531-533 (1998).

Baker et al., "Sequence and characterization of the *gcpE* gene of *Escherichia coli*", FEMS Microbiology Letters, 94:175-180 (1992).

Bayley et al., "Engineering 2,4-D resistance into cotton," Theor Appl Genet, 83:645-649 (1992).

Bentley, R., "The Shikimate Pathway—A Metabolic Tree with Many Branches," Critical Reviews™ in Biochemistry and Molecular Biology; vol. 25, Issue 5, 307-384 (1990).

Bevan, M., "Binary *Agrobacterium* vectors for plant transformation", Nucleic Acids Research, 12:8711-8721 (1984).

Beyer et al., "Phytoene-forming activities in wild-type and transformed rice endosperm," IRRN 21:2-3, p. 44-45 (Aug.-Dec. 1996).

Bork et al., "Go hunting in sequence databases but watch out for the traps", TIG 12, 10:425-427 (Oct. 1996).

Bramley et al., "Biochemical characterization of transgenic tomato plants in which carotenoid synthesis has been inhibited through the expression of antisense RNA to pTOM5," The Plant Journal, 2(3), 343-349 (1992).

Breitenbach et al., "Expression in *Escherichia coli* and properties of the carotene ketolase from *Haematococcus pluvialis*," FEMS Microbiology Letters 140, 241-246 (1996).

Broun et al., "Catalytic Plasticity of Fatty Acid Modification Enzymes Underlying Chemical Diversity of Plant Lipids," Science, 282:1315-1317 (1998).

Buckner et al., "The *y1* Gene of Maize Codes for Phytoene Synthase," Genetics 143:479-488 (May 1996).

Burkhardt et al., "Genetic engineering of provitamin A biosynthesis in rice endosperm," Experientia, 818-821.

Burkhardt et al., "Transgenic rice (*Oryza sativa*) endosperm expressing daffodil (*Narcissus pseudonarcissus*) phytoene synthase accumulates phytoene, a key intermediate of provitamin A biosynthesis" The Plant Journal, 11(5), 1071-1078 (1997).

Cahoon et al., "Production of Fatty Acid Components of Meadowfoam Oil in Somatic Soybean Embryos," Plant Physiology, 124:243-251 (2000).

Chaudhuri et al., "The purification of shikimate dehydrogenase from *Escherichia coli*," Biochem. J., 226:217-223 (1985).

Cheng et al., "Highly Divergent Methyltransferases Catalyze a Conserved Reaction in Tocopherol and Plastoquinone Synthesis in Cyanobacteria and Photosynthetic Eukaryotes", The Plant Cell, 15:2343-2356 (2003).

Collakova et al., "Homogentisate Phytyltransferase Activity is Limiting for Tocopherol Biosynthesis in Arabidopsis", Plant Physiology, 131:632-642 (Feb. 2003).

Collakova et al., "Isolation and Characterization of Tocopherol Prenyl Transferase From Synechocystis and *Arabidopsis*," Poster Abstract see REN-01 -026.

Cook et al., "Nuclear Mutations affecting plastoquinone accumulation in maize", Photosynthesis Research, 31:99-111 (1992).

Cunillera et al., "Characterization of dehydrodolichyl diphosphate synthase of *Arabidopsis thaliana*, a key enzyme in dolichol biosynthesis", FEBS Letters, 477:170-174 (2000).

d'Amato et al., "Subcellular localization of chorismate-mutase isoenzymes in protoplasts from mesophyll and suspension-cultured cells of *Nicotiana silvestris*," Planta, 162:104-108 (1984).

Doerks et al., "Protein annotation: detective work for function prediction", TIG, 14:248-250 (1998).

d'Harlingue et al., "Plastid Enzymes of Terpenoid Biosynthesis, Purification and Characterization of $\gamma$- Tocopherol Methyltransferase from *Capscium* Chromoplasts," The Journal of Biological Chemistry, vol. 260, No. 28, pp. 15200-15203, Dec. 5, 1985.

De Luca, Vincenzo, "Molecular characterization of secondary metabolic pathways", AgBiotech News and Information, 5(6):225N-229N (1993).

Duncan et al., "The overexpression and complete amino acid sequence of *Escherichia coli* 3-dehydroquinase", Biochem. J., 238:475-483 (1986).

Duvold et al., "Incorporation of 2-C-Methyl-D-erythritol, a Putative Isoprenoid Precursor in the Mevalonate-Independent Pathway, into Ubiquinone and Menaquinone of *Escherichia coli*", Tetrahedron Letters, 38(35):6181-6184 (1997).

Elliott, Thomas, "A Method for Constructing Single-Copy *lac* Fusions in *Salmonella typhimurium* and its Application to the *hemA-prfA* Operon", Journal of Bacteriology, 174:245-253 (1992).

Ericson et al., "Analysis of the promoter region of napin genes from *Brassica napus* demonstrates binding of nuclear protein in vitro to a conserved sequence motif", Eur. J. Biochem., 197:741-746 (1991).

Estévez et al., "1-Deoxy-D-xylulose-5-phosphate Synthase, a Limiting Enzyme for Plastidic Isoprenoid Biosynthesis in Plants", The Journal of Biological Chemistry, 276(25):22901-22909 (2001).

Fellermeier et al., "Cell-free conversion of 1-deoxy-D-xylulose 5-phosphate and 2-C-methyl-D-erythritol 4-phosphate into $\beta$-carotene in higher plants and its inhibition by fosmidomycin", Tetrahedron Letters, 40:2743-2746 (1999).

Fourgoux-Nicol et al., "Isolation of rapeseed genes expressed early and specifically during development of the mate gametophyte", Plant Molecular Biology, 40:857-872 (1999).

Fraser et al., "Enzymic confirmation of reactions involved in routes to astaxanthin formation, elucidated using a direct substrate in vitro assay", Eur. J. Biochem., 252:229-236 (1998).

Fraser et al., "In Vitro Characterization of Astaxanthin Biosynthetic Enzymes", The Journal of Biological Chemistry, 272(10) 6128-6135 (1997).

Fray et al., "Constitutive expression of a fruit phytoene synthase gene in transgenic tomatoes causes dwarfism by redirecting metabolites from the gibberellin pathway", The Plant Journal, 8(5):693-701 (1995).

Fray et al., "Identification and genetic analysis of normal and mutant phytoene synthase genes of tomato by sequencing, complementation and co-suppression", Plant Molecular Biology, 22:589-602 (1993).

Fuqua et al., "Characterization of melA: a gene encoding melanin biosynthesis from the marine bacterium Shewanella colwelliana", Gene, 109:131-136 (1991).

Furuya et al., "Production of Tocopherols by Cell Culture of Safflower", Phytochemistry, 26(10):2741-2747 (1987).

Garcia et al., "Subcellular localization and purification of a p-hydroxyphenylpyruvate dioxygenase from cultured carrot cells and characterization of the corresponding cDNA", Biochem. J., 325:761-769 (1997).

Gaubier et al., "A chlorophyll synthetase gene from Arabidopsis thaliana", Mol. Gen. Genet., 249:58-64 (1995).

Goers et al., "Separation and characterization of two chorismate-mutase isoenzymes from Nicotiana silvestris", Planta, 162:109-116 (1984).

Grabse et al., "Loss of α-tocopheral in tobacco plants with decreased geranylgeranyl reductase activity does not modify photosynthesis in optimal growth conditions but increases sensitivity to high-light stress", Planta, 213:620-628 (2001).

Harker et al., "Biosynthesis of ketocarotenoids in transgenic cyanobacteria expressing the algal gene for β-C-4-oxygenase, crtO", FEBS Letters, 404:129-134 (1997).

Harker et al., "Expression of prokaryotic 1-deoxy-D-xylulose-5-phosphatases in Escherichia coli increases carotenoid and ubiquinone biosynthesis", FEBS Letters, 448:115-119 (1999).

Hecht et al., "Studies of the nonmevalonate pathway to terpenes: The role of the GcpE (IspG) protein", PNAS, 98(26):14837-14842 (2001).

Herrmann, K.M., "The Shikimate Pathway as an Entry to Aromatic Secondary Metabolism", Plan Physiol., 107:7-12 (1995).

Kajiwara et al., "Isolation and functional identification of a novel cDNA for astaxanthin biosynthesis from Haematococcus pluvialis, and astaxanthin synthesis in Escherichia coli", Plant Molecular Biology, 29:343-352 (1995).

Kishore et al., "Amino Acid Biosynthesis Inhibitors as Herbicides", Ann. Rev. Biochem., 57:627-663 (1988).

Koziel et al., "Optimizing expression of transgenes with an emphasis on post-transcriptional events", Plant Molecular Biology, 32:393-405 (1996).

Kumagai et al., "Cytoplasmic inhibition of carotenoid biosynthesis with virus-derived RNA", Proc. Natl. Acad. Sci. USA, 92:1679-1683 (1995).

Kuntz et al., "Identification of a cDNA for the plastid-located geranylgeranyl pyrophosphate synthase from Capsicum annuum: correlative increase in enzyme activity and transcript level during fruit ripening", The Plant Journal, 2(1):25-34 (1992).

Lange et al., "Isoprenoid Biosynthesis via a Mevalonate-Independent Pathway in Plants: Cloning and Heterologous Expression of 1-Deoxy-D-xylulose-5-phosphate Reductoisomerase from Peppermint", Archives of Biochemistry and Biophysics, 365(1):170-174 (1999).

Li et al., "Identification of a maize endosperm-specific cDNA encoding farnesyl pyrophosphate synthetase", Gene, 171:193-196 (1996).

Linthorst et al., "Constitutive Expression of Pathogenesis-Related Proteins PR-1,GRP, and PR-S in Tobacco Has No Effect on Virus Infection", The Plant Cell, 1:285-291 (1989).

Lopez et al., "Sequence of the bchG Gene from Chloroflexus aurantiacus: Relationship between Chlorophyll Synthase and other Polyprenyltransferases", Journal of Bacteriology, 178(11):3369-3373 (1996).

Lotan et al., "Cloning and expression in Escherichia coli of the gene encoding β-C-4-oxygenase, that converts β-carotene to the ketocarotenoid canthaxanthin in Haematococcus pluvialis", FEBS Letters, 364:125-128 (1995).

Mahmoud et al., "Metabolic engineering of essential oil yield and composition in mint by altering expression of deoxyxylulose phosphate reductoisomerase and menthofuran synthase", PNAS, 98(15):8915-8920 (2001).

Mandel et al., "CLA1, a novel gene required for chloroplast development, is highly conserved in evolution", The Plant Journal, 9(5):649-658 (1996).

Misawa et al., "Expression of an Erwinia phytoene desaturase gene not only confers multiple resistance to herbicides interfering with carotenoid biosynthesis but also alters xanthophyll metabolism in transgenic plants", The Plant Journal, 6(4):481-489 (1994).

Misawa et al., "Elucidation of the Erwinia uredovora Carotenoid Biosynthetic Pathway by Functional Analysis of Gene Products Expressed in Escherichia coli", Journal of Bacteriology, 172(12):6704-6712 (1990).

Misawa et al., "Functional expression of the Erwinia uredovora carotenoid biosynthesis gene crtI in transgenic plants showing an increase of β-carotene biosynthesis activity and resistance to the bleaching herbicide norflurazon", The Plant Journal, 4(5):833-840 (1993).

Misawa et al., "Structure and Functional Analysis of a Marine Bacterial Carotenoid Biosynthesis Gene Cluster and Astaxanthin Biosynthetic Pathway Proposed at the Gene Level", Journal of Bacteriology, 177(22):6575-6584 (1995).

Nakamura et al., "Structural Analysis of Arabidopsis thaliana Chromosome 5. III. Sequence Features of the Regions of 1,191,918 bp Covered by Seventeen Physically Assigned P1 Clones", DNA Research, 4(6):401-414 (1997).

Oh et al., "Molecular Cloning, Expression, and Functional Analysis of a cis-Prenyltransferase from Arabidopsis thaliana", The Journal of Biological Chemistry, 275(24):18482-18488 (2000).

Oommen et al., "The Elicitor-Inducible Alfalfa Isoflavone Reductase Promoter Confers Different Patterns of Developmental Expression in Homologous and Heterologous Transgenic Plants", The Plant Cell, 6:1789-1803 (1994).

Oster et al., "The G4 Gene of Arabidopsis thaliana Encodes a Chlorophyll Synthase of Etiolated Plants", Bot. Acta, 110:420-423 (1997).

Peisker et al., "Phytol and the Breakdown of Chlorophyll in Senescent Leaves", J. Plant Physiol., 135:428-432 (1989).

Pompliano et al., "Probing Lethal Metabolic Perturbations in Plants with Chemical Inhibition of Dehydroquinate Synthase", J. Am. Chem. Soc., 111:1866-1871 (1989).

Porfirova et al., "Isolation of an Arabidopsis mutant lacking vitamin E and identification of a cyclase essential for all tocopherol biosynthesis", PNAS, 99(19):12495-12500 (2002).

Querol et al., "Functional analysis of the Arabidopsis thaliana GCPE protein involved in plastid isoprenoid biosynthesis", FEBS Letters, 514:343-346 (2002).

Rippert et al., "Molecular and biochemical characterization of an Arabidopsis thaliana arogenate dehydrogenase with two highly similar and active protein domains", Plant Mol. Biol., 48:361-368 (2002).

Rippert et al., "Engineering Plant Shikimate Pathway for Production of Tocotrienol and Improving Herbicide Resistance", Plant Physiology, 134:92-100 (2004).

Rodriguez-Concepción et al., "Elucidation of the Methylerythritol Phosphate Pathway for Isoprenoid Biosynthesis in Bacteria and Plastids. A Metabolic Milestone Achieved through Genomics", Plant Physiology, 130:1079-1089 (2002).

Rodriguez-Concepción et al., "1-Deoxy-D-xylulose 5-phosphate reductoisomerase and plastid isoprenoid biosynthesis during tomato fruit ripening", The Plant Journal, 27(3):213-222 (2001).

Römer et al., "Expression of the Genes Encoding the Early Carotenoid Biosynthetic Enzymes in Capsicum annuum", Biochemical and Biophysical Research Communications, 196(3):1414-1421 (1993).

Ruzafa et al., "The protein encoded by the Shewanella colwelliana melA gene is a p-hydroxyphenylpyruvate dioxygenase", FEMS Microbiology Letters, 124:179-184 (1994).

Sandmann et al., "New functional assignment of the carotenogenic genes crtB and crtE with constructs of these genes from Erwinia species", FEMS Microbiology Letters, 90:253-258 (1992).

Sato et al., "Structural Analysis of *Arabidopsis thaliana* Chromosome 5. IV. Sequence Features of the Regions of 1,456,315 bp Covered by Nineteen Physically Assigned P1 and TAC Clones", DNA Research, 5:41-54 (1998).

Savidge et al., "Isolation and Characterization of Homogentisate Phytyltransferase Genes from *Synechocystis* sp. PCC 6803 and Arabidopsis", Plant Physiology, 129:321-332 (2002).

Schwender et al., "Cloning and heterologous expression of a cDNA encoding 1-deoxy-D-xylulose-5-phosphate reductoisomerase of *Arabidopsis thaliana*", FEBS Letters, 455:140-144 (1999).

Shewmaker et al., "Seed-specific overexpression of phytoene synthase: increase in carotenoids and other metabolic effects", The Plant Journal, 20(4):401-412 (1999).

Shigeoka et al., "Isolation and properties of γ-tocopherol methyltransferase in *Euglena gracilis*", Biochimica et Biophysica Acta, 1128: 220-226 (1992).

Singh et al., "Chorismate Mutase Isoenzymes from *Sorghum bicolor*: Purification and Properties", Archives of Biochemistry and Biophysics, 243(2):374-384 (1985).

Smith, C.J.S. et al., "Antisense RNA inhibition of polygalacturonase gene expression in transgenic tomatoes", Nature, 334:724-726 (1998).

Smith, T.F. et al., The challenges of genome sequence annotation or "the devil is in the details", Nature Biotechnology, 15:1222-1223 (1997).

Soll et al., "Hydrogenation of Geranylgeraniol", Plant Physiol., 71:849-854 (1983).

Soll et al., "2-Methyl-6-Phytylquinol and 2,3-Dimethyl-5-Phytylquinol as Precursors of Tocopherol Synthesis in Spinach Chloroplasts", Phytochemistry, 19:215-218 (1980).

Spurgeon et al., "Biosynthesis of Isoprenoid Compounds", 1:1-45 (1981).

Stam et al., "The Silence of Genes in Transgenic Plants", Annals of Botany, 79:3-12 (1997).

Stocker et al., "Identification of the Tocopherol-Cyclase in the Blue-Green Algae *Anabaena variabilis* Kützing (Cyanobacteria)", Helvetica Chimica Acta, 76:1729-1738 (1993).

Stocker et al., "The Substrate Specificity of Tocopherol Cyclase", Bioorganic & Medicinal Chemistry, 4(7):1129-1134 (1996).

Sun et al., "Cloning and Functional Analysis of the β-Carotene Hydroxylase of *Arabidopsis thaliana*", The Journal of Biological Chemistry, 271(40):24349-24352 (1996).

Suzich et al., "3-Deoxy-D-*arabino*-Heptulosonate 7-Phosphate Synthase from Carrot Root (*Daucus carota*) is a Hysteretic Enzyme", Plant Physiol., 79:765-770 (1985).

Svab et al., "High-frequency plastid transformation in tobacco by selection for a chimeric aadA gene", Proc. Natl. Acad. Sci. USA, 90:913-917 (1993).

Svab et al., "Stable transformation of plastids in higher plants", Proc. Natl. Acad. Sci. USA, 87:8526-8530 (1990).

Takatsuji, H., "Zinc-finger transcription factors in plants", CMLS Cell. Mol. Life Sci., Birkhauser Verlag Basel CH, 54(6):582-596 (1998).

Tjaden et al., "Altered plastidic ATP/ADP-transporter activity influences potato (*Solanum tubersomum* L.) tuber morphology, yield and composition of tuber starch", The Plant Journal, 16(5):531-540 (1998).

Town et al., "Whole genome shotgun sequencing of *Brassica oleracea*, BOGKS71TR BOGK *Brassica oleracea* genomic clone BOGKS71, DNA sequence", Database EMBL Accession No. BH534089 (Dec. 2001).

Town et al, "Whole genome shotgun sequencing of *Brassica oleracea*, BOGAU46TR BOGA *Brassica oleracea* genomic clone BOGAU46, DNA sequence", Database EMBL Accession No. BH248880 (Nov. 2001).

Verwoert et al., "Developmental specific expression and organelle targeting of the *Escherichia coli* fabD gene, encoding malonyl coenzyme A-acyl carrier protein transacylase in transgenic rape and tobacco seeds", Plant Molecular Biology, 26:189-202 (1994).

Xia et al., "The pheA l tyrA l aroF Region from *Erwinia herbicola*: An Emerging Comparative Basis for Analysis of Gene Organization and Regulation in Enteric Bacteria," Database GENBANK on STN, GenBank ACC. No. (GBN): M74133, J. Mol. Evol., 36(2):107-120 Abstract (1993).

Yamamoto, E., "Purification and Metal Requirements of 3-Dehydroquinate Synthase from *Phaseolus Mungo* Seedlings", Phytochemistry, 19:779-781 (1980).

Zaka et al., "Changes in Carotenoids and Tocopherols During Maturation of *Cassia* Seeds", Pakistan J. Sci. Ind. Res., 30(11):812-814 (1987).

Zeidler et al., "Inhibition of the Non-Mevalonate 1-Deoxy-D-xylulose-5-phosphate Pathway of Plant Isoprenoid Biosynthesis by Fosmidomycin", A Journal of Biosciences, Zeitschrift fuer Naturforschung, Section C, 53(11/12):980-986 (Nov./Dec. 1998).

Zhu et al., "Geranylgeranyl pyrophosphate synthase encoded by the newly isolated gene GGPS6 from *Arabidopsis thaliana* is localized in mitochondria", Plant Molecular Biology, 35:331-341 (1997).

Zhu et al., "Cloning and Functional Expression of a Novel Geranylgeranyl Pyrophosphate Synthase Gene from *Arabidopsis thaliana* in *Escherichia coli*", Plant Cell Physiol., 38(3):357-361 (1997).

Kaneko et al., NCBI General Identifier No. 1001725, Accession No. BAA10562 (Feb. 2003).

Alcala et al., Genbank Accession No. Al 897027 (Jul. 1999).

Bevan et al., Database EMBL, Accession No. AL035394 (Feb. 1999).

Bevan et al., TREMBL Database Accession No. O65524 (Aug. 1998).

Campos et al., NCBI General Identifier BAA 18485, Database EMBL, Accession No.: AF148852, (2000).

Chen et al., EMBL Sequence Database Accession No. Al995392 (Sep. 1999).

Desprez et al., Database EMBL, Accession No. Z34566 (Jun. 1994).

Fedenko et al., Abstract: RU 2005353, Derwent Accession No. 1994-253787.

Gaubier et al., Database EMBL, Accession No. Q38833 (Nov. 1996).

Kaneko et al., Database EMBL, Accession No. P73726 (Feb. 1997).

Kaneko et al., Database EMBL, Accession No. P73962 (Jul. 1998).

Kaneko et al., EMBL Sequence Database Accession No. D90909 (Oct. 1996).

Kaneko et al., TREMBL Database Accession No. P73727 (Feb. 1997).

Lange et al., "Mentha x Piperita 1-deoxy-D-xylulose-5-phosphate Reductoisomerase (DXR) mRNA", complete cds, Entrez Report, Accession No. AF116825 (Apr. 1999).

Lin et al., Database EMBL, Accession No. AC003672 (Dec. 1997).

Lin et al., Database EMBL, Accession No. AC003673 (Dec. 1997).

Lin et al., Database EMBL, Accession No. AC004077 (Feb. 1998).

Malakhov et al., Database TREMBL, Accession No. Q55207 (Nov. 1996).

Murata et al., EMBL Sequence Database Accession No. D13960 (Mar. 1996).

Nakamura et al., Database EMBL, Accession No. AB009053, Abstract (Dec. 1997) (1998) (2000).

Nakamura et al., Database EMBL, Accession No. AB005246 (Jul. 1997).

Newman et al., Database EMBL, Accession No. AA586087, Abstract (Sep. 1997).

Newman et al., Database EMBL, Accession No. R30625 (Aug. 1995).

Newman et al., Database EMBL, Accession No. T44803 (Feb. 1995).

Newman et al., DEBEST ID:1262303, Entrez Report, Accession No. AA586087 (Sep. 1997).

Oster et al., Database Biosis, Accession No. PREV199800047824 (Oct. 1997).

Ouyang et al., Database EMBL, Accession No. AF381248 (Jan. 2003).

Rounsley et al., Database EMBL, Accession No. B24116 (Oct. 1997).

Rounsley et al., Database EMBL, Accession No. B29398 (Oct. 1997).

Rounsley et al., Database TREMBL, Accession No. 064684 (Aug. 1998).

Schwender et al., *Arabidopsis thaliana* mRNA for Partial 1-deoxy-d-xylulose-5-phosphate Reductoisomerase (dxr gene), Entrez Report, Accession No. AJ242588 (Aug. 1999).

Scolnik et al., Database EMBL, Accession No. L40577 (Apr. 1995).

Shintani et al., Database NCBI, Accession No. AF104220 (Jan. 1999).

Shoemaker et al., Database EMBL, Accession No. AI748688 (Jun. 1999).

Shoemaker et al., Database EMBL, Accession No. AI938569 (Aug. 1999).

Shoemaker et al., Database EMBL, Accession No. AI988542 (Sep. 1999).

Shoemaker et al., Database EMBL, Accession No. AW306617 (Jan. 2000).

Tabata et al., Database EMBL, Accession No. D64001 (Sep. 1995).

Tabata et al., Database EMBL, Accession No. D64006 (Sep. 1995).

Tabata et al., Database EMBL, Accession No. D90909 (Oct. 1996).

Tabata et al., Database EMBL, Accession No. D90911 (Oct. 1996).

Tabata et al., Database EMBL, Accession No. Q55145 (Nov. 1996).

Tabata et al., Database EMBL, Accession No. Q55500 (Nov. 1996).

Walbot, V., Database EMBL, Accession No. AI795655 (Jul. 1999).

Wing et al., Database EMBL, Accession No. AQ690643 (Jul. 1999).

Xia et al., Database EMBL, Accession No. M74133 (Jun. 1993).

Bevan et al., Accession T4 8445.

International Search Report, PCT/US00/10367, pp. 1-5 (Sep. 15, 2000).

International Search Report, PCT/US00/10368, pp. 1-14 (Jun. 15, 2001).

Written Opinion, PCT/US00/10368, pp. 1-6 (May 9, 2002).

IPER, PCT/US00/10368, pp. 1-5 (Aug. 16, 2002).

Examination Report, New Zealand Patent Application No. 514600, based on PCT/US/00/10368, pp. 1-2 (Apr. 24, 2003).

Communication pursuant to Article 96(2) EPC, Application 00922287.8, based on PCT/US00/10368, pp. 1-6 (Oct. 17, 2003).

Examiner's Report No. 2, Australia Patent Application No. 42492/00, based on PCT/US00/10368, pp. 1-4 (Nov. 12, 2003).

International Search Report, PCT/US01/12334, pp. 1-5 (Apr. 5, 2002).

International Search Report, PCT/US01/24335, pp. 1-8 (Mar. 6, 2003).

International Search Report, PCT/US01/42673, pp. 1-4.

International Search Report, PCT/US02/03294, pp. 1-4 (Mar. 19, 2003).

International Search Report, PCT/US02/13898, pp. 1-3 (Sep. 13, 2002).

IPER, PCT/US02/13898, pp. 1-4 (Apr. 24, 2003).

International Search Report, PCT/US02/14445, pp. 1-6 (Oct. 30, 2003).

International Search Report, PCT/US02/26047, pp. 1-5 (Dec. 5, 2003).

International Search Report, PCT/US02/34079, pp. 1-5 (Jul. 28, 2003).

Written Opinion, PCT/US02/34079, pp. 1-4 (Oct. 23, 2003).

Response to Written Opinion, PCT/US02/34079, pp. 1-6 (Dec. 22, 2003).

sir 1736 cyanobase www.kazusa.com.

Soll et al., "Localization and Synthesis of Prenylquinones in Isolated Outer and Inner Envelope Membranes From Spinach Chloroplasts", Archives of Biochemistry and Biophysics, 238(1):290-299, 1985.

Supplemental European Search Report for EP 02 77 6280.6.

Motohashi et al., Database EMBL, Accession No. AB054257.

Rieger et al., "Putative Chloroplast Inner Envelope Protein", Accession No. Q9LY74.

Karunanandaa et al., "Metabolically enhanced oilseed crops with enhanced seed tocopherol". *Metabol. Eng.* 7:384-400, 2005.

Valentin et al., "The *Arabidopsis* vitamin E pathway gene5-1 Mutant Reveals a Critical Role for Phytol Kinase in Seed Tocopherol Biosynthesis", *Plant Cell* 18:212-224; 2005.

* cited by examiner

TYRA GENES AND USES THEREOF

CROSS-REFERENCE TO RELATED APPLICATION

This application claims the benefit of and priority to U.S. Provisional Application No. 60/289,527, filed May 9, 2001, which is herein incorporated by reference in its entirety.

FIELD OF THE INVENTION

The present invention is in the field of plant genetics and biochemistry. More specifically, the invention relates to genes associated with the tocopherol biosynthesis pathway. The present invention provides and includes nucleic acid molecules, proteins, and antibodies associated with the genes of the tocopherol biosynthesis pathway. The present invention also provides methods for utilizing such agents, for example in gene isolation, gene analysis and the production of transgenic plants. Moreover, the present invention includes transgenic plants modified to express proteins associated with the tocopherol pathway. In addition, the present invention includes methods for the production of products from the tocopherol biosynthesis pathway.

BACKGROUND OF THE INVENTION

Tocopherols are an essential component of mammalian diets. Epidemiological evidence indicates that tocopherol supplementation can result in decreased risk for cardiovascular disease and cancer, can aid in immune function, and is associated with prevention or retardation of a number of degenerative disease processes in humans (Traber and Sies, *Annu. Rev. Nutr.* 16:321-347 (1996)). Tocopherol functions, in part, by stabilizing the lipid bilayer of biological membranes (Skrypin and Kagan, *Biochim. Biophys. Acta* 815:209 (1995); Kagan, *N.Y. Acad. Sci. p* 121, (1989); Gomez-Fernandez et al., *Ann. N.Y. Acad. Sci.* p 109 (1989)), reducing polyunsaturated fatty acid (PUFA) free radicals generated by lipid oxidation (Fukuzawa et al., *Lipids* 17: 511-513 (1982)), and scavenging oxygen free radicals, lipid peroxy radicals and singlet oxygen species (Diplock et al. *Ann. N Y Acad. Sci.* 570: 72 (1989); Fryer, *Plant Cell Environ.* 15(4): 381-392 (1992)).

α-Tocopherol, often referred to as vitamin E, belongs to a class of lipid-soluble antioxidants that includes α, β, γ, and δ-tocopherols and α, β, γ, and δ-tocotrienols. Although α, β, γ, and δ-tocopherols and α, β, γ, and δ-tocotrienols are sometimes referred to collectively as "vitamin E", vitamin E is more appropriately defined chemically as α-tocopherol. α-Tocopherol is significant for human health, in part because it is readily absorbed and retained by the body, and has a higher degree of bioactivity than other tocopherol species (Traber and Sies, *Annu. Rev. Nutr.* 16:321-347 (1996)). However, other tocopherols such as α, β, and δ-tocopherols, also have significant health and nutritional benefits.

Tocopherols are primarily synthesized only by plants and certain other photosynthetic organisms, including cyanobacteria. As a result, mammalian dietary tocopherols are obtained almost exclusively from these sources. Plant tissues vary considerably in total tocopherol content and tocopherol composition, with α-tocopherol the predominant tocopherol species found in green, photosynthetic plant tissues. Leaf tissue can contain from 10-50 μg of total tocopherols per gram fresh weight, but most of the world's major staple crops (e.g., rice, maize, wheat, potato) produce low to extremely low levels of total tocopherols, of which only a small percentage is α-tocopherol (Hess, Vitamin E, α-tocopherol, In *Antioxidants in Higher Plants*, R. Alscher and J. Hess, Eds., CRC Press, Boca Raton. pp. 111-134 (1993)). Oil seed crops generally contain much higher levels of total tocopherols, but α-tocopherol is present only as a minor component (Taylor and Barnes, *Chemy Ind.*, October :722-726 (1981)).

The recommended daily dietary intake of 15-30 mg of vitamin E is quite difficult to achieve from the average American diet. For example, it would take over 750 grams of spinach leaves in which α-tocopherol comprises 60% of total tocopherols, or 200-400 grams of soybean oil to satisfy this recommended daily vitamin E intake. While it is possible to augment the diet with supplements, most of these supplements contain primarily synthetic vitamin E, having six stereoisomers, whereas natural vitamin E is predominantly composed of only a single isomer. Furthermore, supplements tend to be relatively expensive, and the general population is disinclined to take vitamin supplements on a regular basis. Therefore, there is a need in the art for compositions and methods that either increase the total tocopherol production or increase the relative percentage of α-tocopherol produced by plants.

In addition to the health benefits of tocopherols, increased α-tocopherol levels in crops have been associated with enhanced stability and extended shelf life of plant products (Peterson, *Cereal-Chem.* 72(1):21-24 (1995); Ball, *Fat-soluble vitamin assays in food analysis. A comprehensive review*, London, Elsevier Science Publishers Ltd. (1988)). Further, tocopherol supplementation of swine, beef, and poultry feeds has been shown to significantly increase meat quality and extend the shelf life of post-processed meat products by retarding post-processing lipid oxidation, which contributes to the undesirable flavor components (Sante and Lacourt, *J. Sci. Food Agric.* 65(4):503-507 (1994); Buckley et al., *J. of Animal Science* 73:3122-3130 (1995)).

Tocopherol Biosynthesis

The plastids of higher plants exhibit interconnected biochemical pathways leading to secondary metabolites including tocopherols. The tocopherol biosynthetic pathway in higher plants involves condensation of homogentisic acid and phytylpyrophosphate to form 2-methyl-6 phytylplastoquinol (Fiedler et al., *Planta* 155: 511-515 (1982); Soll et al., *Arch. Biochem. Biophys.* 204: 544-550 (1980); Marshall et al., *Phytochem.* 24: 1705-1711 (1985)). This plant tocopherol pathway can be divided into four parts: 1) synthesis of homogentisic acid, which contributes to the aromatic ring of tocopherol; 2) synthesis of phytylpyrophosphate, which contributes to the side chain of tocopherol; 3) cyclization, which plays a role in chirality and chromanol substructure of the vitamin E family; 4) and S-adenosyl methionine dependent methylation of an aromatic ring, which affects the relative abundance of each of the tocopherol species.

Synthesis of Homogentisic Acid

Homogentisic acid is the common precursor to both tocopherols and plastoquinones. In at least some bacteria the synthesis of homogentesic acid is reported to occur via the conversion of chorismate to prephenate and then to p-hydroxyphenylpyruvate via a bifunctional prephenate dehydrogenase. Examples of bifunctional bacterial prephenate dehydrogenase enzymes include the proteins encoded by the tyrA genes of *Erwinia herbicola* and *Escherichia coli*. The tyrA gene product catalyzes the production of prephenate from chorismate, as well as the subsequent dehydrogenation of prephenate to for p-hydroxyphenylpyruvate (p-HPP), the immediate precursor to homogentisic acid. p-HPP is then converted to homogentisic acid by bydroxyphenylpyruvate dioxygenase (HPPD). In contrast, plants are believed to lack prephenate dehydrogenase activity, and it is generally believed that the synthesis of homogentesic acid from chorismate occurs via the synthesis and conversion of the intermediate arogenate. Since pathways involved in homogentesic acid synthesis are also responsible for tyrosine formation, any alterations in these pathways can also result in the alteration in tyrosine synthesis and the synthesis of other aromatic amino acids.

Synthesis of Phytylpyrophosphate

Tocopherols are a member of the class of compounds referred to as the isoprenoids. Other isoprenoids include carotenoids, gibberellins, terpenes, chlorophyll and abscisic acid. A central intermediate in the production of isoprenoids is isopentenyl diphosphate (IPP). Cytoplasmic and plastid-based pathways to generate IPP have been reported. The cytoplasmic based pathway involves the enzymes acetoacetyl CoA thiolase, IMGCoA synthase, HMGCoA reductase, mevalonate kinase, phosphomevalonate kinase, and mevalonate pyrophosphate decarboxylase.

Recently, evidence for the existence of an alternative, plastid based, isoprenoid biosynthetic pathway emerged from studies in the research groups of Rohmer and Arigoni (Eisenreich et al., *Chem. Bio.*, 5:R221-R233 (1998); Rohmer, *Prog. Drug. Res.*, 50:135-154 (1998); Rohmer, *Comprehensive Natural Products Chemistry*, Vol. 2, pp. 45-68, Barton and Nakanishi (eds.), Pergamon Press, Oxford, England (1999)), who found that the isotope labeling patterns observed in studies on certain eubacterial and plant terpenoids could not be explained in terms of the mevalonate pathway. Arigoni and coworkers subsequently showed that 1-deoxyxylulose, or a derivative thereof, serves as an intermediate of the novel pathway, now referred to as the MEP pathway (Rohmer et al., *Biochem. J.*, 295:517-524 (1993); Schwarz, Ph.D. thesis, Eidgenössische Technische Hochschule, Zurich, Switzerland (1994)). Recent studies showed the formation of 1-deoxyxylulose 5-phosphate (Broers, Ph.D. thesis (Eidgenössiche Technische Hochschule, Zurich, Switzerland) (1994)) from one molecule each of glyceraldehyde 3-phosphate (Rohmer, *Comprehensive Natural Products Chemistry*, Vol. 2, pp. 45-68, Barton and Nakanishi, eds., Pergamon Press, Oxford, England (1999)) and pyruvate (Eisenreich et al., *Chem. Biol.*, 5:R223-R233 (1998); Schwarz supra; Rohmer et al., *J. Am. Chem. Soc.*, 118:2564-2566 (1996); and Sprenger et al., *Proc. Natl. Acad. Sci. USA*, 94:12857-12862 (1997)) by an enzyme encoded by the dxs gene (Lois et al., *Proc. Natl. Acad. Sci. USA*, 95:2105-2110 (1997); and Lange et al., *Proc. Natl. Acad. Sci. USA*, 95:2100-2104 (1998)). 1-Deoxyxylulose 5-phosphate can be further converted into 2-C-methylerythritol 4-phosphate (Arigoni et al., *Proc. Natl. Acad. Sci. USA*, 94:10600-10605 (1997)) by a reductoisomerase catalyzed by the dxr gene (Bouvier et al., *Plant Physiol*, 117:1421-1431 (1998); and Rohdich et al., *Proc. Natl. Acad. Sci. USA*, 96:11758-11763 (1999)).

Reported genes in the MEP pathway also include ygbP, which catalyzes the conversion of 2-C-methylerythritol 4-phosphate into its respective cytidyl pyrophosphate derivative and ygbB, which catalyzes the conversion of 4-phosphocytidyl-2C-methyl-D-erythritol into 2C-methyl-D-erythritol, 3,4-cyclophosphate. These genes are tightly linked on the *E. coli* genome (Herz et al., *Proc. Natl. Acad. Sci. U.S.A.*, 97(6):2485-2490 (2000)).

Once IPP is formed by the MEP pathway, it is converted to GGDP by GGDP synthase, and then to phytylpyrophosphate, which is the central constituent of the tocopherol side chain.

Combination and Cyclization

Homogentisic acid is combined with either phytyl-pyrophosphate or solanylpyrophosphate by phytyl/prenyl transferase forming 2-methyl-6-phytyl plastoquinol or 2-methyl-6-solanyl plastoquinol respectively. 2-methyl-6-solanyl plastoquinol is a precursor to the biosynthesis of plastoquinones, while 2-methyl-6-phytyl plastoquinol is ultimately converted to tocopherol.

Methylation of the Aromatic Ring

The major structural difference between each of the tocopherol subtypes is the position of the methyl groups around the phenyl ring. Both 2-methyl-6-phytyl plastoquinol and 2-methyl-6-solanyl plastoquinol serve as substrates for 2-methyl-6-phytylplatoquinol/2-methyl-6-solanylplastoquinol-9 methyltransferase (Methyl Transferase 1 or MT 1), which catalyzes the formation of plastoquinol-9 and γ-tocopherol respectively, by methylation of the 7 position. Subsequent methylation at the 5 position of γ-tocopherol by γ-methyl-transferase generates the biologically active α-tocopherol. Tocopherol methyl transferase 2 (TMT2) shows similar activity to MT1.

There is a need in the art for nucleic acid molecules encoding enzymes involved in tocopherol biosysnthesis, as well as related enzymes and antibodies for the enhancement or alteration of tocopherol production in plants. There is a further need for transgenic organisms expressing those nucleic acid molecules involved in tocopherol biosynthesis, which are capable of nutritionally enhancing food and feed sources.

| Gene ID | Enzyme name |
| --- | --- |
| tyrA | Prephanate dehydrogenase |
| slr1736 | Phytylprenyl transferase from Synechocystis |
| ATPT2 | Phytylprenyl transferase from *Arabidopsis thaliana* |
| DXS | 1-Deoxyxylulose-5-phosphate synthase |
| DXR | 1-Deoxyxylulose-5-phosphate reductoisomerase |
| GGPPS | Geranylgeranyl pyrophosphate synthase |
| HPPD | p-Hydroxyphenylpyruvate dioxygenase |
| AANT1 | Adenylate transporter |
| slr1737 | Tocopherol cyclase |
| IDI | Isopentenyl diphosphate isomerase |
| GGH | Geranylgeranyl reductase |
| MT1 | Methyl transferase 1 |
| tMT2 | Tocopherol methyl transferase 2 |
| GMT | Gamma Methyl Transferase |

As used herein, homogentisate phytyl transferase (HPT), phytylprenyl transferase (PPT), slr1736, and ATPT2, each refer to proteins or genes encoding proteins that have the same enzymatic activity.

SUMMARY OF THE INVENTION

The present invention includes and provides a substantially purified nucleic acid molecule comprising as operably linked components: (A) a promoter region which functions in a plant cell to cause the production of an mRNA molecule; (B) a heterologous nucleic acid molecule that encodes an enzyme with chorismate mutase and prephenate dehydrogenase activities or a fragment thereof of at least 20 contiguous amino acids of said enzyme.

The present invention includes and provides a substantially purified nucleic acid molecule comprising as operably linked components: (A) a promoter region which functions in a plant cell to cause the production of an mRNA molecule; (B) a heterologous nucleic acid molecule that encodes an amino acid sequence selected from the group consisting of SEQ ID NO: 2, SEQ ID NO: 4 and fragments thereof of at least 20 contiguous amino acids.

The present invention includes and provides a nucleic acid molecule comprising as operably linked components: (A) a promoter region which functions in a plant cell to cause the production of an mRNA molecule; (B) a heterologous nucleic acid molecule with a transcribed strand and a non-transcribed strand, wherein said transcribed strand is complementary to a nucleic acid molecule encoding a protein having chorismate mutase and prephenate dehydrogenase activities.

The present invention includes and provides a nucleic acid molecule comprising as operably linked components: (A) a promoter region which functions in a plant cell to cause the production of an mRNA molecule; (B) a heterologous nucleic acid molecule with a transcribed strand and a non-transcribed strand, wherein said transcribed strand is complementary to a nucleic acid molecule encoding a protein comprising an amino acid sequence selected from the group consisting of SEQ ID NOs: 2 and 4.

The present invention includes and provides a transformed plant having a nucleic acid molecule which comprises as operably linked components: (A) a promoter region which functions in a plant cell to cause the production of an mRNA molecule; (B) an exogenous nucleic acid molecule encoding a protein comprising an amino acid sequence selected from the group consisting of SEQ ID NOs: 2 and 4 or fragments thereof encoding at least 20 contiguous amino acids, and (C) a 3' non-translated sequence that functions in said plant cell to cause termination of transcription and addition of polyadenylated ribonucleotides to a 3' end of the mRNA molecule.

The present invention includes and provides a transformed plant having a nucleic acid molecule comprising as operably linked components: (A) an exogenous promoter region which functions in a plant cell to cause the production of a mRNA molecule; which is linked to (B) a transcribed nucleic acid molecule with a transcribed strand and a non-transcribed strand, wherein said transcribed strand is complementary to a nucleic acid molecule encoding a protein comprising an amino acid sequence selected from the group consisting of: SEQ ID NO: 2, SEQ ID NO: 4 and fragments thereof comprising at least 20 contiguous amino acids.

The present invention includes and provides a method of producing a plant having increased tocopherol levels comprising: (A) transforming said plant with a nucleic acid molecule, wherein said nucleic acid molecule comprises a promoter region, wherein said promoter region is linked to a nucleic acid sequence that encodes a protein having an amino acid sequence selected from the group consisting of SEQ ID NOs: 2 and 4; and, growing said plant.

The present invention includes and provides a method for reducing tocopherol levels in a plant comprising: (A) transforming said plant with a nucleic acid molecule, wherein said nucleic acid molecule comprises as operably linked components an exogenous promoter region which functions in plant cells to cause the production of an mRNA molecule, a transcribed nucleic acid molecule having a transcribed strand and a non-transcribed strand, wherein said transcribed strand is complementary to a nucleic acid molecule having a nucleic acid sequence selected from the group consisting of SEQ ID NOs: 1 and 3; and wherein said transcribed nucleic acid molecule is linked to a 3' non-translated sequence that functions in the plant cells to cause termination of transcription and addition of polyadenylated ribonucleotides to a 3' end of the mRNA sequence; and (B) growing said transformed plant.

The present invention includes and provides a method for screening for increased tocopherol levels in a plant comprising interrogating genomic DNA for the presence or absence of a marker molecule that specifically hybridizes to a nucleic acid molecule having a nucleic acid sequence selected from the group consisting of SEQ ID NOs: 1 and 3 and complements thereof; and detecting said presence or absence of said marker.

The present invention includes and provides a method for determining a genomic polymorphism in a plant that is predictive of an increased tocopherol level comprising the steps: (A) incubating a marker nucleic acid molecule and a complementary nucleic acid molecule obtained from said plant under conditions permitting nucleic acid hybridization, wherein said marker nucleic acid molecule specifically hybridizes to a nucleic acid molecule having a nucleic acid sequence selected from the group consisting of SEQ ID NOs: 1 and 3 and complements thereof; (B) permitting hybridization between said marker nucleic acid molecule and said complementary nucleic acid molecule obtained from said plant; and (C) detecting the presence of said polymorphism.

The present invention includes and provides a method for determining a level or pattern of expression of a protein in a plant cell or plant tissue comprising: (A) incubating under conditions permitting nucleic acid hybridization: a marker nucleic acid molecule, said marker nucleic acid molecule having a nucleic acid sequence selected from SEQ ID NO: 1 and SEQ ID NO: 3, complements of either or fragments comprising at least about 20 nucleotides of said sequences, with a complementary nucleic acid molecule obtained from a plant cell or plant tissue, (B) permitting hybridization between said marker nucleic acid molecule and said complementary nucleic acid molecule obtained from said plant cell or plant tissue; and (C) detecting said level or pattern of said complementary nucleic acid, wherein detection of said complementary nucleic acid is predictive of said level or pattern of said expression of said protein.

The present invention includes and provides a method for determining a level or pattern of expression of a protein in a plant cell or plant tissue under evaluation, comprising: assaying a concentration of an indicator molecule in said plant cell or plant tissue under evaluation, wherein said concentration of said indicator molecule is dependent upon expression of a gene, and wherein said gene specifically hybridizes to a nucleic acid molecule having a nucleic acid sequence selected from the group consisting of SEQ ID NOs: 1 and 3 and complements thereof; and, comparing said concentration of said indicator molecule with known concentrations of said indicator molecule that occur in plant cells or plant tissues with known levels or patterns of expression of said protein.

The present invention includes and provides a cell comprising a nucleic acid molecule comprising as operably linked components: (A) a promoter region which functions in a plant cell to cause the production of an mRNA molecule; (B) a heterologous nucleic acid molecule, wherein said heterologous nucleic acid molecule encodes an enzyme with chorismate mutase and prephenate dehydrogenase activities or a fragment of said nucleic acid molecule comprising at least 20 contiguous amino acids.

The present invention includes and provides oil derived from a seed of a transformed plant having a nucleic acid molecule which comprises as operably linked components: (A) a promoter region which functions in a plant cell to cause the production of an mRNA molecule; (B) an exogenous nucleic acid molecule encoding a protein comprising an amino acid sequence selected from the group consisting of SEQ ID NOs: 2 and 4, and (C) a 3' non-translated sequence that functions in said plant cell to cause termination of transcription and addition of polyadenylated ribonucleotides to a 3' end of the mRNA molecule.

The present invention includes and provides a method of preparing tocopherols which comprises: transforming a plant with a nucleic acid comprising as operably linked components: (A) a promoter region which functions in a plant cell to cause the production of an mRNA molecule; (B) an exogenous nucleic acid molecule encoding a protein comprising an amino acid sequence selected from the group consisting of SEQ ID NOs: 2 and 4, and (C) a 3' non-translated sequence that functions in said plant cell to cause termination of transcription and addition of polyadenylated ribonucleotides to a 3' end of the mRNA molecule; and, growing said plant.

The present invention includes and provides a method of preparing homogentesic acid which comprises transforming a plant with a nucleic acid comprising as operably linked components: (A) a promoter region which functions in a plant cell to cause the production of an mRNA molecule; (B) an exogenous nucleic acid molecule encoding a protein comprising an amino acid sequence selected from the group consisting of SEQ ID NOs: 2 and 4, and (C) a 3' non-translated sequence that functions in said plant cell to cause termination of transcription and addition of polyadenylated ribonucleotides to a 3' end of the mRNA molecule.

The present invention includes and provides a method of preparing plastoquinones which comprises transforming a plant with a nucleic acid comprising as operably linked components: (A) a promoter region which functions in a plant cell to cause the production of a mRNA molecule; (B) an exogenous nucleic acid molecule encoding a protein or fragment thereof comprising an amino acid sequence selected from the group consisting of SEQ ID NOs: 2 and 4, and (C) a 3' non-translated sequence that functions in said plant cell to cause termination of transcription and addition of polyadenylated ribonucleotides to a 3' end of the mRNA molecule.

The present invention includes and provides feedstock comprising a transformed plant or part thereof, wherein said transformed plant has an exogenous nucleic acid molecule comprising a sequence selected from the group of SEQ ID NOs: 1 and 3.

The present invention includes and provides a meal comprising plant material manufactured from a transformed plant, wherein said transformed plant contains an exogenous nucleic acid molecule comprising a sequence selected from the group of SEQ ID NOs: 1 and 3.

The present invention includes and provides a transformed plant having an exogenous nucleic acid molecule which comprises a nucleic acid sequence that encodes for a protein having an amino acid sequence of SEQ ID NO: 2 or 4.

The present invention includes and provides a transformed plant having an exogenous nucleic acid molecule that comprises a nucleic acid sequence of SEQ ID NO: 1 or 3.

The present invention includes and provides a method of producing a plant having seeds with increased tocopherol level comprising: (A) transforming said plant with a nucleic acid molecule that encodes a protein with chorismate mutase and prephenate dehydrogenase activities; and (b) growing said transformed plant.

The present invention includes and provides a method of producing a plant having seeds with increased tocopherol level comprising: (A) transforming said plant with a nucleic acid molecule which comprises a nucleic acid sequence that encodes for a protein having an amino acid sequence of SEQ ID NO: 2 or 4; and (b) growing said transformed plant.

The present invention includes and provides a seed derived from a transformed plant having an exogenous nucleic acid molecule that encodes a protein with chorismate mutase and prephenate dehydrogenase activities, wherein said seed has an increased tocopherol level relative to seeds from a plant having a similar genetic background but lacking said exogenous nucleic acid molecule.

The present invention includes and provides a seed derived from a transformed plant having an exogenous nucleic acid molecule which comprises a nucleic acid sequence that encodes for a protein having an amino acid sequence of SEQ ID NO: 2 or 4, wherein said transformed plant has a seed with an increased tocopherol level relative to seeds from a plant having a similar genetic background but lacking said exogenous nucleic acid molecule.

The present invention includes and provides oil derived from a seed of a transformed plant having an exogenous nucleic acid molecule that encodes a protein with chorismate mutase and prephenate dehydrogenase activities, wherein said transformed plant has a seed with an increased tocopherol level relative to seeds from a plant having a similar genetic background but lacking said exogenous nucleic acid molecule.

The present invention includes and provides oil derived from a seed of a transformed plant having an exogenous nucleic acid molecule which comprises a nucleic acid sequence that encodes for a protein having an amino acid sequence of SEQ ID NO: 2 or 4, wherein said transformed plant has a seed with an increased tocopherol level relative to seeds from a plant having a similar genetic background but lacking said exogenous nucleic acid molecule.

The present invention includes and provides feedstock comprising a transformed plant or part thereof, having an exogenous nucleic acid molecule that encodes a protein with chorismate mutase and prephenate dehydrogenase activities, wherein said transformed plant has a seed with an increased tocopherol level relative to seeds from a plant having a similar genetic background but lacking said exogenous nucleic acid molecule.

The present invention includes and provides feedstock comprising a transformed plant or part thereof, having an exogenous nucleic acid molecule which comprises a nucleic acid sequence that encodes for a protein having an amino acid sequence of SEQ ID NO: 2 or 4, wherein said transformed plant has a seed with an increased tocopherol level relative to seeds from a plant having a similar genetic background but lacking said exogenous nucleic acid molecule.

The present invention includes and provides feedstock comprising a transformed plant or part thereof having an exogenous nucleic acid molecule that encodes a protein with chorismate mutase and prephenate dehydrogenase activities, wherein said transformed plant has a seed with an increased tocopherol level relative to seeds from a plant having a similar genetic background but lacking said exogenous nucleic acid molecule.

The present invention includes and provides a meal comprising plant material manufactured from a transformed plant, having an exogenous nucleic acid molecule that encodes a protein with chorismate mutase and prephenate dehydrogenase activities, wherein said transformed plant has a seed with an increased tocopherol level relative to seeds from a plant having a similar genetic background but lacking said exogenous nucleic acid molecule.

The present invention includes and provides a meal comprising plant material manufactured from a transformed plant having an exogenous nucleic acid molecule which comprises a nucleic acid sequence that encodes for a protein having an amino acid sequence of SEQ ID NO: 2 or 4, wherein said transformed plant has a seed with an increased tocopherol level relative to seeds from a plant having a similar genetic background but lacking said exogenous nucleic acid molecule.

The present invention includes and provides a meal comprising plant material manufactured from a transformed plant, having an exogenous nucleic acid molecule that encodes a protein with chorismate mutase and prephenate dehydrogenase activities, wherein said transformed plant has a seed with an increased tocopherol level relative to seeds from a plant having a similar genetic background but lacking said exogenous nucleic acid molecule.

The present invention includes and provides a meal comprising plant material manufactured from a transformed plant having an exogenous nucleic acid molecule which comprises a nucleic acid sequence that encodes for a protein having an amino acid sequence of SEQ ID NO: 2 or 4, wherein said transformed plant has a seed with an increased tocopherol level relative to seeds from a plant having a similar genetic background but lacking the exogenous nucleic acid molecule.

The present invention includes and provides nucleic acid constructs, as well as plants and organisms containing those constructs, having combinations of two or more genes involved in tocopherol and tocotrienol biosynthesis. Any combination of the following genes with tyrA is prefered: slr1736, ATPT2, dxs, dxr, GGH, GGPPS, HPPD, MT1, TMT2, GMT, AANT1, slr 1737, and an antisense construct for homogentisic acid dioxygenase. In a particularly preferred embodiment, tyrA is combined with HPPD and either slr1736 orATPT2.

DESCRIPTION OF THE NUCLEIC AND AMINO ACID SEQUENCES

SEQ ID NO: 1 sets forth a nucleic acid sequence of DNA molecule that encodes an *Erwinia herbicola* bifunctional prephenate dehyrdrogenase.

SEQ ID NO: 2 sets forth a derived amino acid sequence of an *Erwinia herbicola* bifunctional prephenate dehyrdrogenase.

SEQ ID NO: 3 sets forth a nucleic acid sequence of DNA molecule that encodes an *Escherichia coli* bifunctional prephenate dehyrdrogenase.

SEQ ID NO: 4 sets forth a derived amino acid sequence of an *Escherichia coli* bifunctional prephenate dehyrdrogenase.

SEQ ID NO: 5 sets forth a 5' primer used for amplification of an *Erwinia herbicola* tyrA sequence.

SEQ ID NO: 6 sets forth a 3' primer used for amplification of an *Erwinia herbicola* tyrA sequence.

SEQ ID NO: 7 sets forth a 5' primer used for amplification of an *Escherichia coli* tyrA sequence.

SEQ ID NO: 8 sets forth a 3' primer used for amplification of an *Escherichia coli* tyrA sequence.

SEQ ID NO: 9 sets forth a primer sequence.
SEQ ID NO: 10 sets forth a primer sequence.
SEQ ID NO: 11 sets forth a primer sequence.
SEQ ID NO: 12 sets forth a primer sequence.

DETAILED DESCRIPTION

Figure 1:
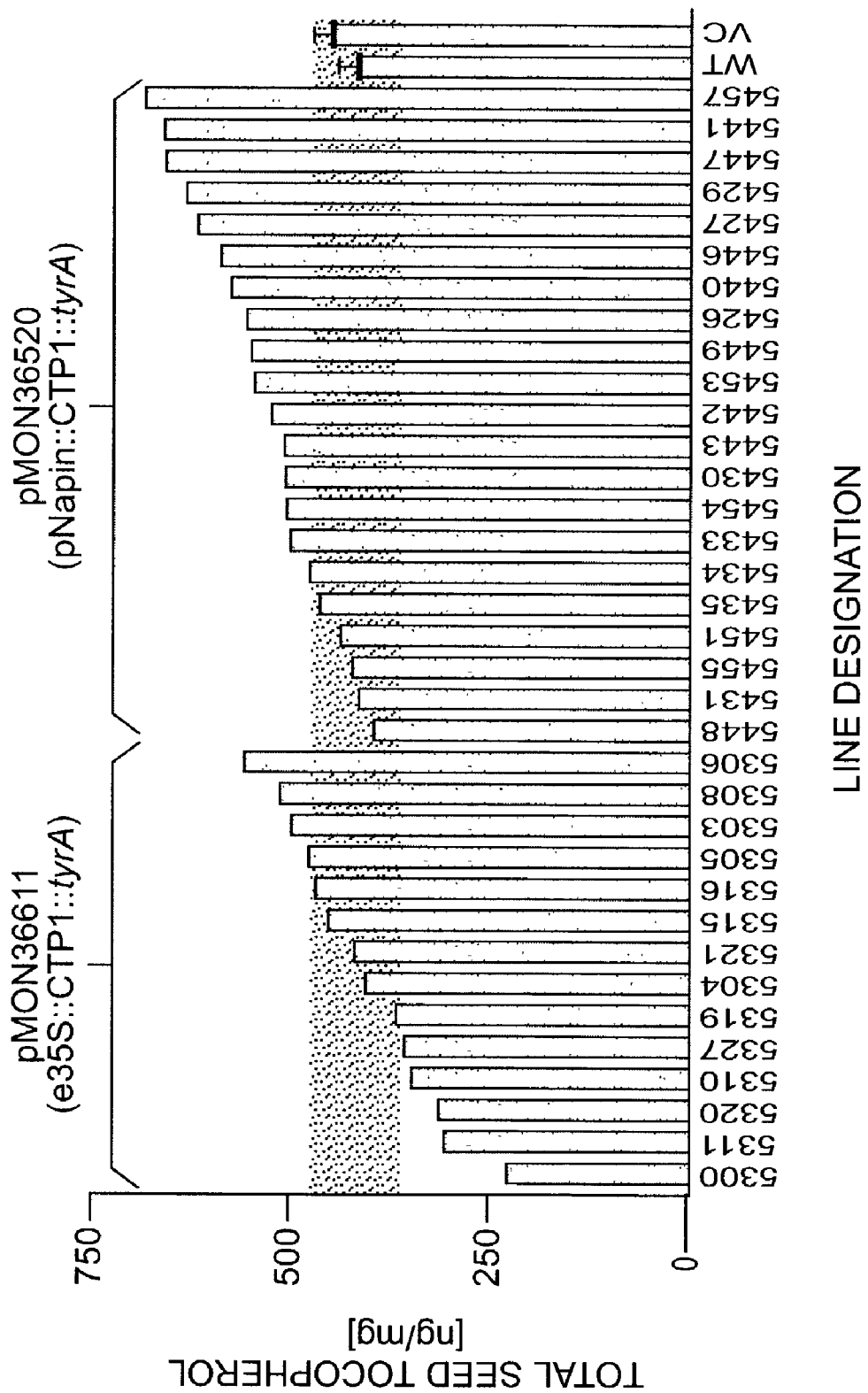
FIG. 1 is a graph comparing total seed tocopherol levels of *Arabidopsis thaliana* lines harboring an *Erwinia herbicola* tyrA expression construct with a plastidal target sequence, a wild type plant, and a plant with a vector control.

Any of the nucleic acid molecules disclosed herein can be enhanced or over-expressed in a variety of organisms, such as plants, which can result in higher levels of tocopherol precursors such as homogentisic acid (HGA) and ultimately in enhanced levels of tocopherols in such organisms. In addition, the enhanced expression or over expression of proteins set forth herein can also result in the production of increased levels of plastoquinones. Moreover, the present invention provides a number of agents, for example, nucleic acid molecules and proteins associated with the production of tocopherols, and provides uses of such agents.

The present invention includes and provides for nucleic acid constructs for expression of bifunctional prephenate dehydrogenases in organisms in which it is desirable to produce an increased yield of homogentisic acid, plastoquinones, or tocopherols. Such nucleic acid constructs may be used in organisms for which an increased level of prephenate dehydrogenase activity is desirable. The invention also includes and provides for nucleic acids constructs for the expression of phytyl prenyltransferases in organisms in which it is desirable to produce an increased yield of plastoquinones, or tocopherols, and the use of constructs producing antisense nucleic acids against phytyl prenyltransferases in organisms in which it is desirable to produce an increased yield of homogentesic acid.

Agents:

The agents of the invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response. The agents will preferably be "substantially purified." The term "substantially purified," as used herein, refers to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the invention may also be recombinant. As used herein, the term recombinant means any agent (e.g., DNA, peptide etc.), that is, or results, however indirectly, from human manipulation of a nucleic acid molecule.

It is understood that the agents of the invention may be labeled with reagents that facilitate detection of the agent (e.g., fluorescent labels, Prober et al., *Science* 238:336-340 (1987); Albarella et al., EP 144914; chemical labels, Sheldon et al., U.S. Pat. No. 4,582,789; Albarella et al., U.S. Pat. No. 4,563,417; modified bases, Miyoshi et al., EP 119448).

Nucleic Acid Molecules

Agents of the invention include nucleic acid molecules which encode a bifunctional prephenate dehydrogenase, having both chorismate mutase and prephenate dehydrogenase activities. In a preferred aspect of the present invention, the nucleic acid molecule comprises a nucleic acid sequence which encodes a bacterial homologue of a bifuntional prephenate dehydrogenase. In a preferred embodiment, the nucleic acid molecule comprises a nucleic acid sequence having SEQ ID NOs: 1 or 3. In another preferred embodiment, the nucleic acid molecule is a fragment of any nucleic acid sequence disclosed herein encoding an amino acid sequence having prephenate dehydrogenase activity.

In another preferred aspect of the present invention the nucleic acid molecule comprises a nucleic acid sequence selected from the group consisting of SEQ ID NOs: 1 and 3, complements thereof, and fragments of either. In a further aspect of the present invention the nucleic acid molecule comprises a nucleic acid sequence encoding an amino acid sequence selected from the group consisting of SEQ ID NOs: 2 and 4, and fragments thereof.

In another preferred aspect of the present invention nucleic acid molecules comprise both a nucleic acid sequence encoding a bifuntional prephenate dehydrogenase and an expression cassette for expressing phyty prenyltransferase. In a further aspect of the present invention, nucleic acid constructs separately encoding a bifunctional prephenate dehydrogenase and phyty prenyltransferase may be employed.

In another preferred aspect of the present invention a nucleic acid molecule comprises nucleotide sequences encoding a plastid transit peptide operably fused to a nucleic acid molecule that encodes a protein or fragment of the present invention.

It is understood that in a further aspect of nucleic acid sequences of the present invention, the nucleic acids can encode a protein that differs from any of the proteins in that one or more amino acids have been deleted, substituted or added without altering the function. For example, it is understood that codons capable of coding for such conservative amino acid substitutions are known in the art.

One subset of the nucleic acid molecules of the invention is fragment nucleic acids molecules. Fragment nucleic acid molecules may consist of significant portion(s) of, or indeed most of, the nucleic acid molecules of the invention, such as those specifically disclosed. Alternatively, the fragments may comprise smaller oligonucleotides (having from about 15 to about 400 nucleotide residues and more preferably, about 15 to about 30 nucleotide residues, or about 50 to about 100 nucleotide residues, or about 100 to about 200 nucleotide residues, or about 200 to about 400 nucleotide residues, or about 275 to about 350 nucleotide residues).

A fragment of one or more of the nucleic acid molecules of the invention may be a probe and specifically a PCR probe. A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3 (www-genome.wi.mit.edu/cgi-bin/primer/primer3.cgi), STSPipeline (www-genome.wi.mit.edu/cgi-bin/www-STS_Pipeline), or GeneUp (Pesole et al., *BioTechniques* 25:112-123 (1998)), for example, can be used to identify potential PCR primers.

Another subset of the nucleic acid molecules of the invention include nucleic acid molecules that encode a protein or fragment thereof.

Nucleic acid molecules or fragments thereof of the present invention are capable of specifically hybridizing to other nucleic acid molecules under certain circumstances. Nucleic acid molecules of the present invention include those that specifically hybridize to nucleic acid molecules having a nucleic acid sequence selected from the group consisting of SEQ ID NOs: 1 and 3, and complements thereof. Nucleic acid molecules of the present invention also include those that specifically hybridize to nucleic acid molecules encoding an amino acid sequences selected from SEQ ID NOs: 2, 4, complements thereof, and fragments of either.

As used herein, two nucleic acid molecules are said to be capable of specifically hybridizing to one another if the two molecules are capable of forming an anti-parallel, double-stranded nucleic acid structure.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning, A Laboratory Manual*, 2nd Ed., Cold Spring Harbor Press, Cold Spring Harbor, N.Y. (1989), and by Haymes et al., *Nucleic Acid Hybridization, A Practical Approach, IRL Press*, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization are, for example, 6.0× sodium chloride/sodium citrate (SSC) at about 45° C., followed by a wash of 2.0×SSC at 20-25° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID NOs: 1 and 3 and complements thereof under moderately stringent conditions, for example at about 2.0×SSC and about 65° C.

In a particularly preferred embodiment, a nucleic acid of the present invention will include those nucleic acid molecules that specifically hybridize to one or more of the nucleic acid molecules set forth in SEQ ID NOs: 1 and 3 and complements thereof under high stringency conditions such as 0.2×SSC and about 65° C.

In one aspect of the present invention, the nucleic acid molecules of the present invention have one or more of the nucleic acid sequences set forth in SEQ ID NOs: 1 and 3 and complements thereof. In another aspect of the present invention, one or more of the nucleic acid molecules of the present invention share between 100% and 90% sequence identity with one or more of the nucleic acid sequences set forth in SEQ ID NOs: 1 and 3 and complements thereof and fragments of either. In a further aspect of the present invention, one or more of the nucleic acid molecules of the present invention share between 100% and 95% sequence identity with one or more of the nucleic acid sequences set forth in SEQ ID NOs: 1 and 3, complements thereof, and fragments of either. In a more preferred aspect of the present invention, one or more of the nucleic acid molecules of the present invention share between 100% and 98% sequence identity with one or more of the nucleic acid sequences set forth in SEQ ID NOs: 1 and 3, complements thereof and fragments of either. In an even more preferred aspect of the present invention, one or more of the nucleic acid molecules of the present invention share between 100% and 99% sequence identity with one or more of the sequences set forth in SEQ ID NOs: 1 and 3, complements thereof, and fragments of either.

In a preferred embodiment the percent identity calculations are performed using the Megalign program of the LASERGENE bioinformatics computing suite (default parameters, DNASTAR Inc., Madison, Wis.).

A nucleic acid molecule of the invention can also encode a homolog protein. As used herein, a homolog protein molecule or fragment thereof is a counterpart protein molecule or fragment thereof in a second species (e.g., maize rubisco small subunit is a homolog of *Arabidopsis* rubisco small subunit). A homolog can also be generated by molecular evolution or DNA shuffling techniques, so that the molecule retains at least one functional or structure characteristic of the original protein (see, for example, U.S. Pat. No. 5,811,238).

In another embodiment, the homolog is selected from the group consisting of alfalfa, *Arabidopsis*, barley, *Brassica campestris*, *Brassica napus*, broccoli, cabbage, canola, citrus, cotton, garlic, oat, onion, flax, an ornamental plant, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, maize, *Phaseolus*, crambe, mustard, castor bean, sesame, cottonseed, linseed, safflower, and oil palm. More particularly, preferred homologs are selected from canola, maize, *Arabidopsis, Brassica campestris, Brassica napus*, soybean, crambe, mustard, castor bean, peanut, sesame, cottonseed, linseed, safflower, oil palm, flax, and sunflower. In an even more preferred embodiment, the homolog is selected from the group consisting of canola, maize, *Arabidopsis, Brassica campestris, Brassica napus*, soybean, sunflower, safflower, oil palms, and peanut. In a preferred embodiment, the homolog is soybean. In a preferred embodiment, the homolog is canola. In a preferred embodiment, the homolog is *Brassica napus*.

In a preferred embodiment, nucleic acid molecules having SEQ ID NOs: 1 and 3, complements thereof, and fragments of either; or more preferably SEQ ID NOs: 1 and 3 and complements thereof, can be utilized to obtain such homologs.

In another further aspect of the present invention, nucleic acid molecules of the present invention can comprise sequences that differ from those encoding a protein or fragment thereof in SEQ ID NOs: 2 and 4 due to fact that a protein can have one or more conservative amino acid changes, and nucleic acid sequences coding for the protein can therefore have sequence differences. It is understood that codons capable of coding for such conservative amino acid substitutions are known in the art.

It is well known in the art that one or more amino acids in a native sequence can be substituted with other amino acid(s), the charge and polarity of which are similar to that of the native amino acid, i.e., a conservative amino acid substitution. Conservative substitutes for an amino acid within the native polypeptide sequence can be selected from other members of the class to which the amino acid belongs. Amino acids can be divided into the following four groups: (1) acidic amino acids, (2) basic amino acids, (3) neutral polar amino acids, and (4) neutral, nonpolar amino acids. Representative amino acids within these various groups include, but are not limited to, (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

Conservative amino acid substitution within the native polypeptide sequence can be made by replacing one amino acid from within one of these groups with another amino acid from within the same group. In a preferred aspect, biologically functional equivalents of the proteins or fragments thereof of the present invention can have ten or fewer conservative amino acid changes, more preferably seven or fewer conservative amino acid changes, and most preferably five or fewer conservative amino acid changes. The encoding nucleotide sequence will thus have corresponding base substitutions, permitting it to encode biologically functional equivalent forms of the proteins or fragments of the present invention.

It is understood that certain amino acids may be substituted for other amino acids in a protein structure without appreciable loss of interactive binding capacity with structures such as, for example, antigen-binding regions of antibodies or binding sites on substrate molecules. Because it is the interactive capacity and nature of a protein that defines that protein's biological functional activity, certain amino acid sequence substitutions can be made in a protein sequence and, of course, its underlying DNA coding sequence and, nevertheless, a protein with like properties can still be obtained. It is thus contemplated by the inventors that various changes may be made in the peptide sequences of the proteins or fragments of the present invention, or corresponding DNA sequences that encode said peptides, without appreciable loss of their biological utility or activity. It is understood that codons capable of coding for such amino acid changes are known in the art.

In making such changes, the hydropathic index of amino acids may be considered. The importance of the hydropathic amino acid index in conferring interactive biological function on a protein is generally understood in the art (Kyte and Doolittle, *J. Mol. Biol.* 157, 105-132 (1982)). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, *J. Mol. Biol.* 157:105-132 (1982)); these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5).

In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101 states that the greatest local average hydrophilicity of a protein, as govern by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (0), threonine (−0.4), proline (−0.5±1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4).

In making such changes, the substitution of amino acids whose hydrophilicity values are within ±2 is preferred, those which are within ±1 are particularly preferred, and those within ±0.5 are even more particularly preferred.

In a further aspect of the present invention, one or more of the nucleic acid molecules of the present invention differ in nucleic acid sequence from those for which a specific sequence is provided herein because one or more codons has been replaced with a codon that encodes a conservative substitution of the amino acid originally encoded.

Agents of the invention include nucleic acid molecules that encode at least about a contiguous 10 amino acid region of a protein of the present invention, more preferably at least about a contiguous 25, 40, 50, 100, or 125 amino acid region of a protein of the present invention.

In a preferred embodiment, any of the nucleic acid molecules of the present invention can be operably linked to a promoter region which functions in a plant cell to cause the production of an mRNA molecule, where the nucleic acid molecule that is linked to the promoter is heterologous with respect to that promoter. As used herein, "heterologous" means not naturally occurring together.

Protein and Peptide Molecules

A class of agents includes one or more of the proteins or fragments thereof or peptide molecules encoded by a nucleic acid agent of the invention. A particular preferred class of proteins is that having an amino acid sequence selected from the group consisting of SEQ ID NOs: 2 and 4 and fragments thereof. Protein or peptide agents may have C-terminal or N-terminal amino acid sequence extensions. One class of N-terminal extensions employed in a preferred embodiment are plastid transit peptides. When employed, plastid transit peptides can be operatively linked to the N-terminal sequence, thereby permitting the localization of the agent peptide or proteins to plastids. In a preferred embodiment the plastid targeting sequence is a CTP1 sequence. In another embodiment the sequence is a CTP2 sequence.

As used herein, the term "protein" or "peptide molecule" includes any molecule that comprises five or more amino acids. It is well known in the art that proteins may undergo modification, including post-translational modifications, such as, but not limited to, disulfide bond formation, glycosylation, phosphorylation, or oligomerization. Thus, as used herein, the term "protein" or "peptide molecule" includes any protein that is modified by any biological or non-biological process. The terms "amino acid" and "amino acids" refer to all naturally occurring L-amino acids. This definition is meant to include norleucine, norvaline, ornithine, homocysteine, and homoserine.

One or more of the protein or fragments thereof or peptide molecules may be produced via chemical synthesis, or more preferably, by expression in a suitable bacterial or eukaryotic host. Suitable methods for expression are described by Sambrook et al., In: *Molecular Cloning, A Laboratory Manual, 2nd Edition, Cold Spring Harbor Press*, Cold Spring Harbor, N.Y. (1989) or similar texts.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin). Fusion protein or peptide molecules of the invention are preferably produced via recombinant means.

Another class of agents comprise protein or peptide molecules or fragments or fusions thereof comprising SEQ ID NOs: 2 and 4 and fragments thereof in which conservative, non-essential or non-relevant amino acid residues have been added, replaced or deleted. Computerized means for designing modifications in protein structure are known in the art (Dahiyat and Mayo, *Science* 278:82-87 (1997)).

A protein of the invention can also be a homolog protein. As used herein, a homolog protein or fragment thereof is a counterpart protein or fragment thereof in a second species. A homolog can also be generated by molecular evolution or DNA shuffling techniques, so that the molecule retains at least one functional or structure characteristic of the original (see, for example, U.S. Pat. No. 5,811,238).

In another embodiment, the homolog is selected from the group consisting of alfalfa, *Arabidopsis*, barley, broccoli, cabbage, canola, citrus, cotton, garlic, oat, onion, flax, an ornamental plant, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, maize, and *Phaseolus*. More particularly, preferred homologs are selected from canola, maize, *Arabidopsis, Brassica campestris, Brassica napus*, soybean, crambe, mustard, castor bean, peanut, sesame, cottonseed, linseed, safflower, oil palm, flax, and sunflower. In an even more preferred embodiment, the homolog is selected from the group consisting of canola, maize, *Arabidopsis, Brassica campestris, Brassica napus*, soybean, sunflower, safflower, oil palms, and peanut. In a preferred embodiment, the homolog is soybean. In a preferred embodiment, the homolog is canola. In a preferred embodiment, the homolog is *Brassica napus*.

In a preferred embodiment, the nucleic acid molecules of the present invention or complements and fragments of either can be utilized to obtain such homologs.

Agents of the invention include proteins and fragments thereof comprising at least about a contiguous 10 amino acid region preferably comprising at least about a contiguous 20 amino acid region, even more preferably comprising at least a contiguous 25, 35, 50, 75 or 100 amino acid region of a protein of the present invention. In another preferred embodiment, the proteins of the present invention include between about 10 and about 25 contiguous amino acid region, more preferably between about 20 and about 50 contiguous amino acid region, and even more preferably between about 40 and about 80 contiguous amino acid region.

Plant Constructs and Plant Transformants

One or more of the nucleic acid molecules of the invention may be used in plant transformation or transfection. Exogenous genetic material may be transferred into a plant cell and the plant cell regenerated into a whole, fertile or sterile plant. Exogenous genetic material is any genetic material, whether naturally occurring or otherwise, from any source that is capable of being inserted into any organism. In a preferred embodiment, the exogenous genetic material encodes a bifunctional prephenate dehydrogenase or fragments thereof, more preferably a bifunctional prephenate dehydrogenase from a prokaryotic organism, and even more preferably a bifunctional prephenate dehydrogenase from *Erwinia herbicola* or *Escherichia coli*. In a preferred embodiment, the exogenous genetic material includes a nucleic acid molecule of the present invention, and preferably a nucleic acid molecule having a sequence selected from the group consisting of SEQ ID NOs: 1 and 3, complements thereof, and fragments of either. In another embodiment, the exogenous genetic material includes a nucleic acid molecule of the present invention, preferably a nucleic acid encoding a protein or fragment thereof having phytyl prenyltransferase activity.

In an embodiment of the present invention, exogenous genetic material comprising a TyrA homolog or fragment thereof is introduced into a plant with one or more additional genes. In one embodiment, preferred combinations of genes include two or more of the following genes: tyrA, slr1736, ATPT2, dxs, dxr, GGH, GGPPS, HPPD, MT1, TMT2, GMT, AANT1, slr 1737, and an antisense construct for homogentisic acid dioxygenase (Krindl et al., *Seed Sci. Res.* 1:209: 219 (1991); Keegstra, *Cell* 56(2):247-53 (1989); Nawrath, et al., *Proc. Natl. Acad. Sci. U.S.A.* 91:12760-12764 (1994); Xia et al., *J. Gen. Microbiol.* 138:1309-1316 (1992); Cyanobase on the world wide web at www.kazusa.or.jp/cyanobase; Lois et al., *Proc. Natl. Acad. Sci. U.S.A.* 95 (5):2105-2110 (1998); Takahashi et al. *Proc. Natl. Acad. Sci. U.S.A.* 95 (17), 9879-9884 (1998); Norris et al., *Plant Physiol.* 117: 1317-1323 (1998); Bartley and Scolnik, *Plant Physiol.* 104: 1469-1470 (1994), Smith et al., *Plant J.* 11: 83-92 (1997); WO 00/32757; WO 00/10380; Saint Guily, et al., *Plant Physiol.*, 100(2):1069-1071 (1992); Sato et al., *J. DNA Res.* 7 (1):31-63 (2000)). In a preferred combination, the nucleic acid construct or constructs encode, in addition to tyrA, HPPD and either slr1736 or ATPT2.

In such combinations, one or more of the gene products can be directed to the plastid by the use of a plastid targeting sequence. Alternatively, one or more of the gene products can be localized in the cytoplasm. Such genes can be introduced, for example, with the TyrA homolog or fragment thereof on a single construct, introduced on different constructs but the same transformation event or introduced into separate plants followed by one or more crosses to generate the desired combination of genes. In such combinations, a preferred promoter is a napin promoter and a preferred plastid targeting sequence is a CTP1 sequence.

Such genetic material may be transferred into either monocotyledons and dicotyledons including, but not limited to canola, maize, soybean, *Arabidopsis* phaseolus, peanut, alfalfa, wheat, rice, oat, sorghum, rye, tritordeum, millet, fescue, perennial ryegrass, sugarcane, cranberry, papaya, banana, safflower, oil palms, flax, muskmelon, apple, cucumber, dendrobium, gladiolus, chrysanthemum, liliacea, cotton, eucalyptus, sunflower, *Brassica campestris, Brassica napus*, turfgrass, sugarbeet, coffee and dioscorea (Christou, In: *Particle Bombardment for Genetic Engineering of Plants*, Biotechnology Intelligence Unit. Academic Press, San Diego, Calif. (1996)), with canola, maize, *Arabidopsis, Brassica campestris, Brassica napus*, soybean, crambe, mustard, castor bean, peanut, sesame, cottonseed, linseed, safflower, oil palm, flax, and sunflower preferred, and canola, maize, *Arabidopsis, Brassica campestris, Brassica napus*, soybean, sunflower, safflower, oil palms, and peanut preferred. In a more preferred embodiment, the genetic material is transferred into canola. In another more preferred embodiment, the genetic material is transferred into *Brassica napus*. In another more preferred embodiment, the genetic material is transferred into soybean.

Transfer of a nucleic acid that encodes a protein can result in expression or overexpression of that protein in a transformed cell or transgenic plant. One or more of the proteins or fragments thereof encoded by nucleic acid molecules of the invention may be overexpressed in a transformed cell or transformed plant. Such expression or overexpression may be the result of transient or stable transfer of the exogenous genetic material.

In a preferred embodiment, expression or overexpression of a protein or fragment thereof of the present invention in a plant provides in that plant, relative to an untransformed plant with a similar genetic background, an increased level of tocotrienols.

In a preferred embodiment, expression or overexpression of a protein or fragment thereof of the present invention in a plant provides in that plant, relative to an untransformed plant with a similar genetic background, an increased level of tocopherols.

In a preferred embodiment, overexpression of a protein or fragment thereof of the present invention in a plant provides in that plant, relative to an untransformed plant with a similar genetic background, an increased level of α-tocopherols.

In a preferred embodiment, overexpression of a protein or fragment thereof of the present invention in a plant provides in that plant, relative to an untransformed plant with a similar genetic background, an increased level of γ-tocopherols.

In a preferred embodiment, overexpression of a protein or fragment thereof of the present invention in a plant provides in that plant, relative to an untransformed plant with a similar genetic background, an increased level of homogentesic acid In a preferred embodiment, overexpression of a protein or fragment thereof of the present invention in a plant provides in that plant, relative to an untransformed plant with a similar genetic background, an increased level of plastoquinols or plastoquinones.

In some embodiments, the levels of one or more products of the tocopherol biosynthesis pathway, including any one or more of tocotrienols, tocopherols, α-tocopherols, γ-tocopherols plastoquinols, plastoquinones or homogentesic acid, are increased by 10%, or more preferably 25%, 50%, 100%, 200%, 250%, 1,000%, 2,000%, or 2,500%. The levels of products may be increased throughout an organism such as a plant or localized in one or more specific organs or tissues of the organism. For example the levels of products may be increased in one or more of the tissues and organs of a plant include without limitation: roots, tubers, stems, leaves, stalks, fruit, berries, nuts, bark, pods, seeds and flowers.

In another embodiment, overexpression of a protein or fragment thereof of the present invention in a plant provides in that plant, or a tissue of that plant, relative to an untransformed plant or plant tissue, with a similar genetic background, an increased level of prephenate dehydrogenase protein.

In another preferred embodiment, overexpression of a protein or fragment thereof of the present invention in a transformed plant may provide tolerance to a variety of stress, e.g. oxidative stress tolerance such as to oxygen or ozone, UV tolerance, cold tolerance, or fungal/microbial pathogen tolerance.

As used herein in a preferred aspect, a tolerance or resistance to stress is determined by the ability of a plant, when challenged by a stress such as cold to produce a plant having a higher yield than one without such tolerance or resistance to stress. In a particularly preferred aspect of the present invention, the tolerance or resistance to stress is measured relative to a plant with a similar genetic background to the tolerant or resistance plant except that the plant expresses or over expresses a protein or fragment thereof of the present invention.

Exogenous genetic material may be transferred into a host cell by the use of a DNA vector or construct designed for such a purpose. Design of such a vector is generally within the skill of the art (*See, Plant Molecular Biology: A Laboratory Manual*, Clark (ed.), Springer, New York (1997)). In some embodiments of this invention a single gene sequence selected from the group consisting of tyrA, slr1736, ATPT2, dxs, dxr, GGH, GGPPS, HPPD, MT1, TMT2, GMT, AANT1, slr 1737, and an antisense construct for homogentisic acid dioxygenase can be transferred into the desired target plant. In a preferred combination, the nucleic acid construct or constructs encode, in addition to tyrA, HPPD and either slr1736 or ATPT2. Target plants expressing the desired activity from the transferred gene sequence can be subject to one or more crosses with plants having been transformed with one or more other gene sequences selected from the group consisting of tyrA, slr1736, ATPT2, dxs, dxr, GGH, GGPPS, HPPD, MT1, TMT2, GMT, AANT1, slr 1737, and an antisense construct for homogentisic acid dioxygenase in order to obtain plants expressing two or more of the desired activities from the transferred gene sequence. In a preferred combination, the nucleic acid construct or constructs encode, in addition to tyrA, HPPD and either slr1736 or ATPT2. In another embodiment, DNA vector constructs may be multiple gene constructs that comprise two or more gene sequences selected from the group consisting of tyrA, slr1736, ATPT2, dxs, dxr, GGH, GGPPS, HPPD, MT1, TMT2, GMT, AANT1, slr 1737, and an antisense construct for homogentisic acid dioxygenase, such that transformation with a single DNA vector construct will result in the expression of the two or more of the gene sequences. In a preferred combination, the nucleic acid construct or constructs encode, in addition to tyrA, HPPD and either slr1736 or ATPT2.

A construct or vector may include a plant promoter to express the protein or protein fragment of choice. In a preferred embodiment, any nucleic acid molecules described herein can be operably linked to a promoter region which functions in a plant cell to cause the production of an mRNA molecule. For example, any promoter that functions in a plant cell to cause the production of an mRNA molecule, such as those promoters described herein, without limitation, can be used. In a preferred embodiment, the promoter is a plant promoter.

A number of promoters that are active in plant cells have been described in the literature. These include the nopaline synthase (NOS) promoter (Ebert et al., Proc. Natl. Acad. Sci. (U.S.A.) 84:5745-5749 (1987)), the octopine synthase (OCS) promoter (which is carried on tumor-inducing plasmids of Agrobacterium tumefaciens), the caulimovirus promoters such as the cauliflower mosaic virus (CaMV) 19S promoter (Lawton et al., Plant Mol. Biol. 9:315-324 (1987)) and the CaMV 35S promoter (Odell et al., Nature 313:810-812 (1985)), the figwort mosaic virus 35S-promoter, the light-inducible promoter from the small subunit of ribulose-1,5-bis-phosphate carboxylase (ssRUBISCO), the Adh promoter (Walker et al., Proc. Natl. Acad. Sci. (U.S.A.) 84:6624-6628 (1987)), the sucrose synthase promoter (Yang et al., Proc. Natl. Acad. Sci. (U.S.A.) 87:4144-4148 (1990)), the R gene complex promoter (Chandler et al., The Plant Cell 1:1175-1183 (1989)) and the chlorophyll a/b binding protein gene promoter, etc. These promoters have been used to create DNA constructs that have been expressed in plants; see, e.g., PCT publication WO 84/02913. The CaMV 35S promoters are preferred for use in plants. Promoters known or found to cause transcription of DNA in plant cells can be used in the invention.

For the purpose of expression in source tissues of the plant, such as the leaf, seed, root or stem, it is preferred that the promoters utilized have relatively high expression in these specific tissues. Tissue-specific expression of a protein of the present invention is a particularly preferred embodiment. For this purpose, one may choose from a number of promoters for genes with tissue- or cell-specific or enhanced expression. Examples of such promoters reported in the literature include the chloroplast glutamine synthetase GS2 promoter from pea (Edwards et al., Proc. Natl. Acad. Sci. (U.S.A.) 87:3459-3463 (1990)), the chloroplast fructose-1,6-biphosphatase (FBPase) promoter from wheat (Lloyd et al., Mol. Gen. Genet. 225:209-216 (1991)), the nuclear photosynthetic ST-LS1 promoter from potato (Stockhaus et al., EMBO J. 8:2445-2451 (1989)), the serine/threonine kinase (PAL) promoter and the glucoamylase (CHS) promoter from Arabidopsis thaliana. Also reported to be active in photosynthetically active tissues are the ribulose-1,5-bisphosphate carboxylase (RbcS) promoter from eastern larch (Larix laricina), the promoter for the cab gene, cab6, from pine (Yamamoto et al., Plant Cell Physiol. 35:773-778 (1994)), the promoter for the Cab-i gene from wheat (Fejes et al., Plant Mol. Biol. 15:921-932 (1990)), the promoter for the CAB-1 gene from spinach (Lubberstedt et al., Plant Physiol. 104:997-1006 (1994)), the promoter for the cab1R gene from rice (Luan et al., Plant Cell. 4:971-981 (1992)), the pyruvate, orthophosphate dikinase (PPDK) promoter from maize (Matsuoka et al., Proc. Natl. Acad. Sci. (U.S.A.) 90: 9586-9590 (1993)), the promoter for the tobacco Lhcb1*2 gene (Cerdan et al., Plant Mol. Biol. 33:245-255 (1997)), the Arabidopsis thaliana SUC2 sucrose-H+symporter promoter (Truernit et al., Planta. 196:564-570 (1995)) and the promoter for the thylakoid membrane proteins from spinach (psaD, psaF, psaE, PC, FNR, atpC, atpD, cab, rbcS). Other promoters for the chlorophyll a/b-binding proteins may also be utilized in the invention, such as the promoters for LhcB gene and PsbP gene from white mustard (Sinapis alba; Kretsch et al., Plant Mol. Biol. 28:219-229 (1995)).

For the purpose of expression in sink tissues of the plant, such as the tuber of the potato plant, the fruit of tomato, or the seed of maize, wheat, rice and barley, it is preferred that the promoters utilized in the invention have relatively high expression in these specific tissues. A number of promoters for genes with tuber-specific or tuber-enhanced expression are known, including the class I patatin promoter (Bevan et al., EMBO J. 8:1899-1906 (1986); Jefferson et al., Plant Mol. Biol. 14:995-1006 (1990)), the promoter for the potato tuber ADPGPP genes, both the large and small subunits, the sucrose synthase promoter (Salanoubat and Belliard, Gene 60:47-56 (1987), Salanoubat and Belliard, Gene 84:181-185 (1989)), the promoter for the major tuber proteins including the 22 kd protein complexes and protease inhibitors (Hannapel, Plant Physiol. 101:703-704 (1993)), the promoter for the granule-bound starch synthase gene (GBSS) (Visser et al., Plant Mol. Biol. 17:691-699 (1991)) and other class I and II patatins promoters (Koster-Topfer et al., Mol. Gen. Genet. 219:390-396 (1989); Mignery et al., Gene. 62:27-44 (1988)).

Other promoters can also be used to express a protein or fragment thereof in specific tissues, such as seeds or fruits. Indeed, in a preferred embodiment, the promoter used is a seed specific promoter. Examples of such promoters include the 5' regulatory regions from such genes as napin (Krindl et al., Seed Sci. Res. 1:209:219 (1991)), phaseolin (Bustos, et al., Plant Cell, 1(9):839-853 (1989)), soybean trypsin inhibitor (Riggs, et al., Plant Cell 1(6):609-621 (1989)), ACP (Baerson, et al., Plant Mol. Biol., 22(2):255-267 (1993)), stearoyl-ACP desaturase (Slocombe, et al., Plant Physiol. 104(4):167-176 (1994)), soybean a' subunit of b-conglycinin (soy 7s, (Chen et al., Proc. Natl. Acad. Sci., 83:8560-8564 (1986))), and oleosin (see, for example, Hong, et al., Plant Mol. Biol., 34(3):549-555 (1997)). Further examples include the promoter for β-conglycinin (Chen et al., *Dev. Genet.* 10: 112-122 (1989)). Also included are the zeins, which are a group of storage proteins found in maize endosperm. Genomic clones for zein genes have been isolated (Pedersen et al., *Cell* 29:1015-1026 (1982), and Russell et al., *Transgenic Res.* 6(2): 157-168) and the promoters from these clones, including the 15 kD, 16 kD, 19 kD, 22 kD, 27 kD and genes, could also be used. Other promoters known to function, for example, in maize include the promoters for the following genes: waxy, Brittle, Shrunken 2, Branching enzymes I and II, starch synthases, debranching enzymes, oleosins, glutelins and sucrose synthases. A particularly preferred promoter for maize endosperm expression is the promoter for the glutelin gene from rice, more particularly the Osgt-1 promoter (Zheng et al., *Mol Cell Biol.* 13:5829-5842 (1993)). Examples of promoters suitable for expression in wheat include those promoters for the ADPglucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins and the aleurone specific proteins. A preferred promoter for expression in the seed is a napin promoter.

Root specific promoters may also be used. An example of such a promoter is the promoter for the acid chitinase gene (Samac et al., *Plant Mol. Biol.* 25:587-596 (1994)). Expression in root tissue could also be accomplished by utilizing the root specific subdomains of the CaMV35S promoter that have been identified (Lam et al., *Proc. Natl. Acad. Sci. (U.S.A.)* 86:7890-7894 (1989)). Other root cell specific promoters include those reported by Conkling et al. (Conkling et al., *Plant Physiol.* 93:1203-1211 (1990)).

Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436. In addition, a tissue specific enhancer may be used (Fromm et al., *The Plant Cell* 1:977-984 (1989)).

Constructs or vectors may also include, with the coding region of interest, a nucleic acid sequence that acts, in whole or in part, to terminate transcription of that region. A number of such sequences have been isolated, including the Tr7 3' sequence and the NOS 3' sequence (Ingelbrecht et al., *The Plant Cell* 1:671-680 (1989); Bevan et al., *Nucleic Acids Res.* 11:369-385 (1983)). Regulatory transcript termination regions can be provided in plant expression constructs of this invention as well. Transcript termination regions can be provided by the DNA sequence encoding the gene of interest or a convenient transcription termination region derived from a different gene source, for example, the transcript termination region which is naturally associated with the transcript initiation region. The skilled artisan will recognize that any convenient transcript termination region which is capable of terminating transcription in a plant cell can be employed in the constructs of the present invention.

A vector or construct may also include regulatory elements. Examples of such include the Adh intron 1 (Callis et al., *Genes and Develop.* 1:1183-1200 (1987)), the sucrose synthase intron (Vasil et al., *Plant Physiol.* 91:1575-1579 (1989)) and the TMV omega element (Gallie et al., *The Plant Cell* 1:301-311 (1989)). These and other regulatory elements may be included when appropriate.

A vector or construct may also include a selectable marker. Selectable markers may also be used to select for plants or plant cells that contain the exogenous genetic material. Examples of such include, but are not limited to: a neo gene (Potrykus et al., *Mol. Gen. Genet.* 199:183-188 (1985)), which codes for kanamycin resistance and can be selected for using kanamycin, RptII, G418, hpt etc.; a bar gene which codes for bialaphos resistance; a mutant EPSP synthase gene (Hinchee et al., *Bio/Technology* 6:915-922 (1988); Reynaerts et al., Selectable and Screenable Markers. In Gelvin and Schilperoort. Plant Molecular Biology Manual, Kluwer, Dordrecht (1988); Reynaerts et al., Selectable and screenable markers. In Gelvin and Schilperoort. Plant Molecular Biology Manual, Kluwer, Dordrecht (1988)), aadA (Jones et al., Mol. Gen. Genet. (1987)),) which encodes glyphosate resistance; a nitrilase gene which confers resistance to bromoxynil (Stalker et al., *J. Biol. Chem.* 263:6310-6314 (1988)); a mutant acetolactate synthase gene (ALS) which confers imidazolinone or sulphonylurea resistance (European Patent Application 154,204 (Sep. 11, 1985)), ALS (D'Halluin et al., Bio/Technology 10: 309-314 (1992)), and a methotrexate resistant DHFR gene (Thillet et al., *J. Biol. Chem.* 263:12500-12508 (1988)). A vector or construct may also include a transit peptide.

Incorporation of a suitable chloroplast transit peptide may also be employed (European Patent Application Publication Number 0218571). Translational enhancers may also be incorporated as part of the vector DNA. DNA constructs could contain one or more 5' non-translated leader sequences which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al., *Plant Mol. Biol.* 32:393-405 (1996). A preferred transit peptide is CTP1. In another embodiment the transit peptide is a CTP2 sequence.

A vector or construct may also include a screenable marker. Screenable markers may be used to monitor expression. Exemplary screenable markers include: a β-glucuronidase or uidA gene (GUS) which encodes an enzyme for which various chromogenic substrates are known (Jefferson, *Plant Mol. Biol, Rep.* 5:387-405 (1987); Jefferson et al., *EMBO J.* 6:3901-3907 (1987)); an R-locus gene, which encodes a product that regulates the production of anthocyanin pigments (red color) in plant tissues (Dellaporta et al., Stadler Symposium 11:263-282 (1988)); a β-lactamase gene (Sutcliffe et al., *Proc. Natl. Acad. Sci. (U.S.A.)* 75:3737-3741 (1978)), a gene which encodes an enzyme for which various chromogenic substrates are known (e.g., PADAC, a chromogenic cephalosporin); a luciferase gene (Ow et al., *Science* 234:856-859 (1986)); a xylE gene (Zukowsky et al., *Proc. Natl. Acad. Sci. (U.S.A.)* 80:1101-1105 (1983)) which encodes a catechol dioxygenase that can convert chromogenic catechols; an α-amylase gene (Ikatu et al., *Bio/Technol.* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins which are detectable, (e.g. by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules such as, for example, by PEG-mediated transformation, by electroporation or by acceleration of DNA coated particles, etc (Potrykus, *Ann. Rev. Plant Physiol. Plant Mol. Biol.* 42:205-225 (1991); Vasil, *Plant Mol. Biol.* 25:925-937 (1994)). For example, electroporation has been used to transform maize protoplasts (Fromm et al., *Nature* 312:791-793 (1986)).

Other vector systems suitable for introducing transforming DNA into a host plant cell include but are not limited to binary artificial chromosome (BIBAC) vectors (Hamilton et al., *Gene* 200:107-116 (1997)); and transfection with RNA viral vectors (Della-Cioppa et al., *Ann. N.Y. Acad. Sci.* (1996), 792 (Engineering Plants for Commercial Products and Applications), 57-61). Additional vector systems also include plant selectable YAC vectors such as those described in Mullen et al., *Molecular Breeding* 4:449-457 (1988).

Technology for introduction of DNA into cells is well known to those of skill in the art. Four general methods for delivering a gene into cells have been described:
(1) chemical methods (Graham and van der Eb, *Virology* 54:536-539 (1973));
(2) physical methods such as microinjection (Capecchi, *Cell* 22:479-488 (1980)), electroporation (Wong and Neumann, *Biochem. Biophys. Res. Commun.* 107:584-587 (1982); Fromm et al., *Proc. Natl. Acad. Sci. (U.S.A.)* 82:5824-5828 (1985); U.S. Pat. No. 5,384,253); the gene gun (Johnston and Tang, *Methods Cell Biol.* 43:353-365 (1994)); and vacuum infiltration (Bechtold et al., *C.R. Acad. Sci. Paris, Life Sci.* 316:1194-1199. (1993)); (3) viral vectors (Clapp, *Clin. Perinatol.* 20:155-168 (1993); Lu et al., *J. Exp. Med.* 178:2089-2096 (1993); Eglitis and Anderson, *Biotechniques* 6:608-614 (1988)); and (4) receptor-mediated mechanisms (Curiel et al., *Hum. Gen. Ther.* 3:147-154 (1992), Wagner et al., *Proc. Natl. Acad. Sci. (USA)* 89:6099-6103 (1992)).

Acceleration methods that may be used include, for example, microprojectile bombardment and the like. One example of a method for delivering transforming nucleic acid molecules into plant cells is microprojectile bombardment. This method has been reviewed by Yang and Christou (eds.), *Particle Bombardment Technology for Gene Transfer*, Oxford Press, Oxford, England (1994)). Non-biological particles (microprojectiles) that may be coated with nucleic acids and delivered into cells by a propelling force. Exemplary particles include those comprised of tungsten, gold, platinum and the like.

A particular advantage of microprojectile bombardment, in addition to it being an effective means of reproducibly transforming monocots, is that neither the isolation of protoplasts (Cristou et al., *Plant Physiol.* 87:671-674 (1988)) nor the susceptibility to *Agrobacterium* infection is required. An illustrative embodiment of a method for delivering DNA into maize cells by acceleration is a biolistics α-particle delivery system, which can be used to propel particles coated with DNA through a screen, such as a stainless steel or Nytex screen, onto a filter surface covered with maize cells cultured in suspension. Gordon-Kamm et al., describes the basic procedure for coating tungsten particles with DNA (Gordon-Kamm et al., *Plant Cell* 2:603-618 (1990)). The screen disperses the tungsten nucleic acid particles so that they are not delivered to the recipient cells in large aggregates. A particle delivery system suitable for use with the invention is the helium acceleration PDS-1000/He gun, which is available from Bio-Rad Laboratories (Bio-Rad, Hercules, Calif.)(Sanford et al., *Technique* 3:3-16 (1991)).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain 1000 or more loci of cells transiently expressing a marker gene. The number of cells in a focus which express the exogenous gene product 48 hours post-bombardment often ranges from one to ten, and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include the particle gun delivery of DNA containing a selectable marker and targeting of the DNA to the plastid genome through homologous recombination (Svab et al., *Proc. Natl. Acad. Sci. (U.S.A.)* 87:8526-8530 (1990); Svab and Maliga, *Proc. Natl. Acad. Sci. (U.S.A.)* 90:913-917 (1993); Staub and Maliga, *EMBO J.* 12:601-606 (1993); U.S. Pat. Nos. 5,451,513 and 5,545,818).

Accordingly, it is contemplated that one may wish to adjust various aspects of the bombardment parameters in small scale studies to fully optimize the conditions. One may particularly wish to adjust physical parameters such as gap distance, flight distance, tissue distance and helium pressure. One may also minimize the trauma reduction factors by modifying conditions that influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example the methods described by Fraley et al., *Bio/Technology* 3:629-635 (1985) and Rogers et al., *Methods Enzymol.* 153:253-277 (1987). Further, the integration of the Ti-DNA is a relatively precise process resulting in few rearrangements. The region of DNA to be transferred is defined by the border sequences and intervening DNA is usually inserted into the plant genome as described (Spielmann et al., *Mol. Gen. Genet.* 205:34 (1986)).

Modem *Agrobacterium* transformation vectors are capable of replication in *E. coli* as well as *Agrobacterium*, allowing for convenient manipulations as described (Klee et al., In: *Plant DNA Infectious Agents*, Hohn and Schell (eds.), Springer-Verlag, New York, pp. 179-203 (1985)). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., *Methods Enzymol.* 153:253-277 (1987)). In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selling) an independent segregant, transgenic plant that contains a single added gene, germinating some of the seed produced and analyzing the resulting plants produced for the gene of interest.

It is also to be understood that two different transgenic plants can also be mated to produce offspring that contain two independently segregating, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation and combinations of these treatments (See, for example, Potrykus et al., *Mol. Gen. Genet.* 205:193-200 (1986); Lorz et al., *Mol. Gen. Genet.* 199:178 (1985); Fromm et al., *Nature* 319:791 (1986); Uchimiya et al., *Mol. Gen. Genet.* 204:204 (1986); Marcotte et al., *Nature* 335:454-457 (1988)).

Application of these systems to different plant strains depends upon the ability to regenerate that particular plant strain from protoplasts. Illustrative methods for the regeneration of cereals from protoplasts are described (Fujimura et al., *Plant Tissue Culture Letters* 2:74 (1985); Toriyama et al., *Theor. Appl. Genet.* 205:34 (1986); Yamada et al., *Plant Cell Rep.* 4:85 (1986); Abdullah et al., *Biotechnology* 4:1087 (1986)).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnology* 6:397 (1988)). In addition, "particle gun" or high-velocity microprojectile technology can be utilized (Vasil et al., *Bio/Technology* 10:667 (1992)).

Using the latter technology, DNA is carried through the cell wall and into the cytoplasm on the surface of small metal particles as described (Klein et al., *Nature* 328:70 (1987); Klein et al., *Proc. Natl. Acad. Sci. (U.S.A.)* 85:8502-8505 (1988); McCabe et al., *Bio/Technology* 6:923 (1988)). The metal particles penetrate through several layers of cells and thus allow the transformation of cells within tissue explants.

Other methods of cell transformation can also be used and include but are not limited to introduction of DNA into plants by direct DNA transfer into pollen (Hess et al., *Intern Rev. Cytol.* 107:367 (1987); Luo et al., *Plant Mol. Biol. Reporter* 6:165 (1988)), by direct injection of DNA into reproductive organs of a plant (Pena et al, *Nature* 325:274 (1987)), or by direct injection of DNA into the cells of immature embryos followed by the rehydration of desiccated embryos (Neuhaus et al., *Theor. Appl. Genet.* 75:30 (1987)).

The regeneration, development and cultivation of plants from single plant protoplast transformants or from various transformed explants is well known in the art (Weissbach and Weissbach, In: *Methods for Plant Molecular Biology*, Academic Press, San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens* and obtaining transgenic plants have been published for cotton (U.S. Pat. No. 5,004,863; U.S. Pat. No. 5,159,135; U.S. Pat. No. 5,518,908); soybean (U.S. Pat. No. 5,569,834; U.S. Pat. No. 5,416,011; McCabe et. al., *Biotechnology* 6:923 (1988); Christou et al., *Plant Physiol.* 87:671-674 (1988)); *Brassica* (U.S. Pat. No. 5,463, 174); peanut (Cheng et al., *Plant Cell Rep.* 15:653-657 (1996), McKently et al., *Plant Cell Rep.* 14:699-703 (1995)); papaya; pea (Grant et al., *Plant Cell Rep.* 15:254-258 (1995)); and *Arabidopsis thaliana* (Bechtold et al., *C.R. Acad. Sci. Paris, Life Sci.* 316:1194-1199 (1993)). The latter method for transforming *Arabidopsis thaliana* is commonly called "dipping" or vacuum infiltration or germplasm transformation.

Transformation of monocotyledons using electroporation, particle bombardment and *Agrobacterium* have also been reported. Transformation and plant regeneration have been achieved in asparagus (Bytebier et al., *Proc. Natl. Acad. Sci.* (*USA*) 84:5354 (1987)); barley (Wan and Lemaux, *Plant Physiol* 104:37 (1994)); maize (Rhodes et al., *Science* 240: 204 (1988); Gordon-Kamm et al., *Plant Cell* 2:603-618 (1990); Fromm et al., *Bio/Technology* 8:833 (1990); Koziel et al., *Bio/Technology* 11:194 (1993); Armstrong et al., *Crop Science* 35:550-557 (1995)); oat (Somers et al., *Bio/Technology* 10:1589 (1992)); orchard grass (Hom et al., *Plant Cell Rep.* 7:469 (1988)); rice (Toriyama et al., *Theor. Appl. Genet.* 205:34 (1986); Part et al., *Plant Mol. Biol.* 32:1135-1148 (1996); Abedinia et al., *Aust. J. Plant Physiol.* 24:133-141 (1997); Zhang and Wu, *Theor. Appl. Genet.* 76:835 (1988); Zhang et al., *Plant Cell Rep.* 7:379 (1988); Battraw and Hall, *Plant Sci.* 86:191-202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *Bio/Technology* 10:691 (1992)) and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454-457 (1988); Marcotte et al., *Plant Cell* 1:523-532 (1989); McCarty et al., *Cell* 66:895-905 (1991); Hattori et al., *Genes Dev.* 6:609-618 (1992); Goff et al., *EMBO J.* 9:2517-2522 (1990)). Transient expression systems may be used to functionally dissect gene constructs (see generally, Mailga et al., *Methods in Plant Molecular Biology*, Cold Spring Harbor Press (1995)).

Any of the nucleic acid molecules of the invention may be introduced into a plant cell in a permanent or transient manner in combination with other genetic elements such as vectors, promoters, enhancers, etc. Further, any of the nucleic acid molecules of the invention may be introduced into a plant cell in a manner that allows for expression or overexpression of the protein or fragment thereof encoded by the nucleic acid molecule.

Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2:279-289 (1990); van der Krol et al., *Plant Cell* 2:291-299 (1990)). Cosuppression may result from stable transformation with a single copy nucleic acid molecule that is homologous to a nucleic acid sequence found with the cell (Prolls and Meyer, *Plant J.* 2:465-475 (1992)) or with multiple copies of a nucleic acid molecule that is homologous to a nucleic acid sequence found with the cell (Mittlesten et al., *Mol. Gen. Genet.* 244:325-330 (1994)). Genes, even though different, linked to homologous promoters may result in the cosuppression of the linked genes (Vaucheret, *C.R. Acad. Sci. III* 316:1471-1483 (1993); Flavell, *Proc. Natl. Acad. Sci.* (*U.S.A.*) 91:3490-3496 (1994)); van Blokland et al., *Plant J.* 6:861-877 (1994); Jorgensen, *Trends Biotechnol.* 8:340-344 (1990); Meins and Kunz, In: *Gene Inactivation and Homologous Recombination in Plants*, Paszkowski (ed.), pp. 335-348, Kluwer Academic, Netherlands (1994)).

It is understood that one or more of the nucleic acids of the invention may be introduced into a plant cell and transcribed using an appropriate promoter with such transcription resulting in the cosuppression of an endogenous protein.

Antisense approaches are a way of preventing or reducing gene function by targeting the genetic material (Mol et al., *FEBS Lett.* 268:427-430 (1990)). The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., In: *Genetic Engineering*, Setlow (ed.), Vol. 11, New York: Plenum 49-63 (1989)).

Antisense RNA techniques involve introduction of RNA that is complementary to the target mRNA into cells, which results in specific RNA:RNA duplexes being formed by base pairing between the antisense substrate and the target mRNA (Green et al., *Annu. Rev. Biochem.* 55:569-597 (1986)). Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression (Takayama and Inouye, *Crit. Rev. Biochem. Mol. Biol.* 25:155-184 (1990)). An antisense vector is constructed by standard procedures and introduced into cells by transformation, transfection, electroporation, microinjection, infection, etc. The type of transformation and choice of vector will determine whether expression is transient or stable. The promoter used for the antisense gene may influence the level, timing, tissue, specificity, or inducibility of the antisense inhibition.

It is understood that the activity of a protein in a plant cell may be reduced or depressed by growing a transformed plant cell containing a nucleic acid molecule whose nontranscribed strand encodes a protein or fragment thereof.

Posttranscriptional gene silencing (PTGS) can result in virus immunity or gene silencing in plants. PTGS is induced by dsRNA and is mediated by an RNA-dependent RNA polymerase, present in the cytoplasm, that requires a dsRNA template. The dsRNA is formed by hybridization of complementary transgene mRNAs or complementary regions of the same transcript. Duplex formation can be accomplished by using transcripts from one sense gene and one antisense gene colocated in the plant genome, a single transcript that has self-complementarity, or sense and antisense transcripts from genes brought together by crossing. The dsRNA-dependent RNA polymerase makes a complementary strand from the transgene mRNA and RNAse molecules attach to this complementary strand (cRNA). These cRNA-RNase molecules hybridize to the endogene mRNA and cleave the single-stranded RNA adjacent to the hybrid. The cleaved single-stranded RNAs are further degraded by other host RNases because one will lack a capped 5' end and the other will lack a poly(A) tail (Waterhouse et al., *PNAS* 95: 13959-13964 (1998)).

It is understood that one or more of the nucleic acids of the invention may be introduced into a plant cell and transcribed using an appropriate promoter with such transcription resulting in the postranscriptional gene silencing of an endogenous transcript.

Antibodies have been expressed in plants (Hiatt et al., *Nature* 342:76-78 (1989); Conrad and Fielder, *Plant Mol. Biol.* 26:1023-1030 (1994)). Cytoplasmic expression of a scFv (single-chain Fv antibody) has been reported to delay infection by artichoke mottled crinkle virus. Transgenic plants that express antibodies directed against endogenous proteins may exhibit a physiological effect (Philips et al., *EMBO J.* 16:4489-4496 (1997); Marion-Poll, *Trends in Plant Science* 2:447-448 (1997)). For example, expressed anti-abscisic antibodies have been reported to result in a general perturbation of seed development (Philips et al., *EMBO J.* 16: 4489-4496 (1997)).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, *Nature Biotechnology* 15:1313-1315 (1997); Baca et al., *Ann. Rev. Biophys. Biomol. Struct.* 26:461-493 (1997)). The catalytic abilities of abzymes may be enhanced by site directed mutagenesis. Examples of abzymes are, for example, set forth in U.S. Pat. No. 5,658,753; U.S. Pat. No. 5,632,990; U.S. Pat. No. 5,631,137; U.S. Pat. No. 5,602,015; U.S. Pat. No. 5,559,538; U.S. Pat. No. 5,576,174; U.S. Pat. No. 5,500,358; U.S. Pat. No. 5,318,897; U.S. Pat. No. 5,298,409; U.S. Pat. No. 5,258,289 and U.S. Pat. No. 5,194,585.

It is understood that any of the antibodies of the invention may be expressed in plants and that such expression can result in a physiological effect. It is also understood that any of the expressed antibodies may be catalytic.

Alterations of plant phenotypes of the present invention can be relative to a plant having a similar genetic background that lacks the introduced nucleic acid of interest. In a preferred aspect, a similar genetic background is a background where the organisms being compared share 50% or greater of their nuclear genetic material. In a more preferred aspect a similar genetic background is a background where the organisms being compared share 75% or greater, even more preferably 90% or greater of their nuclear genetic material. In another even more preferable aspect, a similar genetic background is a background where the organisms being compared are plants, and the plants are isogenic except for any genetic material originally introduced using plant transformation techniques.

The present invention also provides for parts of the plants, particularly reproductive or storage parts, of the present invention. Plant parts, without limitation, include seed, endosperm, ovule and pollen. In a particularly preferred embodiment of the present invention, the plant part is a seed. In one embodiment the seed is a constituent of animal feed.

In another embodiment, the plant part is a fruit, more preferably a fruit with enhanced shelf life. In another preferred embodiment, the fruit has increased levels of a tocopherol.

The present invention also provides a container of over 10,000, more preferably 20,000, and even more preferably 40,000 seeds where over 10%, more preferably 25%, more preferably 50% and even more preferably 75% or 90% of the seeds are seeds derived from a plant of the present invention.

The present invention also provides a container of over 10 kg, more preferably 25 kg, and even more preferably 50 kg seeds where over 10%, more preferably 25%, more preferably 50% and even more preferably 75% or 90% of the seeds are seeds derived from a plant of the present invention.

Any of the plants or parts thereof of the present invention may be processed to produce a feed, meal, protein or oil preparation. A particularly preferred plant part for this purpose is a seed. In a preferred embodiment the feed, meal, protein or oil preparation is designed for ruminant animals. Methods to produce feed, meal, protein and oil preparations are known in the art. See, for example, U.S. Pat. Nos. 4,957,748, 5,100,679, 5,219,596, 5,936,069, 6,005,076, 6,146,669, and 6,156,227. In a preferred embodiment, the protein preparation is a high protein preparation. Such a high protein preparation preferably has a protein content of greater than 5% w/v, more preferably 10% w/v, and even more preferably 15% w/v. In a preferred oil preparation, the oil preparation is a high oil preparation with an oil content derived from a plant or part thereof of the present invention of greater than 5% w/v, more preferably 10% w/v, and even more preferably 15% w/v. In a preferred embodiment the oil preparation is a liquid and of a volume greater than 1, 5, 10 or 50 liters. The present invention provides for oil produced from plants of the present invention or generated by a method of the present invention. Such oil may be a minor or major component of any resultant product. Moreover, such oil may be blended with other oils. In a preferred embodiment, the oil produced from plants of the present invention or generated by a method of the present invention constitutes greater than 0.5%, 1%, 5%, 10%, 25%, 50%, 75% or 90% by volume or weight of the oil component of any product. In another embodiment, the oil preparation may be blended and can constitute greater than 10%, 25%, 35%, 50% or 75% of the blend by volume. Oil produced from a plant of the present invention can be admixed with one or more organic solvents or petroleum distillates.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new cultivars requires the development and selection of varieties, the crossing of these varieties and the selection of superior hybrid crosses. The hybrid seed can be produced by manual crosses between selected male-fertile parents or by using male sterility systems. Hybrids are selected for certain single gene traits such as pod color, flower color, seed yield, pubescence color, or herbicide resistance, which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. A $F_2$ population is produced by selfing one or several $F_1$'s. Selection of the best individuals from the best families is carried out. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seed of a population each generation of inbreeding.

Descriptions of other breeding methods that are commonly used for different traits and crops can be found in one of several reference books (eg. Fehr, Principles of Cultivar Development Vol. 1, pp. 2-3 (1987).

A transgenic plant of the present invention may also be reproduced using apomixis. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucellus, 2) diplospory where the embryo develops from an unreduced egg in an embryo sac derived from the megaspore mother cell, and 3) adventitious embryony where the embryo develops directly from a somatic cell. In most forms of apomixis, pseudogamy or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, U.S. Pat. No. 5,811,636.

Other Organisms

A nucleic acid of the present invention may be introduced into any cell or organism such as a mammalian cell, mammal, fish cell, fish, bird cell, bird, algae cell, algae, fungal cell, fungi, or bacterial cell. A protein of the present invention may be produced in an appropriate cell or organism. Preferred host and transformants include: fungal cells such as *Aspergillus*, yeasts, mammals, particularly bovine and porcine, insects, bacteria, and algae. Methods to transform such cells or organisms are known in the art (EP 0 238 023; Yelton et al., *Proc. Natl. Acad. Sci. (U.S.A.)*, 81:1470-1474 (1984); Malardier et al., *Gene*, 78:147-156 (1989); Becker and Guarente, In: Abelson and Simon (eds.), *Guide to Yeast*

*Genetics and Molecular Biology, Method Enzymol.*, Vol. 194, pp. 182-187, Academic Press, Inc., New York; Ito et al., *J. Bacteriology,* 153:163 (1983) Hinnen et al., *Proc. Natl. Acad. Sci. (U.S.A.)*, 75:1920 (1978); Bennett and LaSure (eds.), *More Gene Manipualtionins in fungi*, Academic Press, CA (1991)). Methods to produce proteins of the present invention are also known (Kudla et al., *EMBO,* 9:1355-1364 (1990); Jarai and Buxton, *Current Genetics,* 26:2238-2244 (1994); Verdier, *Yeast,* 6:271-297 (1990; MacKenzie et al., *Journal of Gen. Microbiol.,* 139:2295-2307 (1993); Hartl et al., *TIBS,* 19:20-25 (1994); Bergenron et al., *TIBS,* 19:124-128 (1994); Demolder et al., *J. Biotechnology,* 32:179-189 (1994); Craig, *Science,* 260:1902-1903 (1993); Gething and Sambrook, *Nature,* 355:33-45 (1992); Puig and Gilbert, *J. Biol. Chem.,* 269:7764-7771 (1994); Wang and Tsou, *FASEB Journal,* 7:1515-1517 (1993); Robinson et al., *Bio/Technology,* 1:381-384 (1994); Enderlin and Ogrydziak, *Yeast,* 10:67-79 (1994); Fuller et al., *Proc. Natl. Acad. Sci. (U.S.A.)*, 86:1434-1438 (1989); Julius et al., *Cell,* 37:1075-1089 (1984); Julius et al., *Cell* 32:839-852 (1983).

In a preferred embodiment, overexpression of a protein or fragment thereof of the present invention in a cell or organism provides in that cell or organism, relative to a cell or organism with a similar genetic background, an increased level of tocotrienols.

In a preferred embodiment, overexpression of a protein or fragment thereof of the present invention in a cell or organism provides in that cell or organism, relative to an untransformed cell or organism with a similar genetic background, an increased level of tocopherols.

In a preferred embodiment, overexpression of a protein or fragment thereof of the present invention in a cell or organism provides in that cell or organism, relative to an untransformed cell or organism with a similar genetic background, an increased level of α-tocopherols.

In a preferred embodiment, overexpression of a protein or fragment thereof of the present invention in a cell or organism provides in that cell or organism, relative to an untransformed cell or organism with a similar genetic background, an increased level of γ-tocopherols.

In a preferred embodiment, overexpression of a protein or fragment thereof of the present invention in a cell or organism provides in that cell or organism, relative to an untransformed cell or organism with a similar genetic background, an increased level of homogentisic acid.

In a preferred embodiment, overexpression of a protein or fragment thereof of the present invention in a cell or organism provides in that cell or organism, relative to an untransformed cell or organism with a similar genetic background, an increased level of plastoquinols or plastoquinones.

Antibodies

One aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in SEQ ID NOs: 2 and 4 or a fragment thereof. In another embodiment, the antibody specifically binds to a fusion protein comprising an amino acid sequence selected from the amino acid sequence set forth in SEQ ID NOs: 2 or 4 or a fragment thereof. In another embodiment the antibody specifically binds to a fusion protein comprising an amino acid sequence selected from the amino acid sequence set forth in SEQ ID NOs: 2 or 4 or a fragment thereof. Antibodies of the invention may be used to quantitatively or qualitatively detect the protein or peptide molecules of the invention, or to detect post translational modifications of the proteins. As used herein, an antibody or peptide is said to "specifically bind" to a protein or peptide molecule of the invention if such binding is not competitively inhibited by the presence of non-related molecules.

Nucleic acid molecules that encode all or part of the protein of the invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments may be a "fusion" molecule (i.e., a part of a larger nucleic acid molecule) such that, upon expression, a fusion protein is produced. It is understood that any of the nucleic acid molecules of the invention may be expressed, via recombinant means, to yield proteins or peptides encoded by these nucleic acid molecules.

The antibodies that specifically bind proteins and protein fragments of the invention may be polyclonal or monoclonal and may comprise intact immunoglobulins, or antigen binding portions of immunoglobulins fragments (such as (F(ab'), F(ab')$_2$), or single-chain immunoglobulins producible, for example, via recombinant means. It is understood that practitioners are familiar with the standard resource materials which describe specific conditions and procedures for the construction, manipulation and isolation of antibodies (see, for example, Harlow and Lane, In: *Antibodies: A Laboratory Manual*, Cold Spring Harbor Press, Cold Spring Harbor, N.Y. (1988)).

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme).

The ability to produce antibodies that bind the protein or peptide molecules of the invention permits the identification of mimetic compounds derived from those molecules. These mimetic compounds may contain a fragment of the protein or peptide or merely a structurally similar region and nonetheless exhibits an ability to specifically bind to antibodies directed against that compound.

Exemplary Uses

Nucleic acid molecules and fragments thereof of the invention may be employed to obtain other nucleic acid molecules from the same species (nucleic acid molecules from maize may be utilized to obtain other nucleic acid molecules from maize). Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules or fragments thereof to screen cDNA or genomic libraries. Methods for forming such libraries are well known in the art.

Nucleic acid molecules and fragments thereof of the invention may also be employed to obtain nucleic acid homologs. Such homologs include the nucleic acid molecules of plants and other organisms, including bacteria and fungi, including the nucleic acid molecules that encode, in whole or in part, protein homologues of other plant species or other organisms, sequences of genetic elements, such as promoters and transcriptional regulatory elements. Such molecules can be readily obtained by using the above-described nucleic acid molecules or fragments thereof to screen cDNA or genomic libraries obtained from such plant species. Methods for forming such libraries are well known in the art. Such homolog molecules may differ in their nucleotide sequences from those found in one or more of SEQ ID NOs: 1 and 3 and complements thereof because complete complementarity is not needed for stable hybridization. The nucleic acid molecules of the invention therefore also include molecules that, although capable of specifically hybridizing with the nucleic acid molecules may lack "complete complementarity."Any of a variety of methods may be used to obtain one or more of the above-described nucleic acid molecules (Zamechik et al., *Proc. Natl. Acad. Sci.* (*U.S.A.*) 83:4143-4146 (1986); Goodchild et al., *Proc. Natl. Acad. Sci.* (*U.S.A.*) 85:5507-5511 (1988); Wickstrom et al., *Proc. Natl. Acad. Sci.* (*U.S.A.*) 85:1028-1032 (1988); Holt et al., *Molec. Cell. Biol.* 8:963-973 (1988); Gerwirtz et al., *Science* 242:1303-1306 (1988); Anfossi et al., *Proc. Natl. Acad. Sci.* (*U.S.A.*) 86:3379-3383 (1989); Becker et al., *EMBO J.* 8:3685-3691 (1989)). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.* 51:263-273 (1986); Erlich et al., European Patent 50,424; European Patent 84,796; European Patent 258,017; European Patent 237,362; Mullis, European Patent 201,184; Mullis et al., U.S. Pat. No. 4,683,202; Erlich, U.S. Pat. No. 4,582,788; and Saiki et al., U.S. Pat. No. 4,683,194) to amplify and obtain any desired nucleic acid molecule or fragment.

Promoter sequences and other genetic elements, including but not limited to transcriptional regulatory flanking sequences, associated with one or more of the disclosed nucleic acid sequences can also be obtained using the disclosed nucleic acid sequence provided herein. In one embodiment, such sequences are obtained by incubating nucleic acid molecules of the present invention with members of genomic libraries and recovering clones that hybridize to such nucleic acid molecules thereof. In a second embodiment, methods of "chromosome walking," or inverse PCR may be used to obtain such sequences (Frohman et al., *Proc. Natl. Acad. Sci.* (*U.S.A.*) 85:8998-9002 (1988); Ohara et al., *Proc. Natl. Acad. Sci.* (*U.S.A.*) 86:5673-5677 (1989); Pang et al., *Biotechniques* 22:1046-1048 (1977); Huang et al., *Methods Mol. Biol.* 69:89-96 (1997); Huang et al., *Method Mol. Biol.* 67:287-294 (1997); Benkel et al., *Genet. Anal.* 13:123-127 (1996); Hartl et al., *Methods Mol. Biol.* 58:293-301 (1996)). The term "chromosome walking" means a process of extending a genetic map by successive hybridization steps.

The nucleic acid molecules of the invention may be used to isolate promoters of cell enhanced, cell specific, tissue enhanced, tissue specific, developmentally or environmentally regulated expression profiles. Isolation and functional analysis of the 5' flanking promoter sequences of these genes from genomic libraries, for example, using genomic screening methods and PCR techniques would result in the isolation of useful promoters and transcriptional regulatory elements. These methods are known to those of skill in the art and have been described (See, for example, Birren et al., *Genome Analysis: Analyzing DNA*, 1, (1997), Cold Spring Harbor Laboratory Press, Cold Spring Harbor, N.Y.). Promoters obtained utilizing the nucleic acid molecules of the invention could also be modified to affect their control characteristics. Examples of such modifications would include but are not limited to enhancer sequences. Such genetic elements could be used to enhance gene expression of new and existing traits for crop improvement.

Another subset of the nucleic acid molecules of the invention includes nucleic acid molecules that are markers. The markers can be used in a number of conventional ways in the field of molecular genetics. Such markers include nucleic acid molecules SEQ ID NOs: 1 and 3, complements thereof, and fragments of either that can act as markers and other nucleic acid molecules of the present invention that can act as markers.

Genetic markers of the invention include "dominant" or "codominant" markers. "Codominant markers" reveal the presence of two or more alleles (two per diploid individual) at a locus. "Dominant markers" reveal the presence of only a single allele per locus. The presence of the dominant marker phenotype (e.g., a band of DNA) is an indication that one allele is in either the homozygous or heterozygous condition. The absence of the dominant marker phenotype (e.g., absence of a DNA band) is merely evidence that "some other" undefined allele is present. In the case of populations where individuals are predominantly homozygous and loci are predominately dimorphic, dominant and codominant markers can be equally valuable. As populations become more heterozygous and multi-allelic, codominant markers often become more informative of the genotype than dominant markers. Marker molecules can be, for example, capable of detecting polymorphisms such as single nucleotide polymorphisms (SNPs).

The genomes of animals and plants naturally undergo spontaneous mutation in the course of their continuing evolution (Gusella, *Ann. Rev. Biochem.* 55:831-854 (1986)). A "polymorphism" is a variation or difference in the sequence of the gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a population may have the original sequence (i.e., the original "allele") whereas other members may have the variant sequence (i.e., the variant "allele"). In the simplest case, only one variant sequence may exist and the polymorphism is thus said to be di-allelic. In other cases, the species' population may contain multiple alleles and the polymorphism is termed tri-allelic, etc. A single gene may have multiple different unrelated polymorphisms. For example, it may have a di-allelic polymorphism at one site and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity analysis (Weber, U.S. Pat. No. 5,075,217; Armour et al., *FEBS Lett.* 307:113-115 (1992); Jones et al., *Eur. J. Haematol.* 39:144-147 (1987); Horn et al., PCT Patent Application WO91/14003; Jeffreys, European Patent Application 370,719; Jeffreys, U.S. Pat. No. 5,175,082; Jeffreys et al., *Amer. J. Hum. Genet.* 39:11-24 (1986); Jeffreys et al., *Nature* 316:76-79 (1985); Gray et al., *Proc. R. Acad. Soc. Lond.* 243:241-253

(1991); Moore et al., *Genomics* 10:654-660 (1991); Jeffreys et al., *Anim. Genet.* 18:1-15 (1987); Hillel et al., *Anim. Genet.* 20:145-155 (1989); Hillel et al., *Genet.* 124:783-789 (1990)).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s) and more preferably within 100 kb of the polymorphism(s) and most preferably within 10 kb of the polymorphism(s) can be employed.

The identification of a polymorphism can be determined in a variety of ways. By correlating the presence or absence of it in a plant with the presence or absence of a phenotype, it is possible to predict the phenotype of that plant. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, organisms that possess a variant sequence can be distinguished from those having the original sequence by restriction fragment analysis. Polymorphisms that can be identified in this manner are termed "restriction fragment length polymorphisms" ("RFLPs") (Glassberg, UK Patent Application 2135774; Skolnick et al., *Cytogen. Cell Genet.* 32:58-67 (1982); Botstein et al., *Ann. J. Hum. Genet.* 32:314-331 (1980); Fischer et al., (PCT Application WO90/13668; Uhlen, PCT Application WO90/11369).

Polymorphisms can also be identified by Single Strand Conformation Polymorphism (SSCP) analysis (Elles, *Methods in Molecular Medicine: Molecular Diagnosis of Genetic Diseases*, Humana Press (1996); Orita et al., *Genomics* 5:874-879 (989)). A number of protocols have been described for SSCP including, but not limited to, Lee et al., *Anal. Biochem.* 205:289-293 (1992); Suzuki et al., *Anal. Biochem.* 192:82-84 (1991); Lo et al., *Nucleic Acids Research* 20:1005-1009 (1992); Sarkar et al., *Genomics* 13:441-443 (1992). It is understood that one or more of the nucleic acids of the invention, may be utilized as markers or probes to detect polymorphisms by SSCP analysis.

Polymorphisms may also be found using a DNA fingerprinting technique called amplified fragment length polymorphism (AFLP), which is based on the selective PCR amplification of restriction fragments from a total digest of genomic DNA to profile that DNA (Vos et al., *Nucleic Acids Res.* 23:4407-4414 (1995)). This method allows for the specific co-amplification of high numbers of restriction fragments, which can be visualized by PCR without knowledge of the nucleic acid sequence. It is understood that one or more of the nucleic acids of the invention may be utilized as markers or probes to detect polymorphisms by AFLP analysis or for fingerprinting RNA.

Polymorphisms may also be found using random amplified polymorphic DNA (RAPD) (Williams et al., *Nucl. Acids Res.* 18:6531-6535 (1990)) and cleaveable amplified polymorphic sequences (CAPS) (Lyamichev et al., *Science* 260:778-783 (1993)). It is understood that one or more of the nucleic acid molecules of the invention, may be utilized as markers or probes to detect polymorphisms by RAPD or CAPS analysis.

Single Nucleotide Polymorphisms (SNPs) generally occur at greater frequency than other polymorphic markers and are spaced with a greater uniformity throughout a genome than other reported forms of polymorphism. The greater frequency and uniformity of SNPs means that there is greater probability that such a polymorphism will be found near or in a genetic locus of interest than would be the case for other polymorphisms. SNPs are located in protein-coding regions and noncoding regions of a genome. Some of these SNPs may result in defective or variant protein expression (e.g., as a result of mutations or defective splicing). Analysis (genotyping) of characterized SNPs can require only a plus/minus assay rather than a lengthy measurement, permitting easier automation.

SNPs can be characterized using any of a variety of methods. Such methods include the direct or indirect sequencing of the site, the use of restriction enzymes (Botstein et al., *Am. J. Hum. Genet.* 32:314-331 (1980); Konieczny and Ausubel, *Plant J.* 4:403-410 (1993)), enzymatic and chemical mismatch assays (Myers et al., *Nature* 313:495-498 (1985)), allele-specific PCR (Newton et al., *Nucl. Acids Res.* 17:2503-2516 (1989); Wu et al., *Proc. Natl. Acad. Sci. USA* 86:2757-2760 (1989)), ligase chain reaction (Barany, *Proc. Natl. Acad. Sci. USA* 88:189-193 (1991)), single-strand conformation polymorphism analysis (Labrune et al., *Am. J. Hum. Genet.* 48: 1115-1120 (1991)), single base primer extension (Kuppuswamy et al., *Proc. Natl. Acad. Sci. USA* 88:1143-1147 (1991), Goelet U.S. Pat. No. 6,004,744; Goelet U.S. Pat. No. 5,888,819), solid-phase ELISA-based oligonucleotide ligation assays (Nikiforov et al., *Nucl. Acids Res.* 22:4167-4175 (1994), dideoxy fingerprinting (Sarkar et al., *Genomics* 13:441-443 (1992)), oligonucleotide fluorescence-quenching assays (Livak et al., *PCR Methods Appl.* 4:357-362 (1995a)), 5'-nuclease allele-specific hybridization TaqMan™ assay (Livak et al., *Nature Genet.* 9:341-342 (1995)), template-directed dye-terminator incorporation (TDI) assay (Chen and Kwok, *Nucl. Acids Res.* 25:347-353 (1997)), allele-specific molecular beacon assay (Tyagi et al., *Nature Biotech.* 16: 49-53 (1998)), PinPoint assay (Haff and Smirnov, *Genome Res.* 7: 378-388 (1997)), dCAPS analysis (Neff et al., *Plant J.* 14:387-392 (1998)), pyrosequencing (Ronaghi et al., *Analytical Biochemistry* 267:65-71 (1999); Ronaghi et al PCT application WO 98/13523; Nyren et al PCT application WO 98/28440; http//www.pyrosequencing.com), using mass spectrometry, e.g. the Masscode™ system (Howbert et al WO 99/05319; Howber et al WO 97/27331; http//www.rapigene.com; Becker et al PCT application WO 98/26095; Becker et al PCT application; WO 98/12355; Becker et al PCT application WO 97/33000; Monforte et al U.S. Pat. No. 5,965,363), invasive cleavage of oligonucleotide probes (Lyamichev et al *Nature Biotechnology* 17:292-296; http//www.twt.com), and using high density oligonucleotide arrays (Hacia et al *Nature Genetics* 22:164-167; http//www.affymetrix.com).

Polymorphisms may also be detected using allele-specific oligonucleotides (ASO), which, can be for example, used in combination with hybridization based technology including southern, northern, and dot blot hybridizations, reverse dot blot hybridizations and hybridizations performed on microarray and related technology.

The stringency of hybridization for polymorphism detection is highly dependent upon a variety of factors, including length of the allele-specific oligonucleotide, sequence composition, degree of complementarity (i.e. presence or absence of base mismatches), concentration of salts and other factors such as formamide, and temperature. These factors are important both during the hybridization itself and during subsequent washes performed to remove target polynucleotide that is not specifically hybridized. In practice, the conditions of the final, most stringent wash are most critical. In addition, the amount of target polynucleotide that is able to hybridize to the allele-specific oligonucleotide is also governed by such factors as the concentration of both the ASO and the target polynucleotide, the presence and concentration of factors that act to "tie up" water molecules, so as to effectively concentrate the reagents (e.g., PEG, dextran, dextran sulfate, etc.), whether the nucleic acids are immobilized or in solution, and the duration of hybridization and washing steps.

Hybridizations are preferably performed below the melting temperature ($T_m$) of the ASO. The closer the hybridization and/or washing step is to the $T_m$, the higher the stringency. $T_m$ for an oligonucleotide may be approximated, for example, according to the following formula: $T_m=81.5+16.6\times(\log10[Na+])+0.41\times(\% \ G+C)-675/n$; where [Na+] is the molar salt concentration of Na+ or any other suitable cation and n=number of bases in the oligonucleotide. Other formulas for approximating $T_m$ are available and are known to those of ordinary skill in the art.

Stringency is preferably adjusted so as to allow a given ASO to differentially hybridize to a target polynucleotide of the correct allele and a target polynucleotide of the incorrect allele. Preferably, there will be at least a two-fold differential between the signal produced by the ASO hybridizing to a target polynucleotide of the correct allele and the level of the signal produced by the ASO cross-hybridizing to a target polynucleotide of the incorrect allele (e.g., an ASO specific for a mutant allele cross-hybridizing to a wild-type allele). In more preferred embodiments of the present invention, there is at least a five-fold signal differential. In highly preferred embodiments of the present invention, there is at least an order of magnitude signal differential between the ASO hybridizing to a target polynucleotide of the correct allele and the level of the signal produced by the ASO cross-hybridizing to a target polynucleotide of the incorrect allele.

While certain methods for detecting polymorphisms are described herein, other detection methodologies may be utilized. For example, additional methodologies are known and set forth, in Birren et al., *Genome Analysis*, 4:135-186, *A Laboratory Manual. Mapping Genomes*, Cold Spring Harbor Laboratory Press, Cold Spring Harbor, N.Y. (1999); Maliga et al., *Methods in Plant Molecular Biology. A Laboratory Course Manual*, Cold Spring Harbor Laboratory Press, Cold Spring Harbor, N.Y. (1995); Paterson, *Biotechnology Intelligence Unit: Genome Mapping in Plants*, R. G. Landes Co., Georgetown, Tex., and Academic Press, San Diego, Calif. (1996); *The Maize Handbook*, Freeling and Walbot, eds., Springer-Verlag, New York, N.Y. (1994); *Methods in Molecular Medicine: Molecular Diagnosis of Genetic Diseases*, Elles, ed., Humana Press, Totowa, N.J. (1996); Clark, ed., *Plant Molecular Biology: A Laboratory Manual*, Clark, ed., Springer-Verlag, Berlin, Germany (1997).

Requirements for marker-assisted selection in a plant breeding program are: (1) the marker(s) should co-segregate or be closely linked with the desired trait; (2) an efficient means of screening large populations for the molecular marker(s) should be available; and (3) the screening technique should have high reproducibility across laboratories and preferably be economical to use and be user-friendly.

The genetic linkage of marker molecules can be established by a gene mapping model such as, without limitation, the flanking marker model reported by Lander and Botstein, *Genetics* 121:185-199 (1989) and the interval mapping, based on maximum likelihood methods described by Lander and Botstein, *Genetics* 121:185-199 (1989) and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, *Genetics* 121:185-199 (1989) and further described by Arús and Moreno-González, *Plant Breeding*, Hayward et al., (eds.) Chapman & Hall, London, pp. 314-331 (1993).

In a preferred embodiment of the present invention the nucleic acid marker exhibits a LOD score of greater than 2.0, more preferably 2.5, even more preferably greater than 3.0 or 4.0 with the trait or phenotype of interest. In a preferred embodiment, the trait of interest is altered tocopherol levels or compositions.

Additional models can be used. Many modifications and alternative approaches to interval mapping have been reported, including the use non-parametric methods (Kruglyak and Lander, *Genetics* 139:1421-1428 (1995)). Multiple regression methods or models can be also be used, in which the trait is regressed on a large number of markers (Jansen, *Biometrics in Plant Breeding*, van Oijen and Jansen (eds.), Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval and at the same time onto a number of markers that serve as 'cofactors,' have been reported by Jansen and Stam, *Genetics* 136:1447-1455 (1994), and Zeng, *Genetics* 136:1457-1468 (1994). Generally, the use of cofactors reduces the bias and sampling error of the estimated QTL positions (Utz and Melchinger, *Biometrics in Plant Breeding*, van Oijen and Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng, *Genetics* 136:1457-1468 (1994)). These models can be extended to multi-environment experiments to analyze genotype-environment interactions (Jansen et al., *Theo. Appl. Genet.* 91:33-37 (1995)).

It is understood that one or more of the nucleic acid molecules of the invention may be used as molecular markers. It is also understood that one or more of the protein molecules of the invention may be used as molecular markers.

In a preferred embodiment, the polymorphism is present and screened for in a mapping population, e.g. a collection of plants capable of being used with markers such as polymorphic markers to map genetic position of traits. The choice of appropriate mapping population often depends on the type of marker systems employed (Tanksley et al., *J.P. Gustafson and R. Appels* (eds.). Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large number of polymorphisms when compared to progeny in a narrow cross (adapted×adapted).

An $F_2$ population is the first generation of selfing (self-pollinating) after the hybrid seed is produced. Usually a single $F_1$ plant is selfed to generate a population segregating for all the genes in Mendelian (1:2:1) pattern. Maximum genetic information is obtained from a completely classified $F_2$ population using a codominant marker system (Mather, Measurement of Linkage in Heredity: Methuen and Co., (1938)). In the case of dominant markers, progeny tests (e.g., $F_3$, $BCF_2$) are required to identify the heterozygotes, in order to classify the population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations e.g. $F_3$ or $BCF_2$ can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually >F5, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter. *Proc. Natl. Acad. Sci.* (*U.S.A.*) 89:1477-1481 (1992)). However, as the distance between markers becomes larger (i.e., loci become more independent), the information in RIL populations decreases dramatically when compared to codominant markers.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., *Proc. Natl. Acad. Sci.* (*U.S.A.*) 89:1477-1481 (1992)). Information obtained from backcross populations using either codominant or dominant markers is less than that obtained from $F_2$ populations because one, rather than two, recombinant gamete is sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) (created by many backcrosses to produce a collection of individuals that is nearly identical in genetic composition except for the trait or genomic region under interrogation) can be used as a mapping population. In mapping with NILs, only a portion of the polymorphic loci is expected to map to a selected region.

Bulk segregant analysis (BSA) is a method developed for the rapid identification of linkage between markers and traits of interest (Michelmore et al., *Proc. Natl. Acad. Sci. U.S.A.* 88:9828-9832 (1991)). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

In an aspect of the present invention, one or more of the nucleic molecules of the present invention are used to determine the level (i.e., the concentration of mRNA in a sample, etc.) in a plant (preferably canola, maize, *Brassica campestris, Brassica napus*, soybean, crambe, mustard, castor bean, peanut, sesame, cottonseed, linseed, safflower, oil palm, flax or sunflower) or pattern (i.e., the kinetics of expression, rate of decomposition, stability profile, etc.) of the expression of a protein encoded in part or whole by one or more of the nucleic acid molecule of the present invention (collectively, the "Expression Response" of a cell or tissue).

As used herein, the Expression Response manifested by a cell or tissue is said to be "altered" if it differs from the Expression Response of cells or tissues of plants not exhibiting the phenotype. To determine whether a Expression Response is altered, the Expression Response manifested by the cell or tissue of the plant exhibiting the phenotype is compared with that of a similar cell or tissue sample of a plant not exhibiting the phenotype. As will be appreciated, it is not necessary to re-determine the Expression Response of the cell or tissue sample of plants not exhibiting the phenotype each time such a comparison is made; rather, the Expression Response of a particular plant may be compared with previously obtained values of normal plants. As used herein, the phenotype of the organism is any of one or more characteristics of an organism (e.g. disease resistance, pest tolerance, environmental tolerance such as tolerance to abiotic stress, male sterility, quality improvement or yield etc.). A change in genotype or phenotype may be transient or permanent. Also as used herein, a tissue sample is any sample that comprises more than one cell. In a preferred aspect, a tissue sample comprises cells that share a common characteristic (e.g. derived from root, seed, flower, leaf, stem or pollen etc.).

In one aspect of the present invention, an evaluation can be conducted to determine whether a particular mRNA molecule is present. One or more of the nucleic acid molecules of the present invention are utilized to detect the presence or quantity of the mRNA species. Such molecules are then incubated with cell or tissue extracts of a plant under conditions sufficient to permit nucleic acid hybridization. The detection of double-stranded probe-mRNA hybrid molecules is indicative of the presence of the mRNA; the amount of such hybrid formed is proportional to the amount of mRNA. Thus, such probes may be used to ascertain the level and extent of the mRNA production in a plant's cells or tissues. Such nucleic acid hybridization may be conducted under quantitative conditions (thereby providing a numerical value of the amount of the mRNA present). Alternatively, the assay may be conducted as a qualitative assay that indicates either that the mRNA is present, or that its level exceeds a user set, predefined value.

A number of methods can be used to compare the expression response between two or more samples of cells or tissue. These methods include hybridization assays, such as northerns, RNAse protection assays, and in situ hybridization. Alternatively, the methods include PCR-type assays. In a preferred method, the expression response is compared by hybridizing nucleic acids from the two or more samples to an array of nucleic acids. The array contains a plurality of suspected sequences known or suspected of being present in the cells or tissue of the samples.

An advantage of in situ hybridization over more conventional techniques for the detection of nucleic acids is that it allows an investigator to determine the precise spatial population (Angerer et al., *Dev. Biol.* 101:477-484 (1984); Angerer et al., *Dev. Biol.* 112:157-166 (1985); Dixon et al., *EMBO J.* 10:1317-1324 (1991)). In situ hybridization may be used to measure the steady-state level of RNA accumulation (Hardin et al., *J. Mol. Biol.* 202:417-431 (1989)). A number of protocols have been devised for in situ hybridization, each with tissue preparation, hybridization and washing conditions (Meyerowitz, *Plant Mol. Biol. Rep.* 5:242-250 (1987); Cox and Goldberg, In: *Plant Molecular Biology: A Practical Approach*, Shaw (ed.), pp. 1-35, IRL Press, Oxford (1988); Raikhel et al., *In situ RNA hybridization in plant tissues*, In: *Plant Molecular Biology Manual*, vol. B9:1-32, Kluwer Academic Publisher, Dordrecht, Belgium (1989)).

In situ hybridization also allows for the localization of proteins within a tissue or cell (Wilkinson, *In Situ Hybridization*, Oxford University Press, Oxford (1992); Langdale, *In Situ Hybridization* In: *The Maize Handbook*, Freeling and Walbot (eds.), pp. 165-179, Springer-Verlag, New York (1994)). It is understood that one or more of the molecules of the invention, preferably one or more of the nucleic acid molecules or fragments thereof of the invention or one or more of the antibodies of the invention may be utilized to detect the level or pattern of a protein or mRNA thereof by in situ hybridization.

Fluorescent in situ hybridization allows the localization of a particular DNA sequence along a chromosome, which is useful, among other uses, for gene mapping, following chromosomes in hybrid lines, or detecting chromosomes with translocations, transversions or deletions. In situ hybridization has been used to identify chromosomes in several plant species (Griffor et al., *Plant Mol. Biol.* 17:101-109 (1991); Gustafson et al., *Proc. Natl. Acad. Sci. (U.S.A.)* 87:1899-1902 (1990); Mukai and Gill, *Genome* 34:448-452 (1991); Schwarzacher and Heslop-Harrison, *Genome* 34:317-323 (1991); Wang et al., *Jpn. J. Genet.* 66:313-316 (1991); Parra and Windle, *Nature Genetics* 5:17-21 (1993)). It is understood that the nucleic acid molecules of the invention may be used as probes or markers to localize sequences along a chromosome.

Another method to localize the expression of a molecule is tissue printing. Tissue printing provides a way to screen, at the same time on the same membrane many tissue sections from different plants or different developmental stages (Yomo and Taylor, *Planta* 112:35-43 (1973); Harris and Chrispeels, *Plant Physiol.* 56:292-299 (1975); Cassab and Varner, *J. Cell. Biol.* 105:2581-2588 (1987); Spruce et al., *Phytochemistry* 26:2901-2903 (1987); Barres et al., *Neuron* 5:527-544 (1990); Reid and Pont-Lezica, *Tissue Printing: Tools for the Study of Anatomy, Histochemistry and Gene Expression*, Academic Press, New York, N.Y. (1992); Reid et al., *Plant Physiol.* 93:160-165 (1990); Ye et al., *Plant J.* 1:175-183 (1991)).

One skilled in the art can refer to general reference texts for detailed descriptions of known techniques discussed herein or equivalent techniques. These texts include *Current Protocols in Molecular Biology* Ausubel, et al., eds., John Wiley & Sons, N.Y. (1989), and supplements through September (1998), *Molecular Cloning, A Laboratory Manual*, Sambrook et al, $2^{nd}$ Ed., Cold Spring Harbor Press, Cold Spring Harbor, N.Y. (1989), *Genome Analysis: A Laboratory Manual* 1. *Analyzing DNA*, Birren et al., Cold Spring Harbor Press, Cold Spring Harbor, N.Y. (1997); *Genome Analysis: A Laboratory Manual* 2. *Detecting Genes*, Birren et al., Cold Spring Harbor Press, Cold Spring Harbor, N.Y. (1998); *Genome Analysis: A Laboratory Manual* 3: *Cloning Systems*, Birren et al., Cold Spring Harbor Press, Cold Spring Harbor, N.Y. (1999); *Genome Analysis: A Laboratory Manual* 4: *Mapping Genomes*, Birren et al., Cold Spring Harbor Press, Cold Spring Harbor, N.Y. (1999); *Plant Molecular Biology: A Laboratory Manual*, Clark, Springer-Verlag, Berlin, (1997), *Methods in Plant Molecular Biology*, Maliga et al., Cold Spring Harbor Press, Cold Spring Harbor, N.Y. (1995). These texts can, of course, also be referred to in making or using an aspect of the invention. It is understood that any of the agents of the invention can be substantially purified and/or be biologically active and/or recombinant.

Having now generally described the invention, the same will be more readily understood through reference to the following examples which are provided by way of illustration, and are not intended to be limiting of the present invention, unless specified.

Each periodical, patent, and other document or reference cited herein is herein incorporated by reference in its entirety.

EXAMPLE 1

Cloning of tyrA from *Erwinia herbicola*

Figure 2:
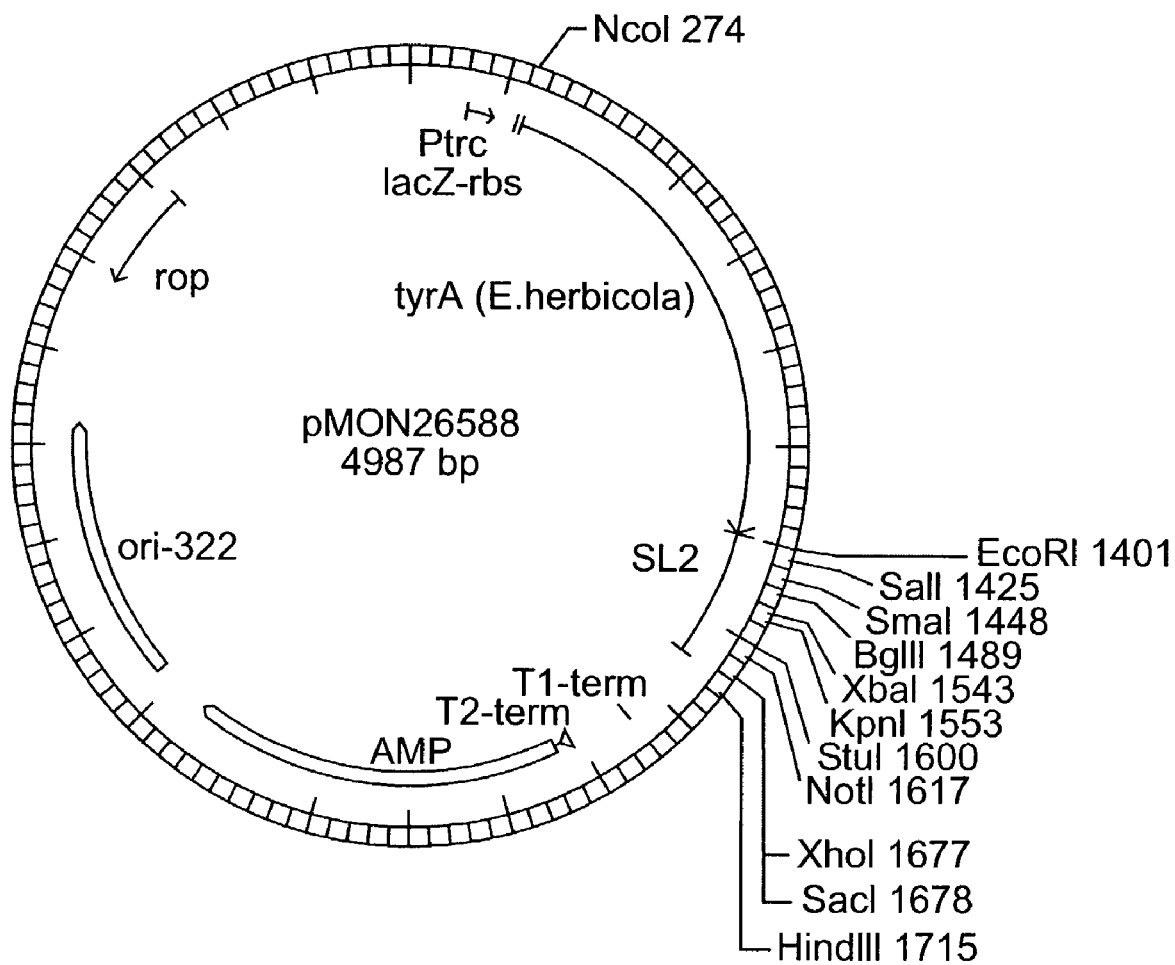
FIG. 2 is a schematic of construct pMON26588.

Vectors pJX1, pJX181, and pJX184 are obtained (Zhao and Jensen of Molecular Evolution 36(2):107-20 (1993)). The tyrA gene is amplified by PCR using primers tyrA5' (ACT GCC ATG GTG GCT GAA CTG ACC G (SEQ ID NO: 5)) and tyrA3' (ACT GGA ATT CTT ATT ATG GGC GGC TGT CAT TG (SEQ ID NO: 6)) and plasmid DNA from vectors pJX1, pJX181, and pJX184 as template DNA. PCR reactions using the Expand™ high fidelity PCR kit from Boehringer Mannheim are performed in a total volume of 50 µl according to the manufacturer's protocol. The tyrA gene is amplified by 30 PCR cycles under the following conditions: 10 min incubation at 95° C., followed by 30 cycles of 1 min at 95° C., 1 min annealing at 56° C. and 1.5 min extension at 72° C. These reactions were followed by a 5 min incubation at 72° C. The PCR product form pJX184 is chosen for gene cloning and digested with NcoI and EcoRI. The gel purified restriction fragment is ligated into NcoI/EcoRI-digested and gel purified pSE280 (Invitrogen Co., Carlsbad, Calif.) resulting in the formation of pMON26588 (FIG. 2). The tyrA insert in pMON26588 is verified by DNA sequencing.

EXAMPLE 2

Cloning of tyrA from *Escherichia coli*

Figure 3:
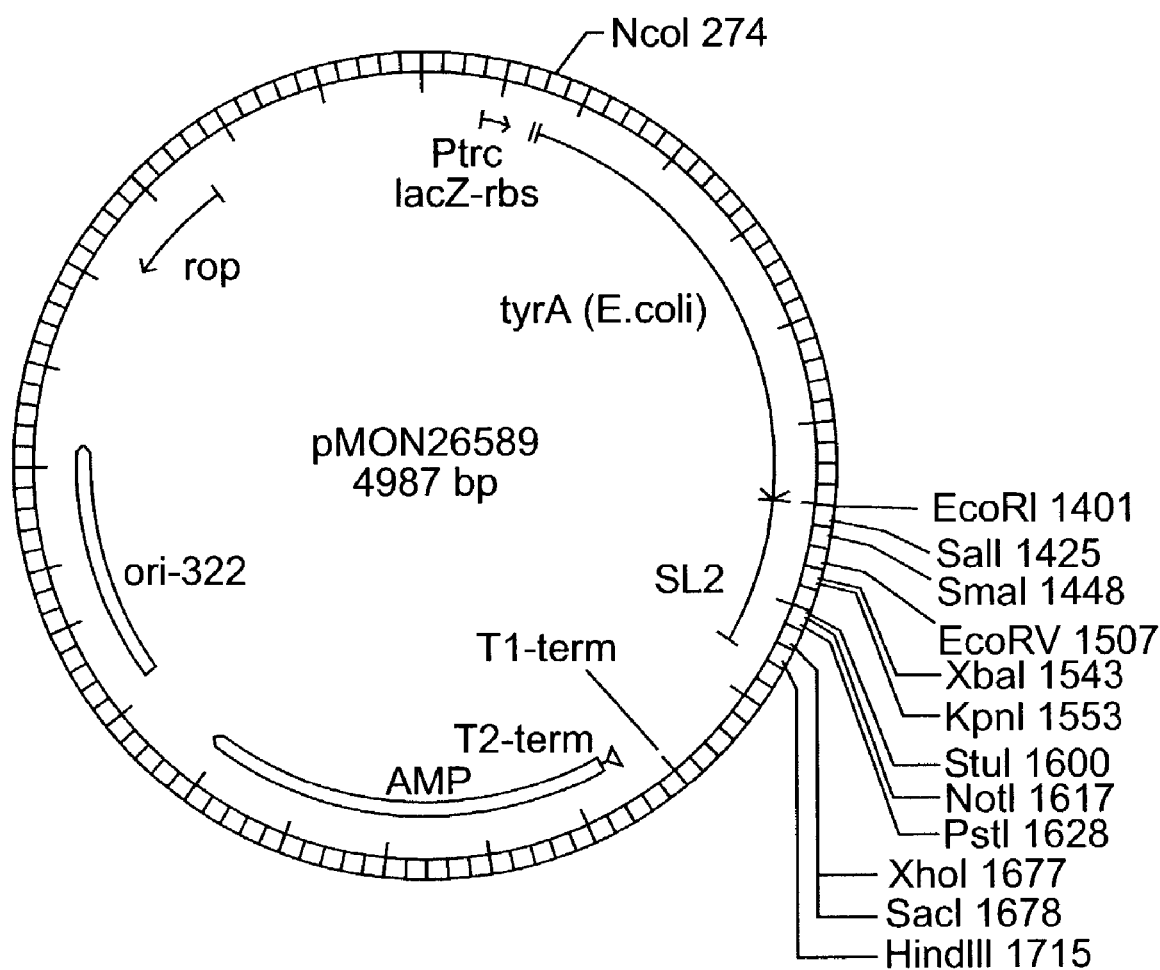
FIG. 3 is a schematic of construct pMON26589.

The tyrA gene from *E. coli* is amplified by PCR using primers tyrAecoli5' (ACT GCC ATG GTT GCT GAA TTG ACC G (SEQ ID NO: 7)) and tyrAecoli3' (ACT GGA ATT CTT ATT ACT GGC GAT TG (SEQ ID NO:8)) and *E. coli* DH5α total genomic DNA as template DNA. *E. coli* total genomic DNA is isolated using the Qiaamp Tissue Kit from Qiagen (Qiagen Inc. Valencia, Calif.). PCR reactions using the Expand™ high fidelity PCR kit from Boehringer Mannheim are performed in a total volume of 50 μl according to the manufacturer's protocol. The tyrA gene is amplified by 30 PCR cycles under the following conditions: 10 min incubation at 95° C., followed by 30 cycles of 1 min at 95° C., 1 min annealing at 56° C. and 1.5 min extension at 72° C. These reactions are followed by a 5 min incubation at 72° C. The PCR product is digested with NcoI and EcoRI. The gel purified restriction fragment is ligated into NcoI/EcoRI-digested and gel purified pSE280 (Invitrogen Co., Carlsbad, Calif.) resulting in the formation of pMON26589 (FIG. 3). The tyrA insert in pMON26589 is verified by DNA sequencing.

EXAMPLE 3

Expression of Bifunctional Prephenate Dehydrogenase in *E. coli*

Vectors pMON26588 and pMON26589 are transformed into *E. coli* DH5α and cells are grown in a 15 ml LB culture to an optical density at 600 nm of about 0.6, and induced by adding IPTG to a final concentration of 0.66 μM. After incubation for 2 to 3 hours, cells are harvested. The cell pellet iss resuspended in 0.5 ml 25 mM Tris/HCl, pH8.2 and cells are disrupted by sonication. Membranes and cell debris are sedimented by centrifugation at 100,000×g for three hours. The supernatant is used in enzyme assays as a crude cell extract. Prephenate dehydrogenase activity is measured in a final volume of 1.5 ml containing 1 mM EDTA, 1 mM DTE, 1 mM NAD, and 1 mM prephenate (Ba-salt) in 25 mM Tris/HCl pH 8.2. The specific activity of prephenate dehydrogenase is determined by monitoring the conversion of $NAD^+$ to NADH as described in Methods in Enzymology Vol. 17 (Part A) pages 564-574 (1970). Results are shown in table 1, below.

TABLE 1

| Vector Designation | Gene | Specific activity μmole/mg × min |
|---|---|---|
| Wild type control | | $2 \times 10^{-5}$ |
| pMON26588 | tyrA *Erwinia herbicola* | 5.75 |
| pMON26589 | tyrA *Escherichia coli* | 3.44 |

EXAMPLE 4

Placing the tyrA Gene Under the Control of the T7 Promoter

Figure 4:
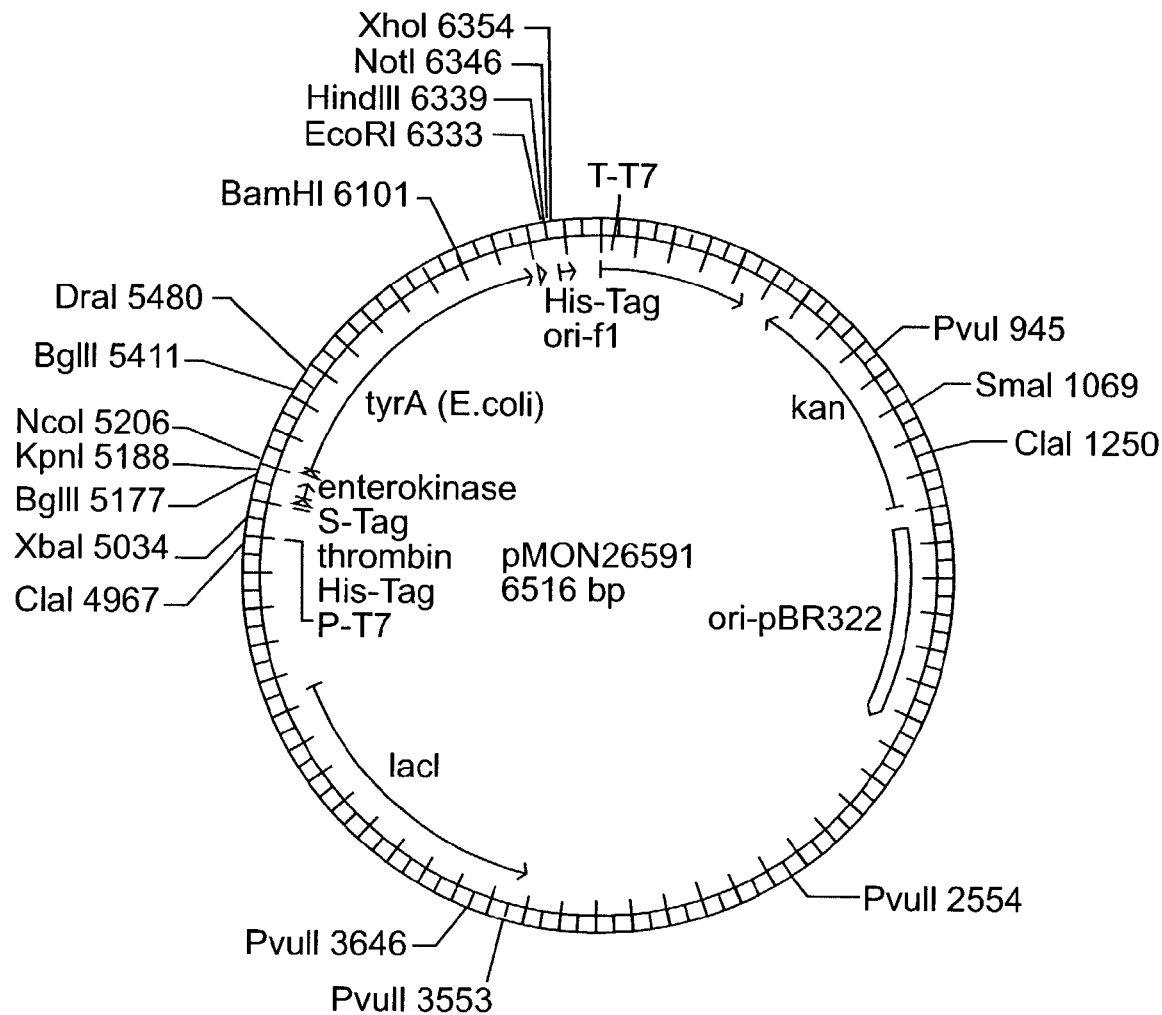
FIG. 4 is a schematic of construct pMON26591.
Figure 5:
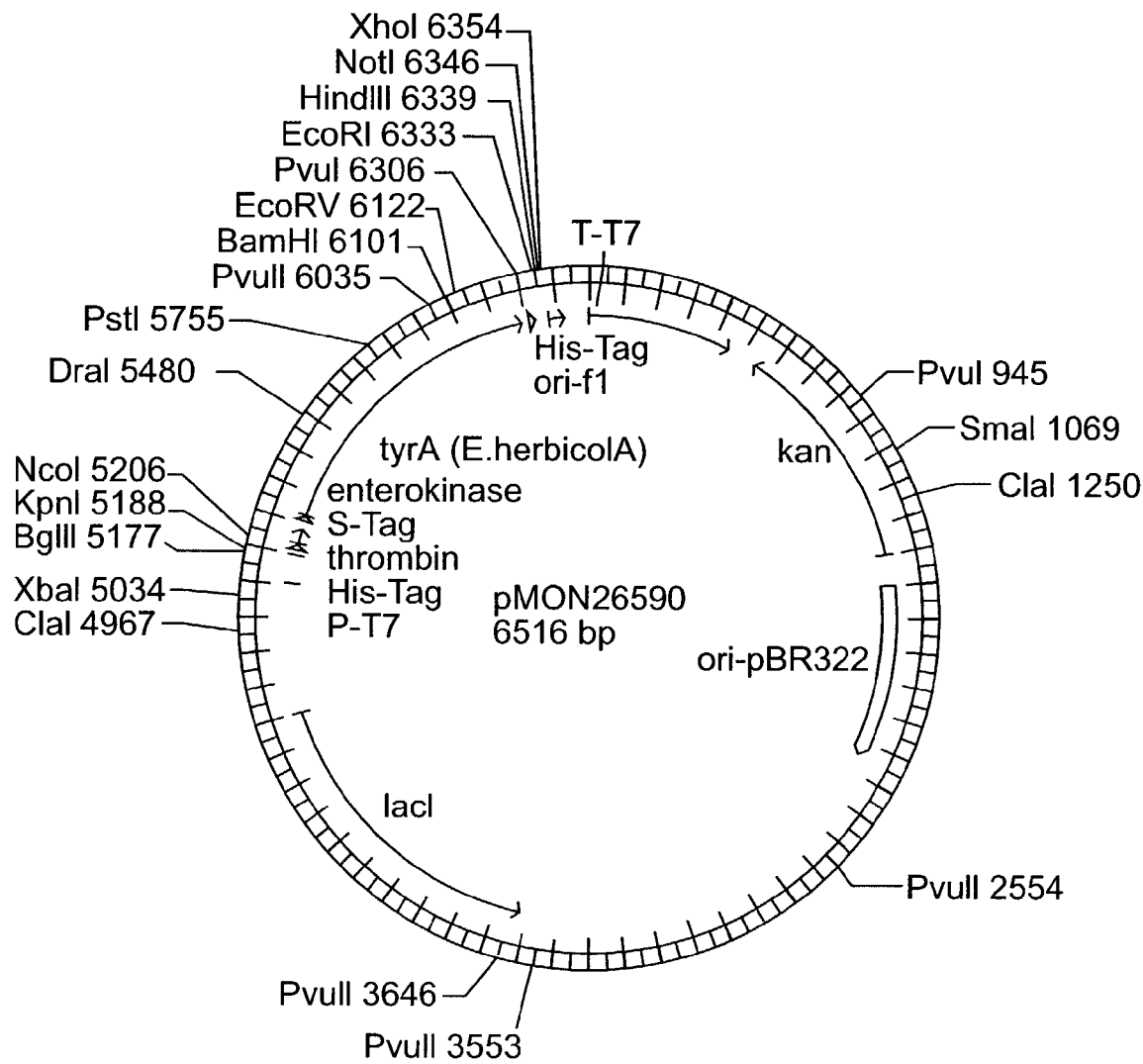
FIG. 5 is a schematic of construct pMON26590.
Figure 28:
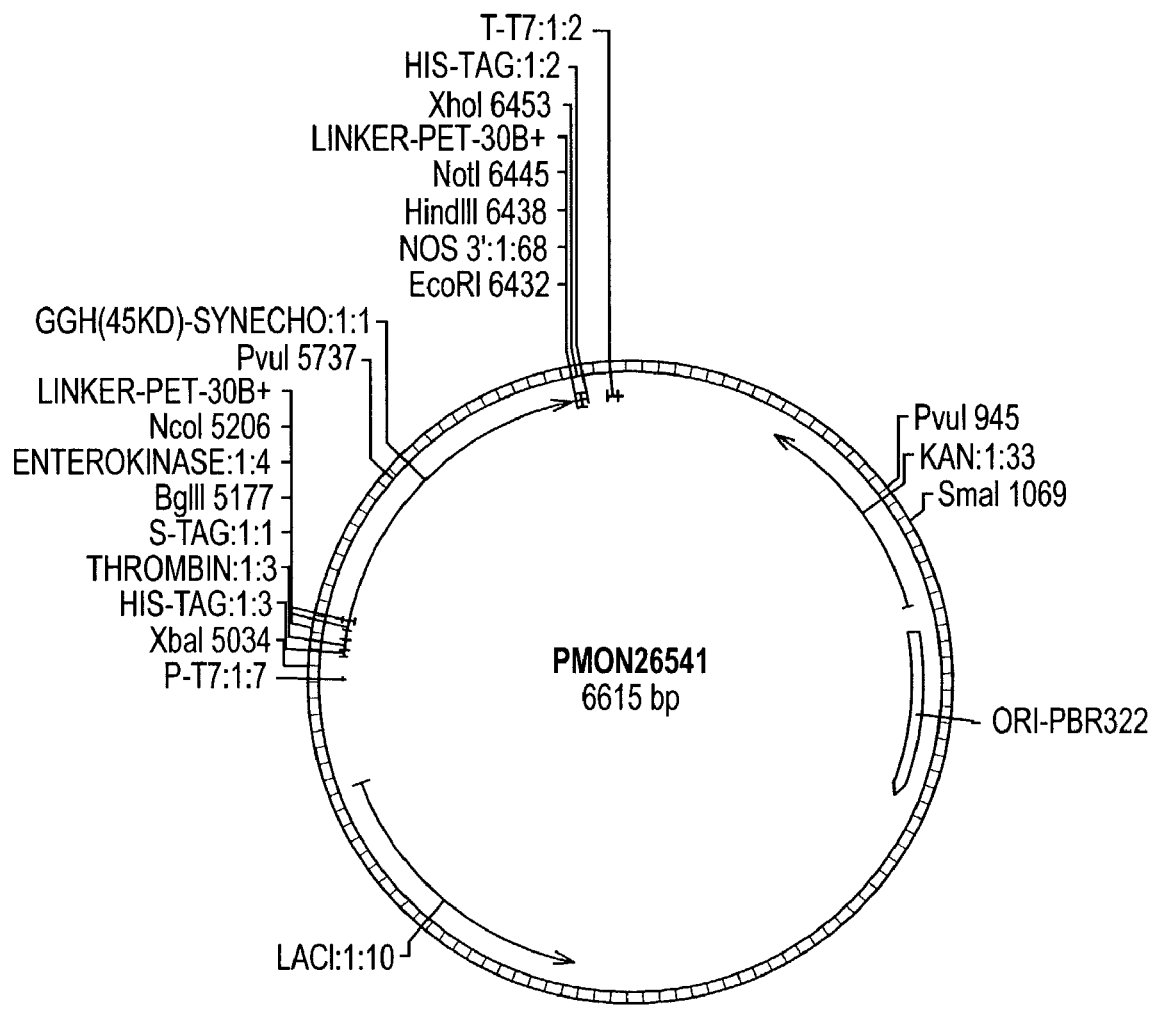
FIG. 28 is a schematic of construct pMON26541.

The *E. coli* and *E. herbicola* tyrA genes are cleaved as NcoI/EcoRI fragments from pMON26589 and pMON26588, gel purified, and cloned into NcoI/EcoRI-digested and gel purified pMON26541 (FIG. 28), resulting in the formation of pMON26591 and pMON26590, respectively (FIGS. 4 and 5). These vectors place the tyrA gene under the control of the T7 promoter.

EXAMPLE 5

Preparation of a Plant Expression Vector with tyrA

Figure 6:
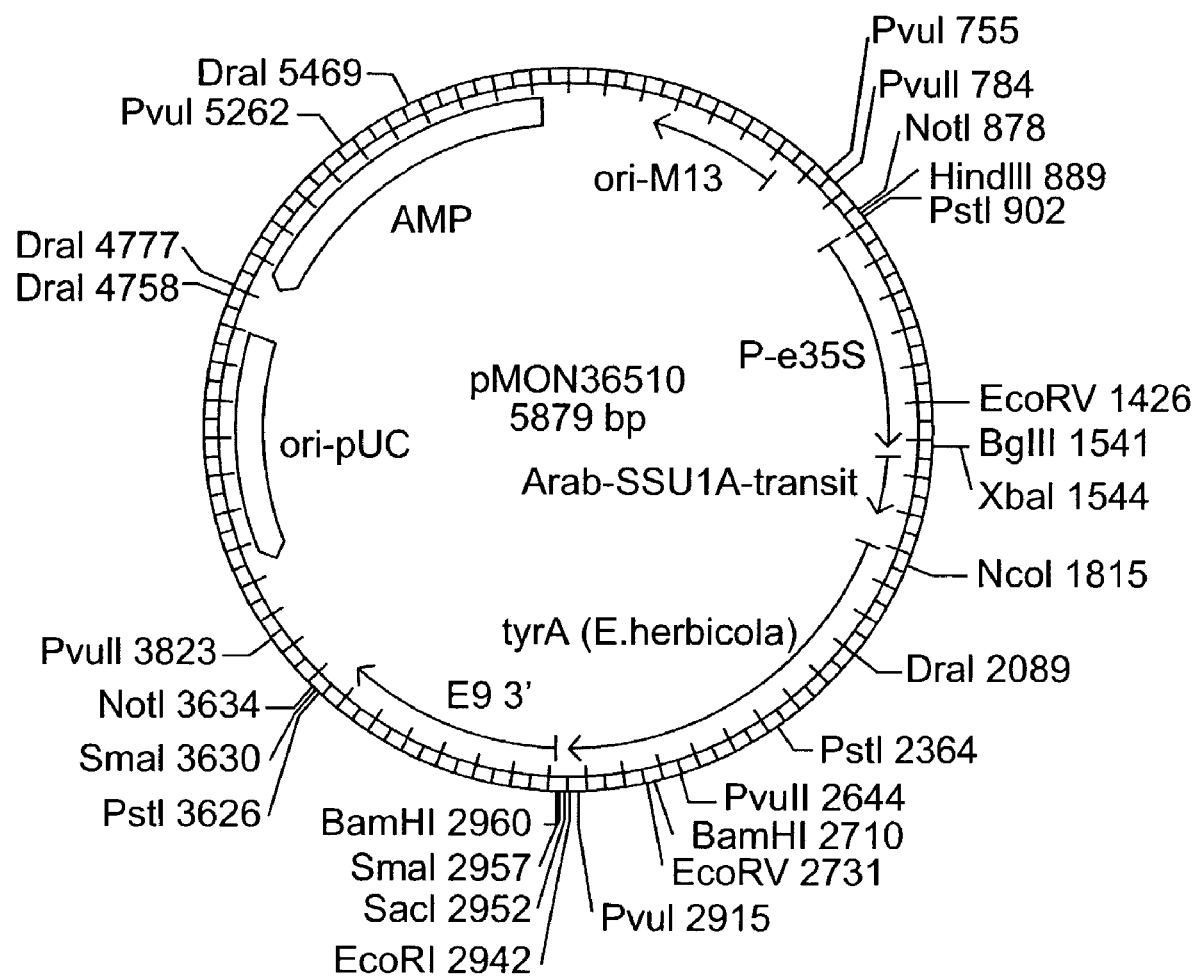
FIG. 6 is a schematic of construct pMON36510.

The *E. herbicola* tyrA gene is chosen for plant expression. The gene is cleaved from pMON26590 by NcoI/EcoRI restriction digest, gel purified, and ligated into NcoI/EcoRI-digested and gel purified pMON26541 resulting in the formation of the shuttle vector pMON36510 (FIG. 6). These ligations fuse the bacterial tyrA gene to CTP1, which is the chloroplast target peptide of the small subunit of the ribulose bisphosphate carboxylase from *Arabidopsis*, and place it under e35S promoter control.

Figure 7:
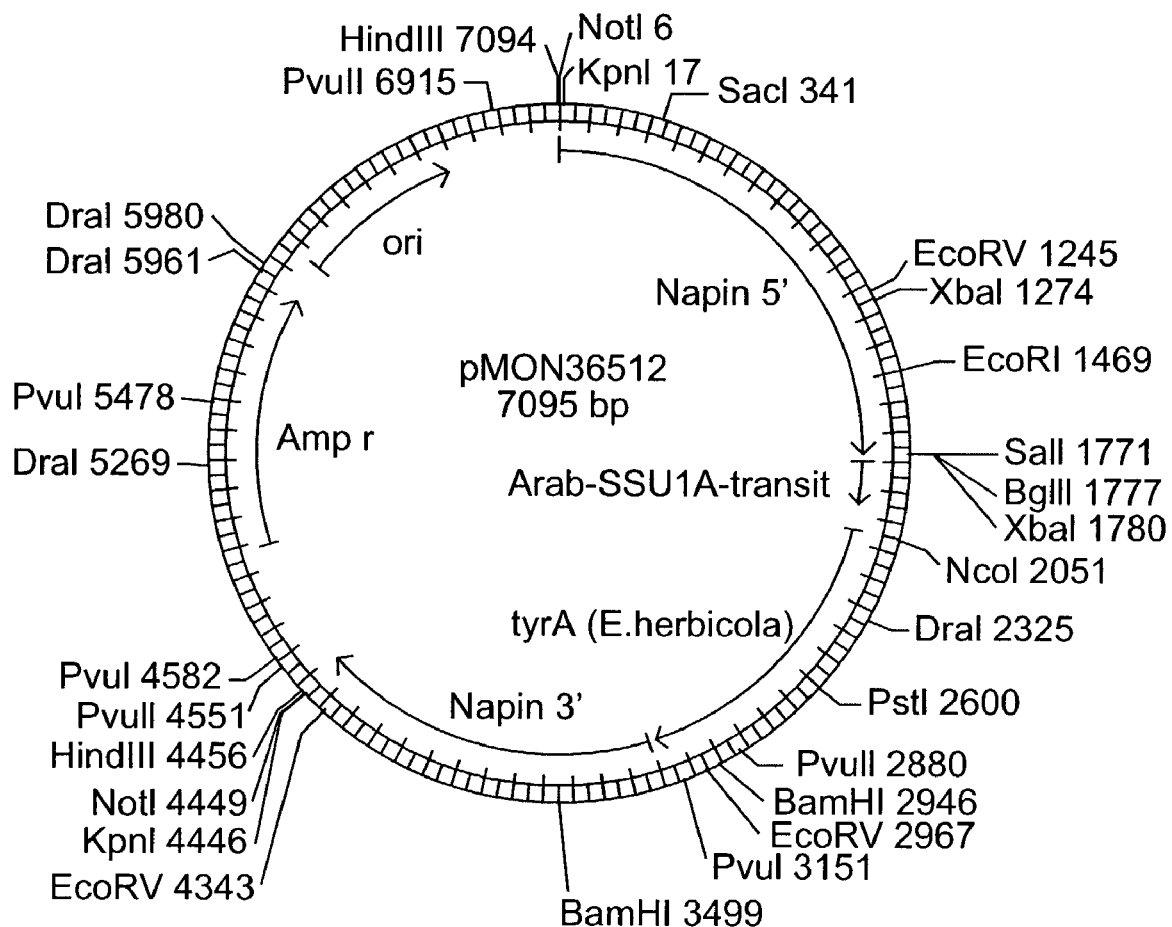
FIG. 7 is a schematic of construct pMON36512.
Figure 45:
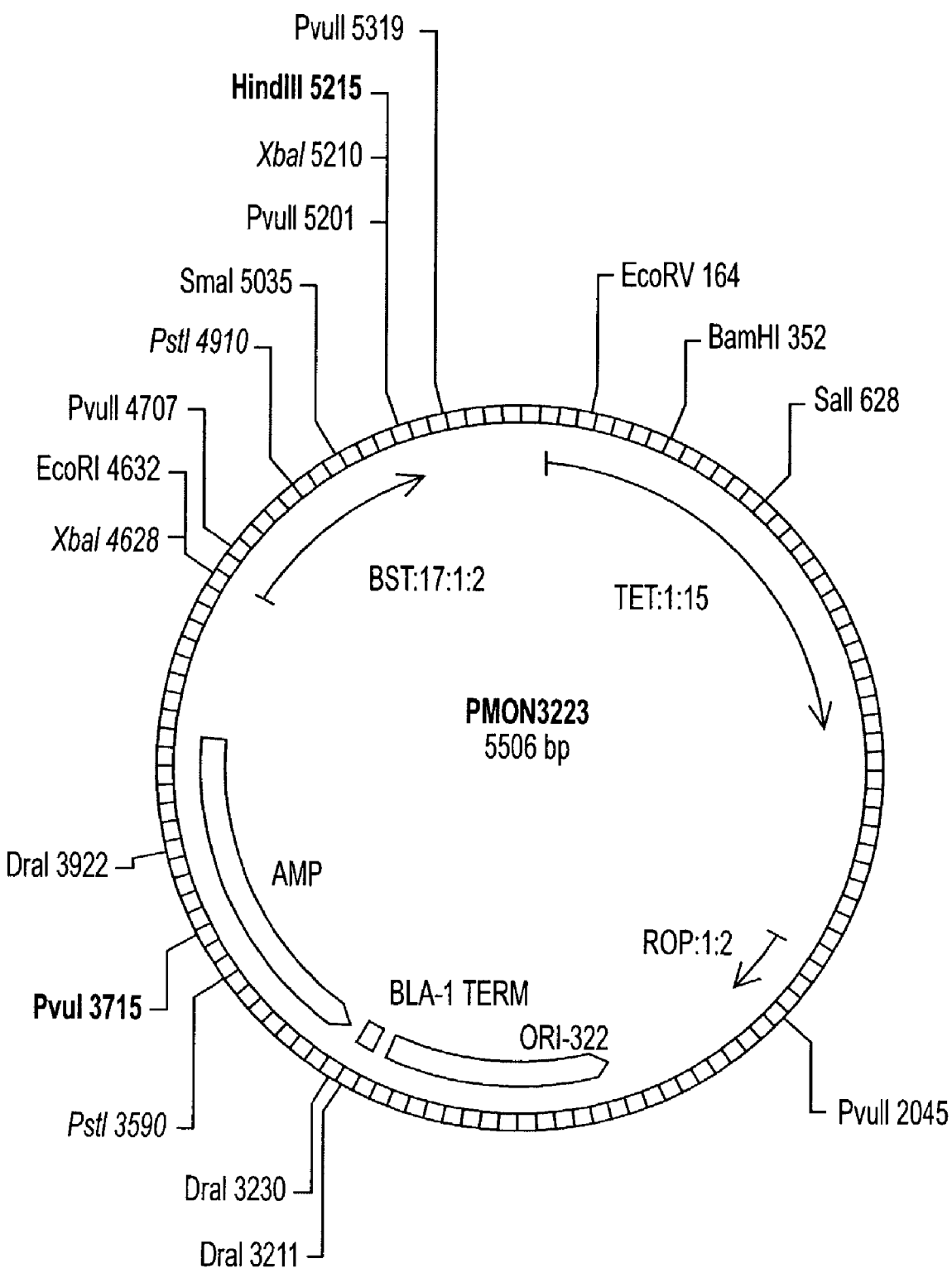
FIG. 45 is a schematic of construct pCGN3223.

To place the tyrA gene under Napin promoter control, pMON36510 is digested with EcoRI, ends are filled in using the Klenow fragment (Maniatis), and the gel purified vector is digested with Bgl II. The smaller fragment encoding the tyrA gene fused to CTP1 is gel purified and ligated for ligation into digested and gel purified pCGN3223 (FIG. 45). To perform this ligation, pCGN3224 is digested with PstI, ends are filled in with Klenow fragment (Maniatis) and subsequently the vector is digested with Bgl II and gel purified. Ligation of the purified vector and the purified CTP1:tyrA fusion results in the formation of pMON36512 (FIG. 7).

Figure 8:
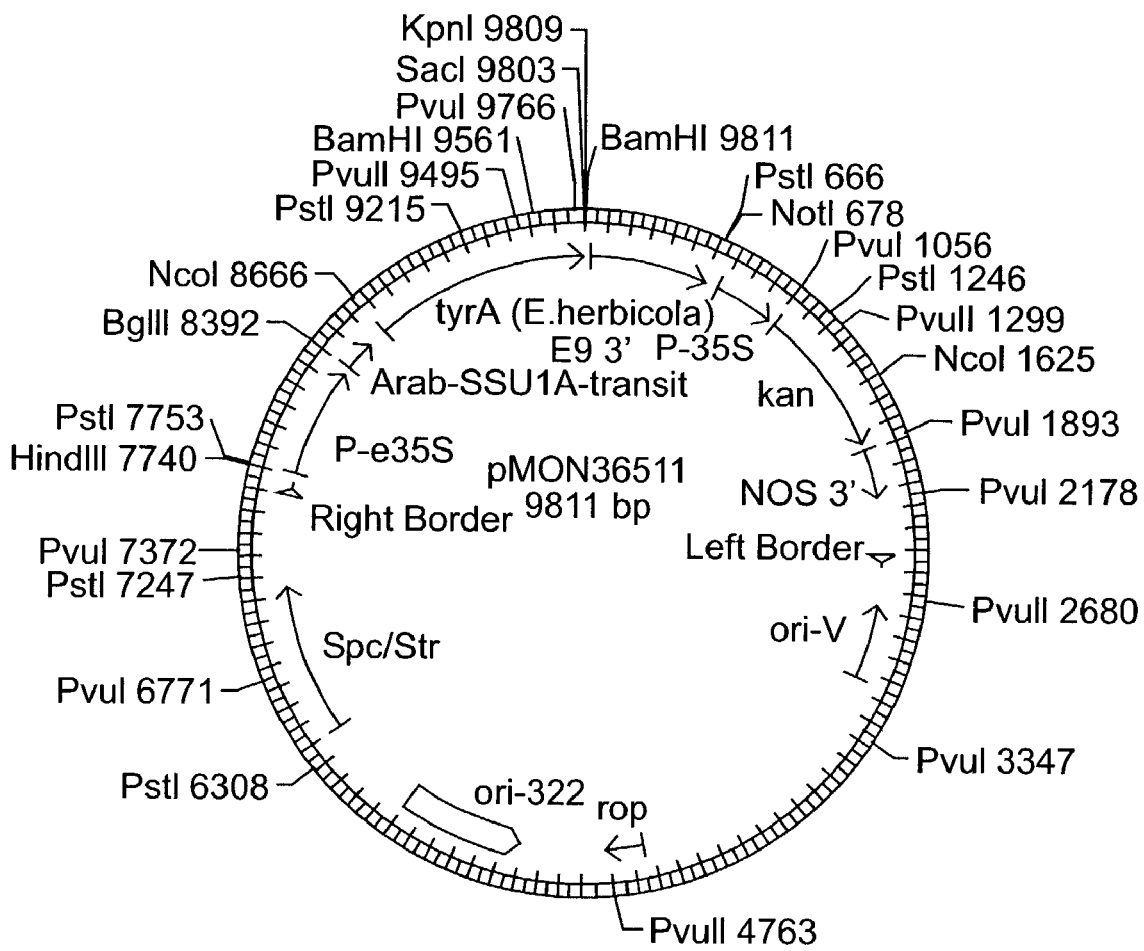
FIG. 8 is a schematic of construct pMON36511.
Figure 9:
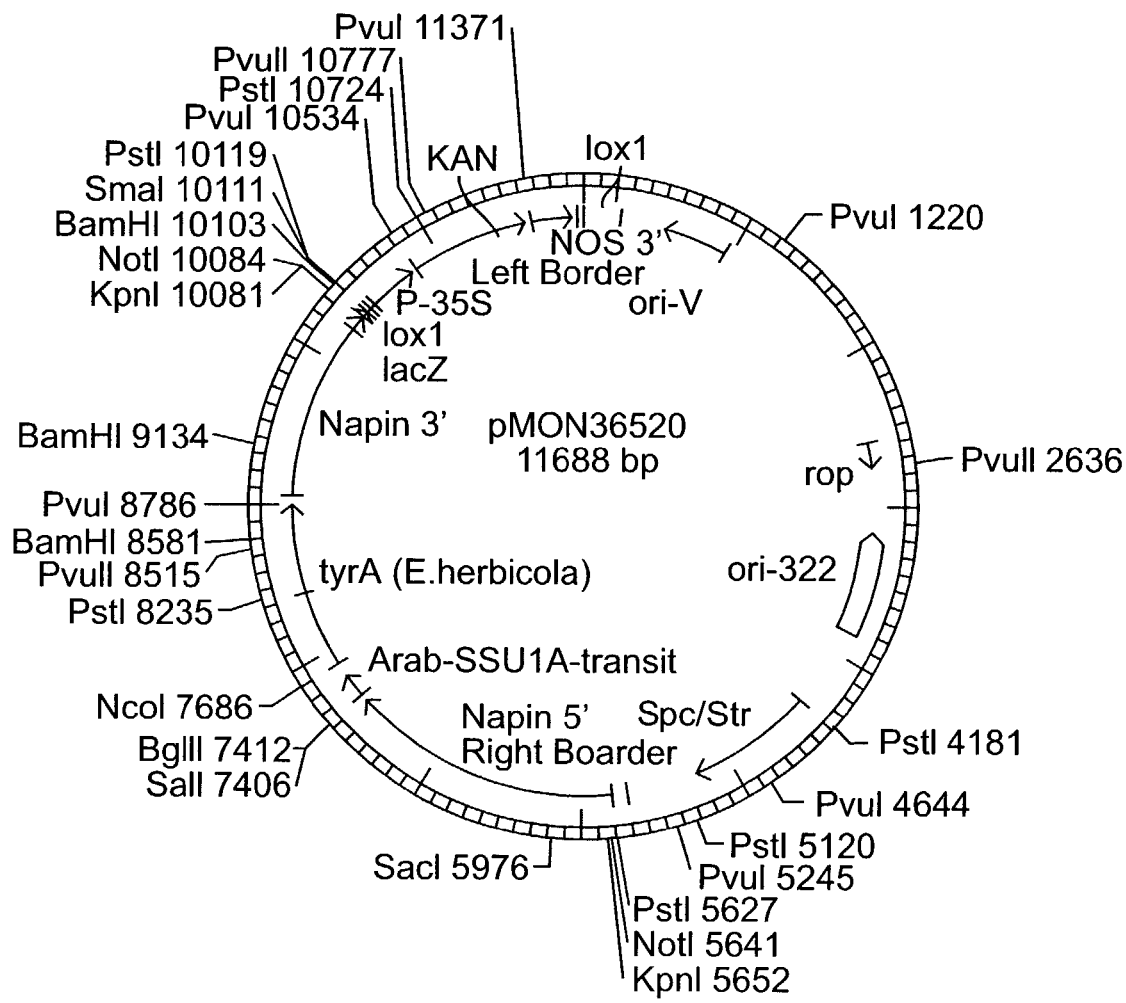
FIG. 9 is a schematic of construct pMON36520.
Figure 10:
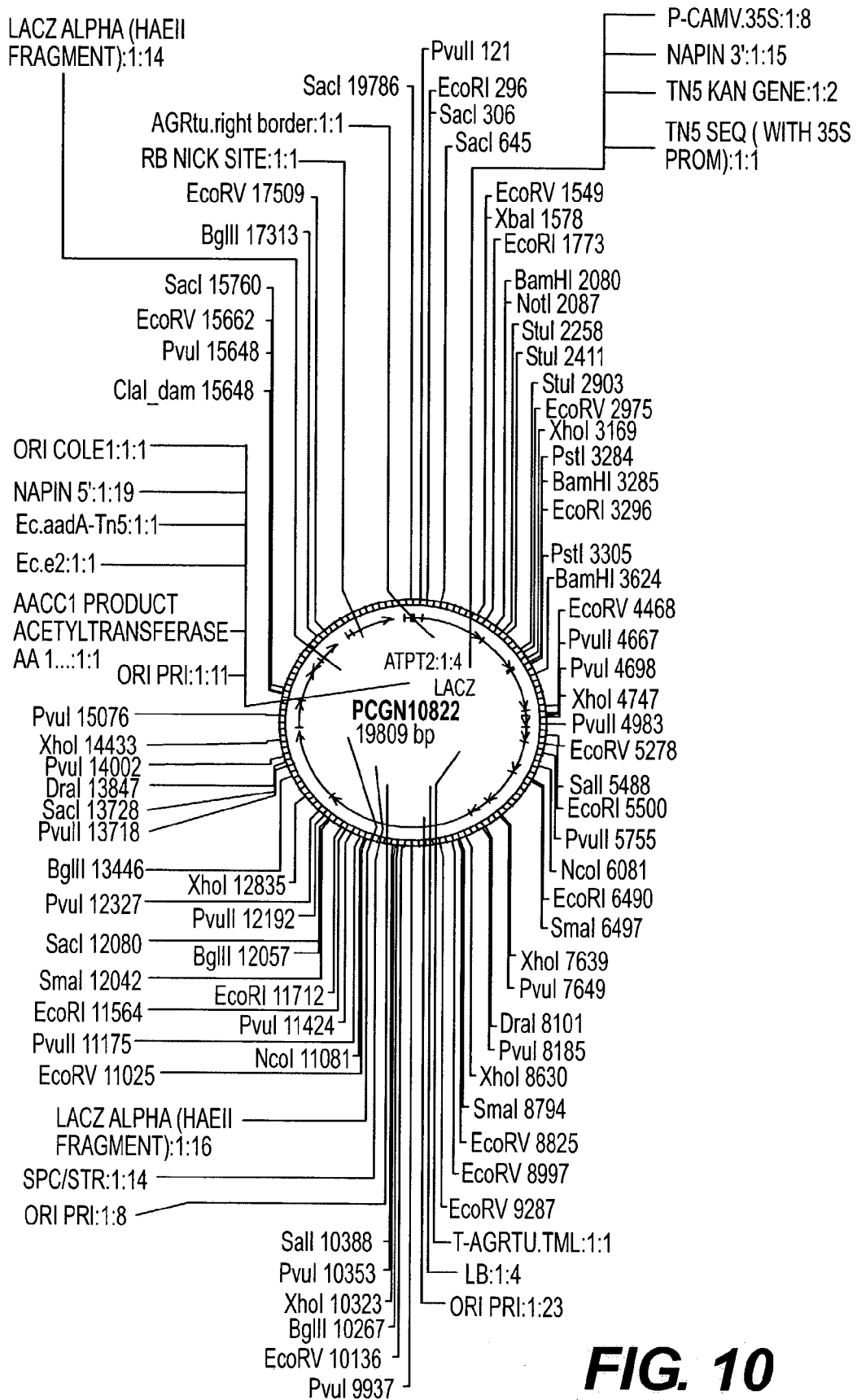
FIG. 10 is a schematic of construct pCGN1822.
Figure 11:
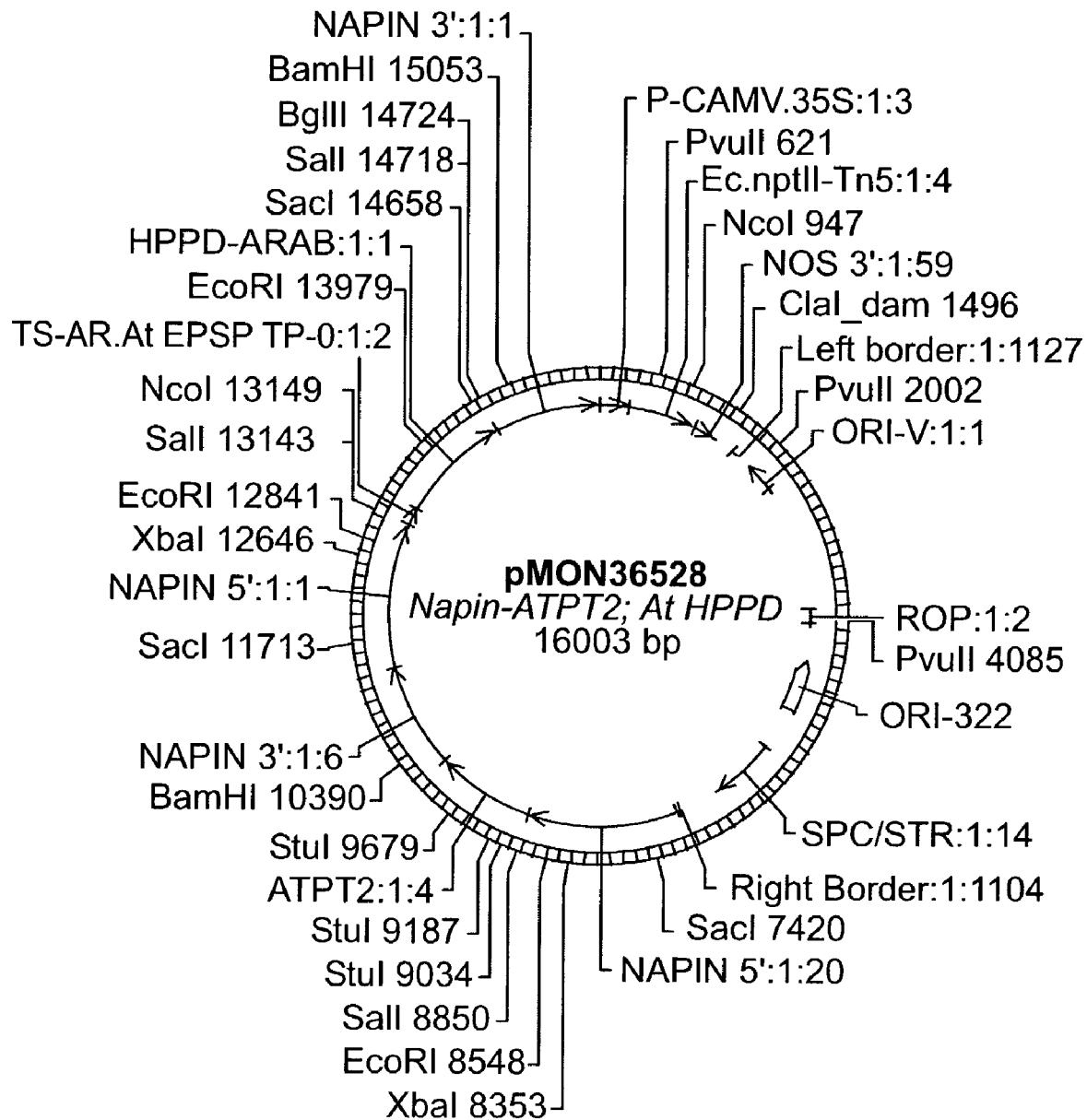
FIG. 11 is a schematic of construct pMON36528.
Figure 29:
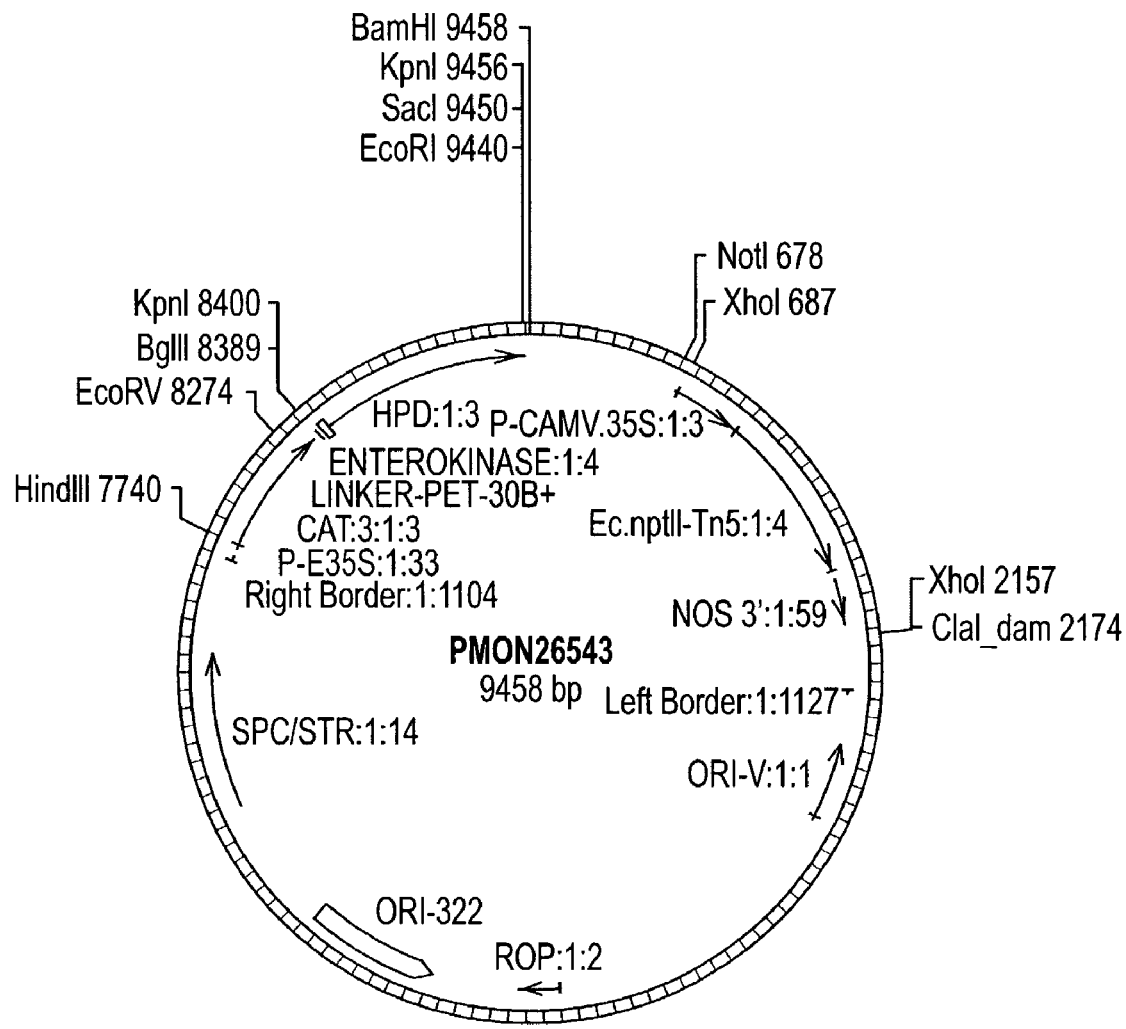
FIG. 29 is a schematic of construct pMON26543.
Figure 30:
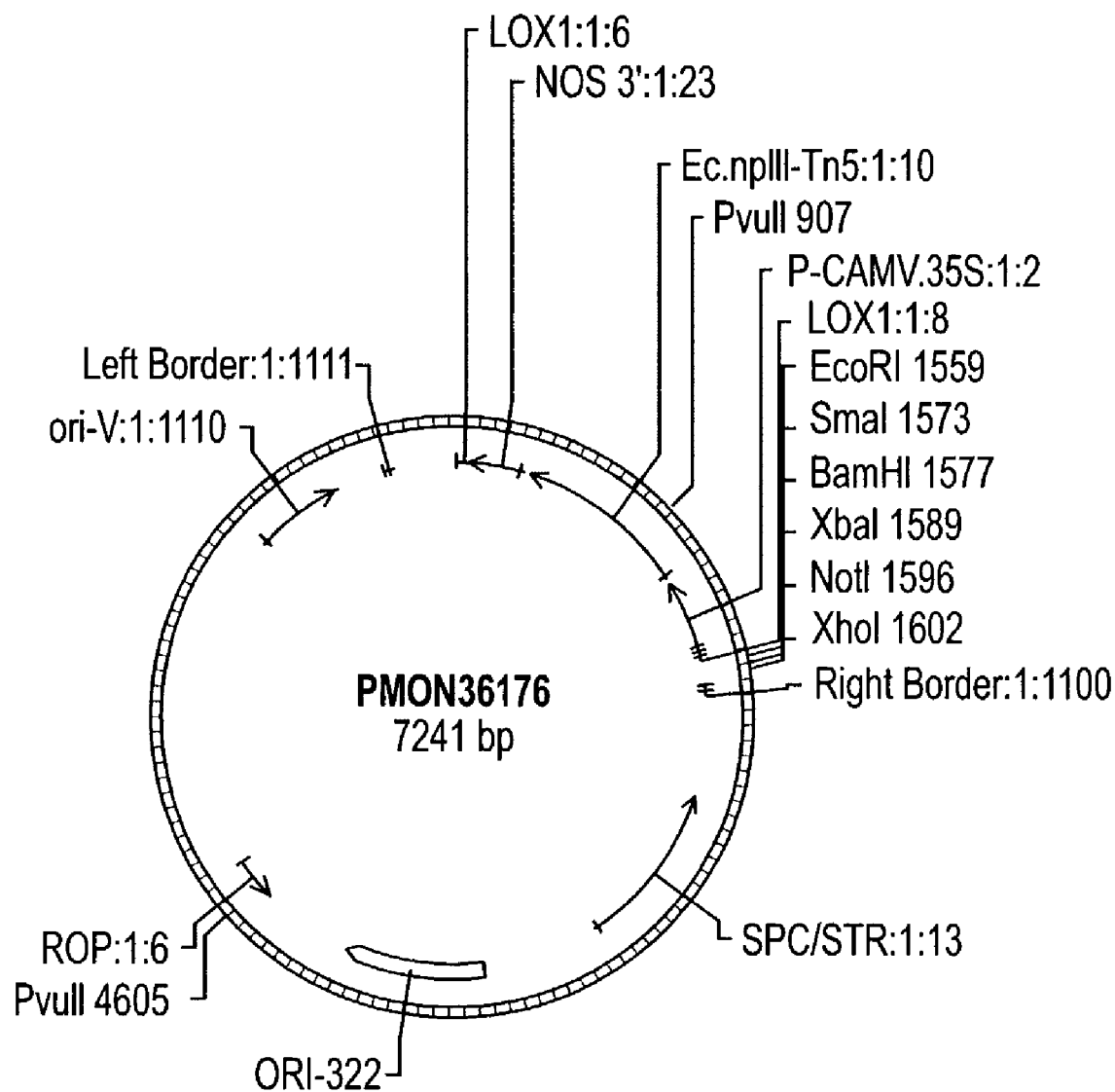
FIG. 30 is a schematic of construct pMON36176.
Figure 31A:
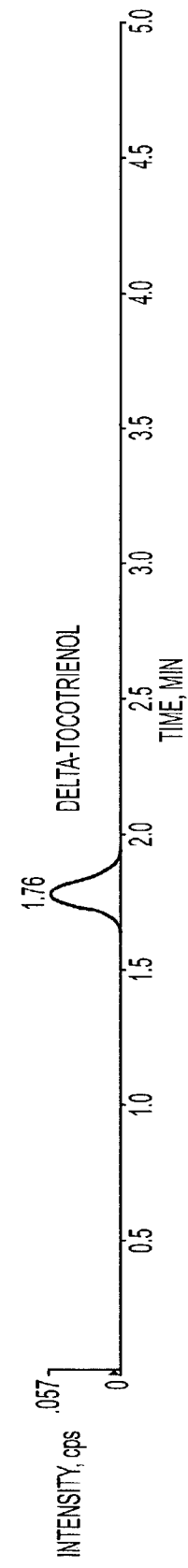
FIG. 31 is an LC/MS standard graph.
Figure 31A:
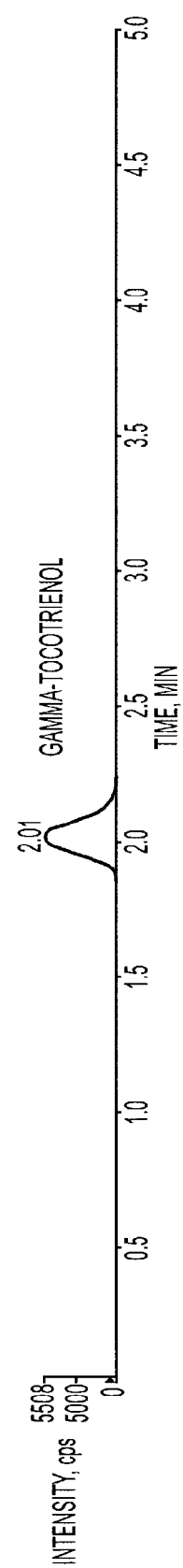
Figure 31A:
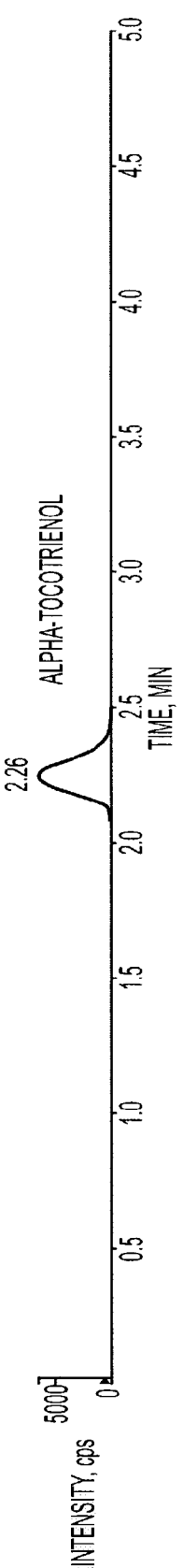
Figure 31B:
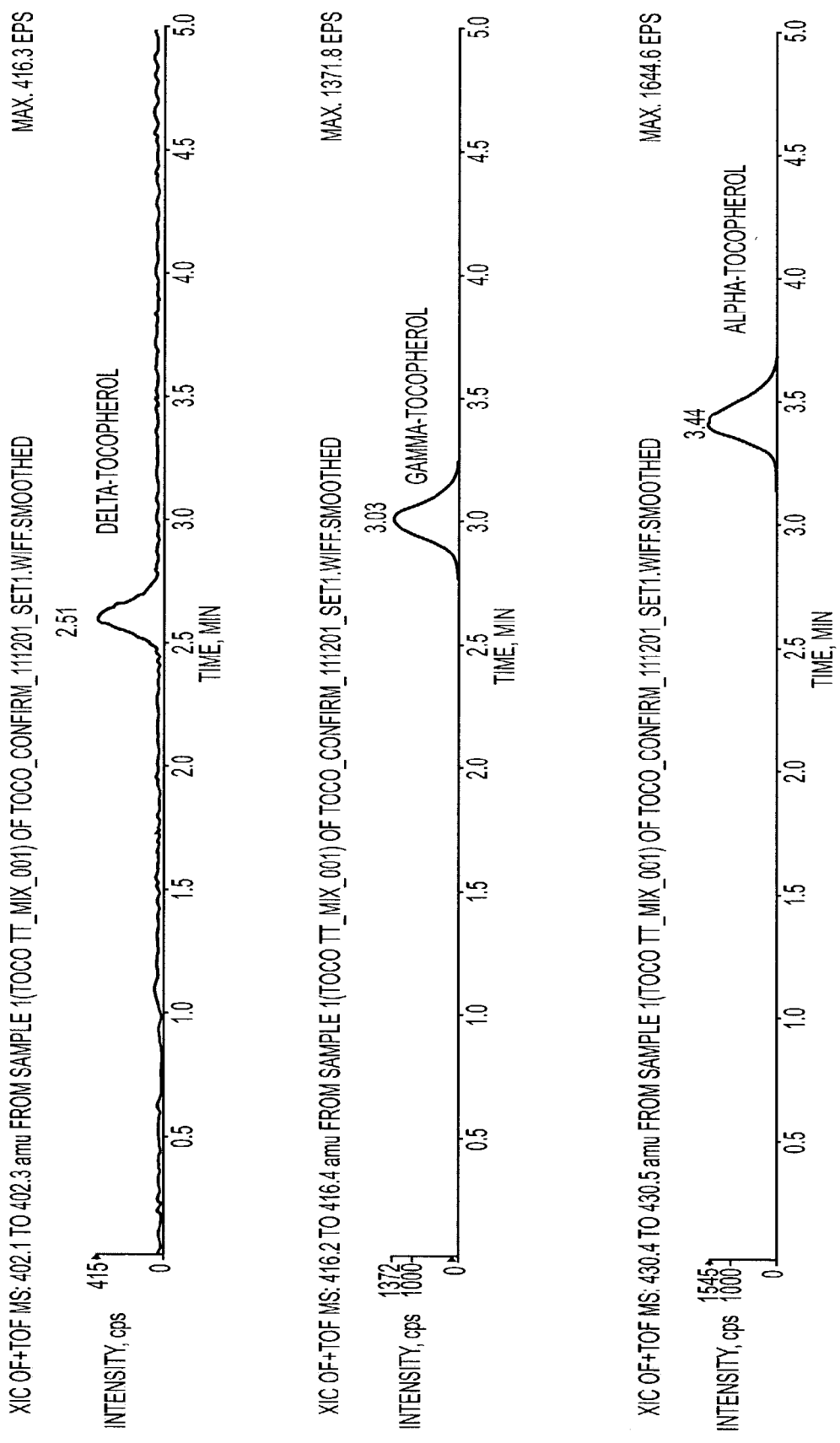
Figure 32A:
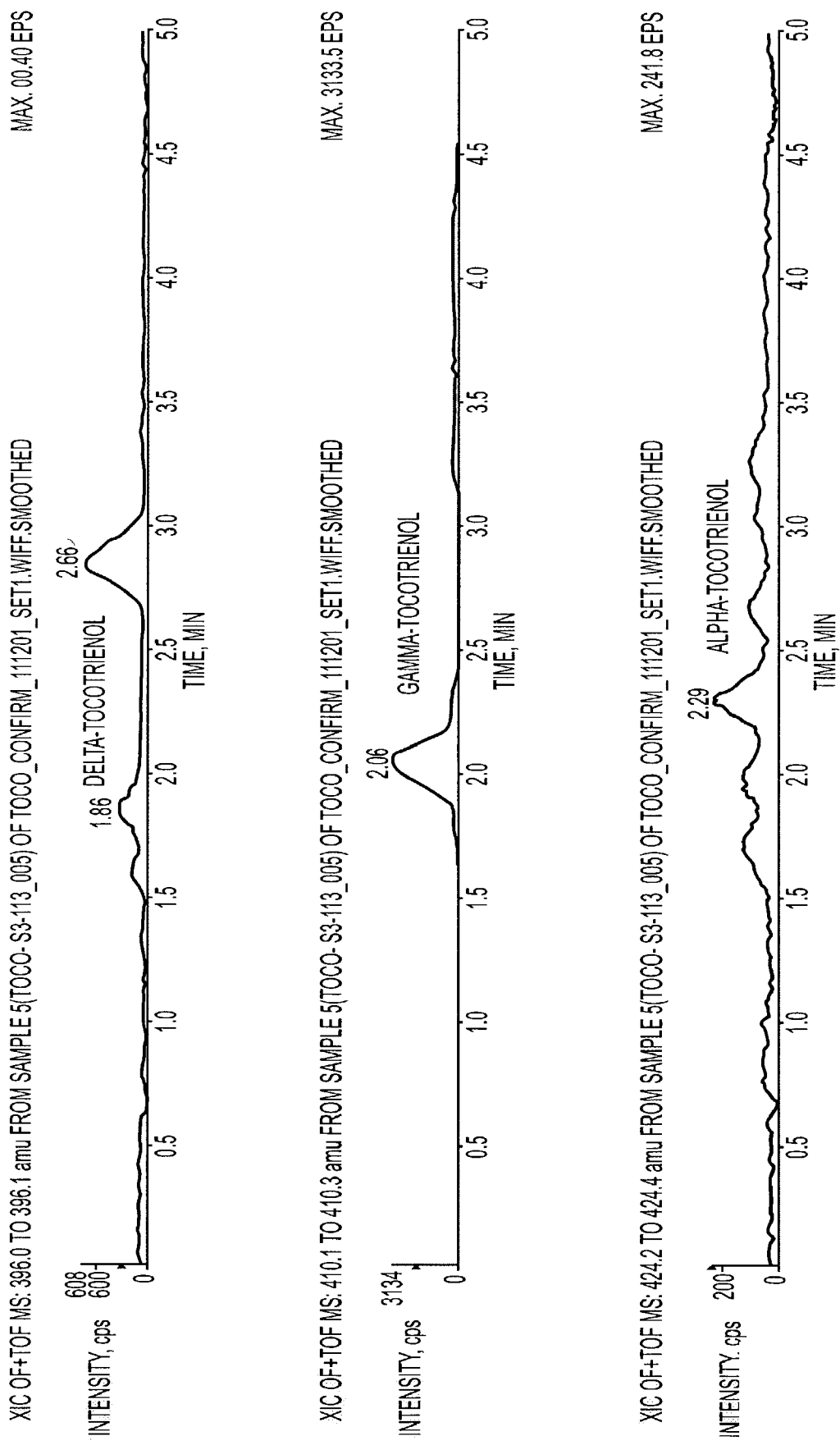
FIG. 32 is an LC/MS graph.
Figure 32B:
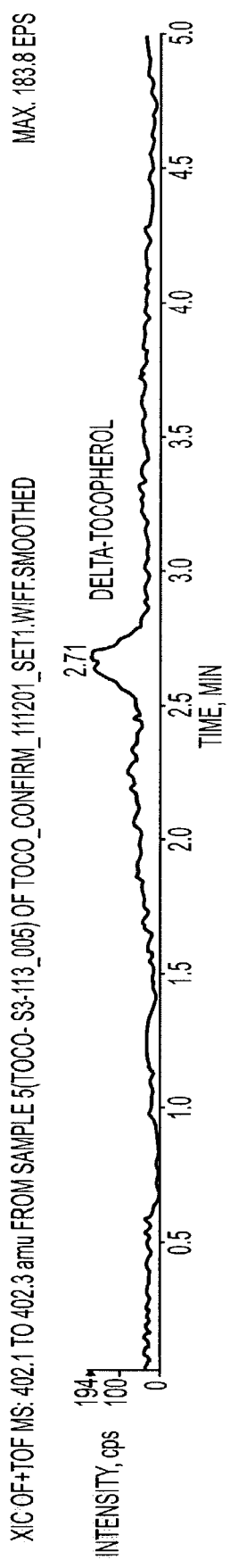
Figure 32B:
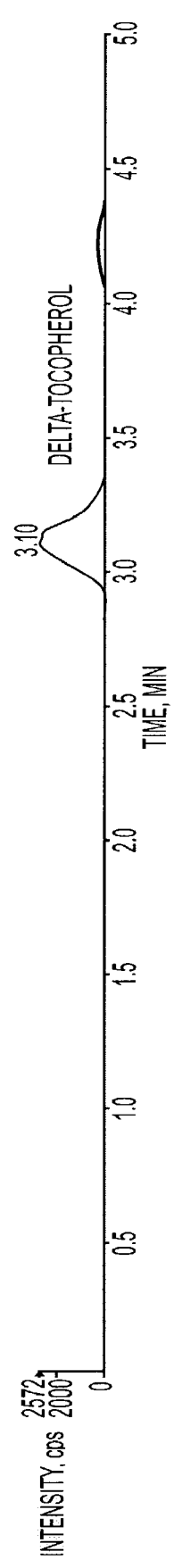
Figure 32B:
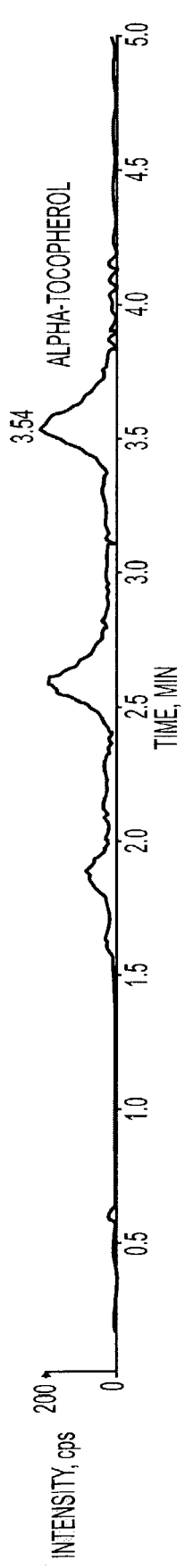

To transfer the *E. herbicola* tyrA gene into an *Arabidopsis* binary vector pMON36510 is digested with HindIII and Sac I and the gel purified fragment carrying the e35S promoter is fused to CTP1 and tyrA is ligated into HindIII/SacI-digested and gel purified pMON26543 (FIG. 29), which results in the formation of pMON36511 (FIG. 8). This vector contains tyrA under e35S promoter control. The pNapin binary expression vector is obtained by ligating the gel purified NotI fragment harboring the pNapin::CTP1::tyrA::napin 3' expression cassette into NotI digested pMON36176 (FIG. 30), which results in the formation of pMON36520 (FIG. 9).

EXAMPLE 6

Transformation of *Arabidopsis* with pMON36520 and pMON36511 *Agrobacterium* that have been transformed with pMON36520 and pMON36511 are prepared as follows. 100 μl of an overnight culture are spread on an agar LB plate with antibiotics. The plate is placed upside down in a 30° C. chamber overnight. The plates are removed after colonies have grown (24-48 hours).

A small scale culture is started by placing 10 ml of liquid LB media in a 50 ml tube. 10 μl Kanamycin (50 μg/μL), 10 μl Spectinomycin (75-100 μg/μL), and 10 μl Chloramphenicol (25 μg/μL) are added. Agrobacterium is added from a plate, and the tube is shaken and placed in a 30° C. shaker overnight.

Following overnight growth of the 10 ml culture, the culture is removed to a 500 ml flask. 200 ml of liquid LB is placed in a flask, 200 μl Kanamycin (50 μg/mL), 200 μl Spectinomycin (75-100 μg/μL), and 200 μl of Chloramphenicol (25 μg/μL) are added, and the entire 10 ml overnight culture is then added. The 500 ml flask is placed in a 30° C. shaker and grown overnight.

The entire 200 ml culture is placed in a centrifuge tube and centrifuged for 25 minutes at 3,750 rpm and 19° C. After centrifugation, the liquid is poured off and the pellet is resuspended in 25 ml of 5% Sucrose (0.05% Silwet) solution.

900 µl of the sucrose solution and 100 µl of the 25 ml bacterial culture are placed in a cuvette, and the cuvette is shaken with a covering of parafilm. A blank OD reading is taken with a 1 ml of sucrose solution, and then readings of all the bacterial solutions are taken. The OD (at a wavelength of 600) of each culture is recorded. The following calculations are then performed:

$C_1V_1=C_2V_2$; $C_1V_1=(0.8)(200$ ml$)$; $C_1V_1=160$; $V_1=160/C_1$; and $V_1=X$ ml/10 to determine $OD_{600}=0.8$ of an *Agrobacterium* culture.

Plants are soaked for at least 30 minutes in water prior to dipping. The bacterial solution is poured into a shallow plastic container, and above ground parts of the plant (bolts, rosettes) are dipped into the solution for 3-5 seconds with gentle agitation. Dipped plants are placed on their side in a diaper lined black tray, and covered by a dome overnight (16-24 hours) to maintain a high humidity. The cover is removed and normal plant growth conditions are resumed for 4 weeks.

Following the transformation and high humidity treatment, plants are maintained at 22° C., 60% RH, and a 16 hour photoperiod for 4 weeks. 5-7 days after transformation, plants are coned. Fertilization with a weak 20-20-20 fertilizer is done weekly. After 4 weeks of growth, plants are placed in the greenhouse and all watering is stopped to encourage plant dry down for seed harvest. Plants are ready for seed harvest after 1-1.5 weeks of dry down.

Seeds are harvested by cutting the base of the plant below the cones, holding the plant over a seed sieve and a white piece of paper, running bolts through the cone hole, and collecting clean seeds through sieving.

Seeds are sterilized by connecting a vacuum dessicator hose to a vacuum in a fume hood/flow bench. 100 ml of bleach is placed in a 250 ml beaker, and 3 ml of concentrated HCl is added to the bleach. The beaker is placed in the dessicator, and seeds in seed tubes in a tube holder are placed in the dessicator. A cover is placed on the dessicator, and the vacuum is operated. The dessicator is left overnight but no longer than 16 hours.

Once sterilized, seeds are plated on selection media (prepared by adding 10 g (2 g/L) Phyta-Gel, 10.75 g (2.15 g/L) MS Basal Salts (M-5524 from Sigma), 50 g (10 g/L) Sucrose, and 6 ml (1.2 ml/L) Kanamycin solution (950 mg/ml), 5 ml (1 ml/L) Cefotaxime Solution (250 mg/ml), and 5 ml (1 ml/L) Carbenecillin Solution (250 mg/ml) to a total volume of 5 liters at a pH or 5.7). Seed tubes are tapped lightly over a plate in order to distribute the seeds sparsely. The plates are wrapped in parafilm and placed in a 4° C. refrigerator for 1-2 days of cold treatment. After this cold treatment the plates are placed in a 28° C. chamber for germination.

Selected plantlets are green and have secondary leaves developing. The selected plantlets are moved to soil after secondary leaves have developed.

The plantlets are potted in soil and covered with a dome for 5 days to maintain high humidity. The plantlets are moved to a greenhouse after the bottom siliques begin to turn yellow.

Seeds from the selected plantlets are grown in 2.5 inch pots with soil (½ Metro-200; ½ PGX Mix). The soil is mounded and the pot is covered with mesh screen. The screen is fastened to the pot with a rubber band. Seeds are sown and covered with a germination dome.

The seedlings are grown in a 12 hr. photoperiod in 70% relative humidity at 22° C. Water is supplied every other day as needed and Peter's 20-20-20 fertilizer is applied from below, bi-weekly.

EXAMPLE 7

Transformed seed plants from Example 6 representing 20 independent transformation events are grown and seeds harvested to produce $T_2$ seeds. The $T_2$ seeds are grown and tested for tocopherol levels. In FIG. 1, tocopherol levels are expressed as nanograms of total tocopherol per milligram of seed. Tocopherol levels are determined by adding 10 to 15 mg of *Arabidopsis* seed into a 2 mL microtube. A mass of 1 g of 0.5 mm microbeads (Biospecifics Technologies Corp., Lynbrook, N.Y.) and 500 µl 1% pyrogallol (Sigma Chem, St. Louis, Mo.) in ethanol containing 5 µg/mL tocol, are added to the tube. The sample is shaken twice for 45 seconds in a FastPrep (Bio101/Savant) at a speed of 6.5. The extract is filtered (Gelman PTFE acrodisc 0.2 µm, 13 mm syringe filters, Pall Gelman Laboratory Inc, Ann Arbor, Mich.) into an autosampler tube. HPLC is performed on a Zorbax silica HPLC column, 4.6 mm×250 mm (5 µm) with a fluorescent detection using a Hewlett Packard HPLC (Agilent Technologies, Palo Alto Calif.). Sample excitation is performed at 290 nm, and emission is monitored at 336 nm. Tocopherols are separated with a hexane methyl-t-butyl ether gradient using an injection volume of 20 µl, a flow rate of 1.5 m/min, and a run time of 12 min (40° C.). Tocopherol concentration and composition is calculated based on standard curves for α, β, δ, and γ-tocopherol and α, β, δ, and γ-tocotrienols using Chemstation software (Agilent Technologies, Palo Alto Calif.).

EXAMPLE 8

Transformed Plants with TyrA and Other Tocopherol Biosynthesis Genes

Canola, *Brassica napes, Arabidopsis* and soybean plants are transformed with a variety of DNA constructs using a particle bombardment approach essentially as set forth in Christou, In *Particle Bombardment for the Genetic Engineering of Plants*, Biotechnology Intelligence Unit Academic Press, San Diego, Calif. (1996) or using *Agrobacterium* mediated transformation. Two sets of DNA constructs are produced. The first set of constructs are "single gene constructs". Each of the following genes is inserted into a separate plant DNA construct under the control of a napin promoter (Krindl et al., *Seed Sci. Res.* 1:209:219 (1991)) and the products of the genes can be targeted to the plastid by an encoded plastid target peptide such as CTP 1 (Keegstra, *Cell* 56(2):247-53 (1989); Nawrath, et al., *Proc. Natl. Acad. Sci. U.S.A* 91: 12760-12764 (1994)) or CTP2): an *E. herbicola* tyrA gene (Xia et al., *J. Gen. Microbiol.* 138:1309-1316 (1992)), an slr1736 gene (in Cyanobase on the world wide web at: kazusa.orjp/cyanobase), a plant ATPT2 gene (Smith et al., *Plant J.* 11: 83-92 (1997)), a dxs gene (Lois et al. *Proc. Natl. Acad. Sci. U.S.A.* 95 (5):2105-21 10 (1998)), a dxr gene (Tkahashi et al. Proc. Natl. Acad. Set. U.S.A. 95 (17), 9879-9884 (1998)), an *Arabidopsis thaliana* HPPD gene (Norris et al., *Plant Physiol.* 117:1317-1323 (1998)), a GGH gene (Keller et al., *Eur. J. Biochem.* 251:413-417 (1998)), an *Arabidopsis thaliana* GGPPS gene (Bartley and Scolnik, *Plant Physiol.* 104:1469-1470 (1994)), a AANT1 gene (Saint Guily, et al., *Plant Physiol.*, 100(2):1069-1071 (1992)), an MT1 gene (The seqence of the Synechocystis MT1 (NCBI General Identifier Number_1653572) was used in a blast search against ESTs of *Anabaena* sp. strain PCC 7120 (Kaneko 2001). A sequence with substantial homology to the Synechocystis MT1 was found in a blast search against ESTs of *Anabaena* sp. strain PCC 7120

(Kaneko et al., DNA Research 8(5): 205-213 (2001)), a TMT2 gene (as disclosed in U.S. Application Ser. No. 60/330,563, filed on Oct. 25, 2001, which is herein incorporated by reference in its entirety), a GMT gene (as disclosed in U.S. Application Ser. No. 60/312,758, filed on Aug. 17, 2001, which is herein incorporated by reference in its entirety); WO 00/32757, WO 00/10380), and a slr1737 gene (in Cyanobase (on the world wide web at kazusa.orjp/cyanobase), and an antisense construct for homogentisic acid dioxygenase (Sato et al., J. DNA Res. 7 (1):31-63 (2000)). Each construct is transfonned into at least one canola, Brassica napus, Arabidopsis and soybean plant. Plants expressing each of these genes are selected to participate in additional crosses. The tocopherol composition and level in each plant is also analyzed using the method set forth in example 7. Crosses are carried out for each species to generate transgenic plants having one or more of the following combination of introduced genes: tyrA, slr1736, ATP2 dxs, dxr, GGH, GGPPS, HPPD, MT1, TMT2, GMT, AANT1, slr 1737, and an antisense construct for homogentisic acid dioxygenase. In a preferred combination, the nucleic acid construct or constructs encode, in addition to tyrA, HPPD and either slr1736 or ATPT2.

The tocopherol composition and level in each plant generated by the crosses (including all intermediate crosses) is also analyzed using the method set forth in example 7. Progeny of the transformants from these constructs will be crossed with each other to stack the additional genes to reach the desired level of tocopherol.

A second set of DNA constructs is generated and referred to as the "multiple gene constructs." The multiple gene constructs contain multiple genes each under the control of a napin promoter (Krindl et al., Seed Sci. Res. 1:209:219 (1991)) and the products of each of the genes are targeted to the plastid by an encoded plastid target peptide. The multiple gene construct can have two or more of the following genes: tyrA, slr1736, ATPT2, dxs, dxr, GGH, GGPPS, HPPD, MT1, TMT2, GMT, AANT1, slr 1737, and an antisense construct for homogentisic acid dioxygenase. In a preferred combination, the nucleic acid construct or constructs encode, in addition to tyrA, HPPD and either slr1736 or ATPT2.

Each construct is then transformed into at least one canola, Brassica napus, Arabidopsis and soybean plant. The tocopherol composition and level in each plant is also analyzed using the method set forth in example 7. Progeny of the transformants from these constructs are crossed with each other to stack the additional genes to reach the desired level of tocopherol.

EXAMPLE 9

Figure 12:
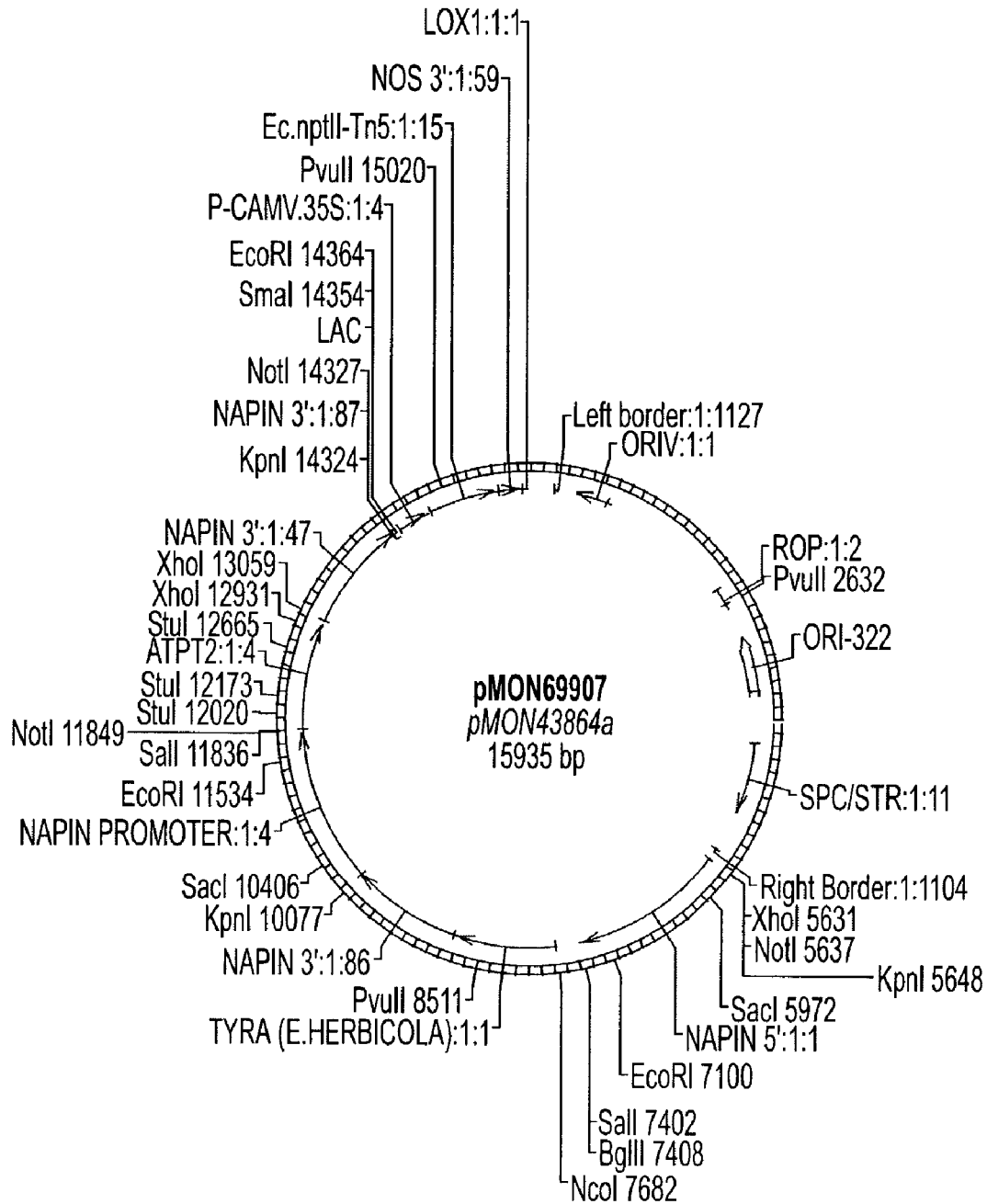
FIG. 12 is a schematic of construct pMON69907.
Figure 13:
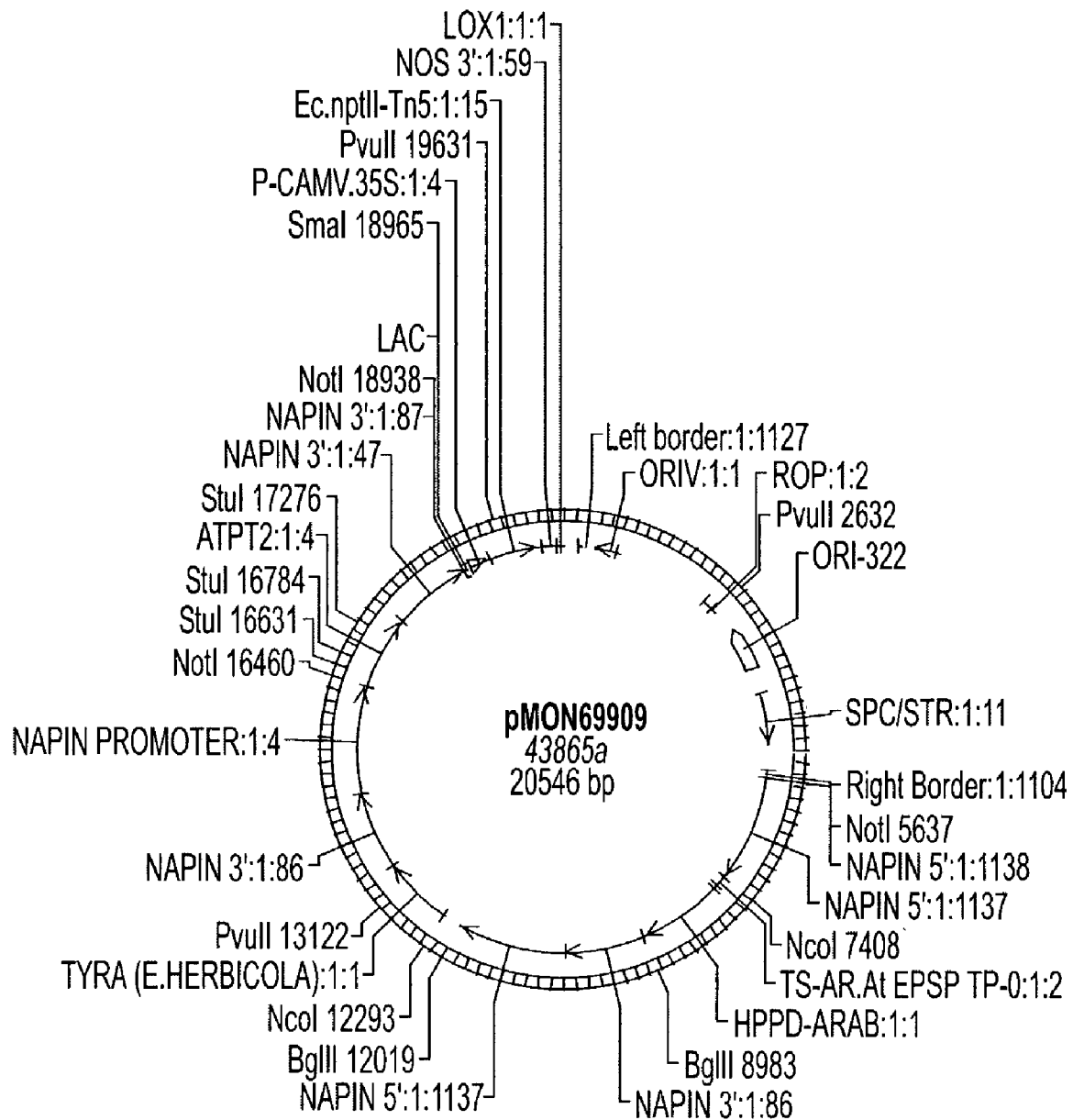
FIG. 13 is a schematic of construct pMON69909.
Figure 14:
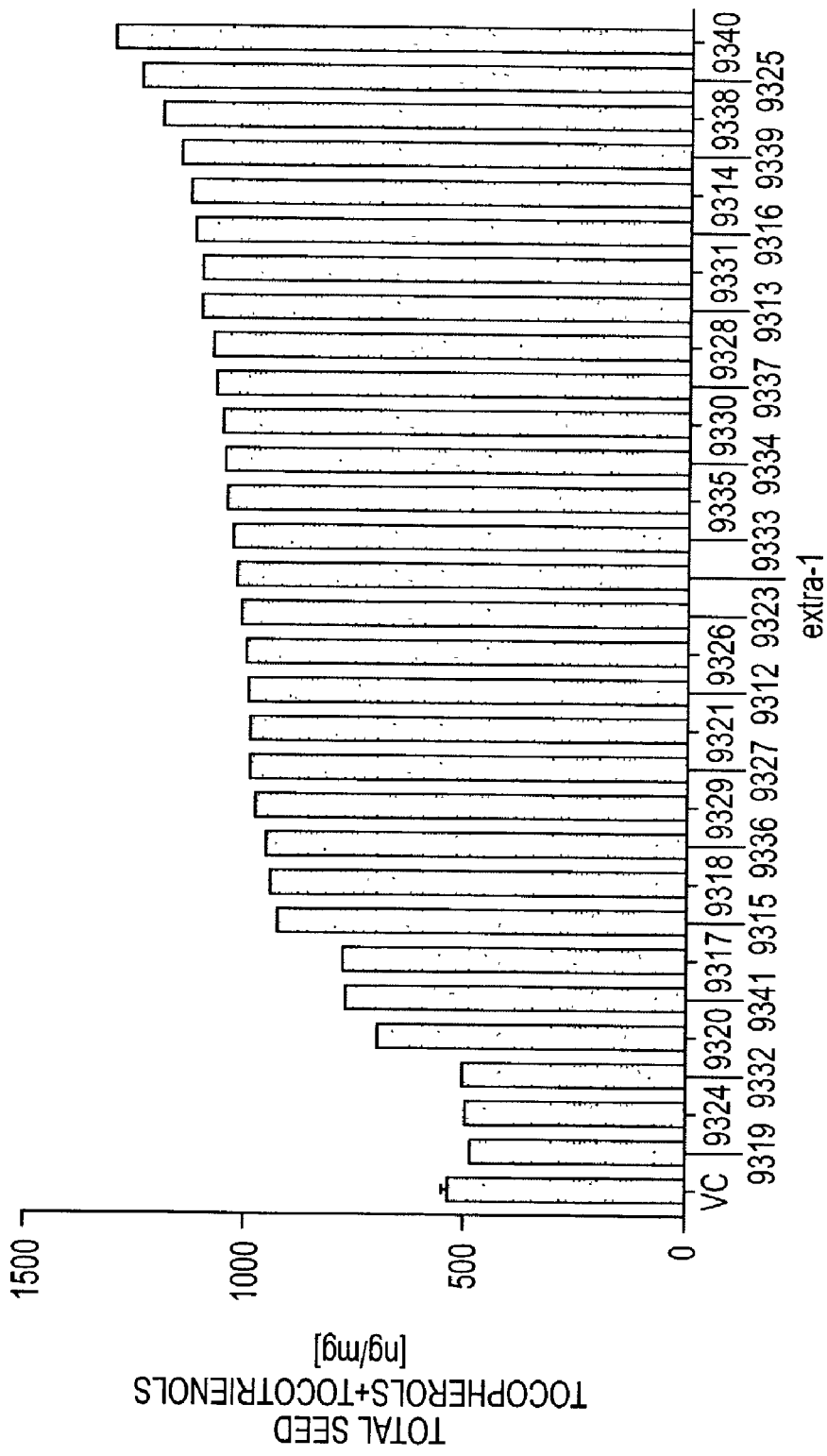
FIG. 14 depicts the total tocopherol and tocotrienol content of *Arabidopsis* seeds from wild type plants and several plant lines transformed with the plasmid vector pMON69907.
Figure 15:
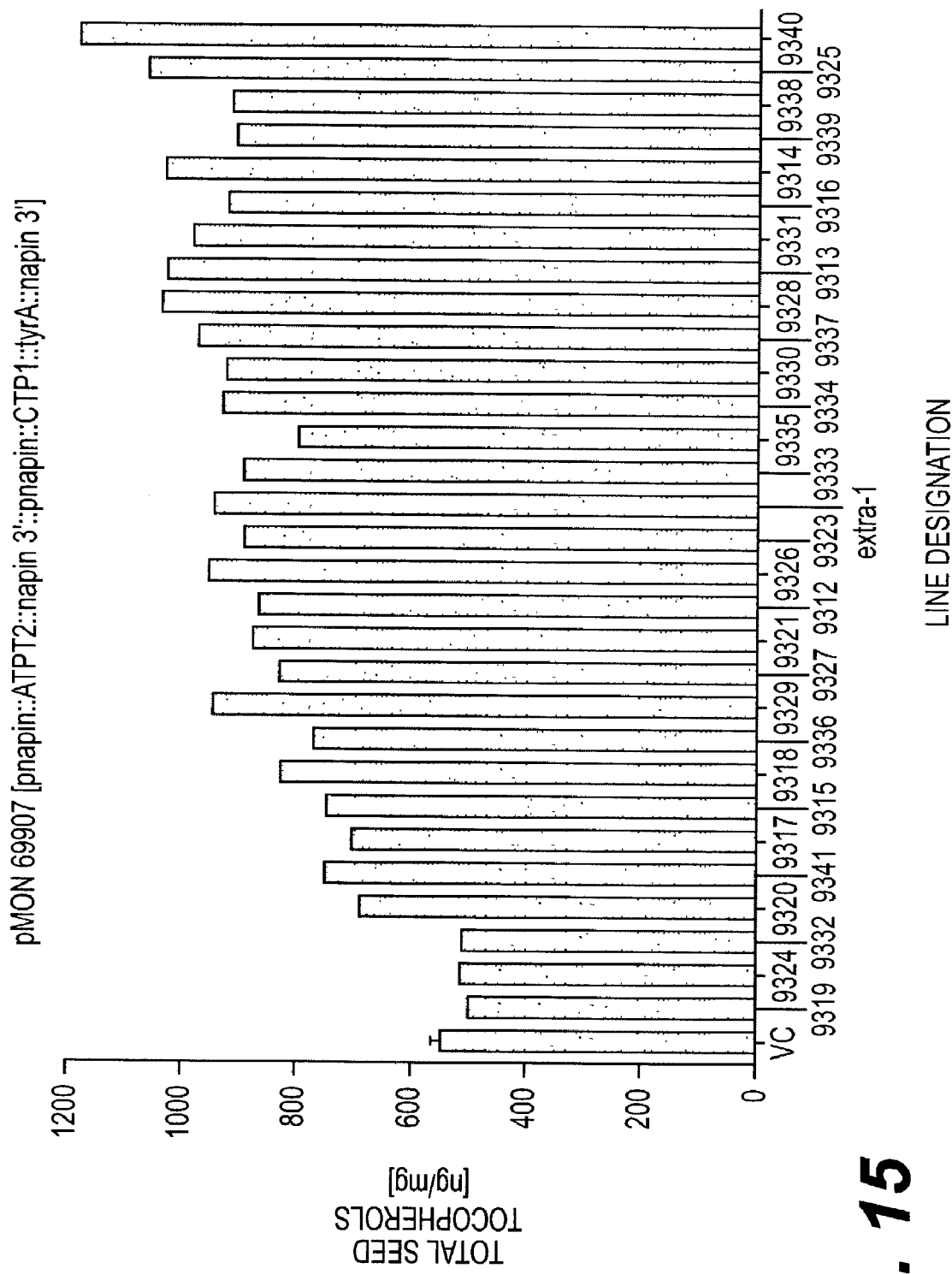
FIG. 15 depicts the total tocopherol content of *Arabidopsis* seeds from wild type plants and several plant lines transformed with the plasmid vector pMON69907.
Figure 33:
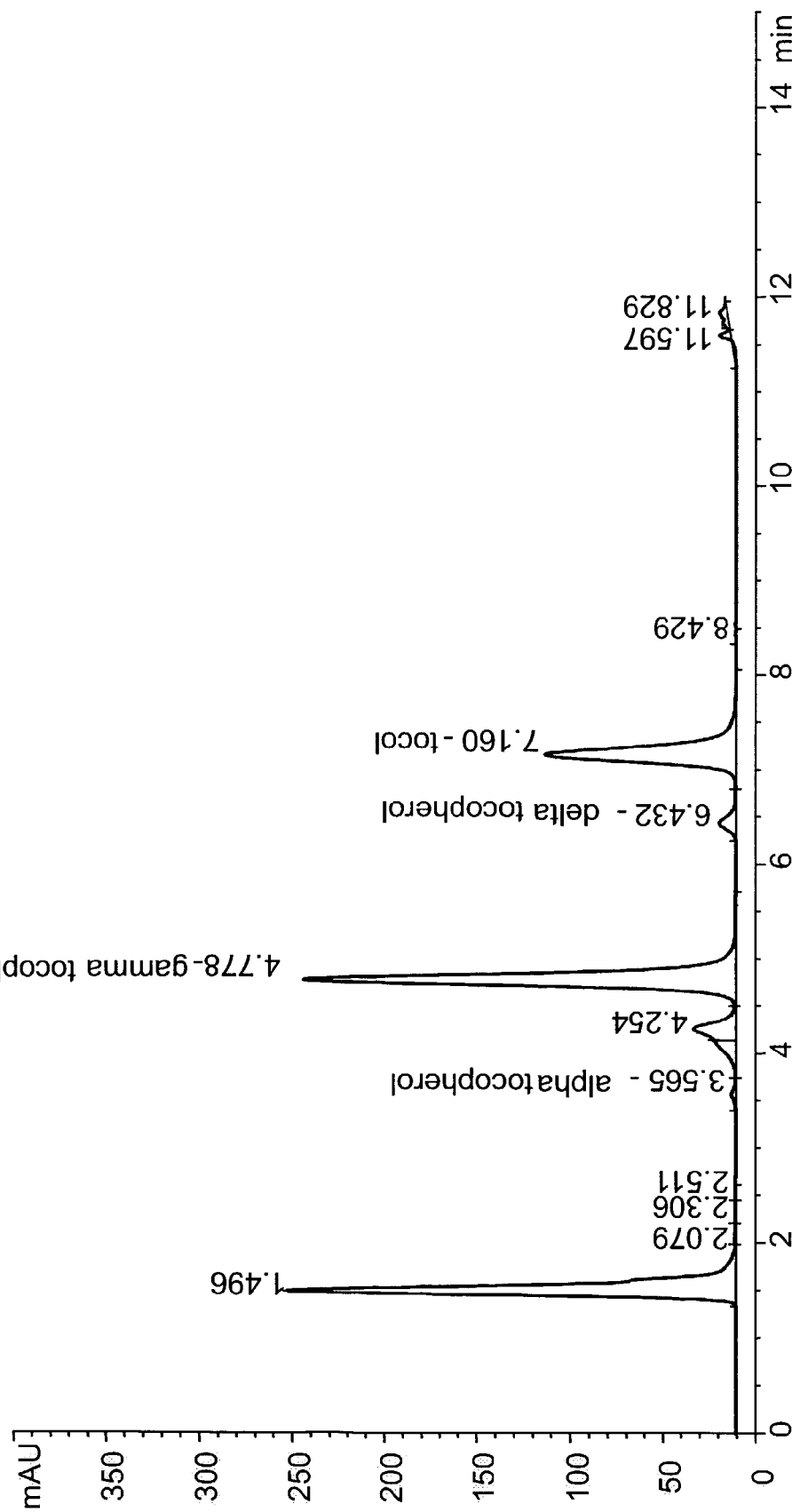
FIG. 33 is an HPLC chromatograph.
Figure 34:
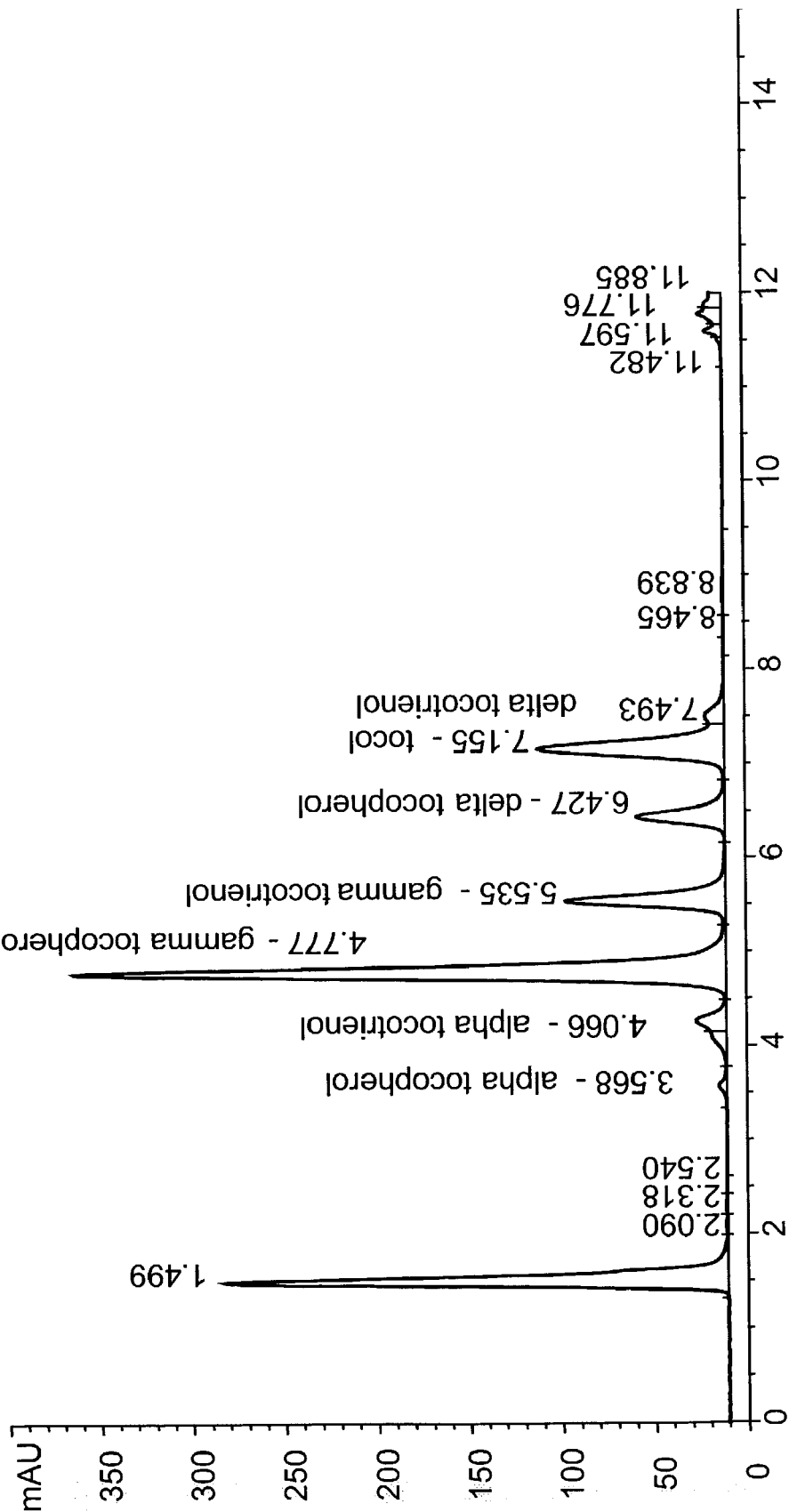
FIG. 34 is an HPLC chromatograph.

Transformed Arabidopsis Plants with tyrA, ATPT2, and Other Tocopherol Biosynthesis Genes Wild type Arabidopsis plants and Arabidopsis plant lines are transformed with the plasmid vector pMON69907 (FIG. 12), are grown, and seed is collected as described in the above examples, and the seed is analyzed for tocopherol and tocotrienol content as described above. Plasmid pMON69907 encodes a bifunctional prephenate dehydrogenase (tyrA) and a phytyl prenyltransferase (ATPT2). FIG. 14 depicts the total tocopherol and tocotrienol content of Arabidopsis seeds from wild type plants and several plant lines transformed with the plasmid vector pMON69907. FIG. 15 depicts the total tocopherol content of Arabidopsis seeds from a wild type plant and several plant lines transformed with the plasmid vector pMON69907. FIG. 31 shows LC/MS standards for tocopherol and tocotrienol. FIG. 32 shows LC/MS results for selected lines, showing presence of tocotrienols. FIG. 33 shows an HPLC/FLD chromatogram of control seed extract showing no presence of tocotrienols. FIG. 34 shows an HPLC/FLD chromatogram of control seed extract showing the presence of tocotrienols in selected lines.

EXAMPLE 10

Transformed Arabidopsis Plants with tyrA and Other Tocopherol Biosynthesis Genes Expression constructs pCGN10822, pMON36528, pMON69907 and pMON69909, shown in FIGS. 10-13 respectively are prepared.

Figure 16A:
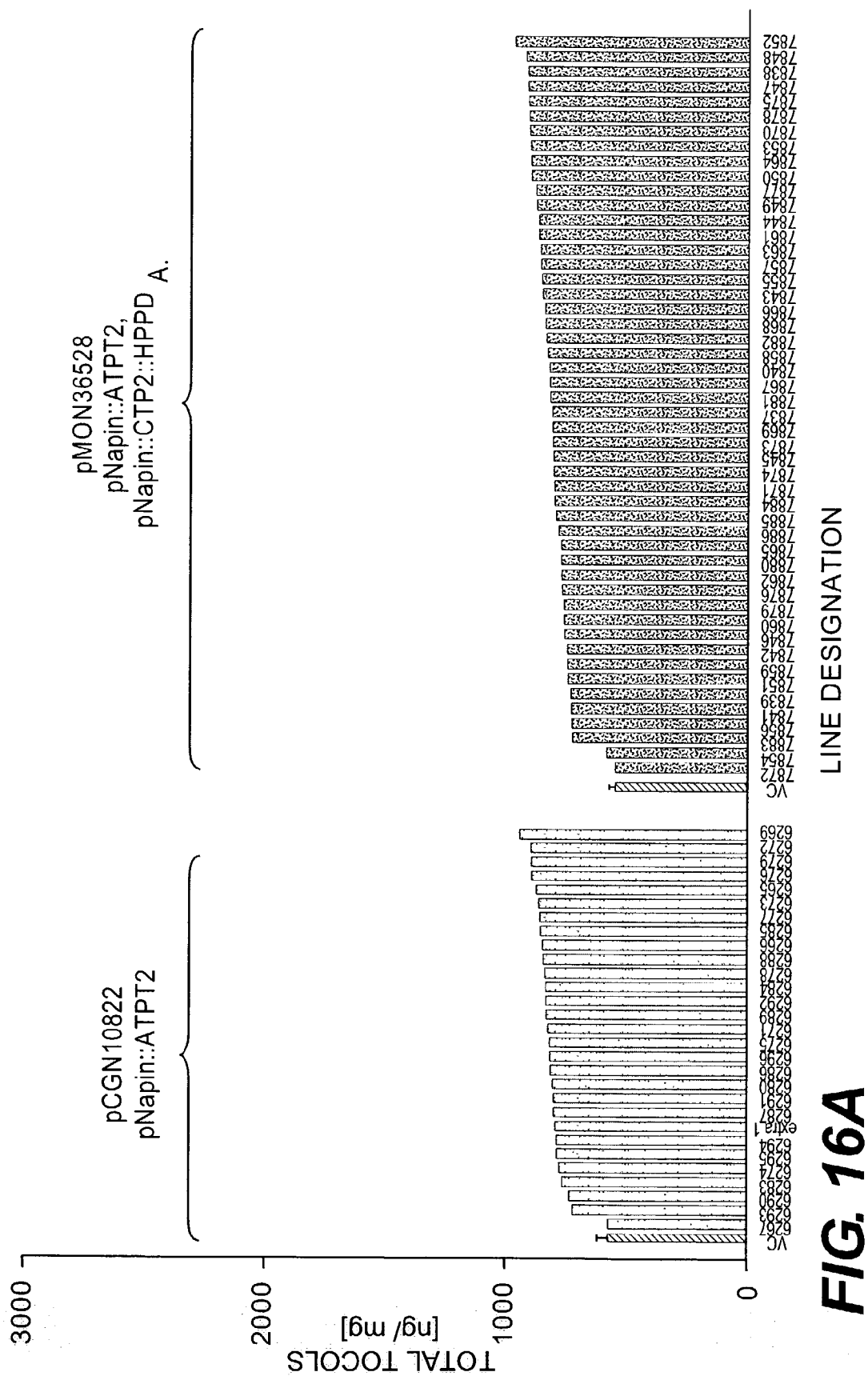
FIG. 16 depicts the total tocopherol and tocotrienol content of *Arabidopsis thaliana* seeds from wild type plants and several plant lines separately transformed with the plasmid vectors pCGN10822, pMON36528, pMON69907 and pMON69909.
Figure 16B:
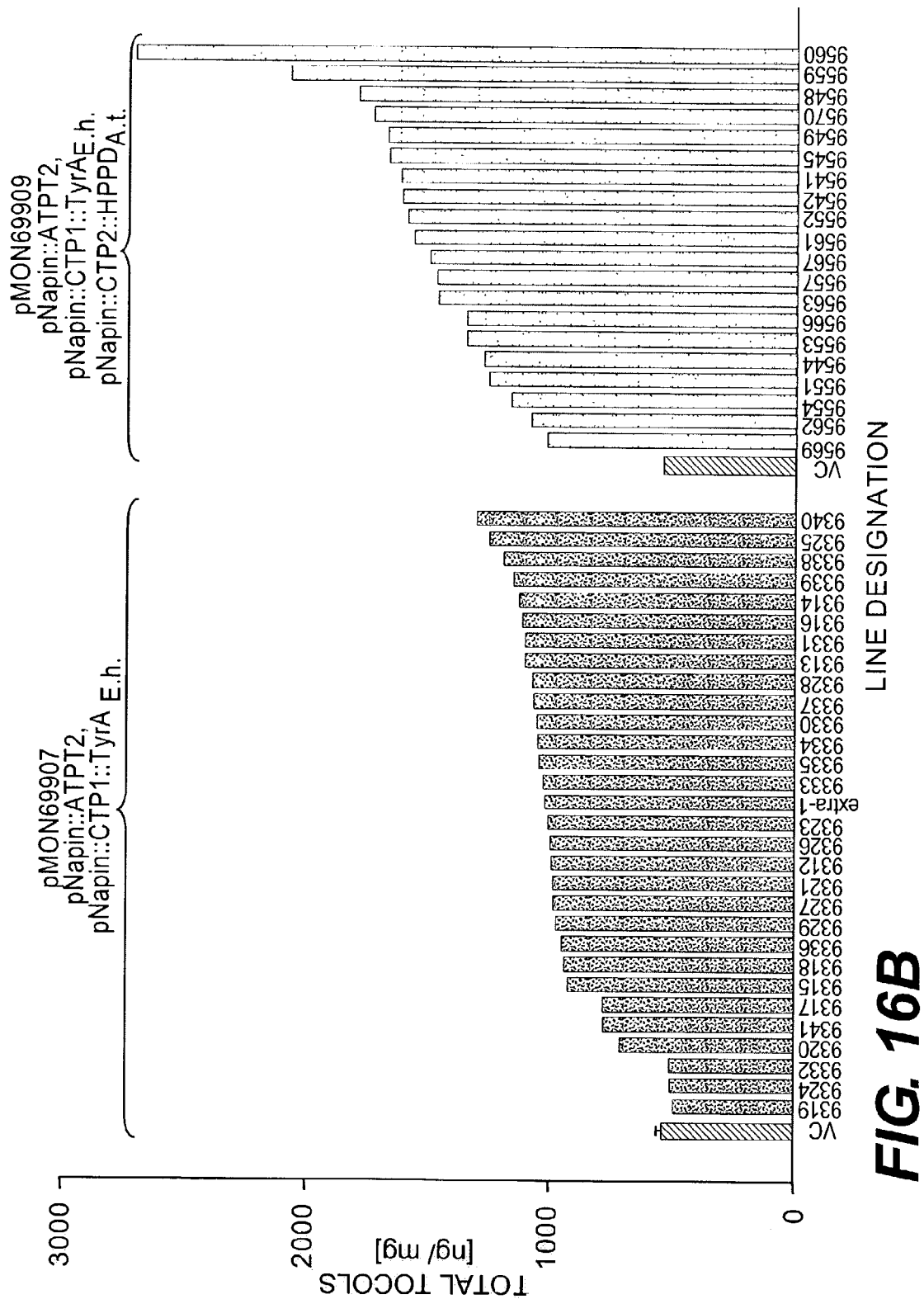
Figure 17A:
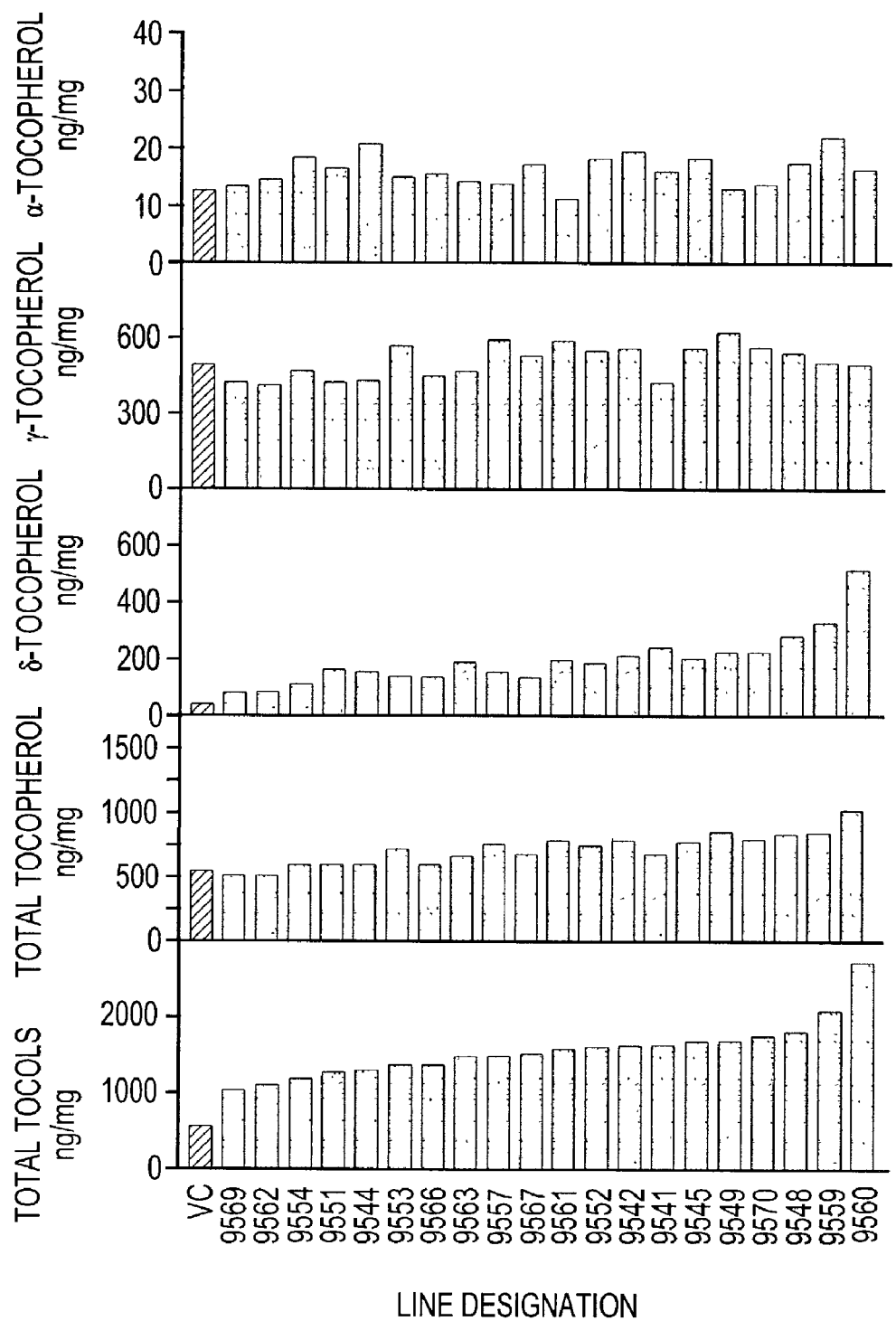
FIG. 17 depicts a detailed analysis of tocopherol and tocotrienol content of *arabidopsis* seeds from plant lines transformed with the vector pMON69909 relative to wild type plant seeds.
Figure 17B:
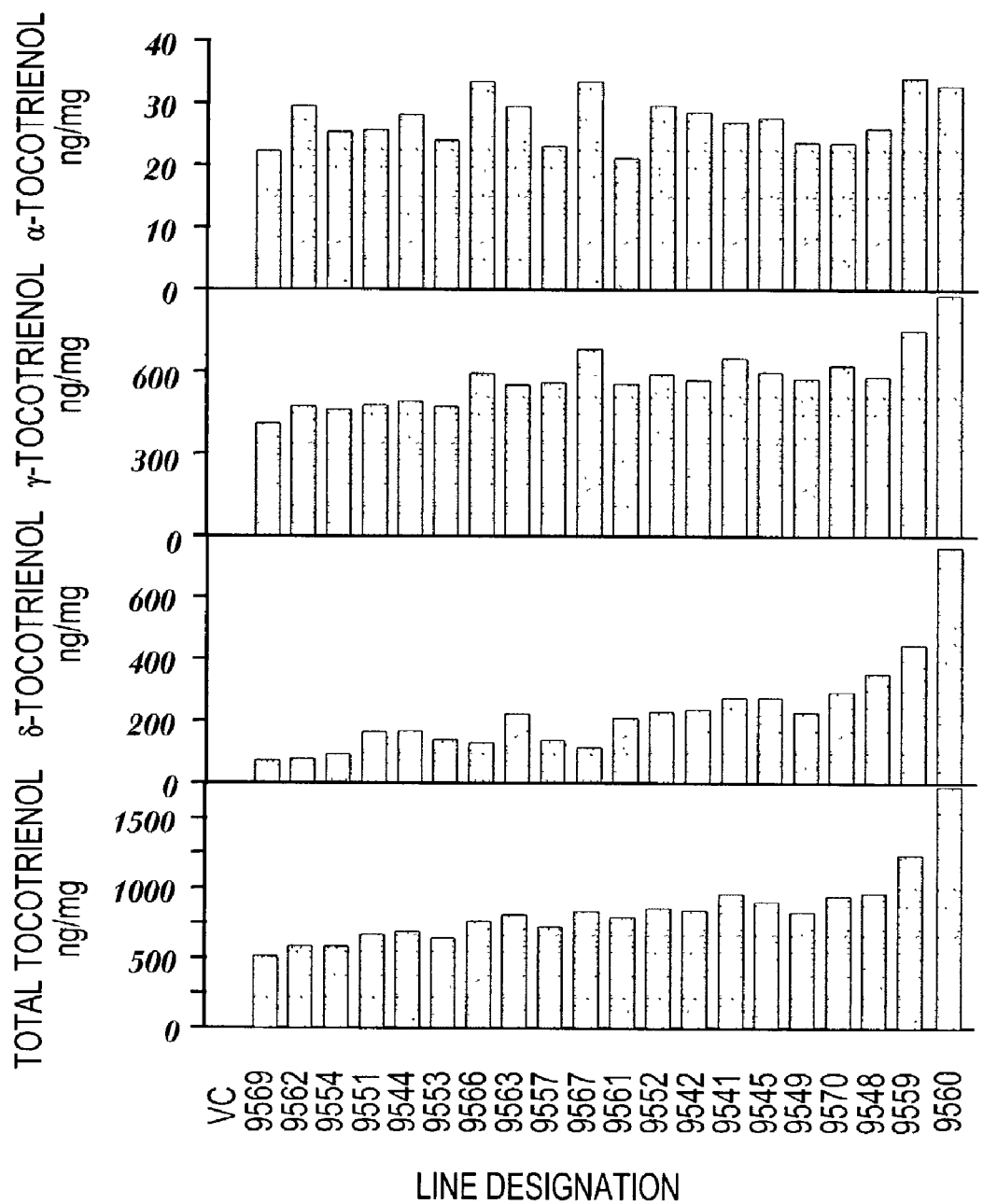

Arabidopsis plants are transformed with the indicated vectors using the transformation techniques described in Example 8. Transformants are isolated and grown into individual lines by self pollination and seed from each line collected. The total tocopherol and tocotrienol composition of the seeds from each line are analyzed using the method set forth in Example 7. FIG. 16 shows total tocopherol and tocotrienol levels for plant lines harboring the described contructs or a control. An analysis of T2 seeds from plant lines derived by transformation with the vector pMON69909 relative to wild type is shown in FIG. 17. Plant lines transformed with pMON69909 demonstrate a substantial increase in total tocopherols and total tocotrienols, with the largest increases in delta tocopherol, alpha tocotrieneol, delta tocotrienol, and gamma tocotrienol. Some seed from plants harboring the vector pMON69909 show a dark coloration as the result of homogentisic acid accumulation, which is confirmed by LC/MS analysis (see FIGS. 31 and 32).

Heterologous expression of tyrA in seeds of transgenic Arabidopsis plants produces a 1.6-fold increase in seed tocopherol levels as compared to control lines. Another key enzyme essential for tocopherol biosynthesis is HPT, which is involved in the condensation of phytyl pyrophosphate (PPP) and homogentisate (HGA) to produced 2-methyl-6-phytylplastoquinol (2M6PPQ), a precursor for synthesis of four different isoforms of tocopherols. Overexpression of $HPT_{Arabidopsis}$ (ATPT2) and the $HPT_{Synechocystis}$ (slr1736) independently in seeds of transgenic A. thaliana results in a 1.6-fold increase in seed tocopherols. A putative adenylate transporter from A. thaliana (AANT1) expressed as a single gene is shown to increase seed tocopherol levels to 1.4-fold in A. thaliana. To test whether a combination of these genes would result in synergistic effect on tocopherol biosynthesis, various combinations are tested in A. thaliana.

Figure 35:
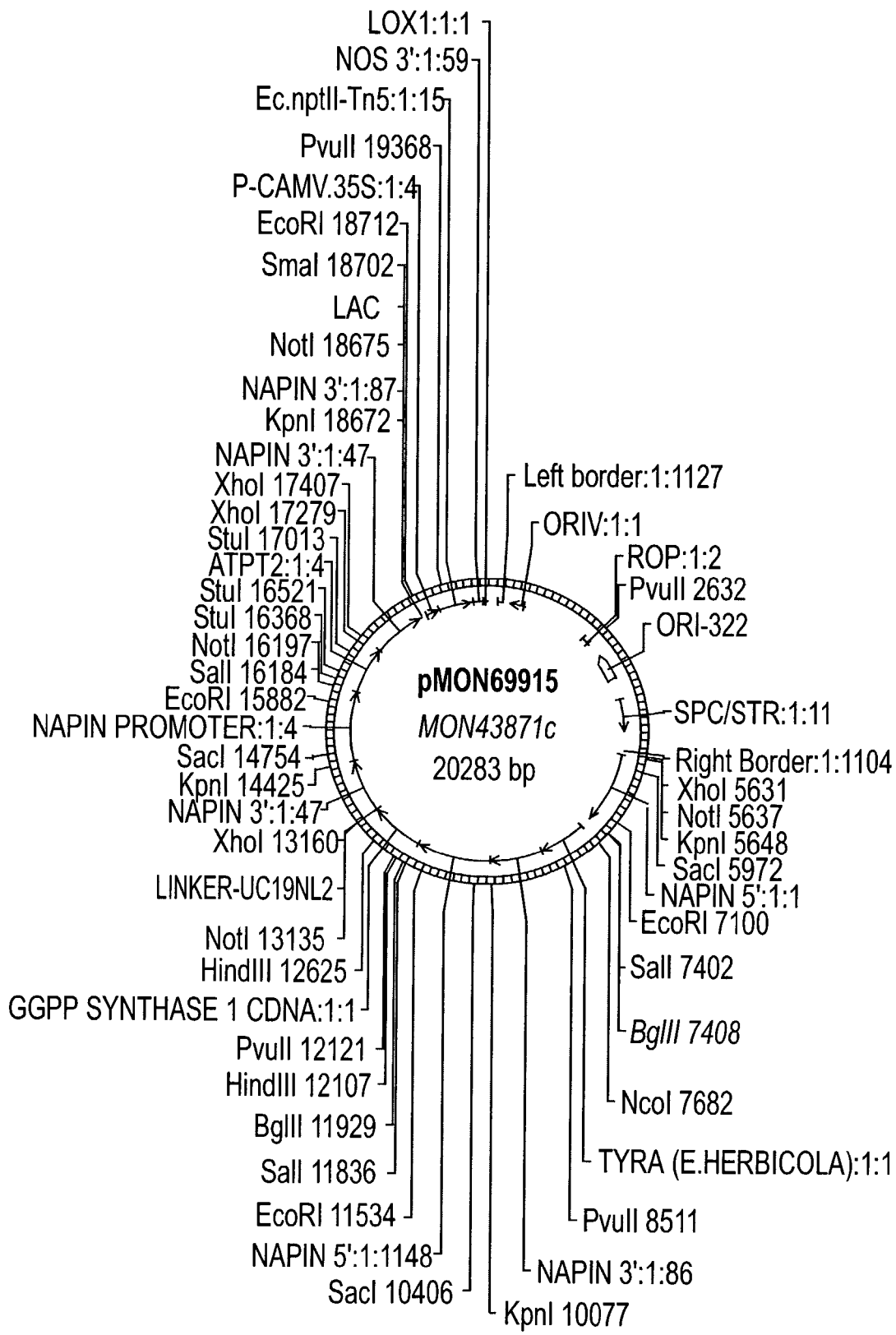
FIG. 35 is a schematic of construct pMON69915.
Figure 36:
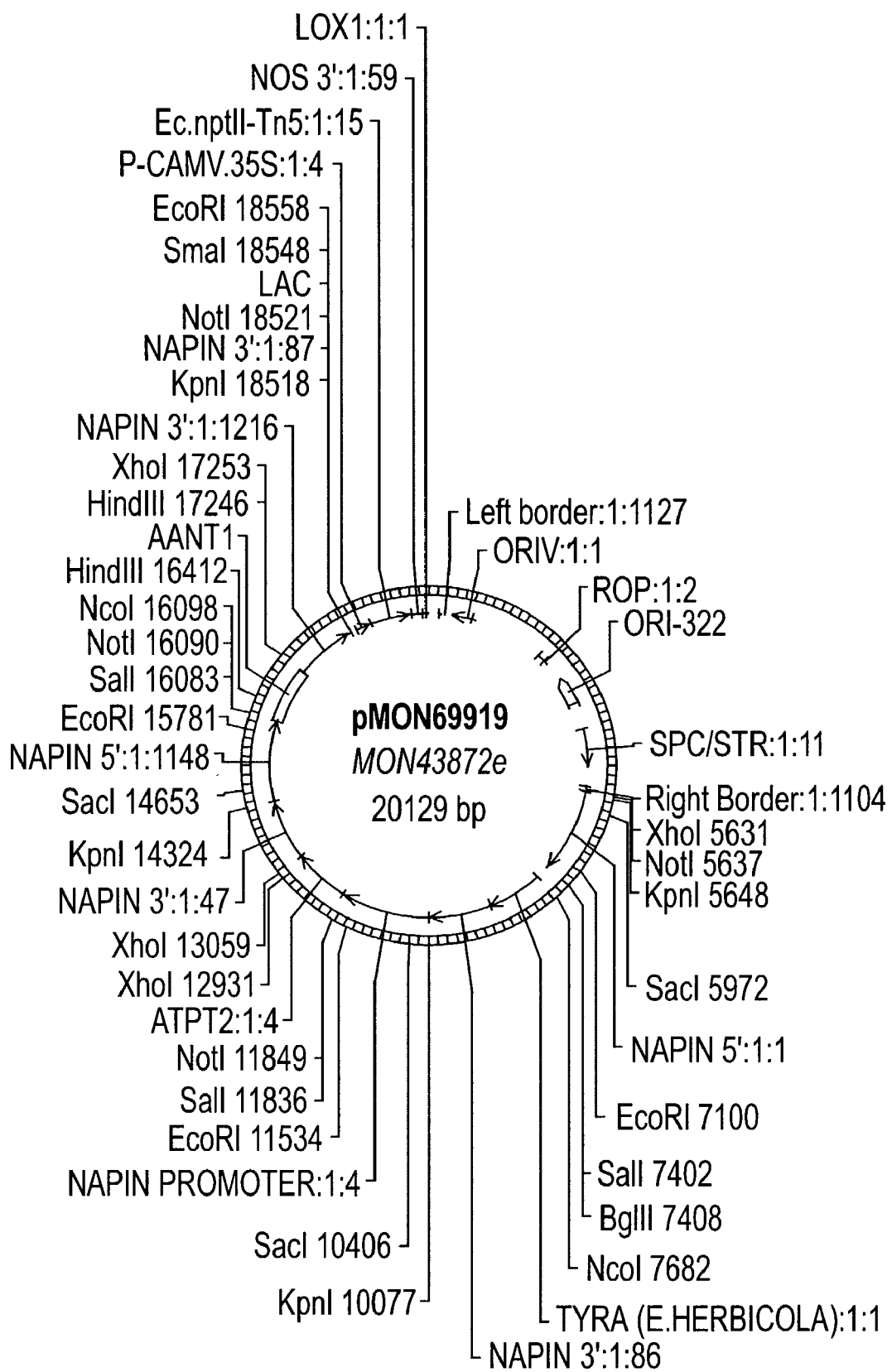
FIG. 36 is a schematic of construct pMON69919.

T2 Arabidopsis seeds harboring ATPT2 and tyrA double gene constructs (pMON69907), ATPT2, tyrA, and HPPD triple gene constructs (pMON69909), ATPT2, tyrA, and GGPPS triple gene constructs (pMON69915 (FIG. 35)), and ATPT2, tyrA, and AANT1 triple gene constructs (pMON69919 (FIG. 36)), are analyzed for seed tocopherol content and composition. Total seed tocopherol and tocotrienol content increases to approximately 2.4-fold in lines transformed with pMON69907 (double gene vector) and up to 5-fold in the lines carrying the triple gene vector (pMON69909) (See FIGS. 16 and 17). HPPD expressed as a single gene in A. thaliana result in a barely detectable increase of tocopherol levels. The combination of HPPD with ATPT2 does not result in a further increase of tocopherol levels as compared to lines harboring ATPT2 alone (data not shown). In contrast, when HPPD is combined with tyrA and ATPT2, tocopherol and tocotrienol levels double compared to the tyrA, ATPT2 combination. Seeds harboring the triple gene construct pMON69909 appear much darker in color than control seeds.

Furthermore, it is known that wild-type dicotyledonous plants do not accumulate tocotrienols. However, the transgenic *A. thaliana* seeds harboring all four constructs accumulates substantial levels of tocotrienols (confirmed by HPLC, and for selected samples by LC-MS, (See FIGS. 31, 32, 33, and 34). The tocopherol and tocotrienol content of seeds harboring the triple gene expression construct, pMON69909, consist of 60% tocotrienols and 40% tocopherols. When the availability of endogenous HGA is elevated by overexpression of the HGA biosynthetic enzymes (tyra & HPPD) along with HPT, the HPT would utilize geranylgeranyl pyrophosphate (GGPP) and HGA to produce tocotrienols instead of tocopherols under conditions limited by the availability of endogenous level of geranylgeranyl reductase (GGH). The GGH functions on hydrogenating the GGPP to PPP, a substrate for HPT in tocopherol synthesis. Hence, increased tocotrienols accumulation seen in the constructs tested can be overcome by overexpression of GGH in combination with tyrA, HPPD, and HPT.

EXAMPLE 11

Transformed Plants with tyrA and Other Tocopherol Biosynthesis Genes

Plants are transformed with the DNA constructs shown in tables 2 and 3 below, employing the techniques described in Example 8. The constructs contain one or more genes under the control of a napin promoter (Krindl et al., *Seed Sci. Res.* 1:209:219 (1991)), the 7Sα' promoter (Chen et al., *PNAS* 83(22):8560-8564 (1998)) or the Arc5 promoter (Goossens et al., *Plant Physiol.* 120:1095-1104 (1999)). The products of the genes can be targeted to the plastid by an encoded plastid target peptide such as CTP1 (Keegstra, *Cell* 56(2): 247-53 (1989); Nawrath, et al., *Proc. Natl. Acad. Sci. U.S.A.* 91:12760-12764 (1994)) or CTP2. One or more of the following genes are used: an *E. herbicola* tyrA gene (Xia et al., *J. Gen. Microbiol.* 138:1309-1316 (1992)), an slr1736 gene (in Cyanobase on the world wide web at: kazusa.org.jp/cyanobase), an ATPT2 gene (Smith et al., *Plant J.* 11: 83-92 (1997)), an *E. coli* dxs gene (Lois et al., *Proc. Natl. Acad. Sci. U.S.A.* 95 (5):2105-2110 (1998)), a dxr gene (Takahashi et al. *Proc. Natl. Acad. Sci. U.S.A.* 95 (17), 9879-9884 (1998)), an HPPD gene (Norris et al., *Plant Physiol.* 117: 1317-1323 (1998)), a GGH gene (Keller et al., *Eur. J. Biochem.* 251:413-417 (1998)), an *Arabidopsis thaliana* GGPPS gene (Bartley and Scolnik, *Plant Physiol.* 104:1469-1470 (1994)), an AANT1 gene (Saint Guily, et al., *Plant Physiol.*, 100(2):1069-1071 (1992)), an MT1 gene (as above for Example 8), a TMT2 gene (as above for example 8), a GMT gene (as above for example 8, and WO 00/32757, WO 00/10380), an slr1737 gene (in Cyanobase on the world wide web at kazusa.org.jp/cyanobase), and an antisense construct for homogentisic acid dioxygenase (denoted $HGD_{AS}$)(Sato et al., *J. DNA Res.* 7 (1):31-63 (2000)). Each construct is transformed into at least one canola, *Brassica napus, Arabidposis*, and soybean plant. The tocopherol composition and level in each plant is also analyzed using the method set forth in example 7. Examples of transformed plants with tyrA and other tocopherol biosynthesis genes include *Arabidopsis* plants transformed with the constructs set forth in Table 2 and soy plants transformed with the constructs in Table 3.

Plants with desired characteristics may be subject to further crosses to generate transgenic plants having one or more of the following combination of introduced genes: tyrA, slr1736, ATPT2, dxs, dxr, GGH, GGPPS, HPPD, MT1, TMT2, GMT, AANT1, slr 1737, and an antisense construct for homogentisic acid dioxygenase. Alternatively the plants may be crossed to stack multiple copies of one or more of the aforementioned genes in a transgenic plant.

TABLE 2

The following gene combinations are prepared and tested in *Arabidopsis thaliana*

1 pNapin::CTP1::TyrA*E. herbicola*::Napin 3'/pNapin::CTP2::HPPD*A. thaliana*::Napin3'/pNapin::ATPT2*A. thaliana*::Napin 3'
2 pNapin::CTP1::TyrA*E. herbicola*::Napin 3'/pNapin::AANT1*A. thaliana*::Napin3'/pNapin::ATPT2*A. thaliana*::Napin 3'
3 pNapin::CTP1::TyrA*E. herbicola*::Napin 3'/pNapin::GGPPS*A. thaliana*::Napin3'/pNapin::ATPT2*A. thaliana*::Napin 3'
4 pNapin::CTP1::TyrA*E. herbicola*::Napin 3'/pNapin::CTP1::DXS*E. coil*::Napin3'/pNapin::ATPT2*A. thaliana*::Napin 3'/pNapin::GGH::Napin 3'
5 pNapin::CTP1::tyrA*E. herbicola*::Napin 3'/pNapin::CTP1::DXR*E. coil*::Napin3'/PNaPin::ATPT2*A. thaliana*::Napin 3'/pNapin::GGH::Napin 3'
6 pNapin::CTP1::TyrA*E. herbicola*::Napin 3'/pNapin::HGDAs::Napin3'
7 pNapin::CTP1::TyrA*E. herbicola*::Napin 3'/pNapin::HGDAS::Napin3'/pNapin::ATPT2*A. thaliana*
8 pNapin::CTP1::TyrA*E. herbicola*::Napin 3'/pNapin::HGDAS::Napin3'/pNapin::ATPT2*A. thaliana*::Napin 3'/pNapin::GGH::Napin 3'
9 pNapin::CTP1::TyrA*E. herbicola*::Napin 3'/pNapin::HGDAS::Napin3'/pNapin::ATPT2*A. thaliana*::Napin 3'/pNapin::CTP1::DXS*E. coil*::Napin 3'/pNapin::GGH::Napin 3'

TABLE 3

The following gene combinations are prepared and tested in *Glycine max*

1 p7S::CTP2::HPPD::E9 3'/p7Sα'::CTP1::TyrA::E9 3'
2 pArc5::ATPT2::Arc 3'/p7Sα'::CTP1::TyrA::E9 3'/pNapin::GGH::Napin3'
3 pArc5::ATPT2::Arc 3'/p7S::CTP1::TyrA::E9 3'/pNapin::GGH::Napin3'/pNapin::CTP1::DXS::Napin 3'

EXAMPLE 12

Figure 18A:
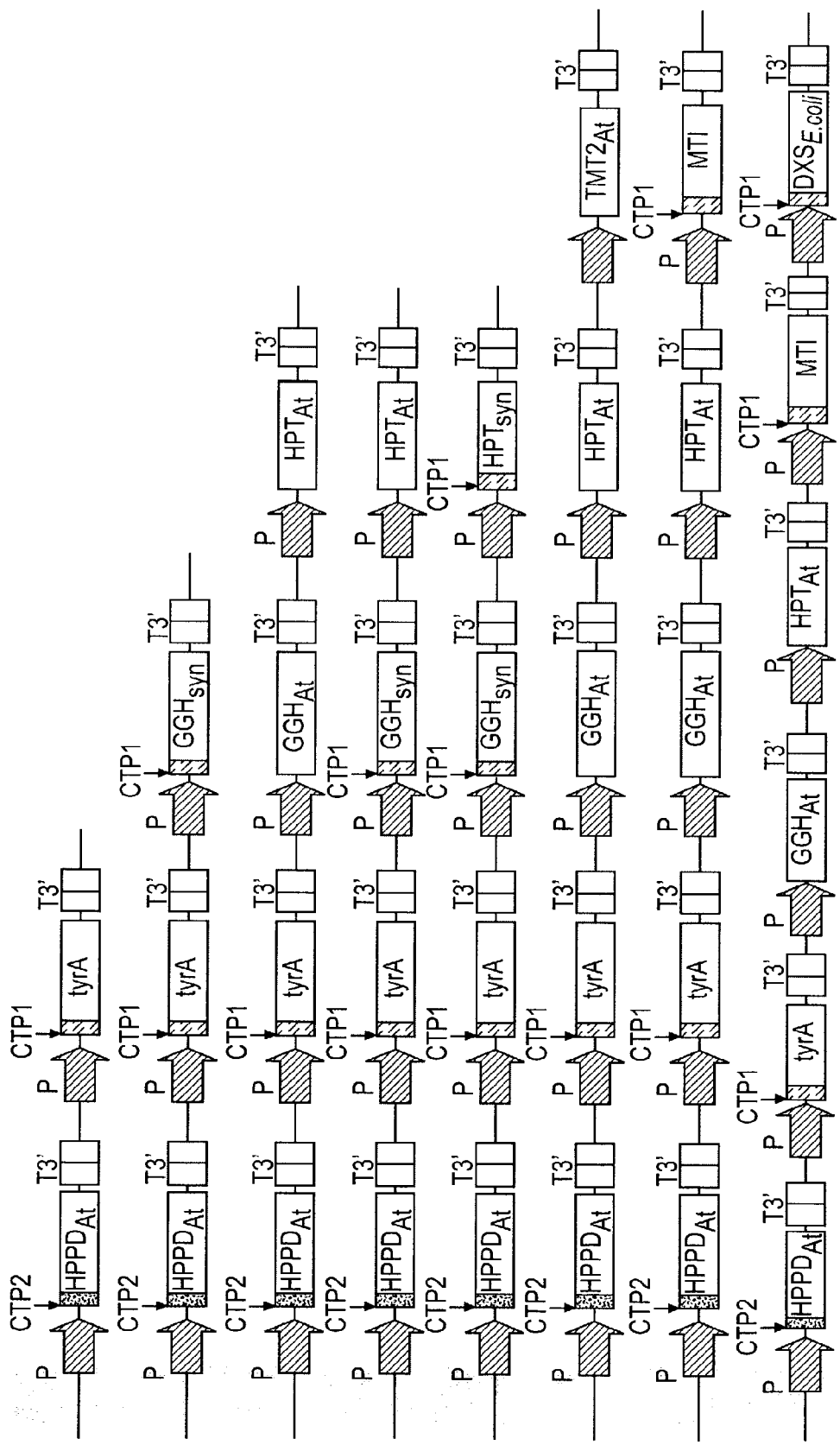
FIGS. 18a and 18b show exepmlary constructs for transformation into plants.
Figure 18B:
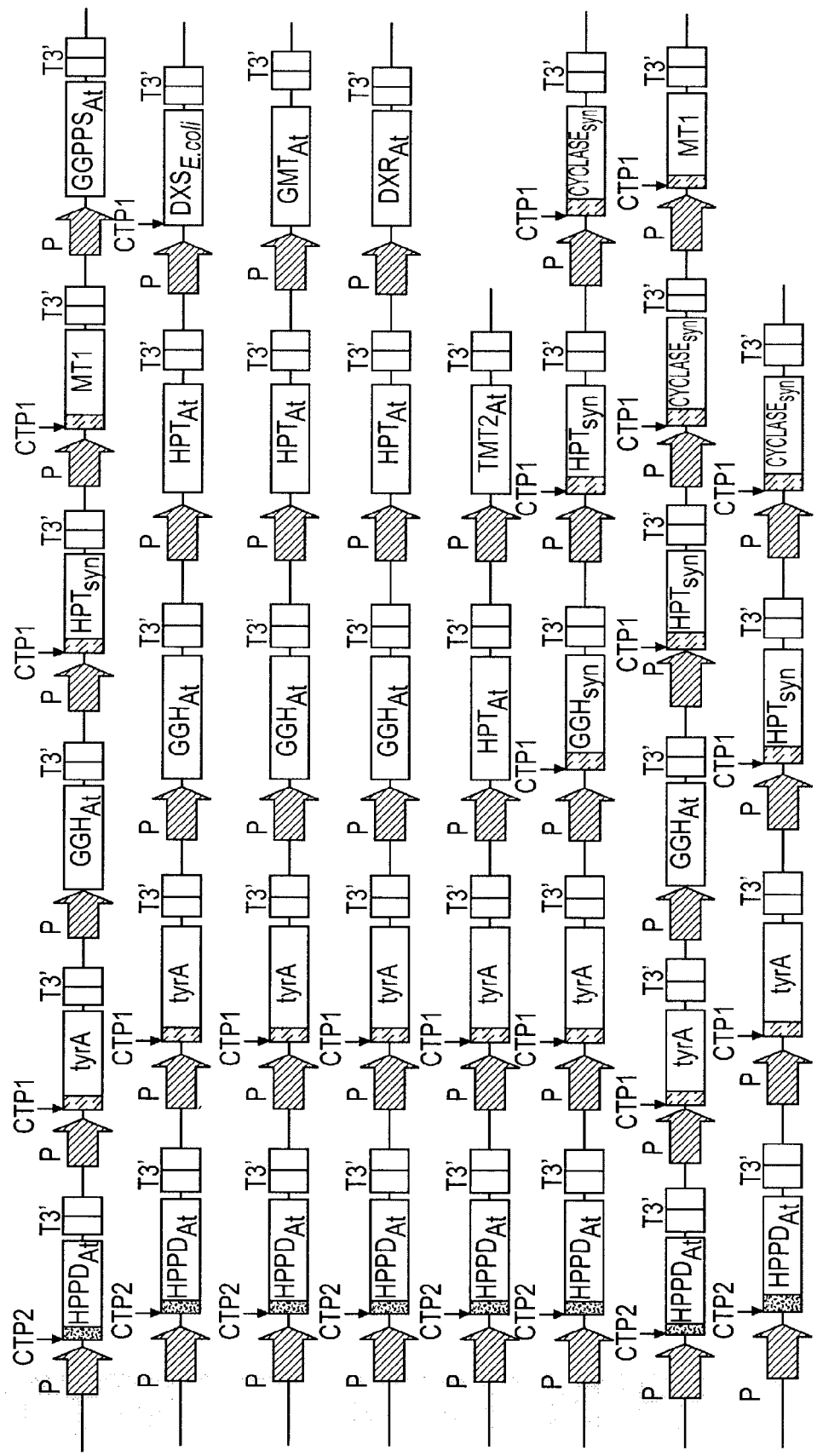

Construction of Plant Binary Vectors Harboring Combinations of tyrA with Other Tocopherol Synthesis Genes Components of each gene expression cassette include a promoter, in this example the napin promoter, a terminator, a plastid target peptide (which can be the native plastid target peptide or an N-terminal fused chloroplast target peptide), and a gene of interest, as shown in FIGS. 18a and 18b. The expression cassettes can be oriented head to tail, head to head, or the orientation can vary.

Figure 20:
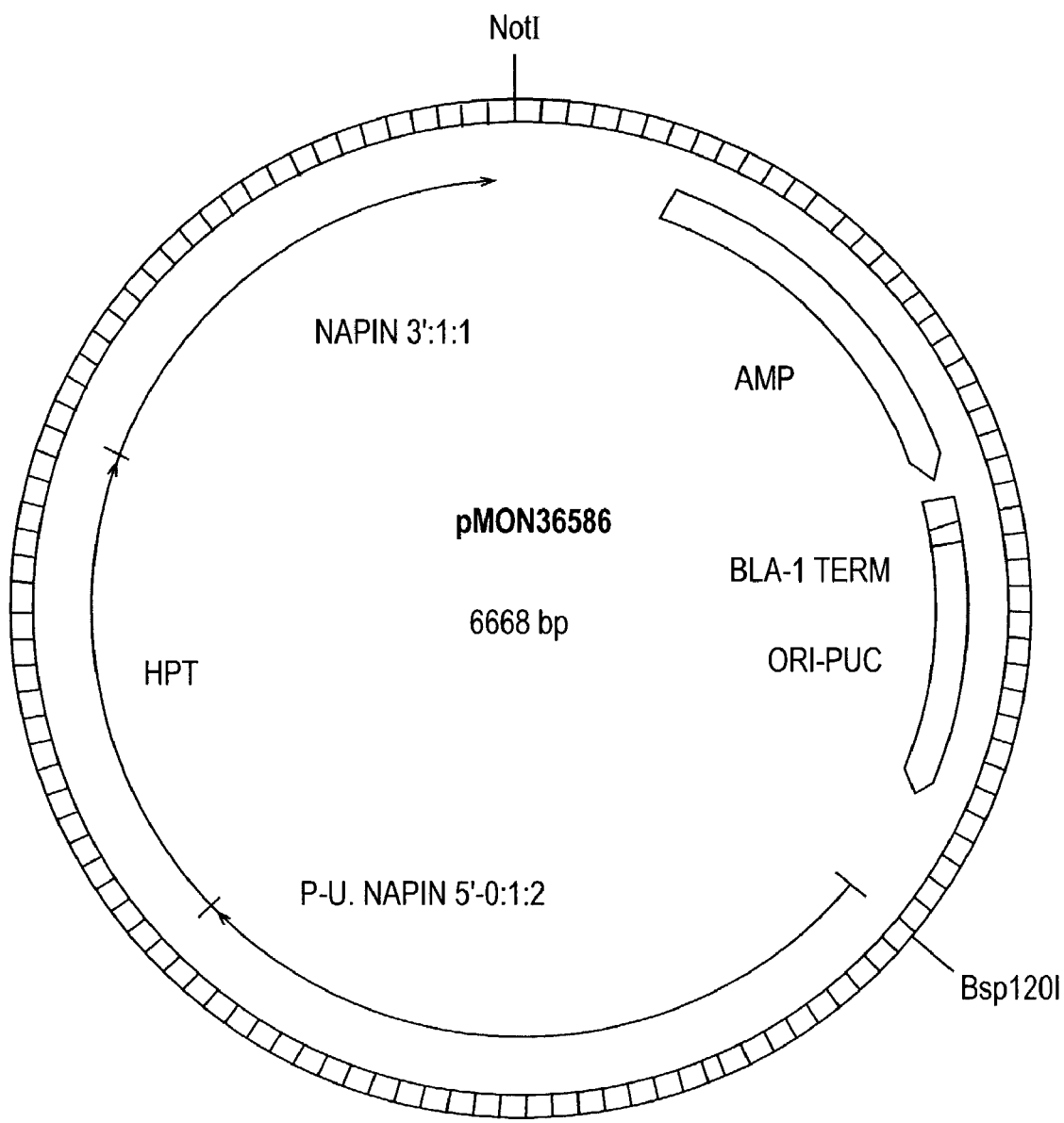
FIG. 20 is an example of a shuttle vector (pMON36586) harboring an expression cassette of the *Arabidopsis* homogentisate phytyltransferase (HPT) as a Bsp120I/Not I cassette. The napin promoter and napin terminator are fused to the 5' and 3' ends, respectively, to drive seed specific expression.

Cloning is performed using expression cassettes flanked by Bsp120 I and Not I restriction sites. A shuttle vector (pMON36582 (FIG. 19)) is constructed by annealing primers SV MCS 1A and SV MCS 1B:

Bsp120 I/Not I cassette is shown as pMON36586 in FIG. 20. This vector is obtained as described above.

Figure 21A:
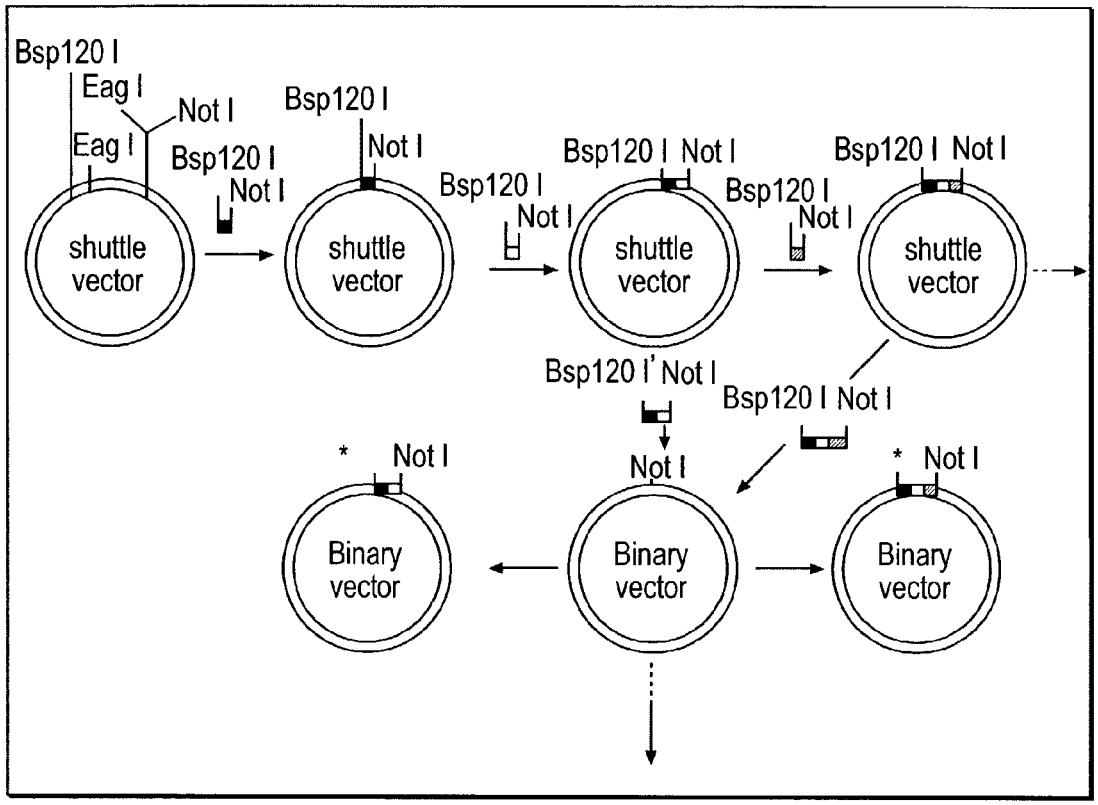
FIG. 21 represents various gene expression cassettes shown in a shuttle vector (A) or in a binary vector (B).
Figure 21B:
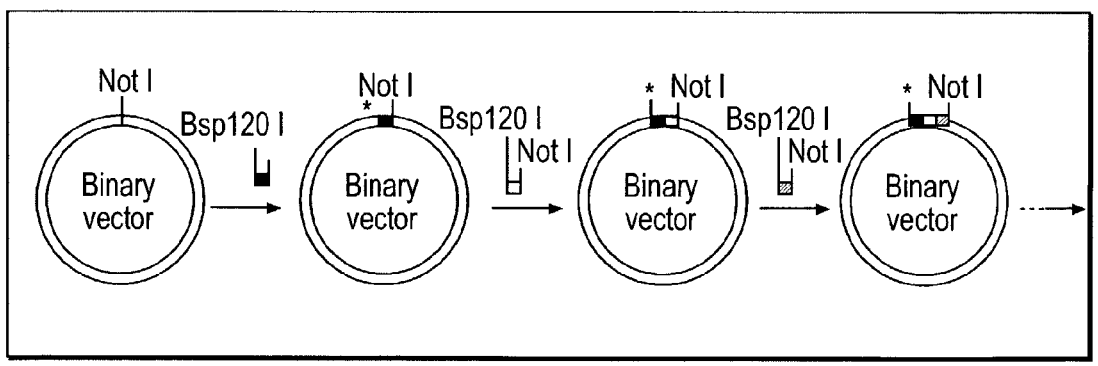
Figure 22:
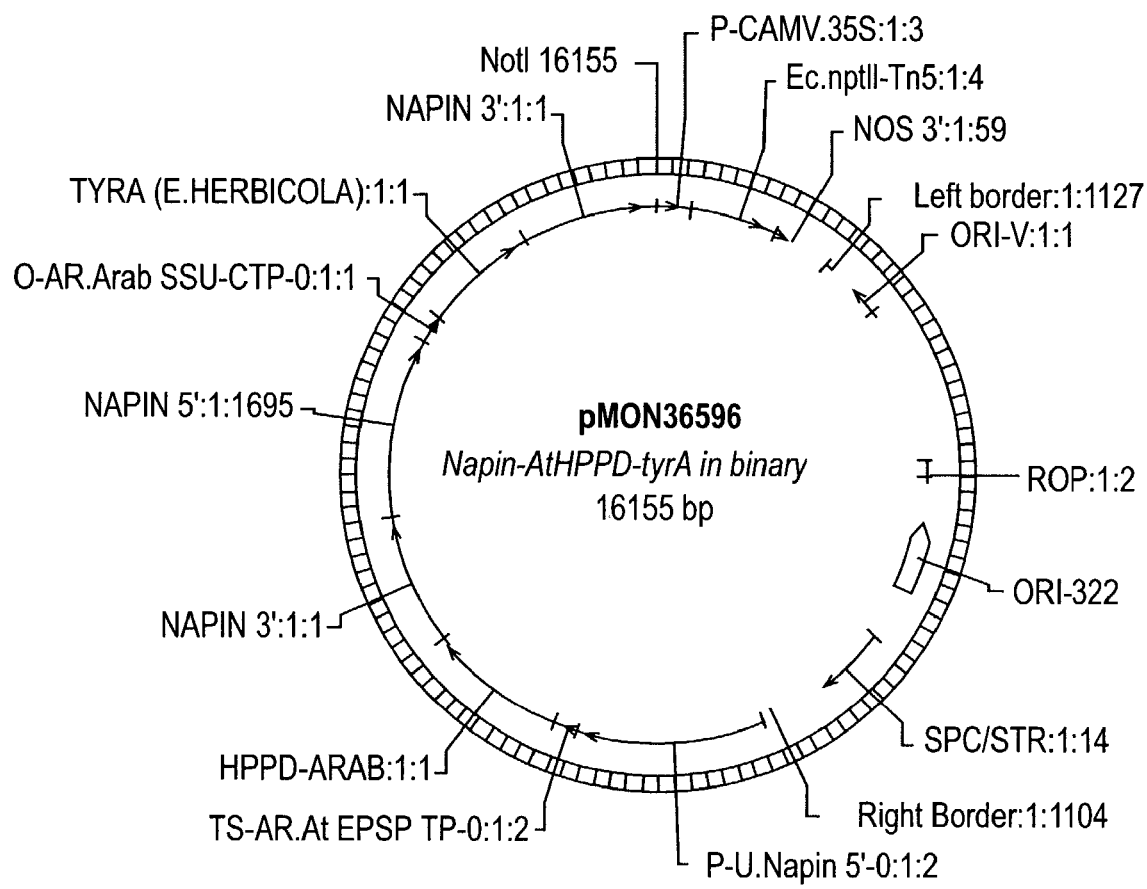
FIG. 22 is a schematic of construct pMON36596.
Figure 23:
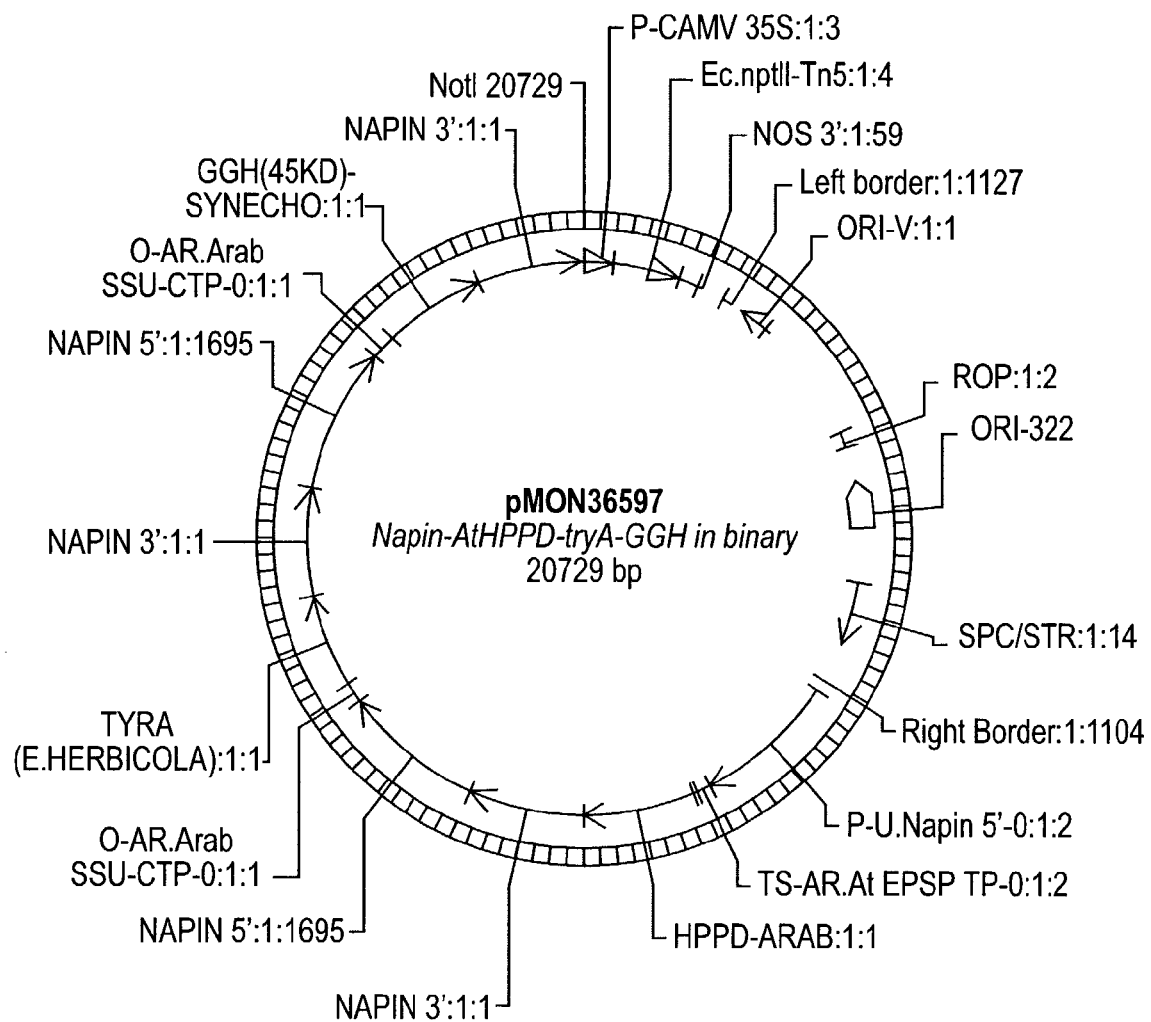
FIG. 23 is a schematic of construct pMON36597.
Figure 24:
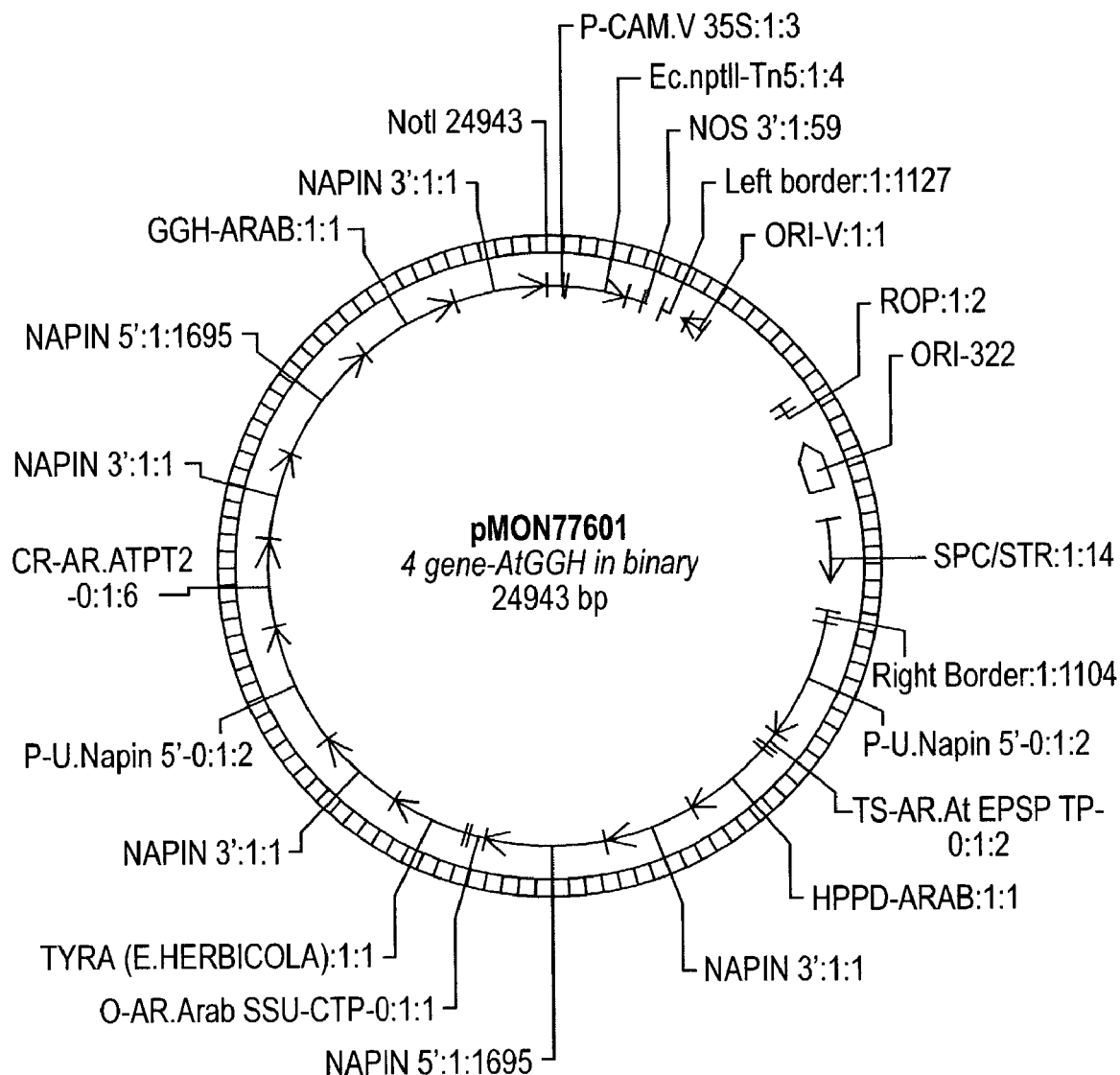
FIG. 24 is a schematic of construct pMON77601.
Figure 25:
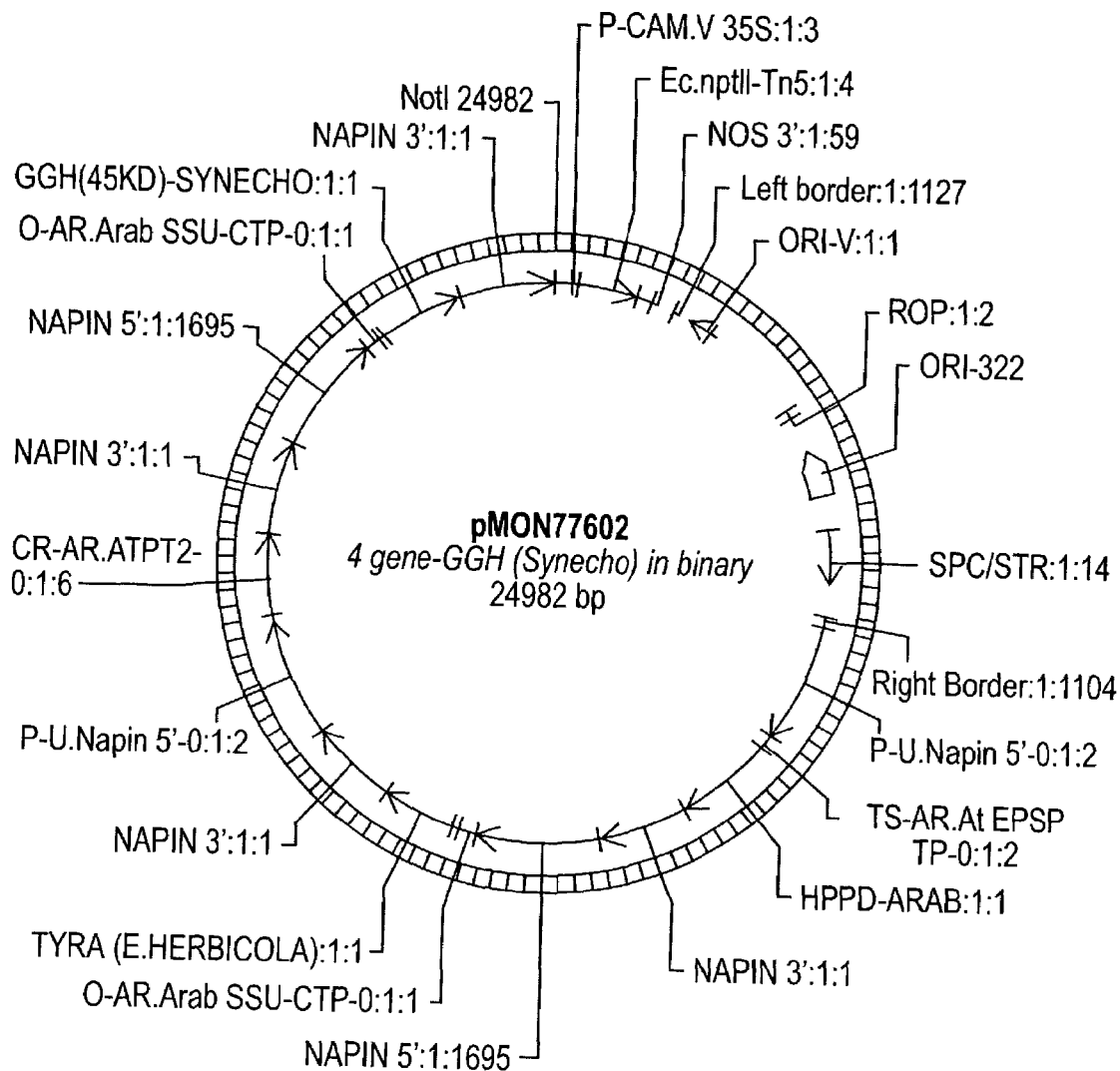
FIG. 25 is a schematic of construct pMON77602.
Figure 26:
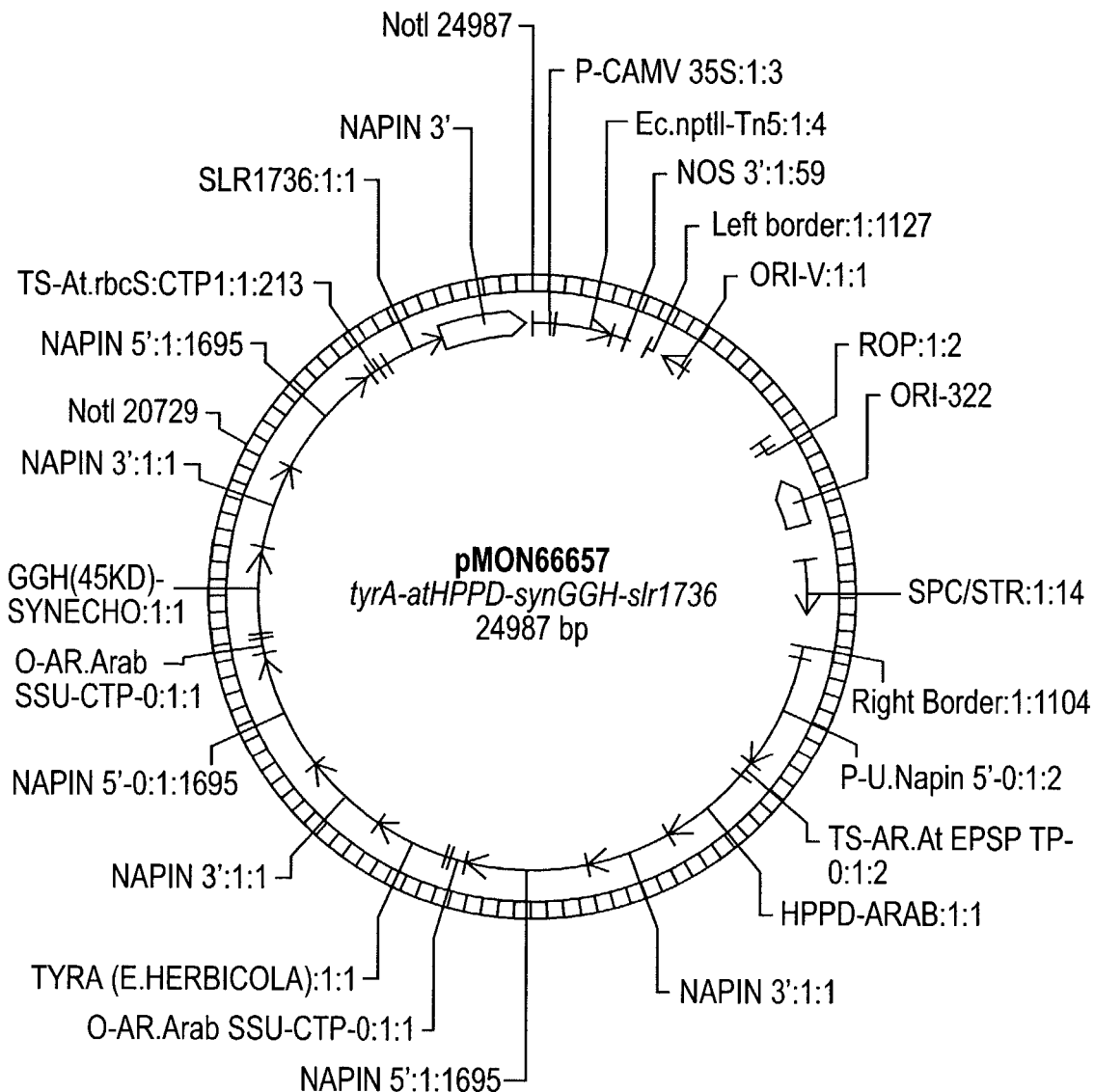
FIG. 26 is a schematic of construct pMON66657.
Figure 27:
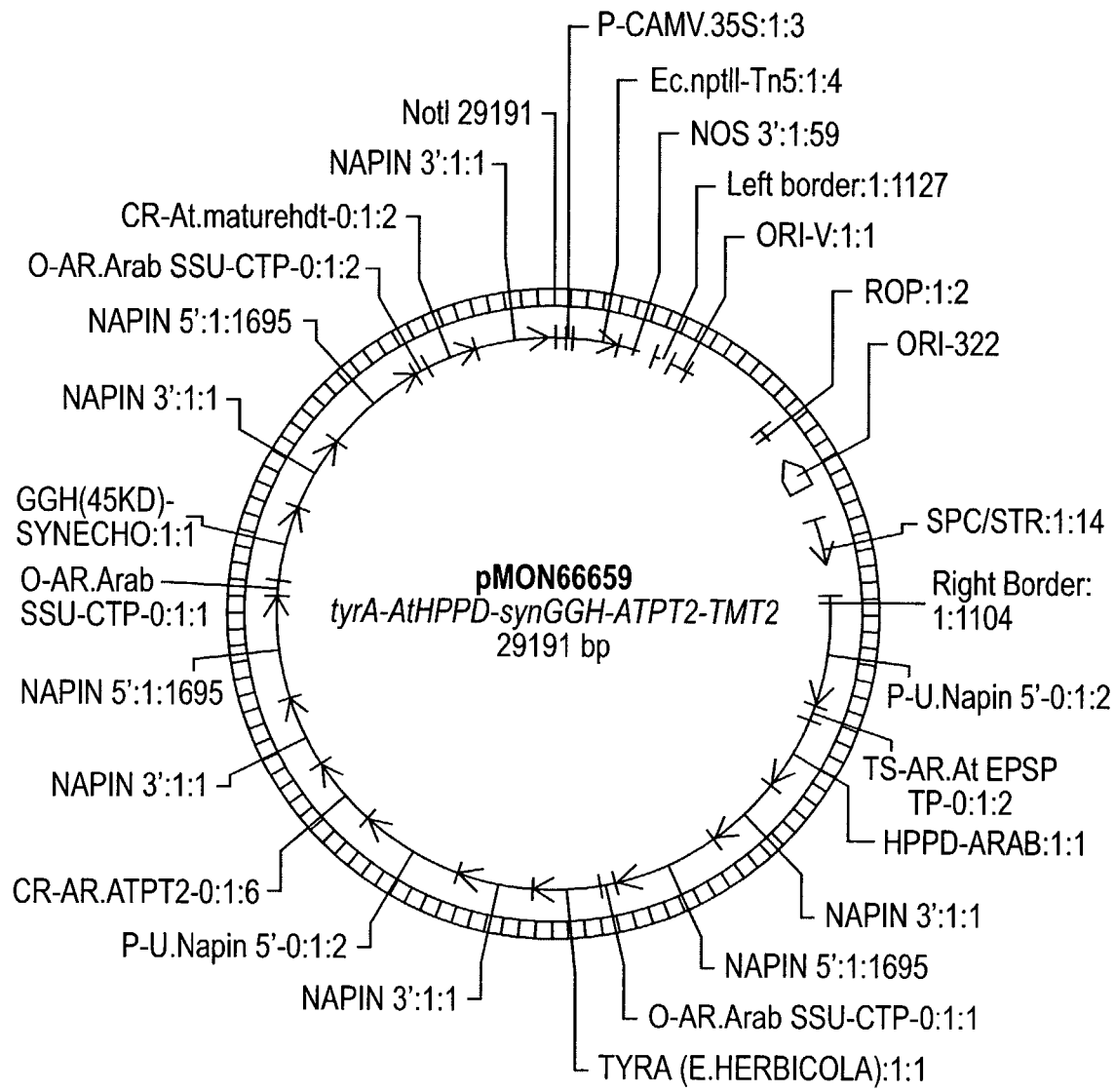
FIG. 27 is a schematic of construct pMON66659.
Figure 37:
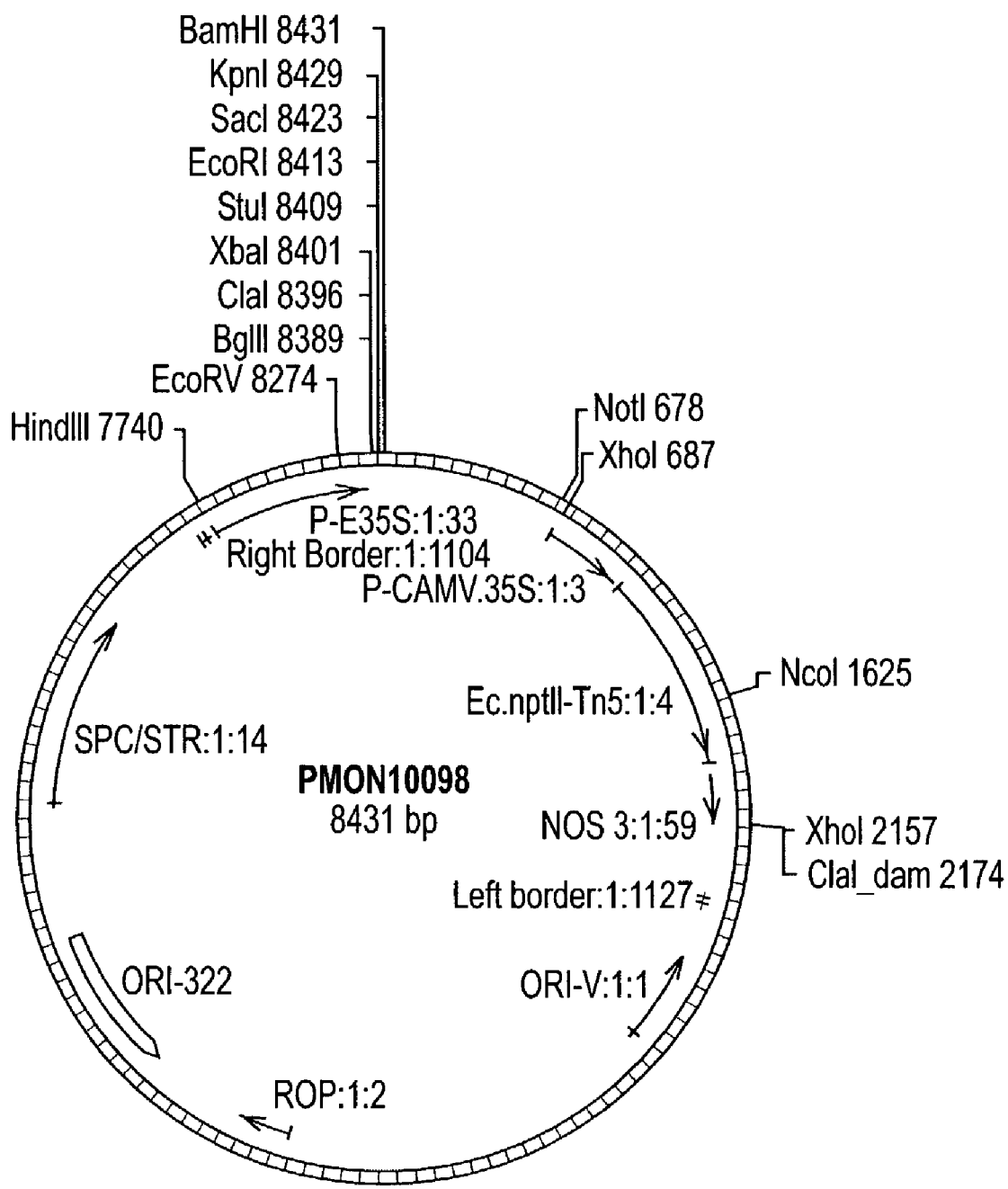
FIG. 37 is a schematic of construct pMON10098.

The assembly of expression cassettes are performed in a shuttle vector, such as pMON36586. Gene expression cassettes are released from other shuttle vectors by Bsp120I/Not I digests, and ligated into a shuttle vector such as pMON36586, which has been digested with Not I. The resulting vector harbors one additional gene expression cassette and a single Not I site. This procedure can be repeated as required. Upon completion of the gene assembly, the combined expression cassettes can be released by Bsp120 I/Not I digest (pMON10098 (FIG. 37)). The resulting fragment carrying the expression cassettes is then purified and ligated into a single Not I site of a binary vector. Alternatively the assembly of gene expression cassettes can be performed directly in a binary vector (FIG. 21). A binary

```
                 Xma I   Bsp120 I  Eag    Xba I  EcoRI    Not I     Asc I   Age Iv
SV MCS 1A    GATCT CCCGGG AA GGGCCC CGGCCG TCTAGA GAATTC GCGGCCGC GGCGCGCC ACCGGT     (SEQ ID NO:9)

Figure 19:
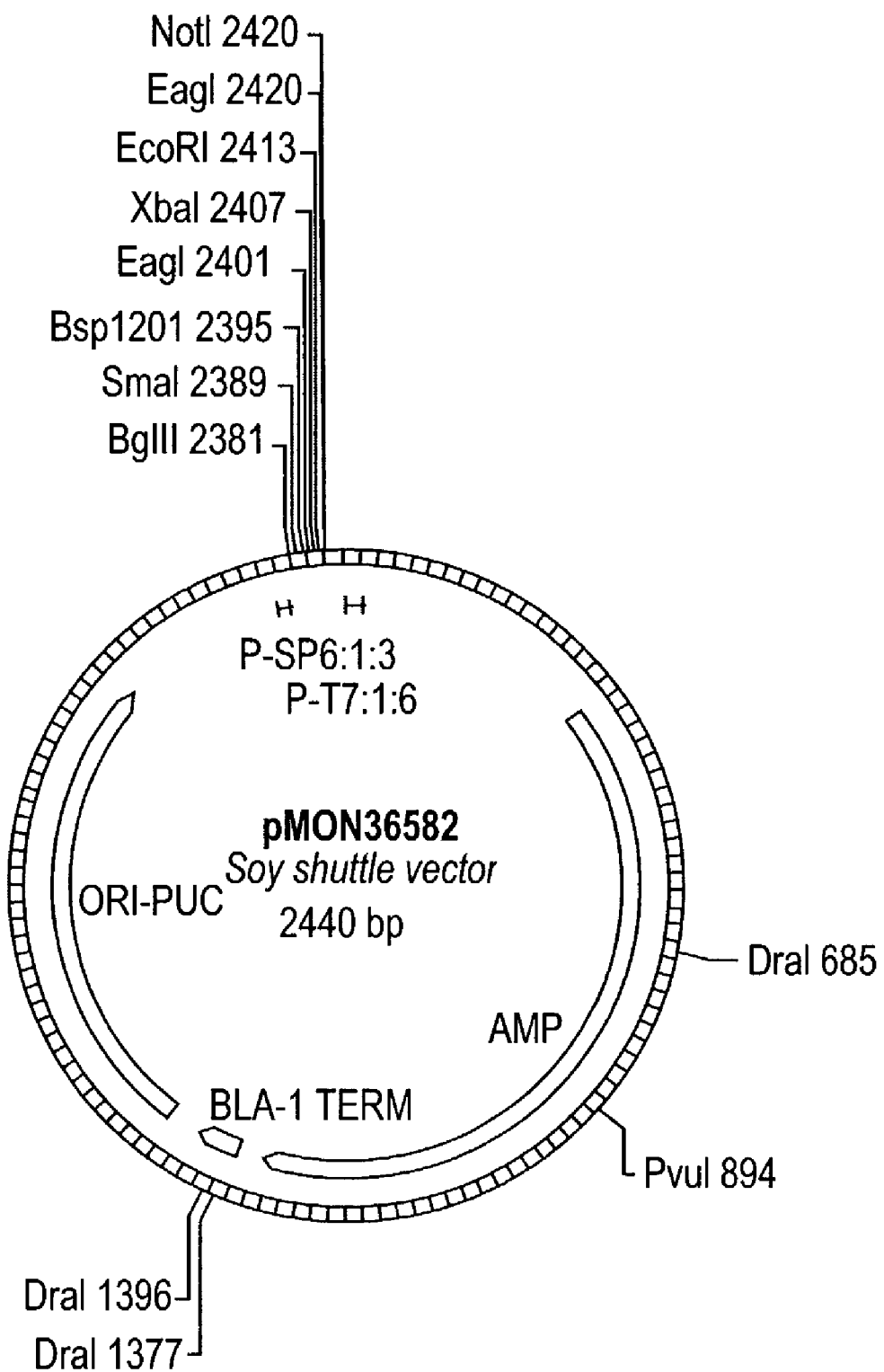
FIG. 19 is a schematic construct of pMON36582.

Xma I   Bsp120 I  Eag    Xba I  EcoRI    Not I     Asc I   Age I
SV MCS 1B    TCGA ACCGGT GGCGCGCC GCGGCCG GAATTC TCTAGA CGGCCG GGGCCC TT CCCGGG A     (SEQ ID NO: 10)
``` and ligating them into Bgl II and Xho I digested and gel purified pSP72 (Promega, www.promega.com). The resulting vector is designated pMON36582 (FIG. 19). The vector is confirmed by DNA sequencing.

All gene expression cassettes are set up to be flanked by Not I restriction sites. These cassettes are isolated by digesting the previous vectors with Not I, followed by gel purification of the expression cassettes. pMON36582 is digested with Eag I, which cuts twice in this vector, once within the Not I site, and once 19 bp upstream of the Not I site. Both overhangs are compatible with Not I. The Not I expression cassettes are ligated into gel purified Eag I digested pMON36582, resulting in a vector with a single Not I site. The expression cassette is therefore available as a Bsp120I/Not I cassette. An example of an expression cassette for the Arabidopsis homogentisate phytyltransferase available as a vector is defined by the presence of the right and left border sequences, which are necessary for DNA transfer from Agrobacterium into plant cells. All chemical reagents and enzymes for this manipulation are molecular grades. These reagents and enzymes are utilized according to the supplier's instructions. Standard molecular cloning techniques are used.

Several examples of plant binary constructs, their components and plasmid maps are depicted. The examples depicted containing tyrA combinations with other genes of interest for tocopherol pathway engineering are listed in FIGS. 18a and 18b.

Components of these constructs are also provided in the Table 4. Vector maps shown as FIGS. 22-27 represent various constructs.

TABLE 4

List of binary vectors to be transformed into *Arabidopsis thaliana* to engineer tocopherol biosynthesis

| pMON # | Gene Combination | Genetic Elements |
|---|---|---|
| 36596 | $HPPD_{At}$/tyrA | Napin 5' & Napin 3'; CTP1&2 |
| 36597 | $HPPD_{At}$/tyrA/$GGH_{syn}$ | Napin 5' & Napin 3'; CTP1&2; native CTPs |
| 77601 | $HPPD_{At}$/tyrA/$GGH_{At}$/ATPT2 | Napin 5' & Napin 3'; CTP1&2; native CTPs |
| 77602 | $HPPD_{At}$/tyrA/$GGH_{syn}$/ATPT2 | Napin 5' & Napin 3'; CTP1&2; native CTPs |
| 66657 | $HPPD_{At}$/tyrA/$GGH_{syn}$/slr1736 | Napin 5' & Napin 3'; CTP1&2; native CTPs |
| 66659 | $HPPD_{At}$/tyrA/$GGH_{At}$/ATPT2/TMT2 | Napin 5' & Napin 3'; CTP1&2; native CTPs |
|  | $HPPD_{At}$/tyrA/$GGH_{syn}$/ATPT2/MT1 | Napin 5' & Napin 3'; CTP1&2; native CTPs |
|  | $HPPD_{At}$/tyrA/ATPT2/TMT2 | Napin 5' & Napin 3'; CTP1&2; native CTPs |
|  | $HPPD_{At}$/tyrA/$GGH_{At}$/ATPT2/MT1/DxS | Napin 5' & Napin 3'; CTP1&2; native CTPs |
|  | $HPPD_{At}$/tyrA/$GGH_{At}$/ATPT2/DxS*E. coli* | Napin 5' & Napin 3'; CTP1&2; native CTPs |
|  | $HPPD_{At}$/tyrA/$GGH_{At}$/slr1736/MT1/$GGPPS_{At}$ | Napin 5' & Napin 3'; CTP1&2; native CTPs |
|  | $HPPD_{At}$/tyrA/ATPT2/$GGH_{At}$/$DxR_{At}$ | Napin 5' & Napin 3'; CTP1&2; native CTPs |
|  | $HPPD_{At}$/tyrA/$GGH_{At}$/slr1736/$Cyclase_{syn}$/MT1 | Napin 5' & Napin 3'; CTP1&2; native CTPs |
|  | $HPPD_{At}$/tyrA/$GGH_{syn}$/slr1736/$Cyclase_{syn}$ | Napin 5' & Napin 3'; CTP1&2; native CTPs |
|  | $HPPD_{At}$/tyrA/slr1736/$Cyclase_{syn}$ | Napin 5' & Napin 3'; CTP1&2; native CTPs |
|  | $HPPD_{At}$/tyrA/$GGH_{At}$/ATPT2/$GMT_{At}$ | Napin 5' & Napin 3'; CTP1&2; native CTPs |

EXAMPLE 13

Construction of Vectors Encoding Multiple Enzymes

This example set forth the use of a prephenate dehydrogenase (tyrA) such as the *Erwinia herbicola* tyrA in combination with other key enzymes in the tocopherol biosynthetic pathway to enhance tocopherol production in transgenic plant seeds such as *Arabidopsis thaliana* seeds. The enzymes combined with tyrA include ATPT2, p-hydroxyphenylpyruvate dioxygenase (HPPD$_{Arabidopsis}$), and geranylgeranylpyrophosphate synthase (GGPPS$_{Arabidopsis}$) from *Arabidopsis thaliana*. In addition tyrA was also tested in combination with ATPT2 and a putative adenylate transporter (AANT1$_{Arabidopsis}$) from *Arabidopsis thaliana*.

Figure 38:
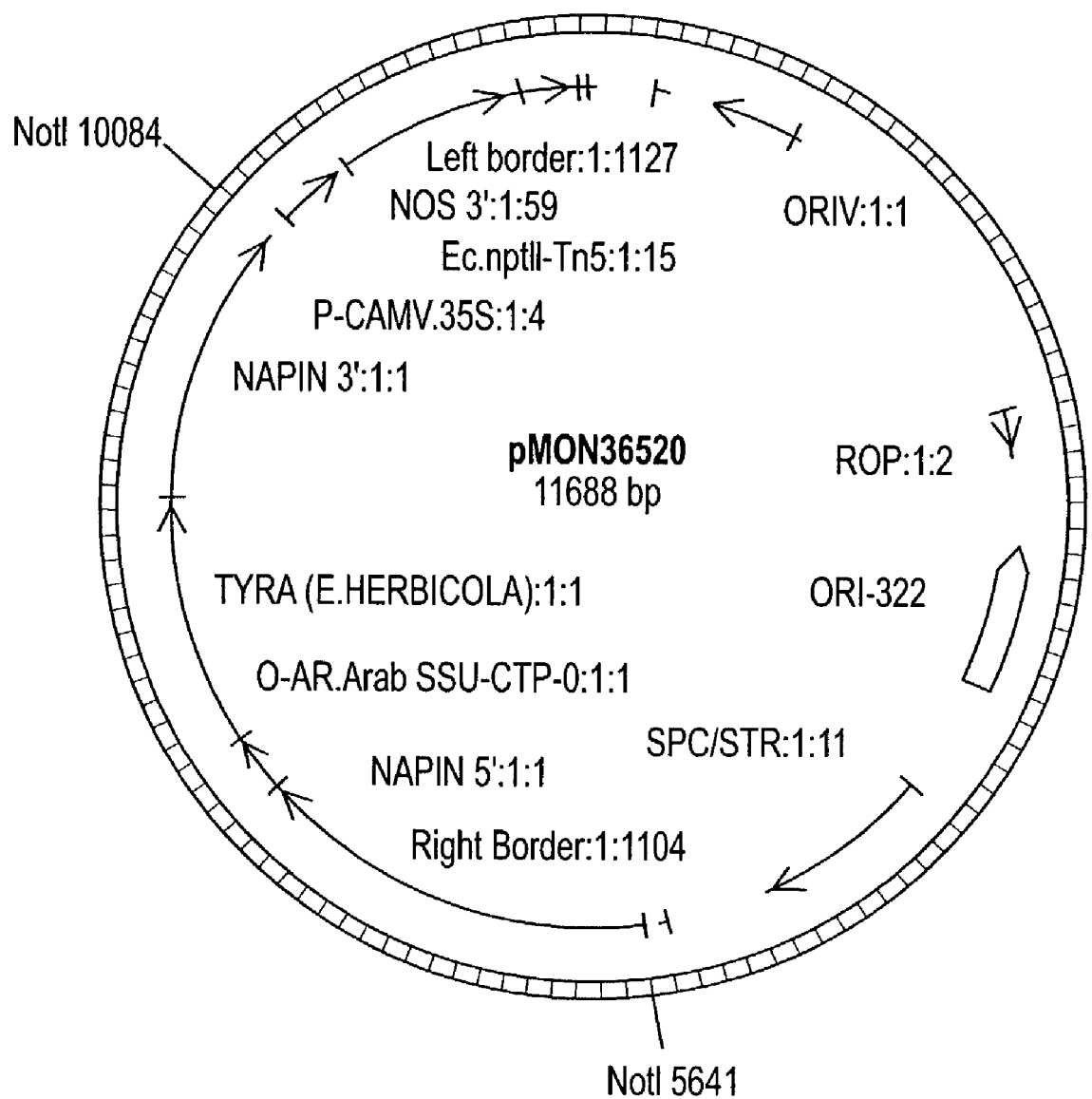
FIG. 38 is a schematic of construct pMON36520.
Figure 39:
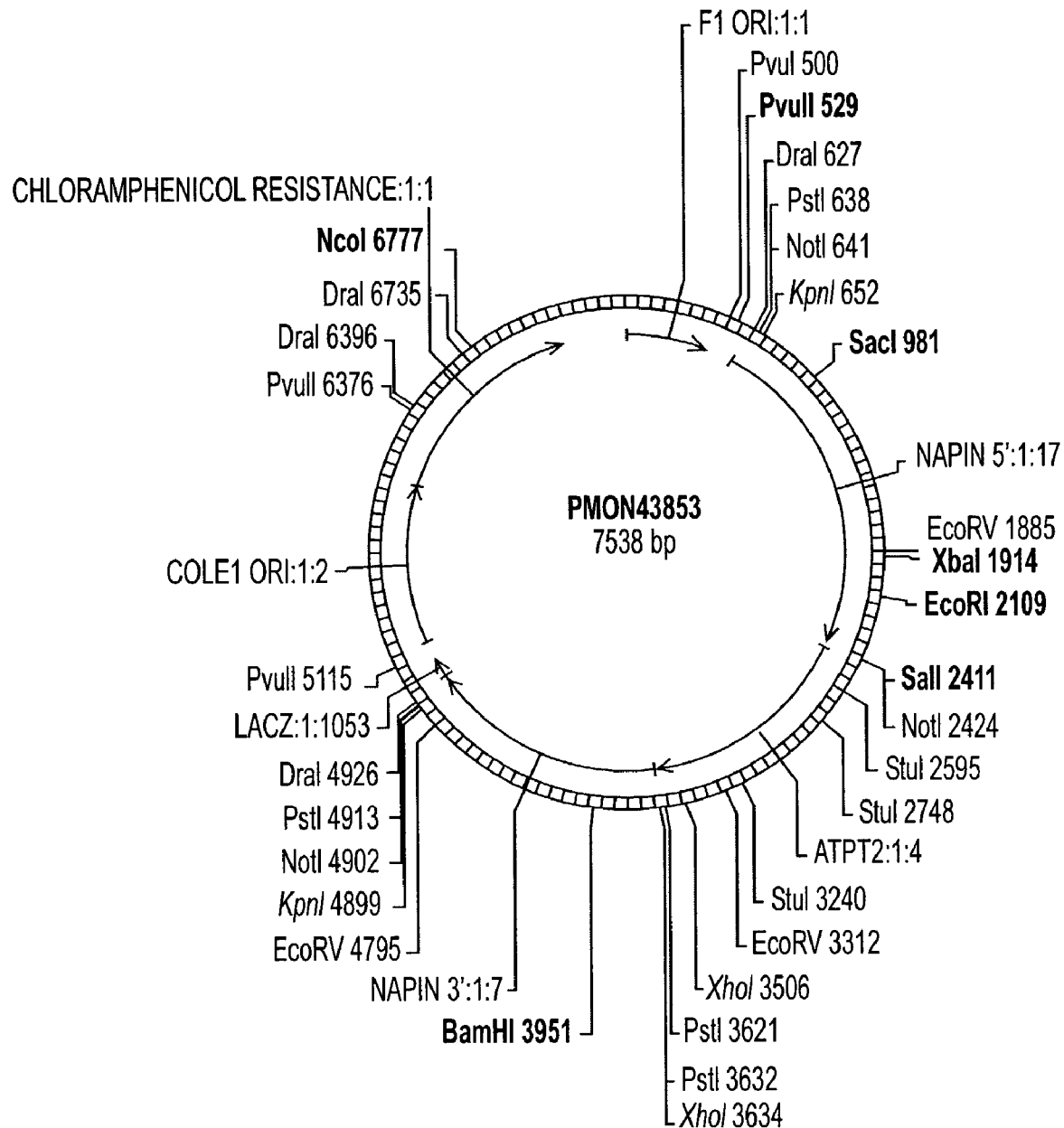
FIG. 39 is a schematic of construct pMON43853.

Construction of a double gene vector harboring seed specific tyrA and ATPT2 expression cassettes is performed as follows. Purified plasmid DNA of pMON36520 (FIG. 38) is subjected to a partial KpnI digest and ligated with a 4.2 kbp gel purified Kpn I-fragment isolated from pMON43853 (FIG. 39). The 4.2 kb insert from pMON43853 contains the PPT gene expression cassette (pNapin::ATPT2::Napin 3'). The resulting plant binary vector pMON69907 (FIG. 12) is used for transformation of *Arabidopsis thaliana* to test the combinatorial effect of seed specific expression of tyrA and ATPT2.

Figure 40:
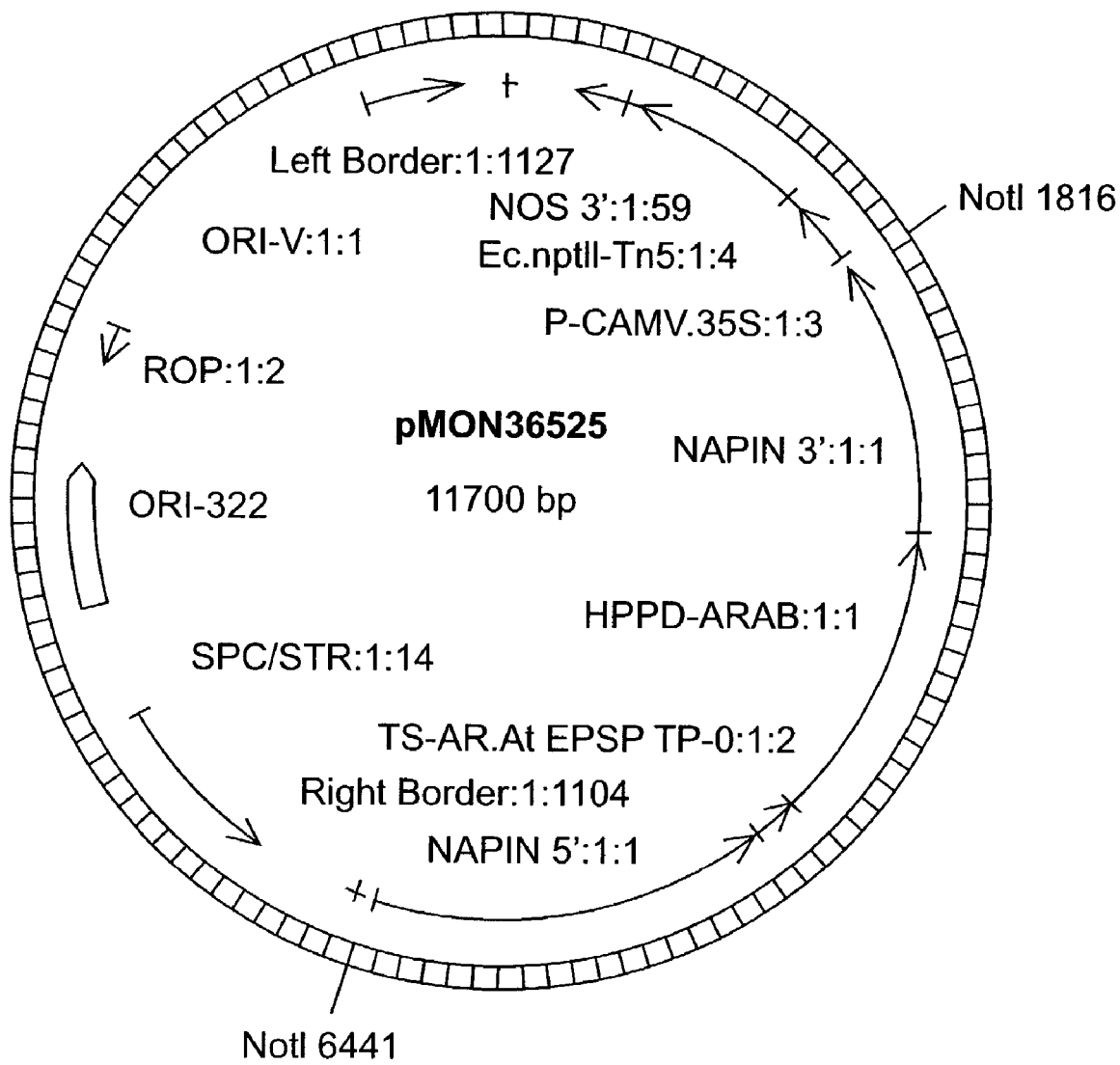
FIG. 40 is a schematic of construct pMON36525.

To further increase tocopherol biosyntheses the HPPD$_{Arabidopsis}$ is expressed in addition to tyrA, and ATPT2 in *Arabidopsis thaliana* seed. This was achieved by adding a seed specific expression cassette for HPPD$_{Arabidopsis}$ to pMON69907 resulting in the formation of pMON69909. The binary vector pMON69909 is constructed by partially digesting pMON69907 with KpnI. The single KpnI-cut pMON69907 is gel purified and ligated with a 4.6 kb KpnI/KpnI insert isolated from pMON36525 (FIG. 40). The 4.6 kb KpnI/KpnI insert from pMON36525 contains the HPPD gene expression cassette, pNapin::CTP2::HPPD$_{Arabidopsis}$::Napin 3' to direct seed specific plastid targeted expression of HPPD. The CTP2 is a chloroplast-target signal from the *Arabidopsis* 5-enolpyruvylshikimate-3-phosphate synthase (EPSPS) gene.

Figure 41:
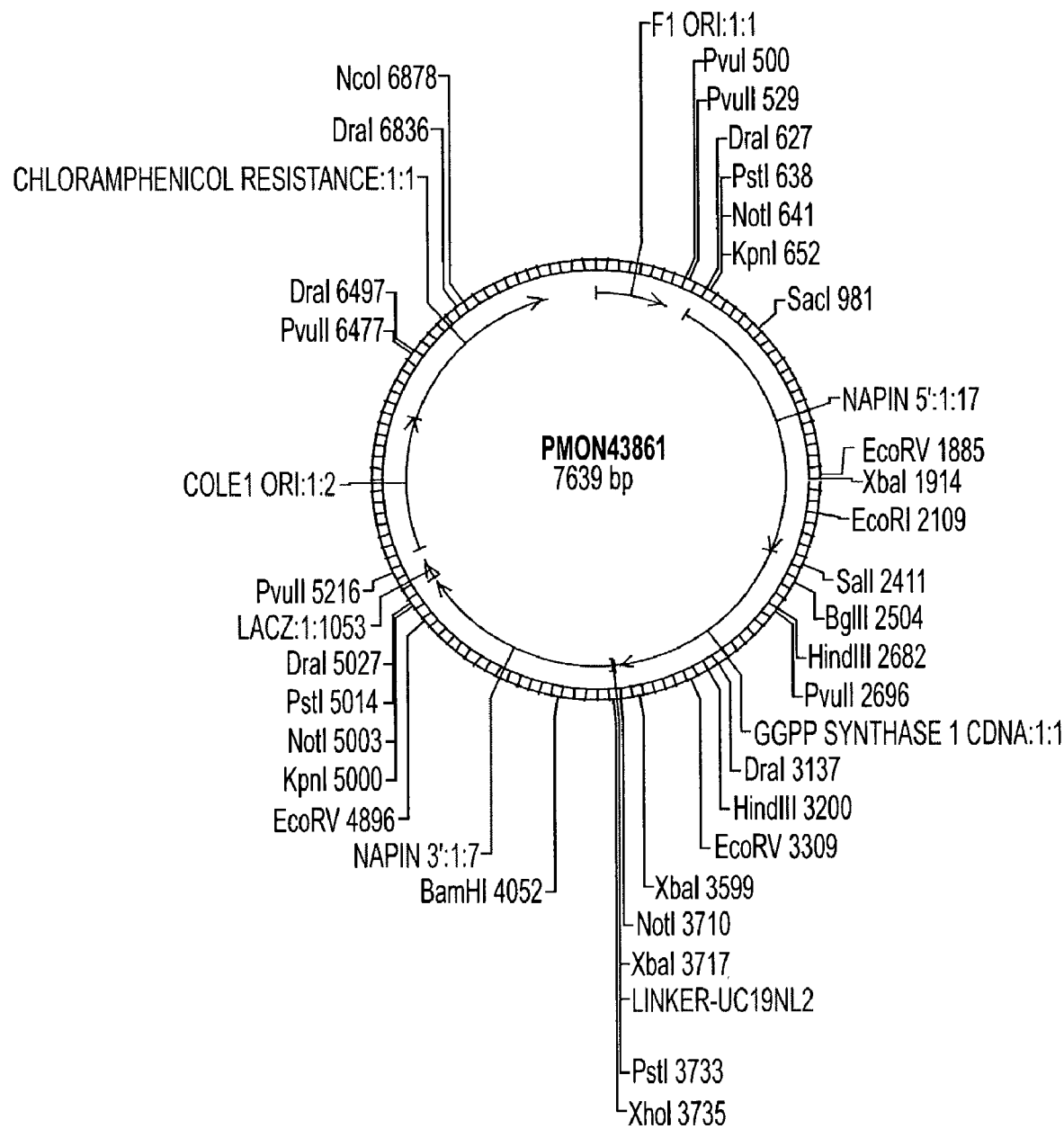
FIG. 41 is a schematic of construct pMON43861.
Figure 42:
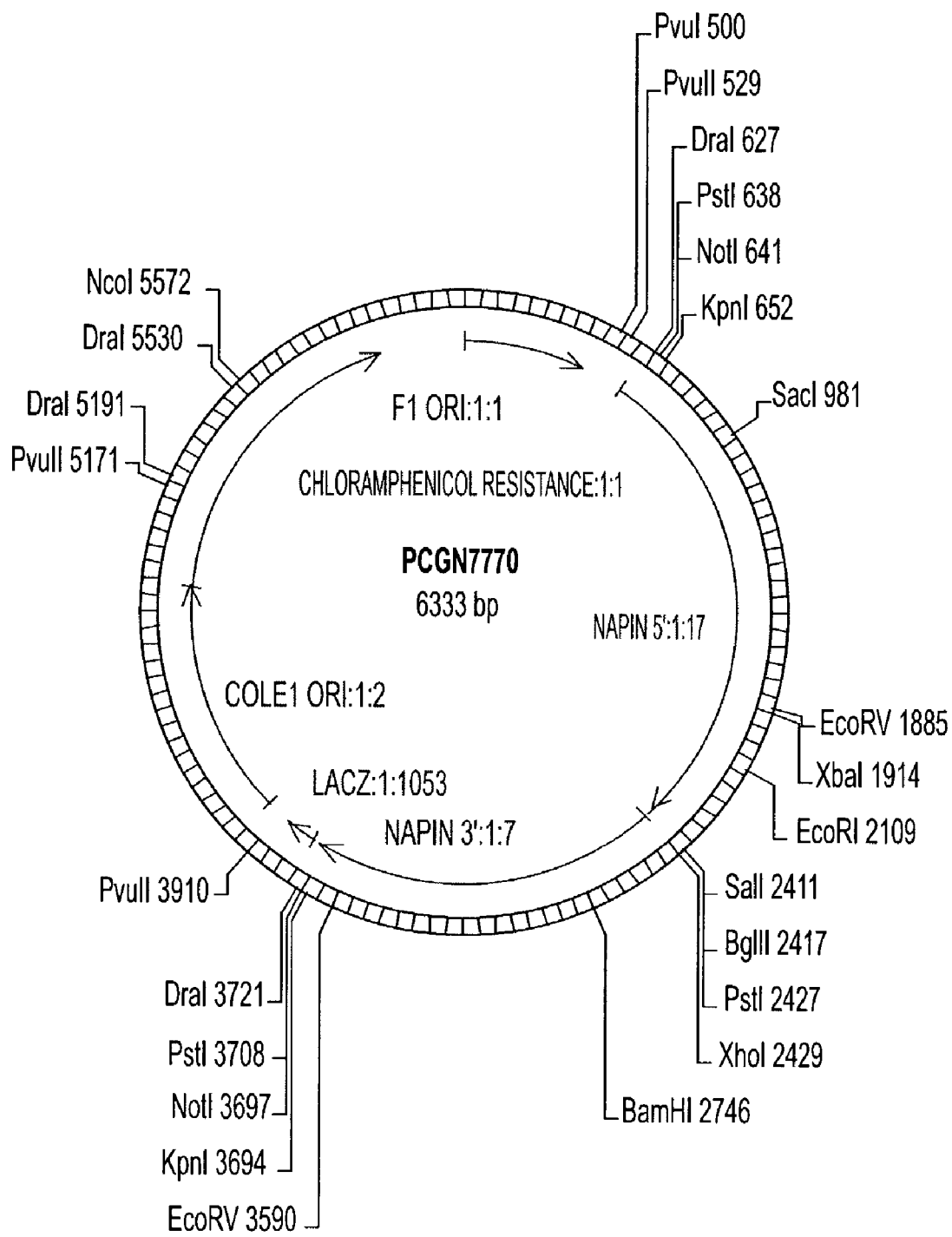
FIG. 42 is a schematic of construct pCGN7770.

The binary vector pMON69915 (FIG. 35) is constructed to test the effect of three gene combinations, tyrA, ATPT2, and GGPPS$_{Arabidopsis}$ on seed tocopherol production. Vector pMON69907 is digested partially with KpnI. Single KpnI-cut pMON69907 is gel purified and ligated with a gel purified 4.3 kb, KpnI/KpnI fragment from pMON43861 (FIG. 41) to create pMON69915. The KpnI fragment from pMON43861 contains the gene expression cassette for the *Arabidopsis* geranylgeranyldiphosphate synthase from *Arabidopsis thaliana* (pNapin::GGPPS$_{Arabidopsis}$::Napin 3'). The GGPPS cDNA is identified as an EST clone, by searching an EST database with sequence information available in the literature (Okada et al., *Plant Physiol.* 122:1045-1056 (2000)). The EST clone is digested with NcoI and blunt-ended by filling the 5' overhang with the klenow-fragment. Subsequently the clone is digested with BamHI and to excise the cDNA fragment. The gel purified BamHI/blunt cDNA fragment is ligated with BglII/SalI digested and (SalI blunt-ended) vector pCGN7770 (FIG. 42) to create pMON43861.

Figure 43:
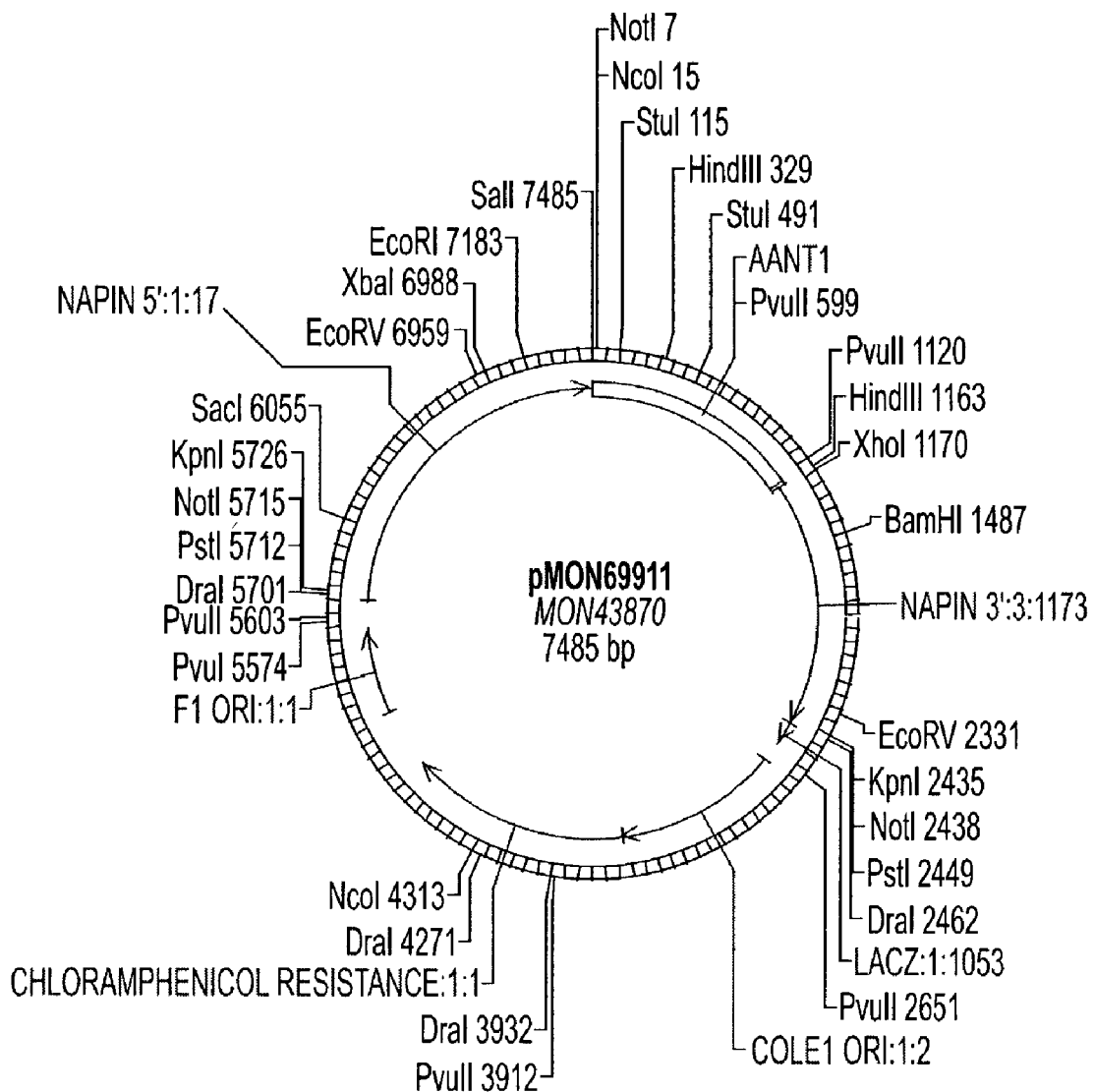
FIG. 43 is a schematic of construct pMON69911.
Figure 44:
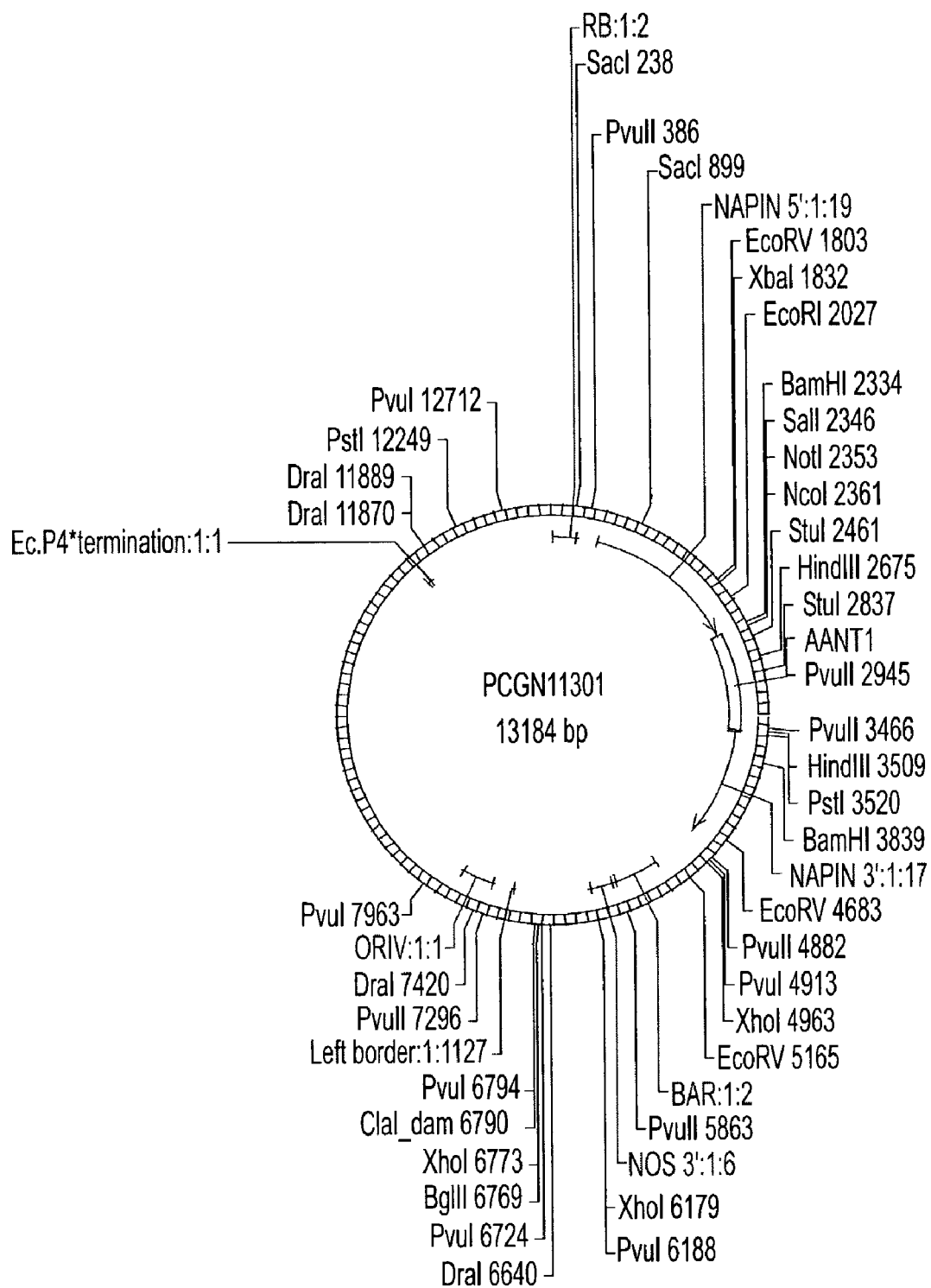
FIG. 44 is a schematic of construct pCGN11301.

The plant binary vector pMON69919 (FIG. 36) is constructed to test combined expression of tyrA, ATPT2, and AANT1$_{Arabidopsis}$ on seed tocopherol levels. To generate this vector, pMON69907 is partially digested with KpnI. Single KpnI-cut pMON69907 is gel purified, and ligated with a 4.2 kb gel-purified KpnI/KpnI fragment from pMON69911 (FIG. 43). The 4.2 kb fragment contains a seed specific expression cassette for the *Arabidopsis* adenylate transporter AANT1 (pNapin::AANT1$_{Arabidopsis}$::napin 3'). pMON69911 is generated by excising the AANTI fragment from pCGN11301 (FIG. 44) with SalI and PstI (the PstI site is blunted by removing 3' overhang with Klenow) and then ligated to SalI/XhoI digested (XhoI blunt-ended) pCGN7770.

Using the published partial sequence of AANT1 (Saint-Guily et al., *Plant Physiol.* 100(2):1069-1071 (1992)) several full-length clones are identified in EST databases. The AANT1 coding region is PCR-amplified using primers, AANT1F 5'-GGATCC GCGGCCGCACCATGGTTGATCAAGTTCAGCA (SEQ ID NO: 11) and AANT1R 5'-GAGCT CCTGCAGGAAGCTTTTAGGCACCTCCTGATCCGT-3' (SEQ ID NO: 12). The NotI site (underlined) is placed upstream of the start codon (italics) in primer AANT1F while the Sse8387I site (underlined) was placed downstream of the stop codon (italics) in AANT1R. The PCR products are first cloned into pCR2.1 and the inserts are verified by sequencing of both strands. Subsequently, the NotI/Sse8387I fragments are inserted into the NotI/Sse8387I sites of the napin expression cassette in pCGN9979 in sense orientation with respect to the napin promoter to generate pCGN11301. The plant expression constructs are used for transformation of *Arabidopsis thaliana* by *Agrobacterium* mediated transformation as described in above.

EXAMPLE 14

Expression of Vectors Encoding Multiple Enzymes in Plants

Figure 75:
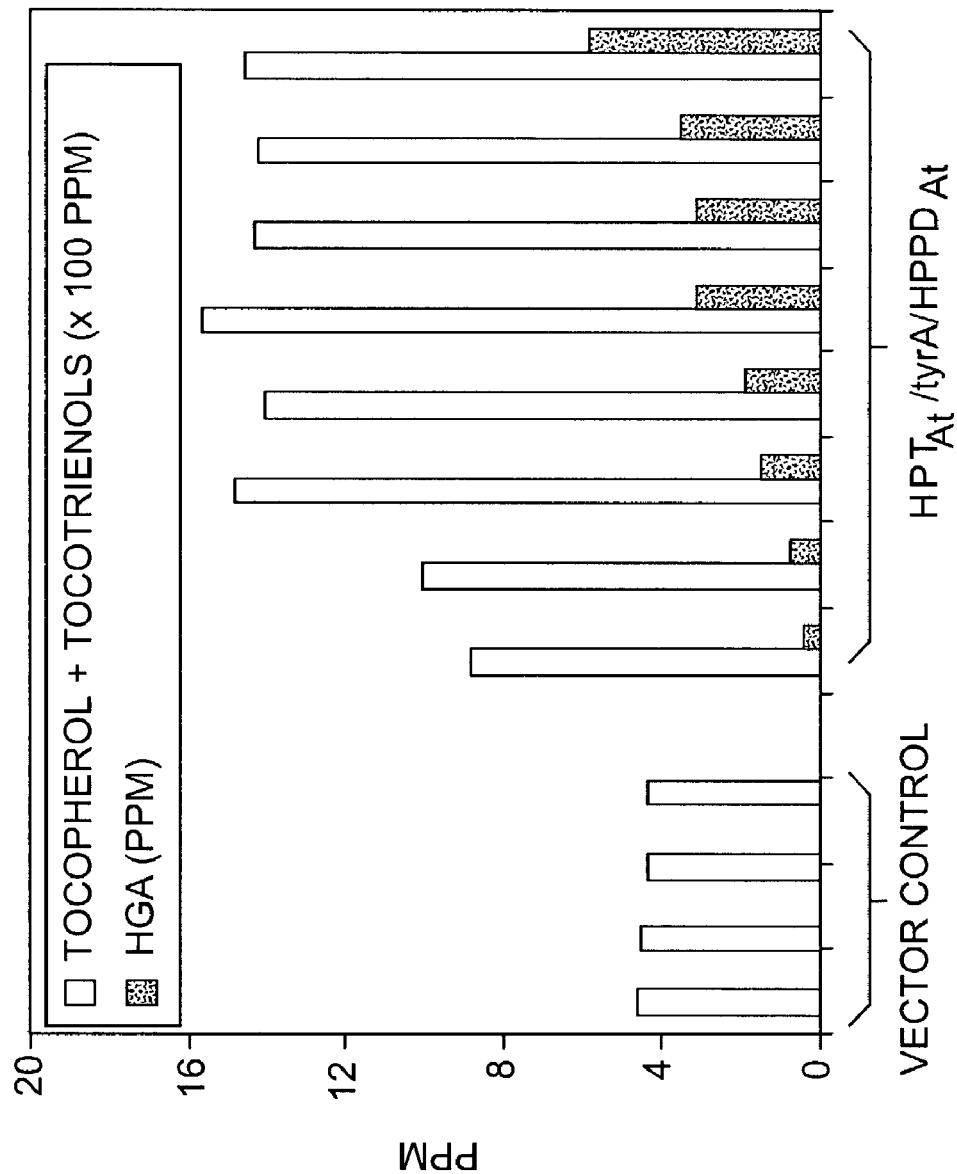
FIG. 75 shows tocopherol and tocotrienol as well as HGA levels in selected lines.
Figure 76:
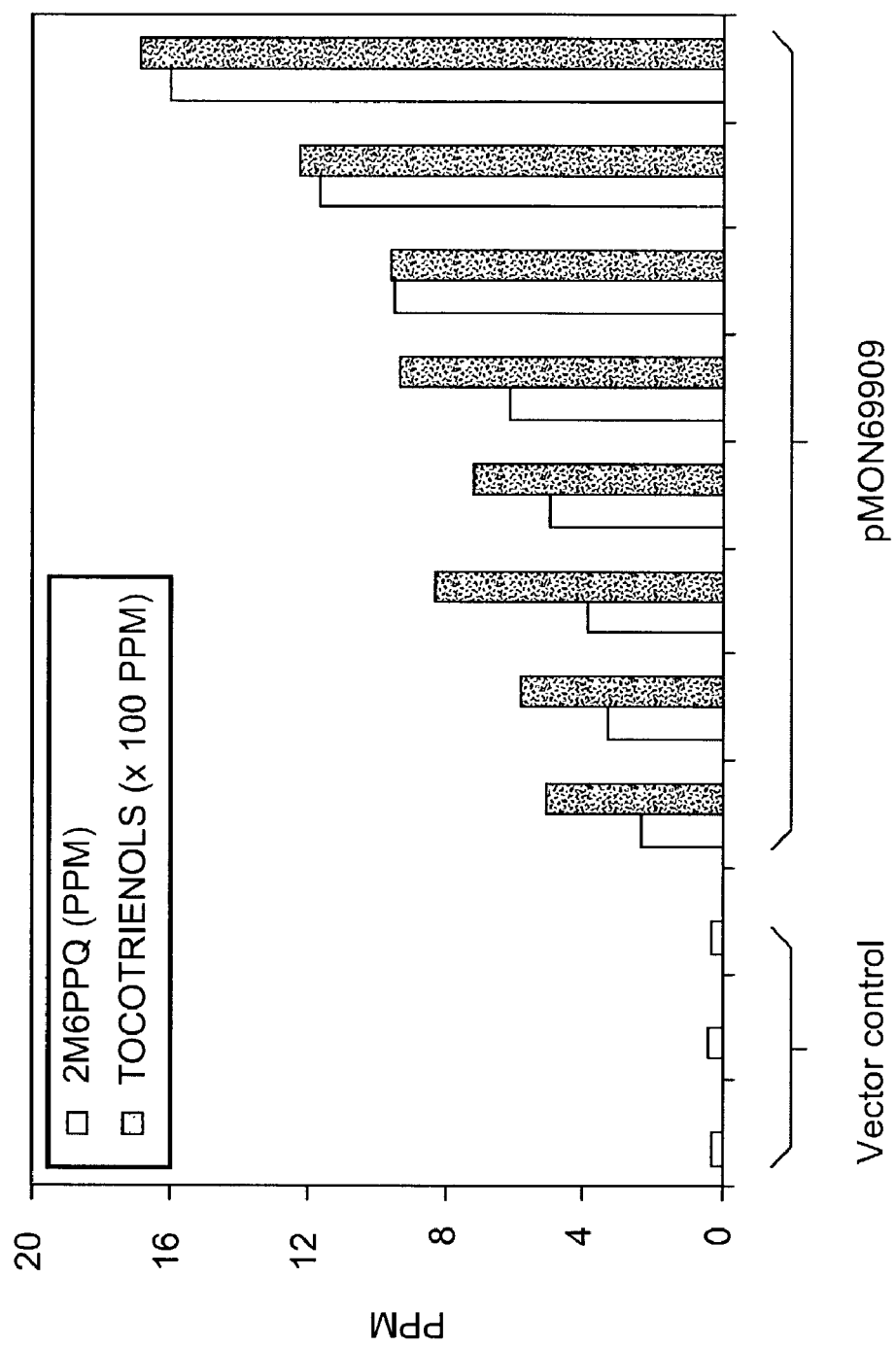
FIG. 76 shows tocotrienol and 2M6PPQ levels in selected lines.

Using the transformation technique given in Example 8, *Arabidopsis thaliana* plants are transformed with the vectors from Example 13. Results for pMON69909 are given in FIGS. 14, 15, 16, 17 and 31-34. Further results are given in the table below and in FIGS. 75 and 76, which show tocopherol, tocotrienol, homogentisate, and 2-methylphytylplastoquinol levels for transformed plants having pMON69909.

| Construct | Genetic elements | Tocopherol/Tocotrienol increase | % tocopherol | % tocotrienol |
|---|---|---|---|---|
| pMON69907 | pNapin::HPT*Arabidopsis*::napin 3'/ pNapin::CTP1::tyrA*Erwinia herbicola*::napin 3' | 2.4-fold | 91 | 9 |

-continued

| Construct | Genetic elements | Tocopherol/ Tocotrienol increase | % tocopherol | % tocotrienol |
|---|---|---|---|---|
| pMON69909 | pNapin::HPTArabidopsis::napin 3'/ pNapin::CTP1::tyrAErwinia herbicola::napin 3'/ pNapin::CTP2::HPPDArabidopsis::napin 3' | 5-fold | 38 | 62 |
| pMON69915 | pNapin::HPTArabidopsis::napin 3'/ pNapin::CTP1::tyrAE. herbicola::napin 3'/ pNapin::GGPPSArabidopsis::napin3' | 2.9-fold | 86 | 14 |
| pMON69919 | pNapin::HPTArabidopsis::napin 3'/pNapin::CTP1::tyrAE. herbicola::napin 3'/ pNapin::AANT1Arabidopsis::napin3' | 3-fold | 89 | 11 |

EXAMPLE 15

Expression of Constructs in Soybean

This example describes the method involved in preparation of plant binary vectors to test tyrA alone and in combination with other key enzymes in the tocopherol biosynthetic pathway to enhance tocopherol production in transgenic *Glycine max* seeds.

The table below describes the plant binary vectors prepared for *G. max* transformation with their respective gene of interest expression cassettes for seed-specific expression of the transgenes.

List of Constructs Transformed to *G. Max*.

| Construct number | Genetic elements |
|---|---|
| pMON36575 | p7Sα'::CTP1::tyrAE herbicola::E9 3' |
| pMON69924 | p7Sα'::CTP2::HPPDArabidopsis::E9 3'/p7Sα'::CTP1::tyrAE. herbicola::E9 3' |
| pMON69943 | p7Sα'::CTP2::HPPDArabidopsis::E9 3'/p7Sα'::CTP1::tyrAE. herbicola::E9 3'/ pArcelin-5::CTP1::slr1736::Arcelin 3' |
| pMON69945 | p7Sα'::CTP2::HPPDArabidopsis::E9 3'/p7Sα'::CTP1::tyrAE. herbicola::E9 3'/ pArcelin-5::CTP1::slr1736::Arcelin 3'/ pNapin::GGHAArabidopsis::napin 3' |

Figure 46:
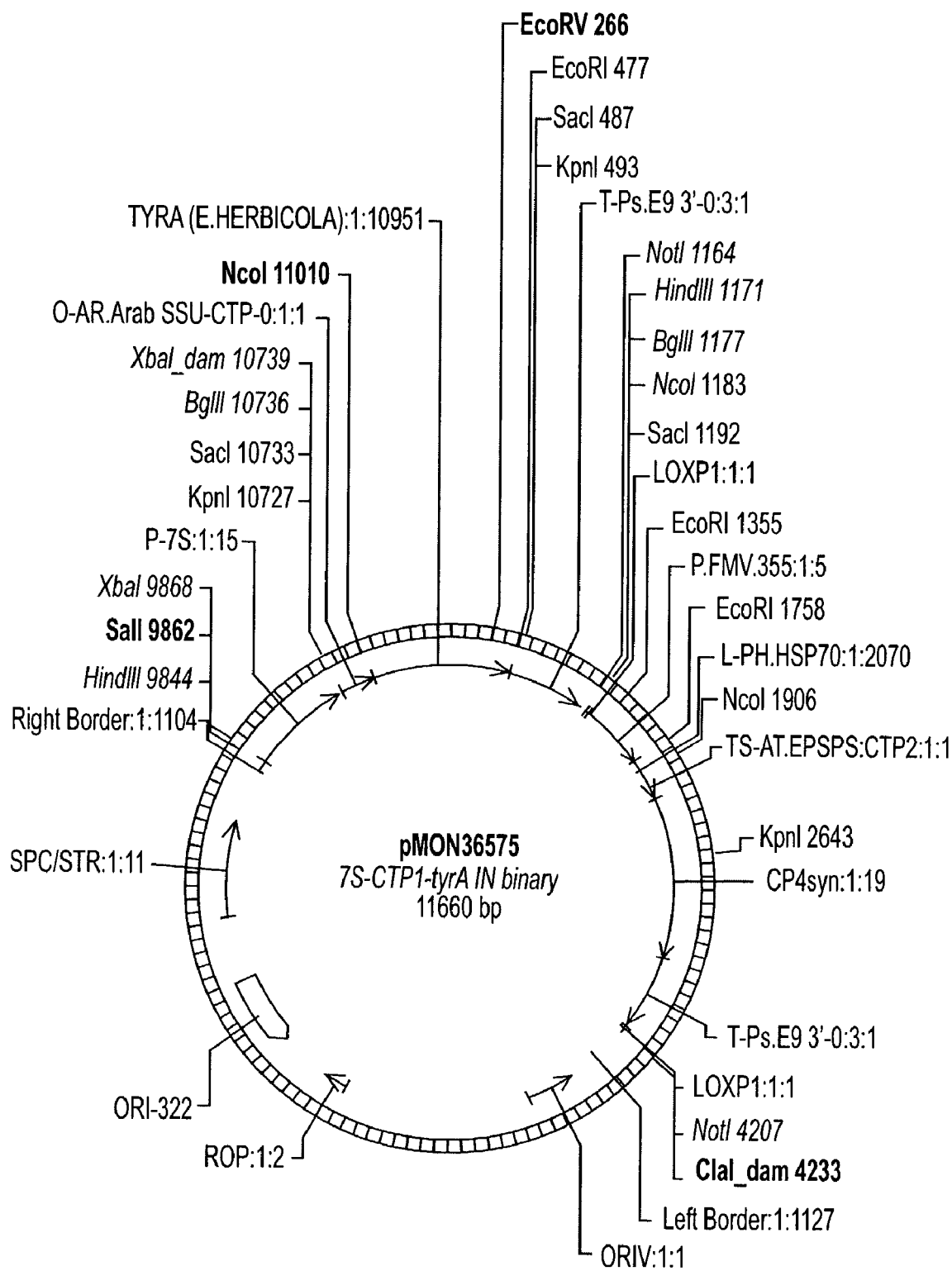
FIG. 46 is a schematic of construct pMON36575.
Figure 47:
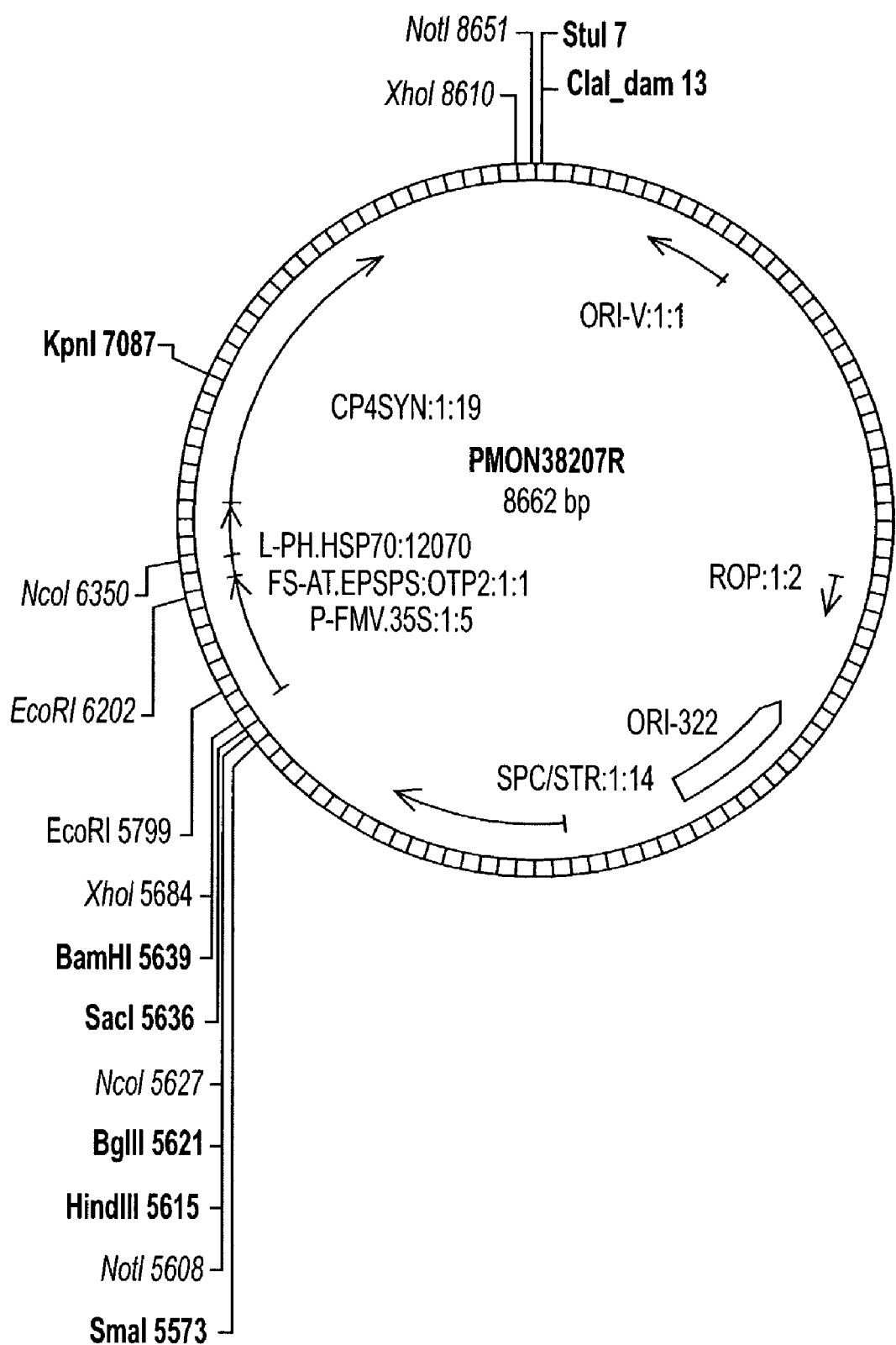
FIG. 47 is a schematic of construct pMON38207R.
Figure 48:
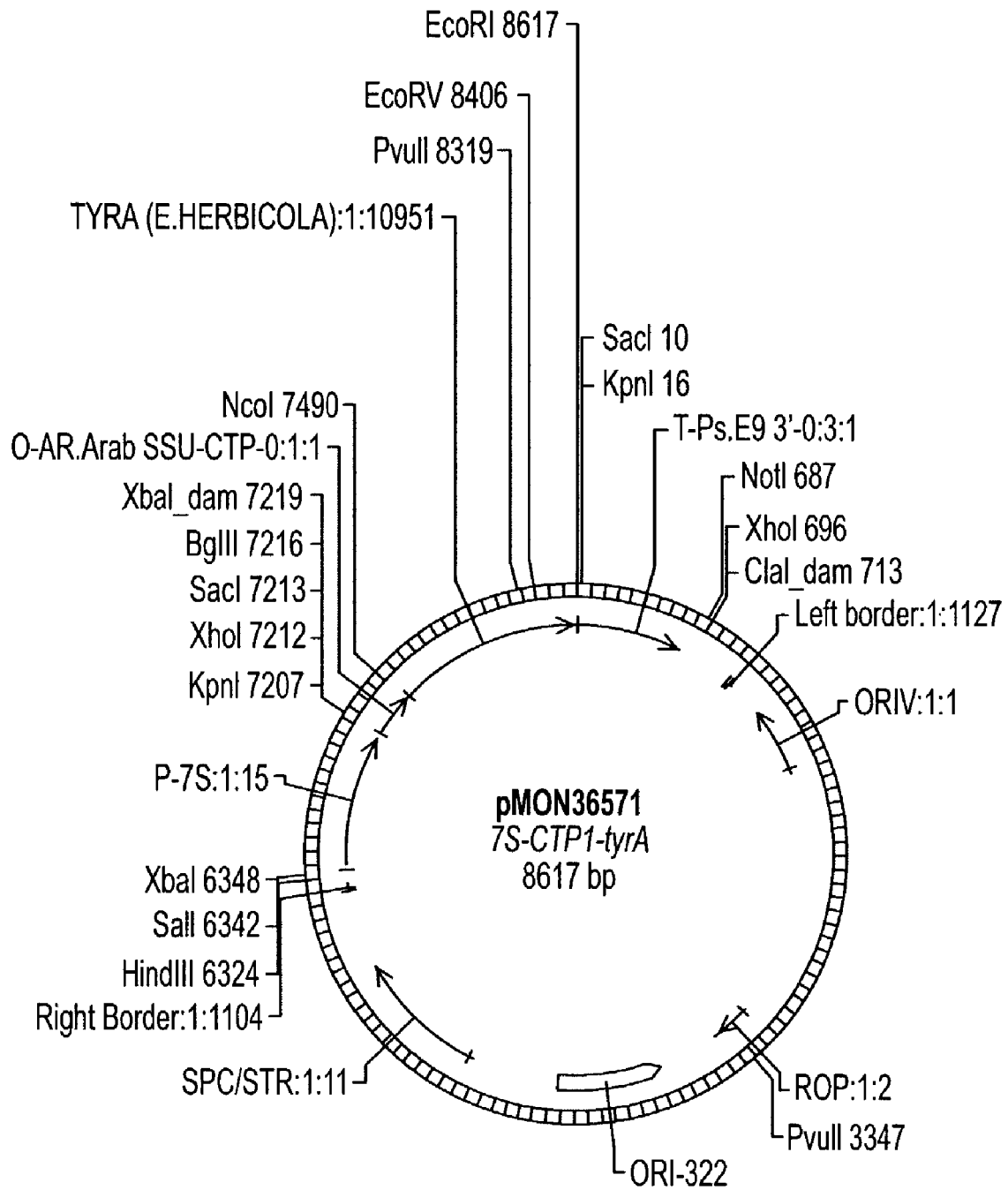
FIG. 48 is a schematic of construct pMON36571.
Figure 49:
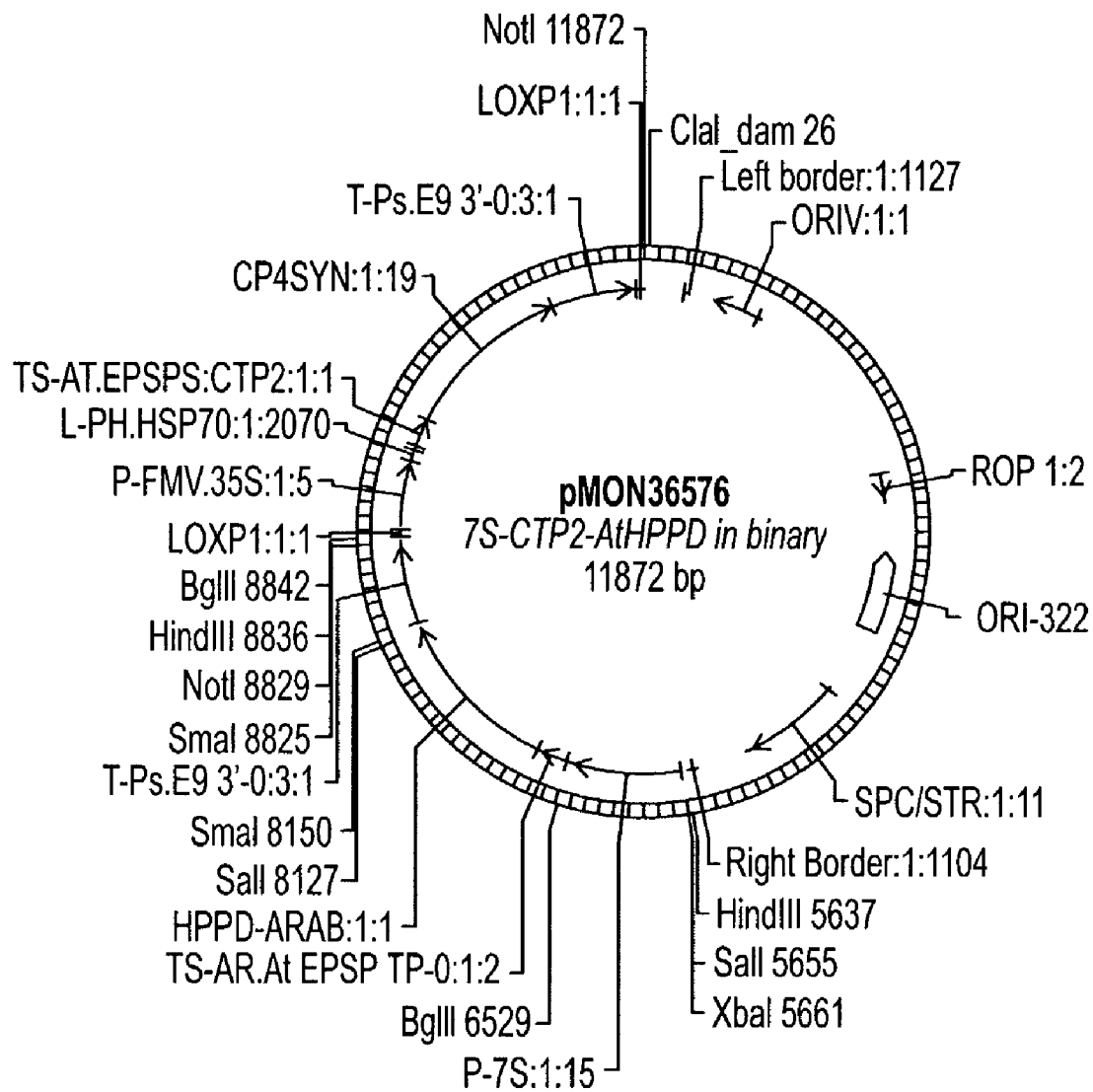
FIG. 49 is a schematic of construct pMON36576.
Figure 50:
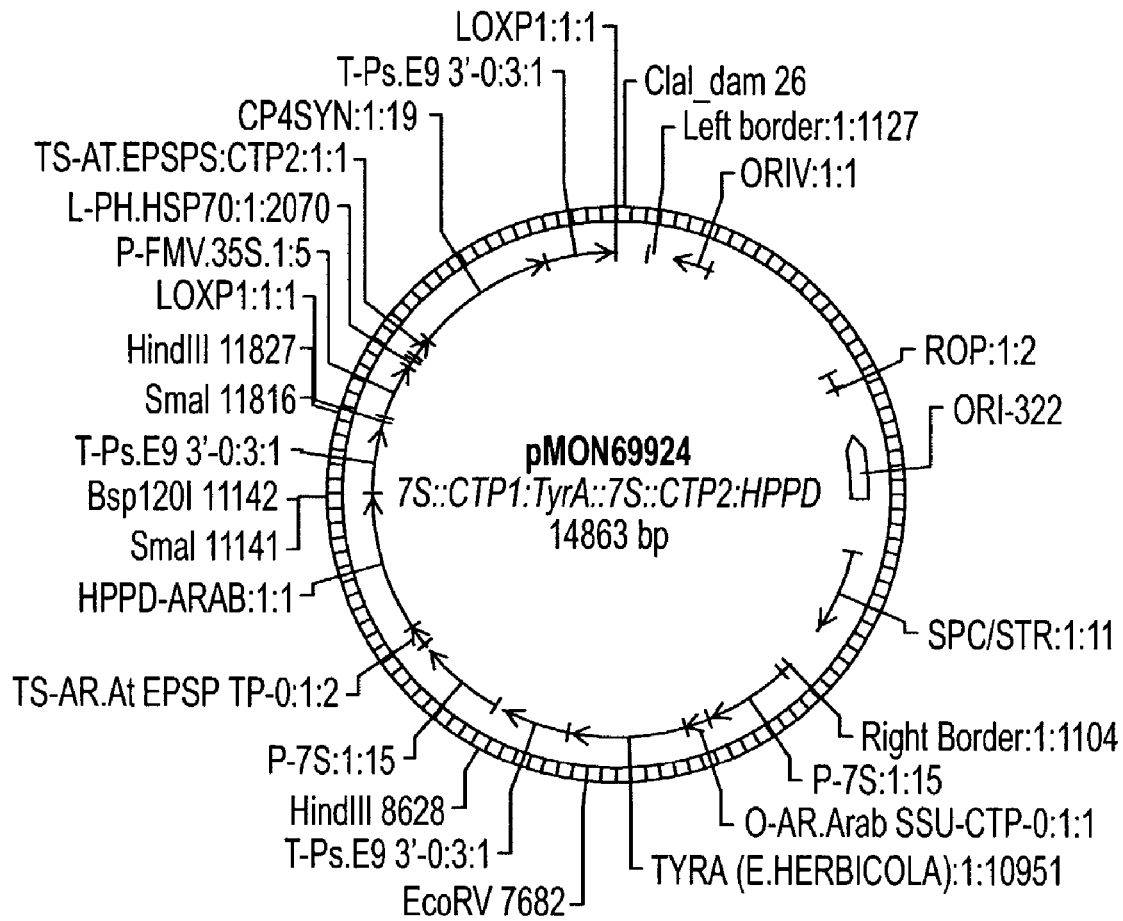
FIG. 50 is a schematic of construct pMON69924.

The pMON36575 (FIG. 46) is prepared by ligating the 3 kb gel purified NotI fragment from pMON38207R (FIG. 47) at the NotI site of pMON36571 (FIG. 48) that contains the p7Sα'::CTP1::tyrA$_{E.\ herbicola}$::E9 3' expression cassette. The CTP1 encodes the chloroplast-target signal sequence from the *Arabidopsis* RUBISCO small subunit. The 3 kb NotI fragment contains the selectable marker cassette, pFMV::CTP2::CP4syn::E9 3'. The CTP2 encodes the chloroplast-target signal sequence from the *Arabidopsis* 5-enolpyruvylshikimate-3-phosphate synthase (EPSPS). The CP4syn is an EPSPS synthetic gene. Vector pMON36575 is further digested with HindIII to release 3 kb fragment containing the p7Sα'-::CTP1::tyrA$_{E.\ herbicola}$::E9 3' expression cassette. The fragment is blunt-ended by filling the 5' overhangs with the klenow-fragment, gel purified and ligated at the PmeI site of pMON36576 (FIG. 49) which carries the expression cassette of p7Sα'::CTP2::HPPD$_{Arabidopsis}$::E9 3' to generate the pMON69924 (FIG. 50).

Figure 51:
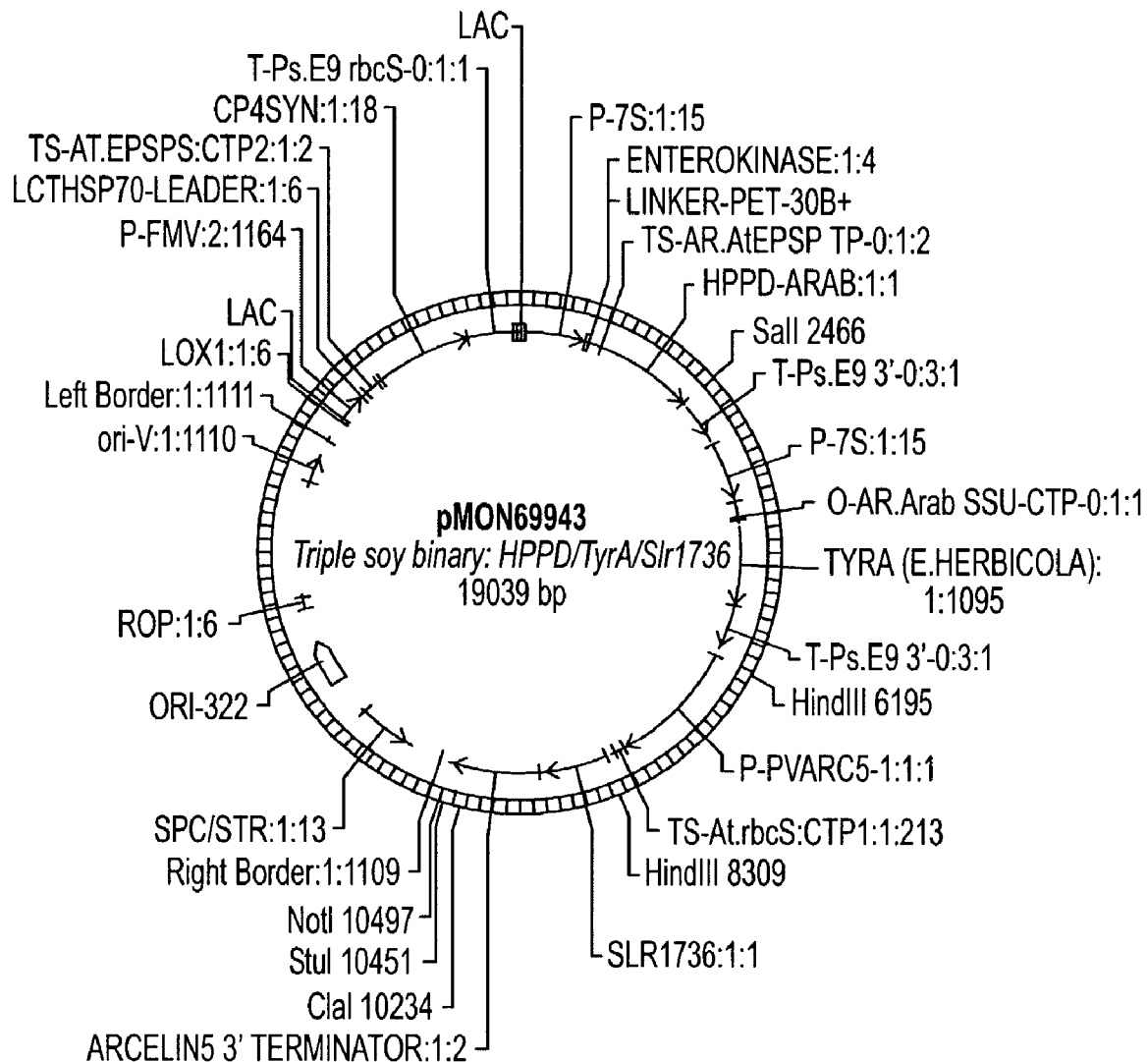
FIG. 51 is a schematic of construct pMON69943.
Figure 52:
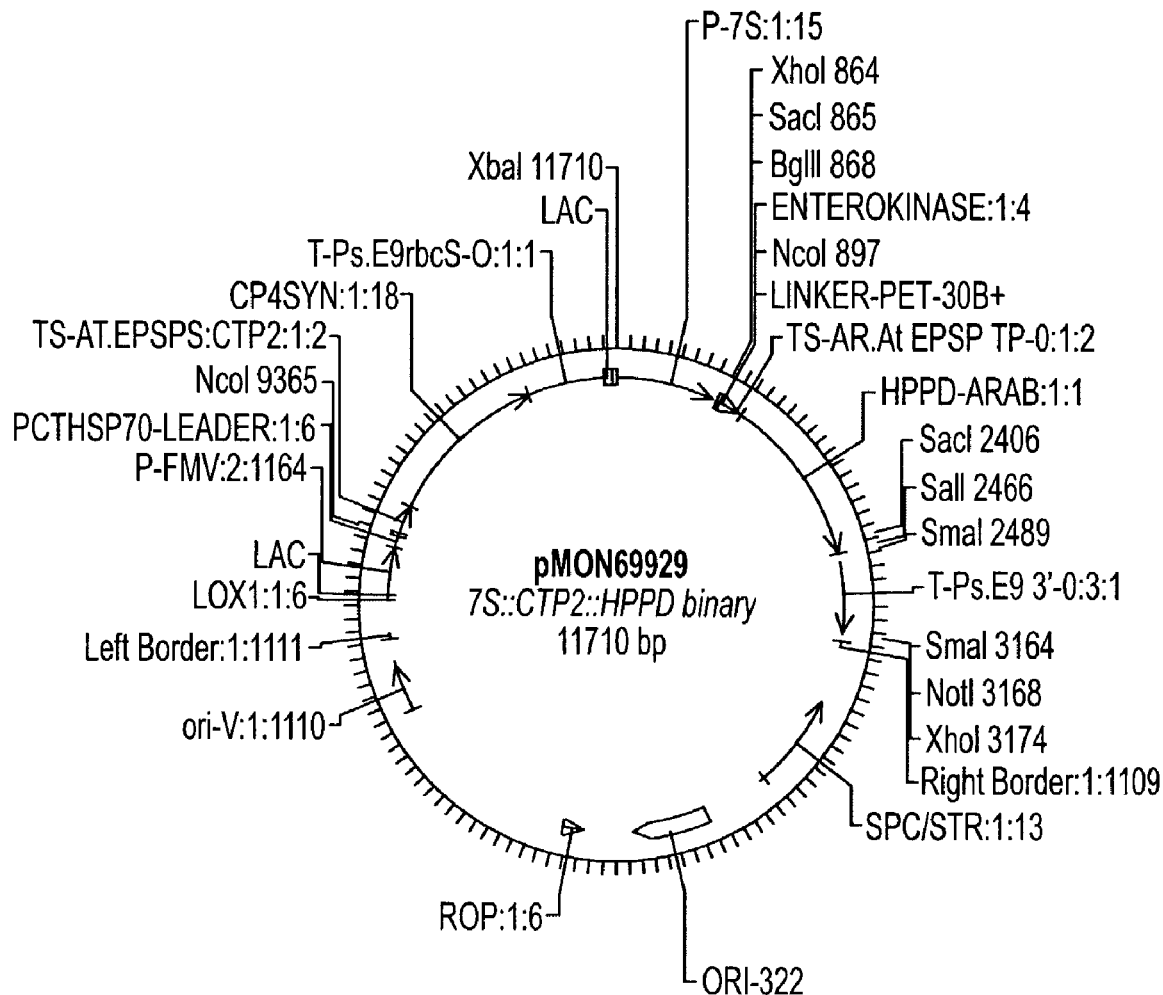
FIG. 52 is a schematic of construct pMON69929.
Figure 53:
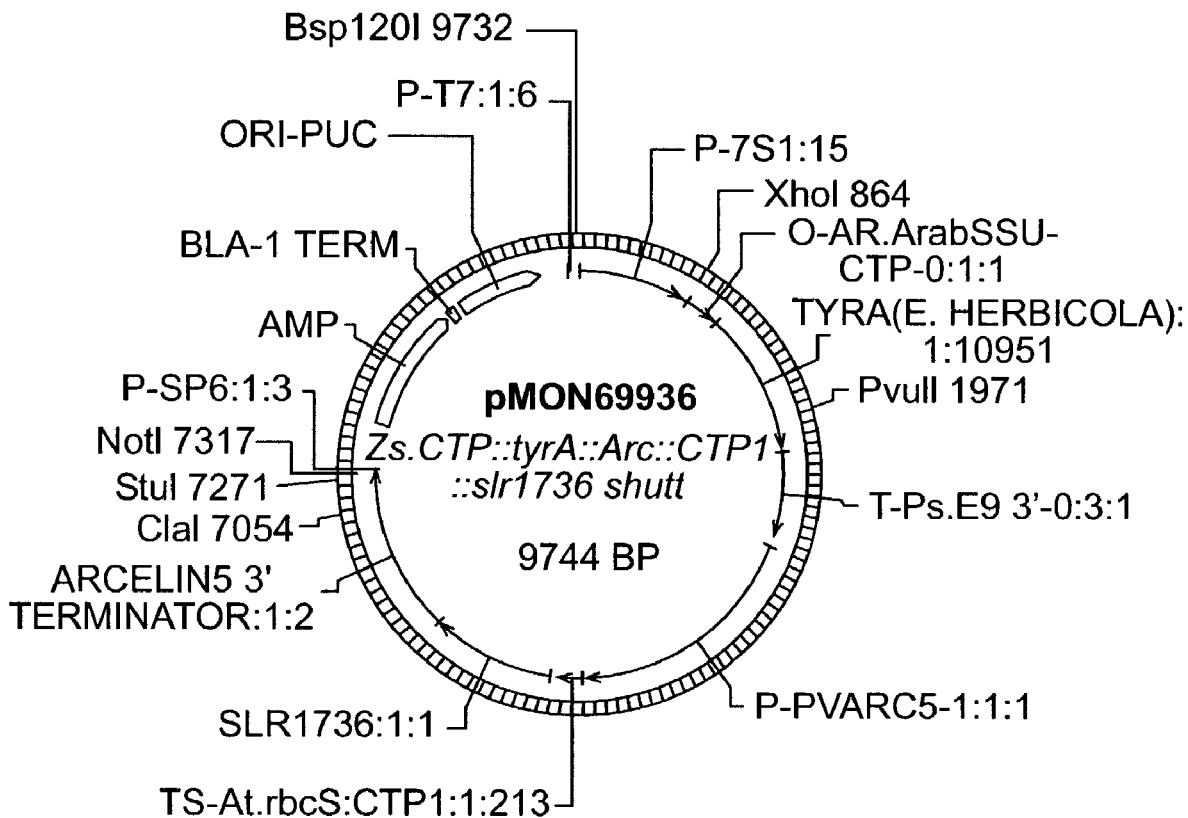
FIG. 53 is a schematic of construct pMON69936.
Figure 54:
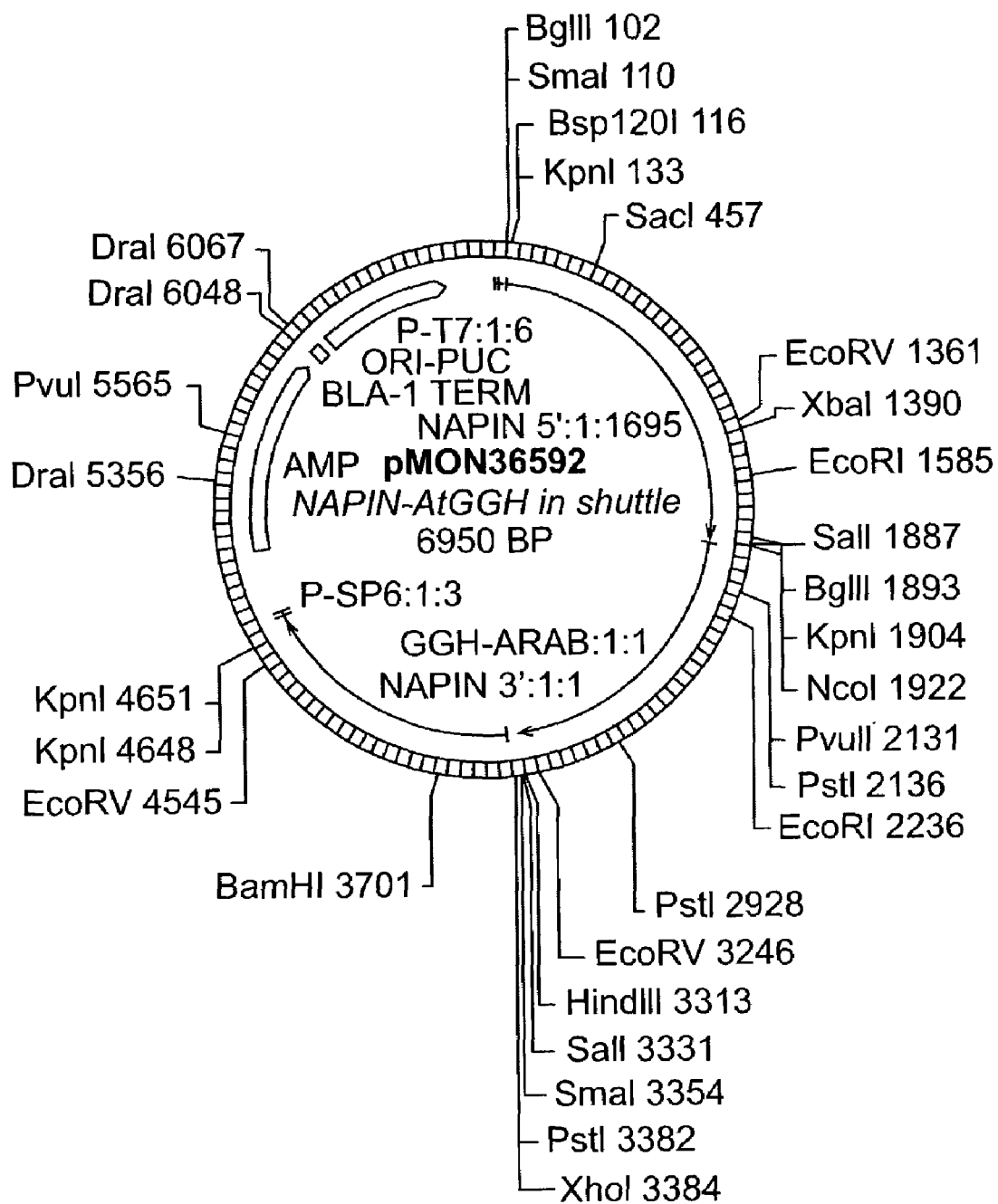
FIG. 54 is a schematic of construct pMON36592.
Figure 55:
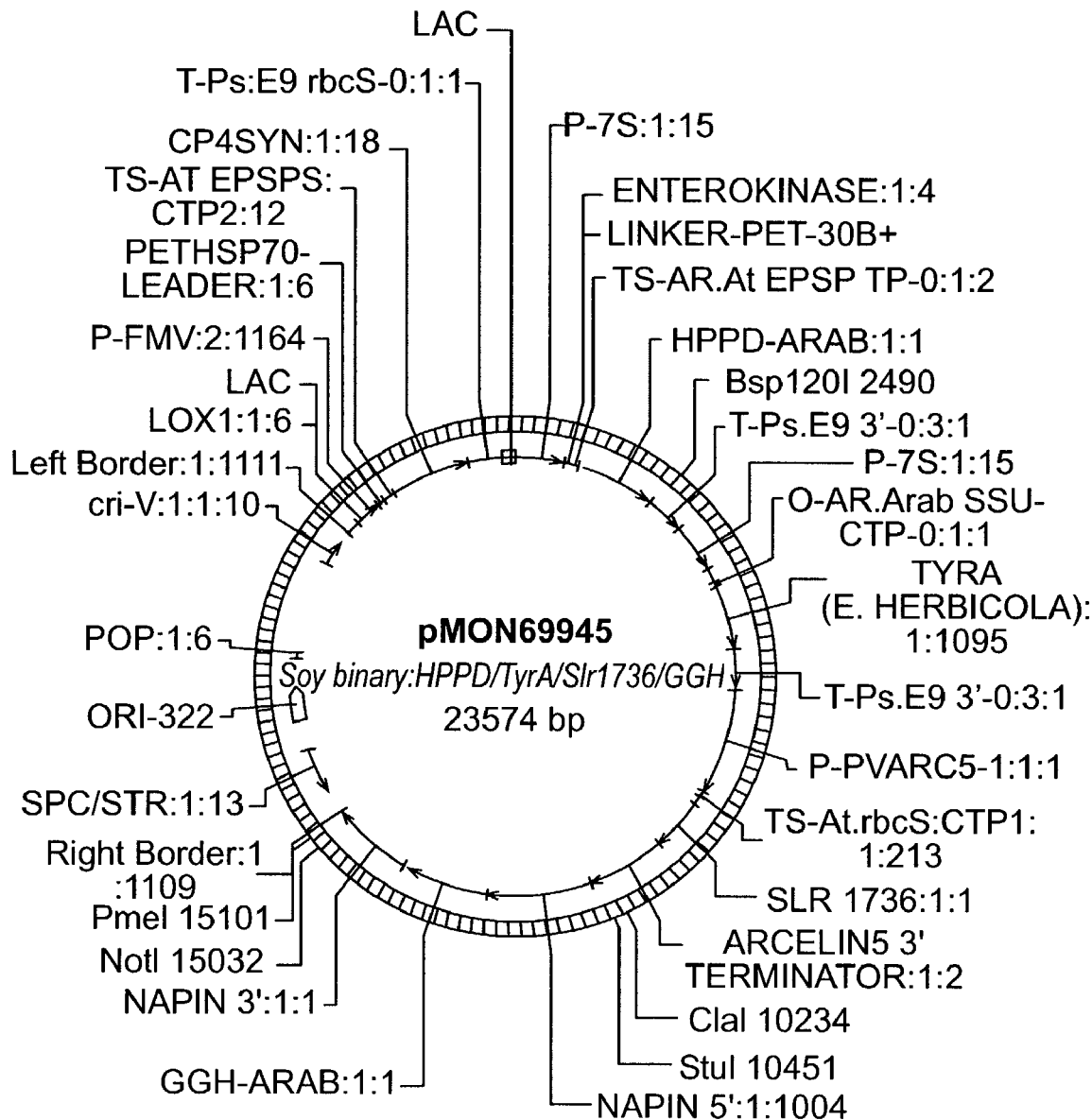
FIG. 55 is a schematic of construct pMON69945.

The plant binary vector pMON69943 (FIG. 51) is prepared by digesting pMON69929 (FIG. 52), containing the p7Sα'::CTP2::HPPD$_{Arabidopsis}$::E9 3' expression cassette, with NotI and ligating with 7.3 kb gel purified fragment generated by digestion of pMON69936 (FIG. 53) with Bsp120I and NotI. This fragment contains the expression cassettes of p7Sα'::CTP1::tyrA$_{E.\ herbicola}$::E9 3' and pArcelin-5::CTP1::slr1736::Arcelin 3'. Vector pMON69943 is further digested with NotI and ligated with a 4.5 kb Bsp120I/NotI gel purified fragment from pMON36592 (FIG. 54) to generate pMON69945 (FIG. 55). The fragment from pMON36592 contains the expression cassette of pNapin::GGH$_{Arabidopsis}$::napin 3'.

*Gluycine max* is transformed with the described vectors according to the procedure set forth in WO 00/61771 A3 on pages 99-100.

EXAMPLE 16

Multiple gene combinations expressed in canola.

All gene expression cassettes used for expression in canola are prepared as Not I cassettes containing the napin promoter, a gene of interest, and the napin terminator. Genes of interest are N-terminally fused to a chloroplast target peptide, unless a natural chloroplast target peptide is present. All gene combinations are assembled in a single multi gene vector.

Figure 56:
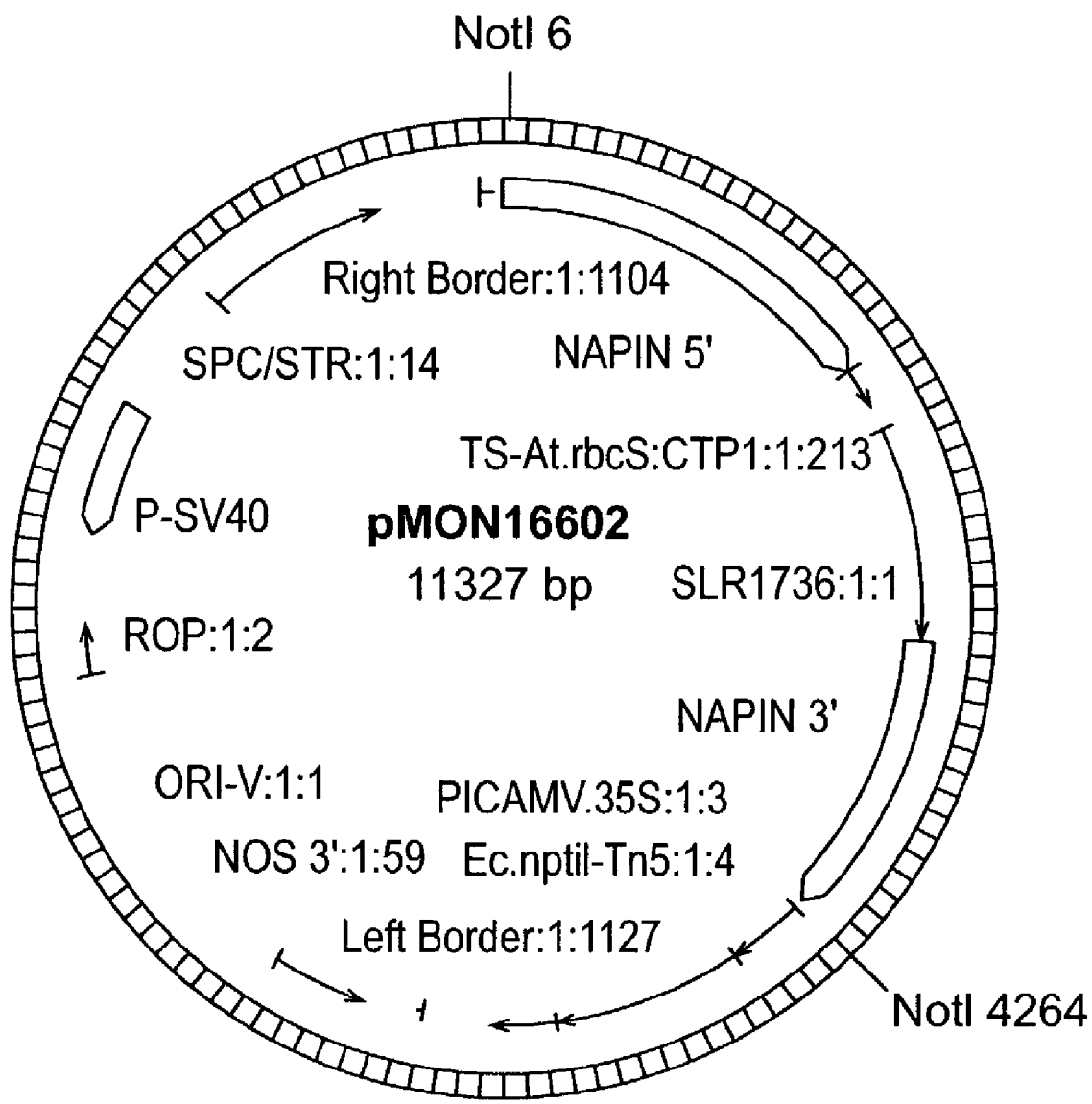
FIG. 56 is a schematic of construct pMON16602.
Figure 57:
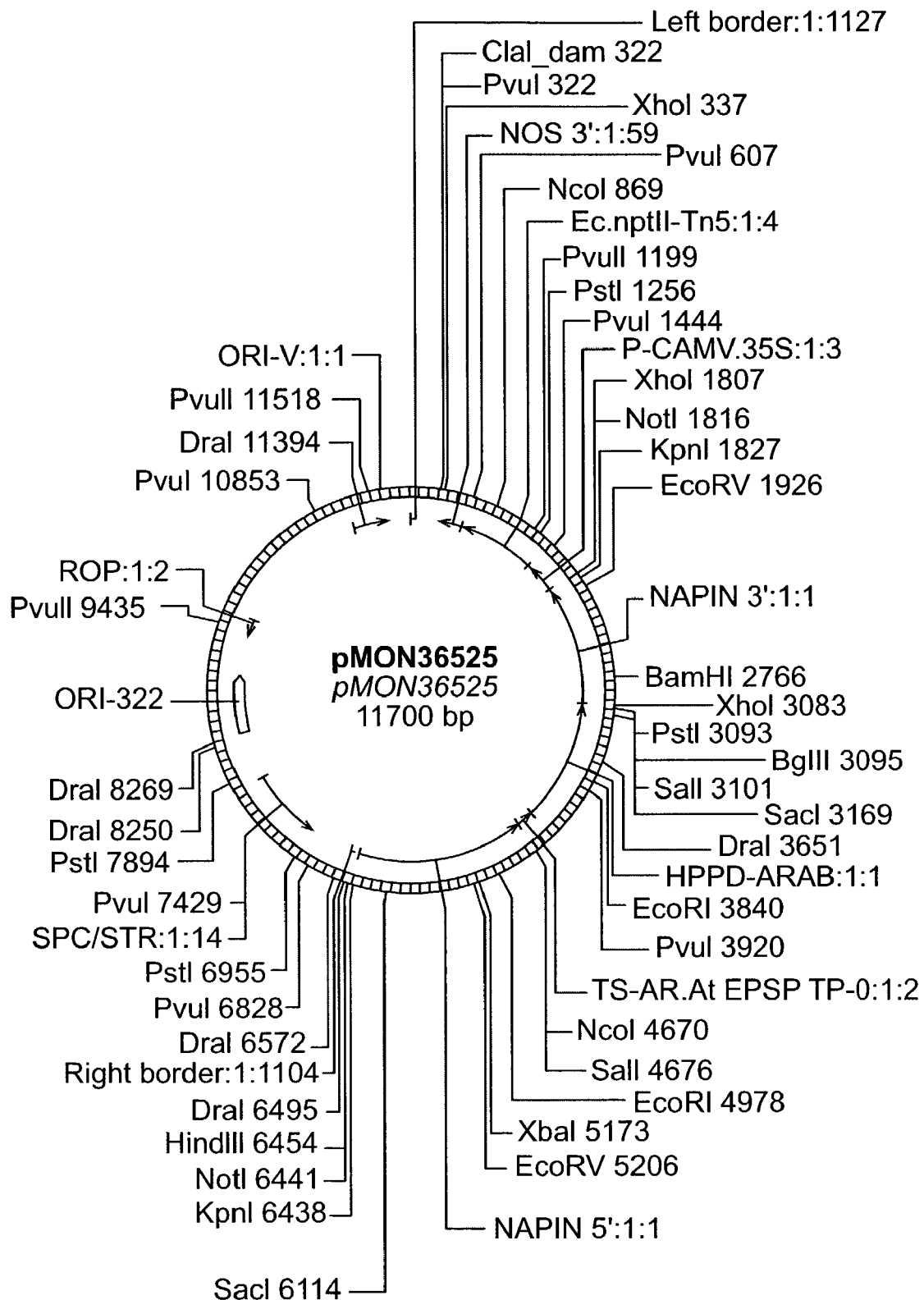
FIG. 57 is a schematic of construct pMON36525.
Figure 58:
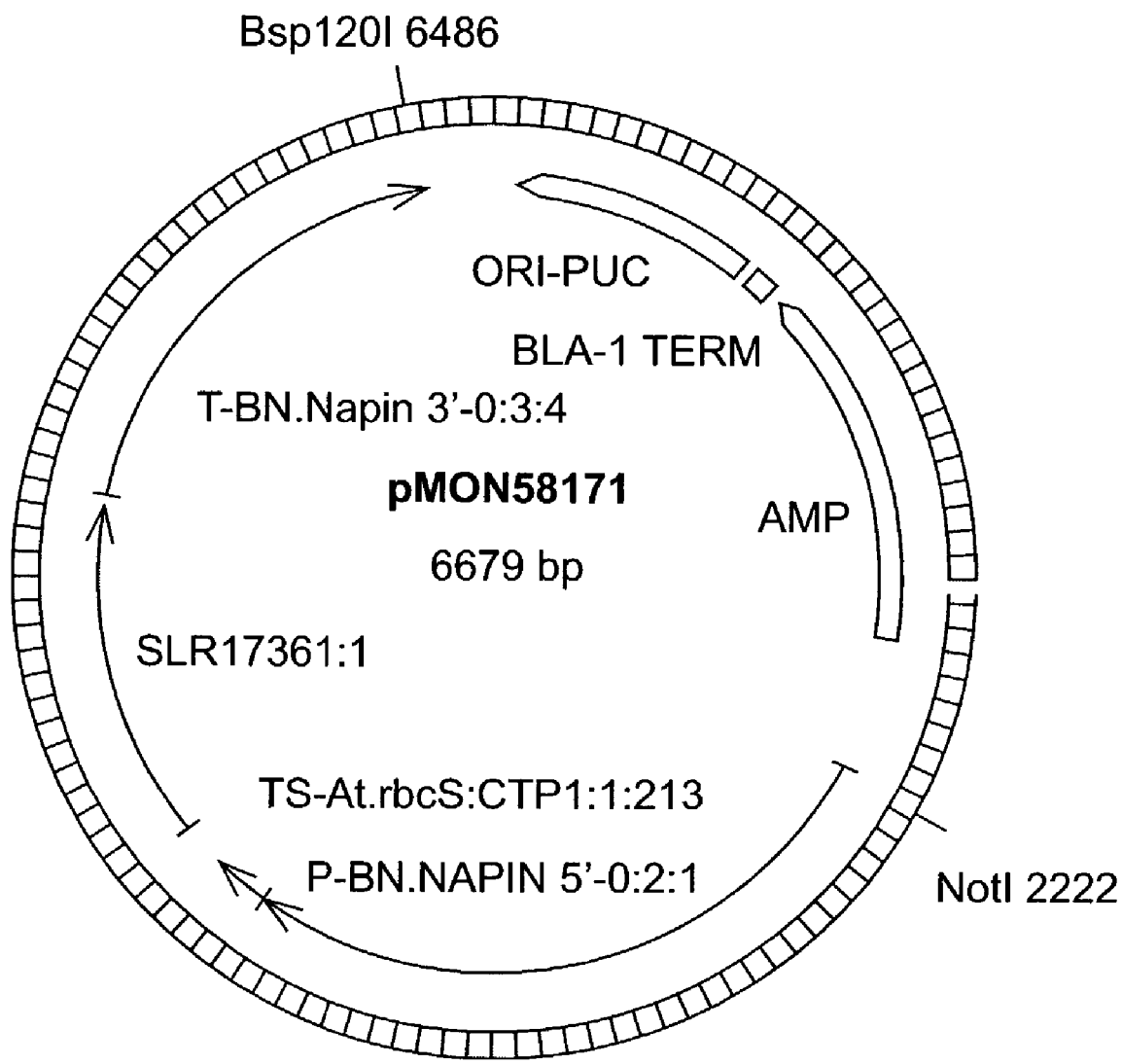
FIG. 58 is a schematic of construct pMON58171.
Figure 59:
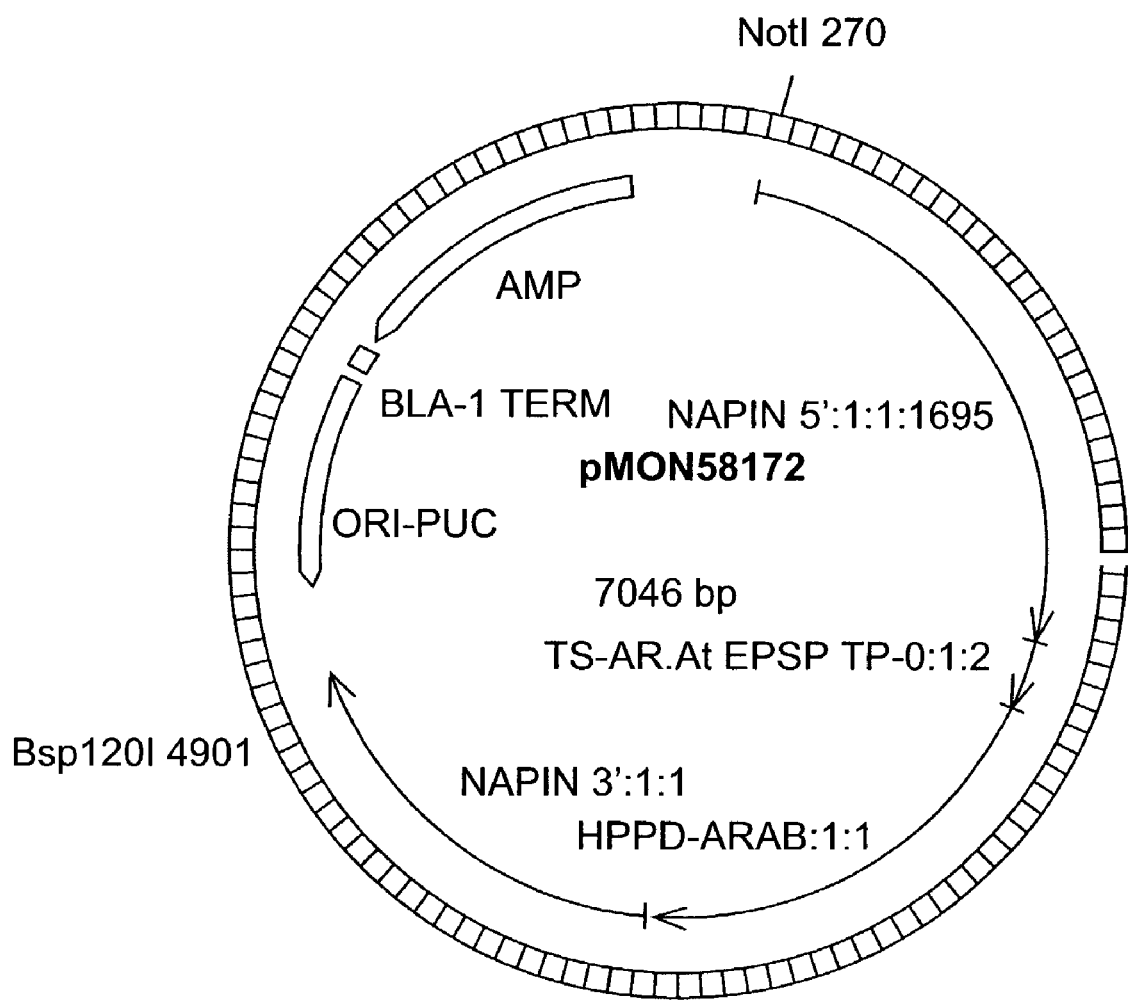
FIG. 59 is a schematic of construct pMON58172.
Figure 60:
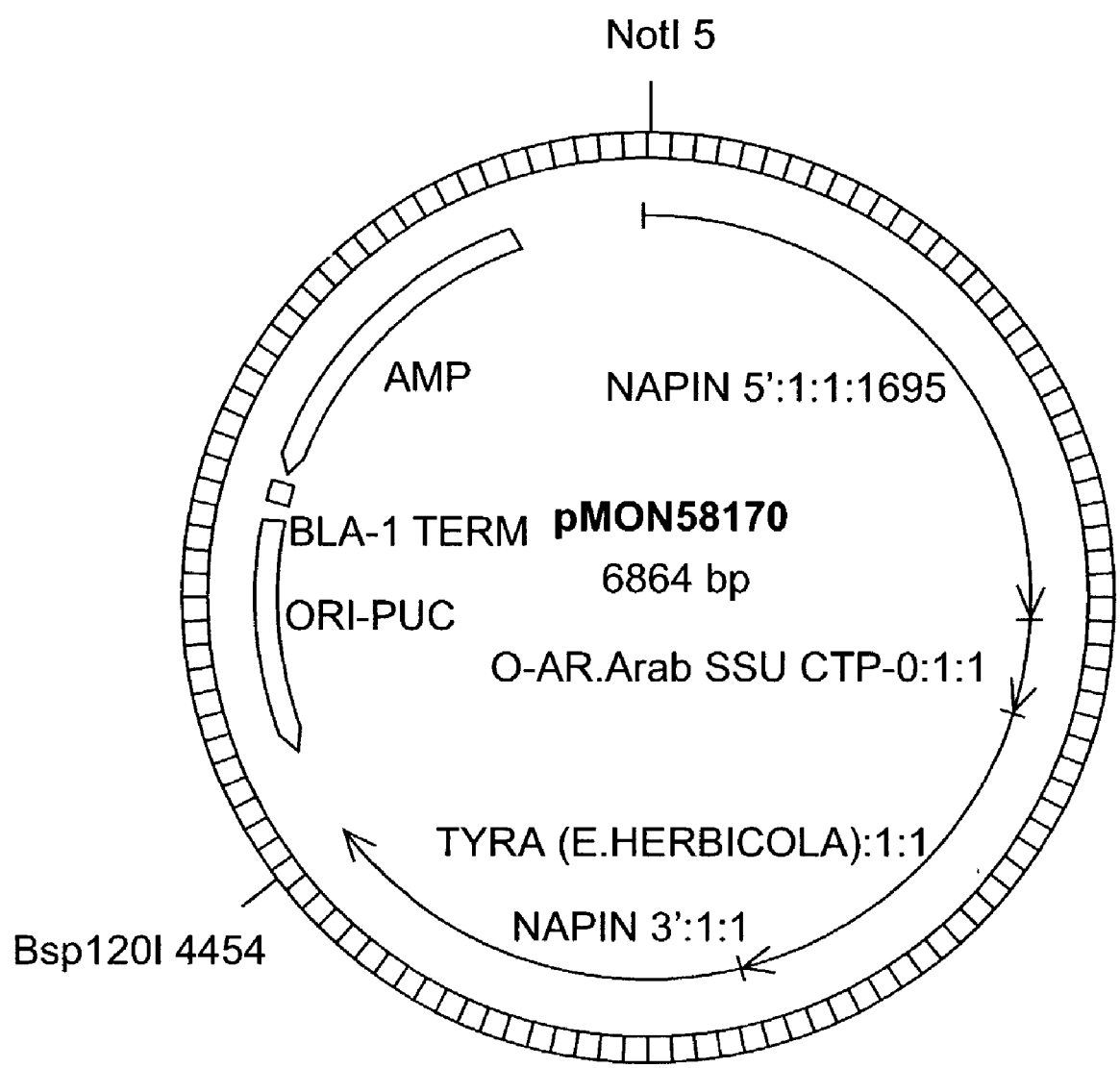
FIG. 60 is a schematic of construct pMON58170.

In order to ease the construction of multi gene vectors, the Not I expression cassettes are isolated by Not I digestion from pMON16602 (FIG. 56), pMON36525 (FIG. 57), pMON36520 (FIG. 38) and cloned into Eag I digested and gel purified pMON36582 (FIG. 19), resulting in the formation of pMON58171 (FIG. 58)(slr1736 expression cassette), pMON58172 (FIG. 59)(HPPD$_{Arabidopsis}$ expression cassette), and pMON58170 (FIG. 60) (tyrA$_{E.\ herbicola}$ expression cassette). All of the resulting expression cassettes are flanked by Bsp120 I and Not I.

Figure 61:
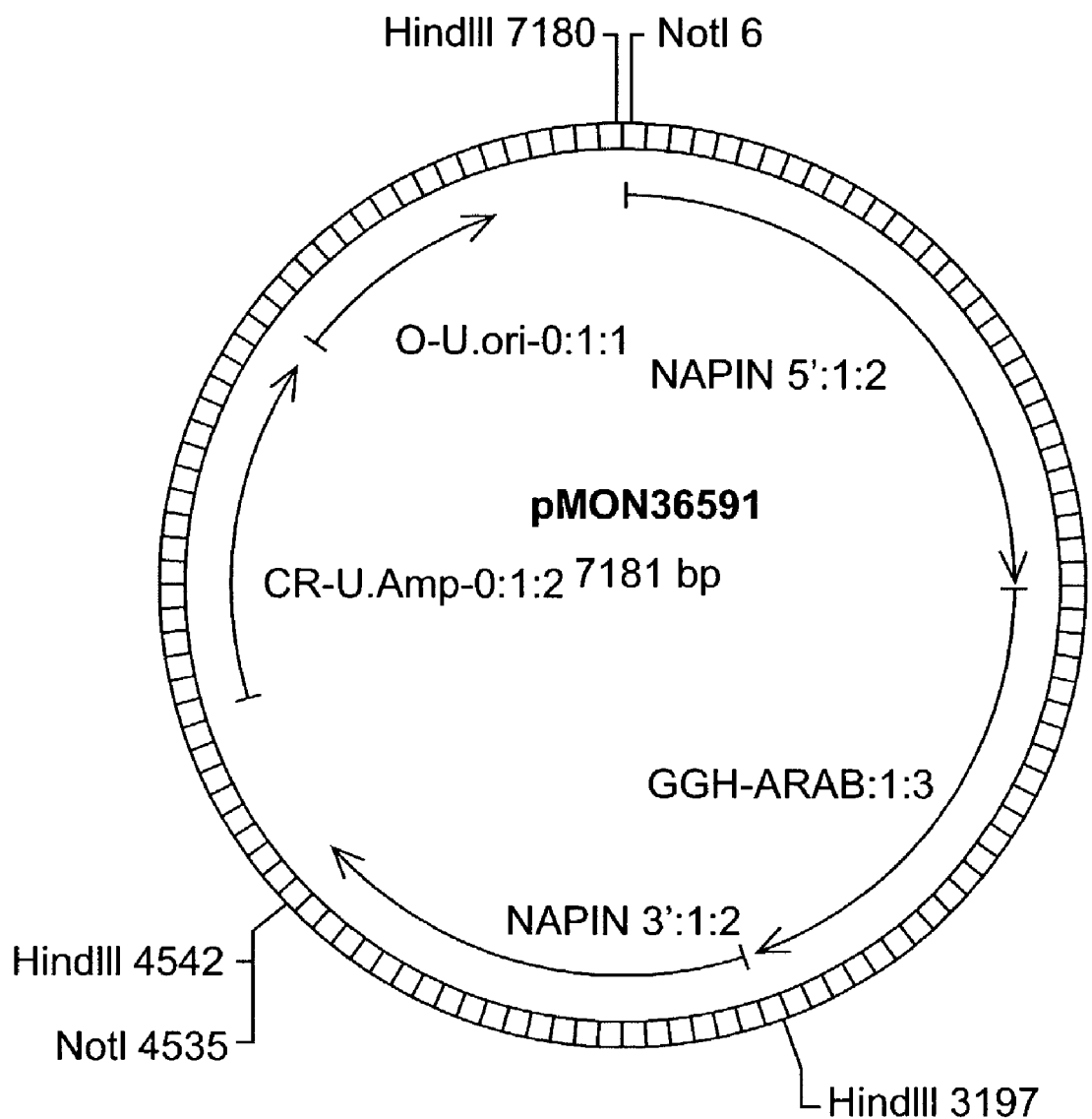
FIG. 61 is a schematic of construct pMON36591.
Figure 62:
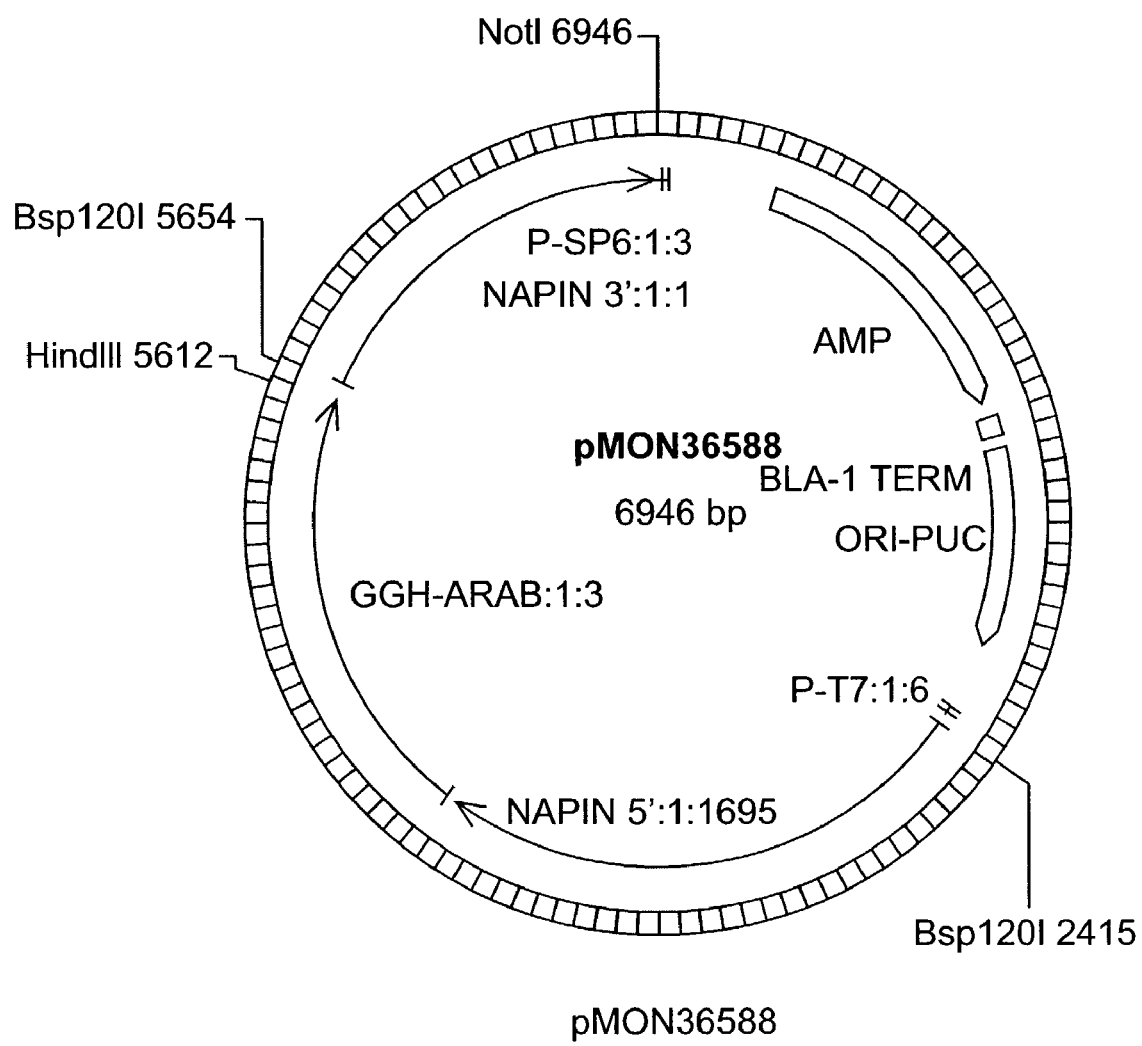
FIG. 62 is a schematic of construct pMON36588.
Figure 63:
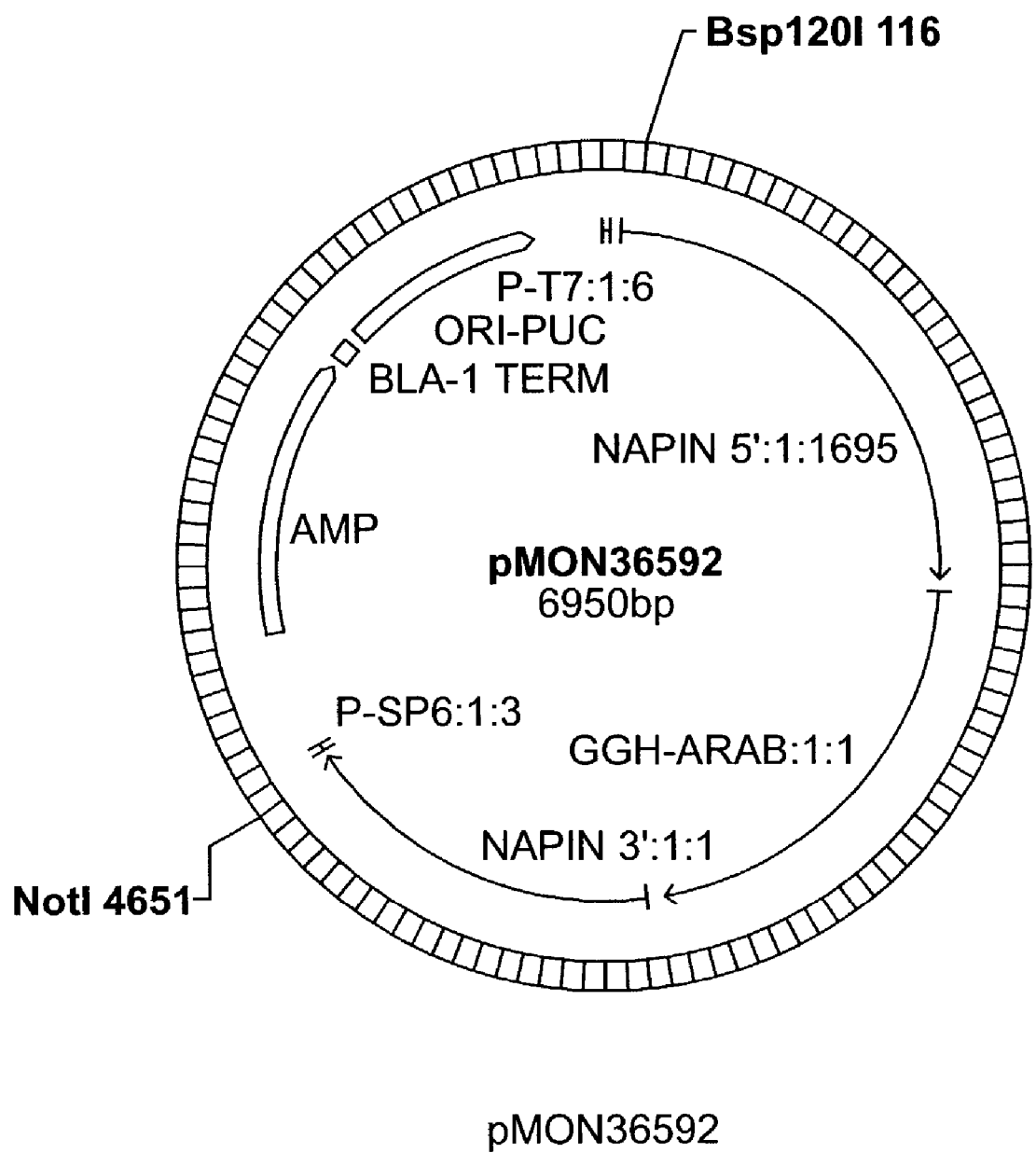
FIG. 63 is a schematic of construct pMON36592.
Figure 64:
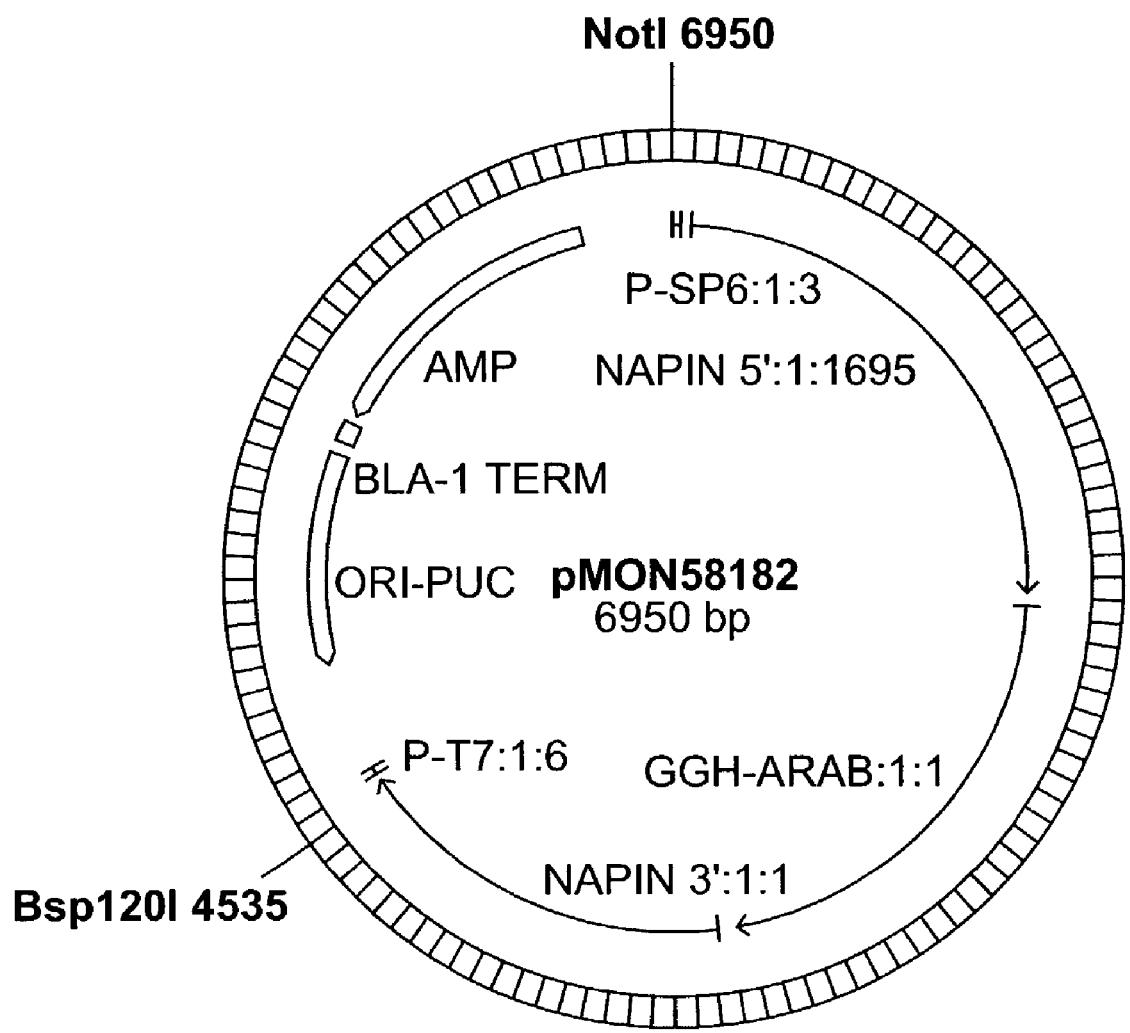
FIG. 64 is a schematic of construct pMON58182.

A napin driven expression cassette for the *Arabidopsis* GGH is obtained by isolation and gel purification of a 3191 bp Not I/Hind III fragment from pMON36591 (FIG. 61) and a 5612 bp Not I/Hind III-fragment from pMON36588 (FIG. 62). These two purified fragments are ligated, resulting in the formation of pMON36592 (FIG. 63). Vector pMON36592 is digested with Bsp120I and Not I, the GGH expression cassette is gel purified, and ligated into Eag I digested and gel purified pMON36582 (FIG. 19), resulting in the formation of pMON58182 (FIG. 64).

Figure 65:
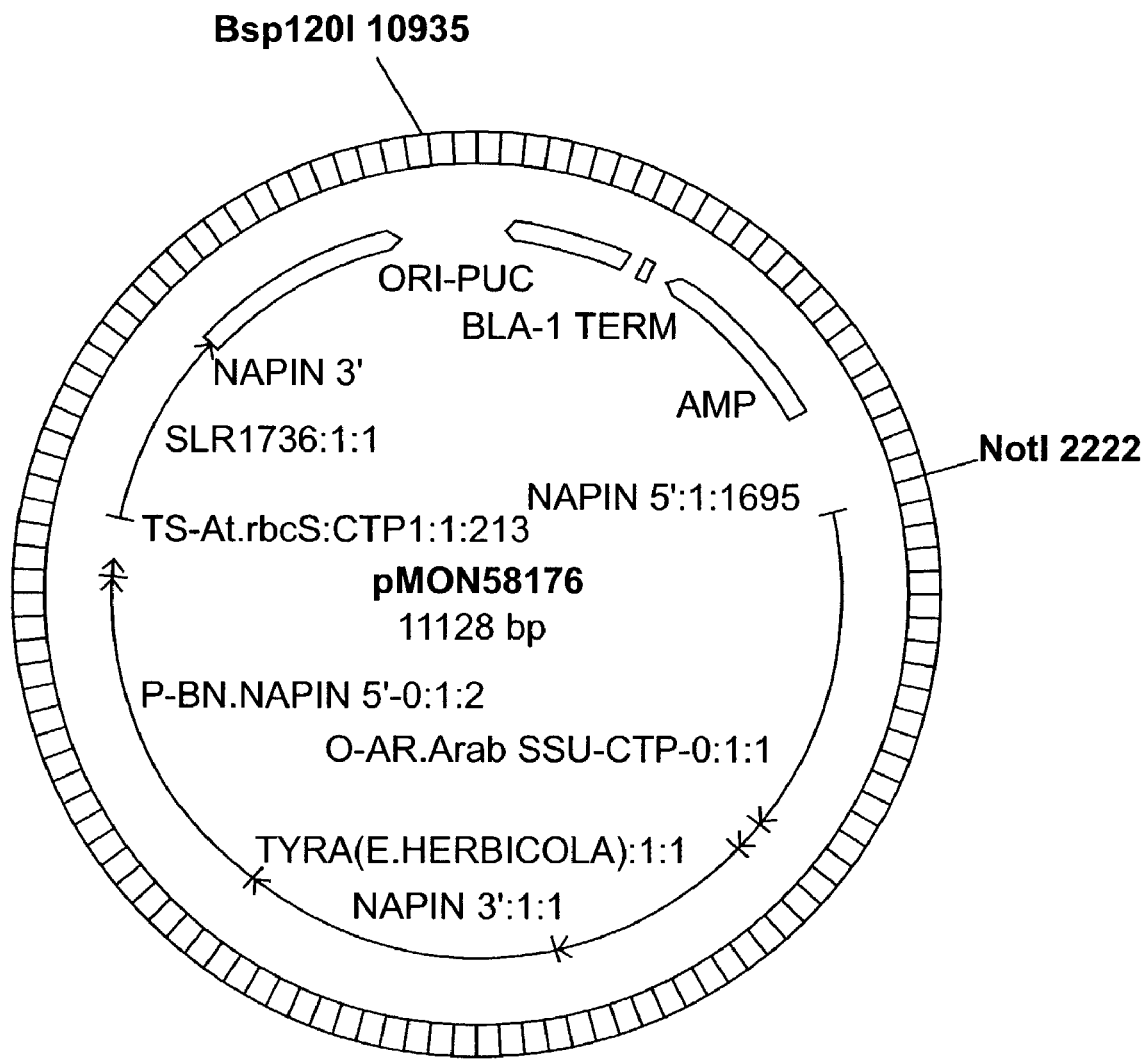
FIG. 65 is a schematic of construct pMON58176.
Figure 66:
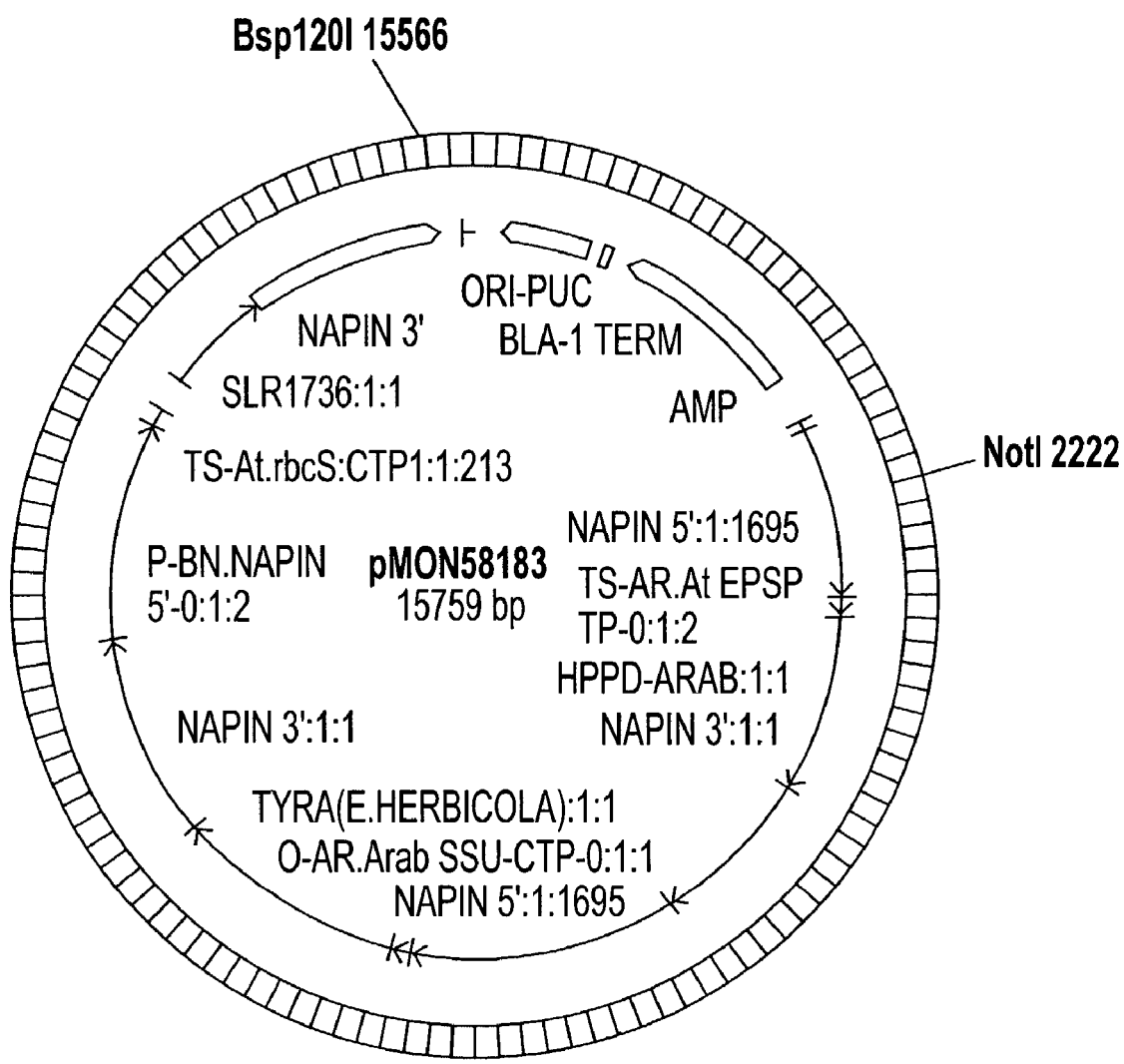
FIG. 66 is a schematic of construct pMON58183.
Figure 67:
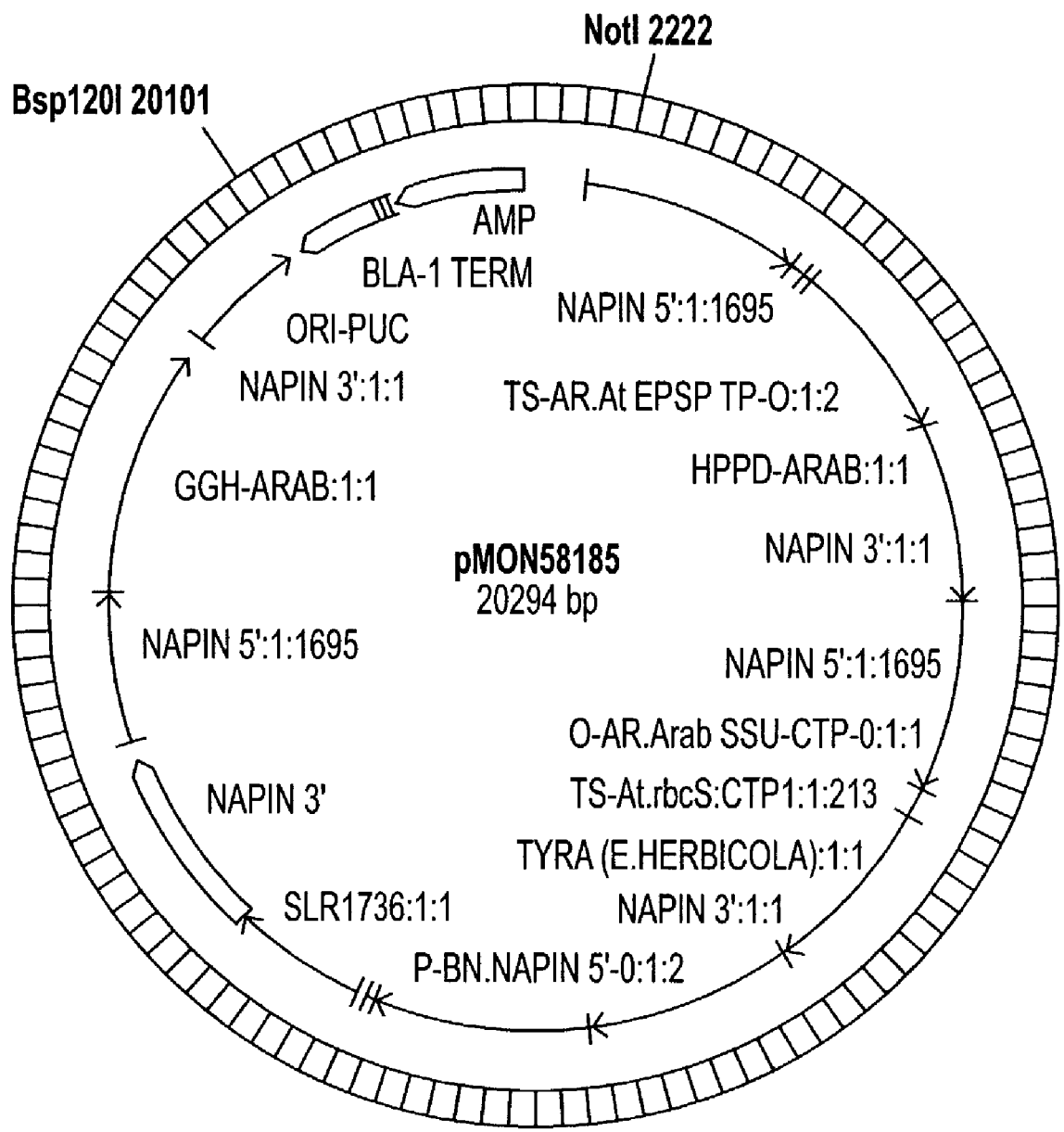
FIG. 67 is a schematic of construct pMON58185.

Multi gene vectors combining these four genes are obtained by digesting vectors pMON58171, pMON58172, pMON58170, and pMON58182 with Bsp120I and Not I, followed by gel purification of the larger fragments from each construct. These fragments contain the slr1736, HPPD, tyrA, and GGH expression cassettes, respectively. The tyrA expression cassette from pMON58170 is ligated into Not I digested and alkaline phosphatase treated pMON58171, resulting in the formation of the double gene vector pMON58176 (FIG. 65) containing gene expression cassettes for tyrA and slr1736, respectively. This vector is again digested with Not I, alkaline phosphatase treated, and ligated with the HPPD expression cassette from pMON58172. The resulting triple gene vector pMON58183 (FIG. 66) contains the HPPD, tyrA, and slr1736 expression cassettes. Also pMON58183 is digested with Bsp120 I, alkaline phosphatase treated, and ligated with the gel purified GGH expression cassette (see purification above), resulting in the formation of pMON58185 (FIG. 67).

Figure 68:
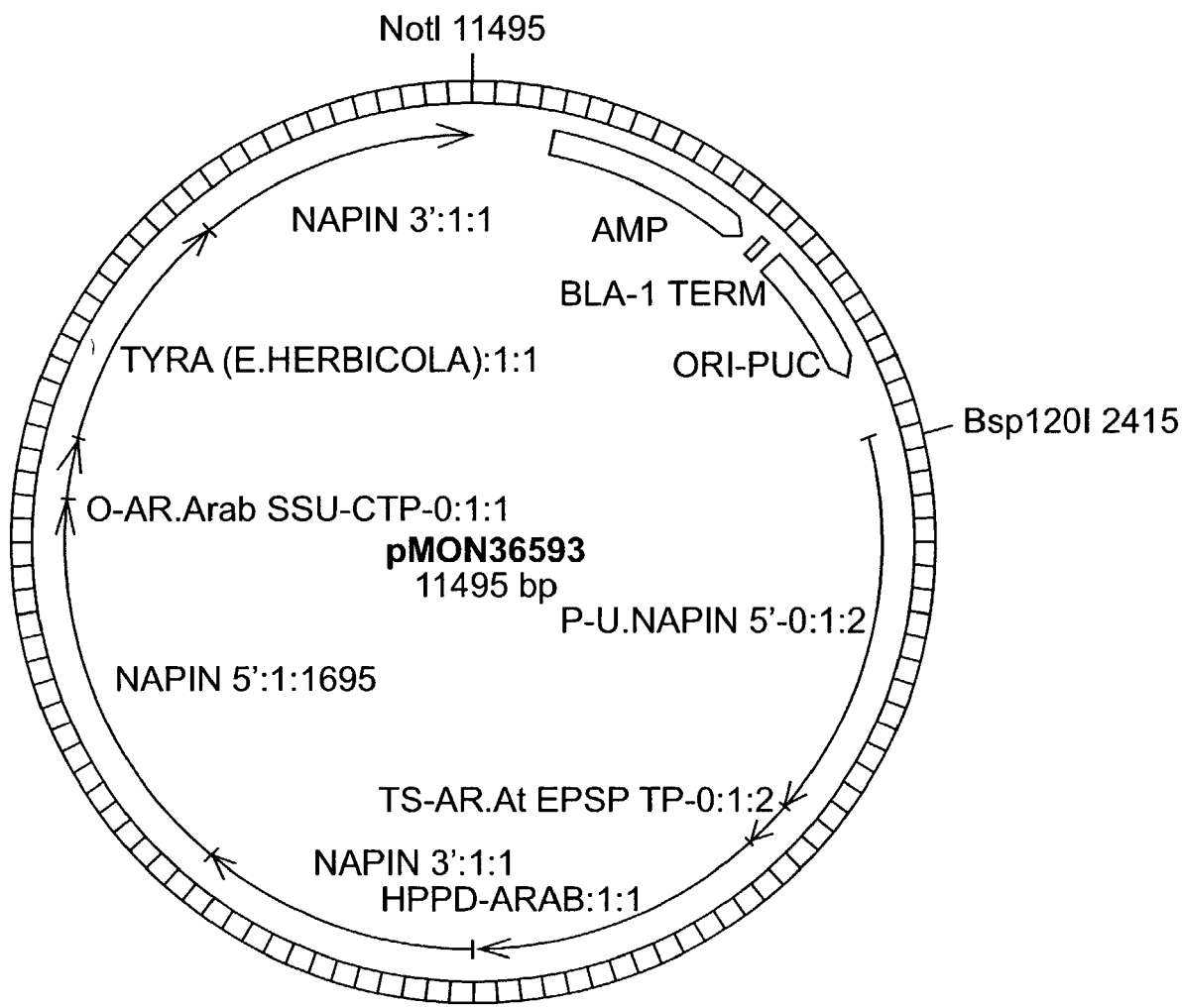
FIG. 68 is a schematic of construct pMON36593.
Figure 69:
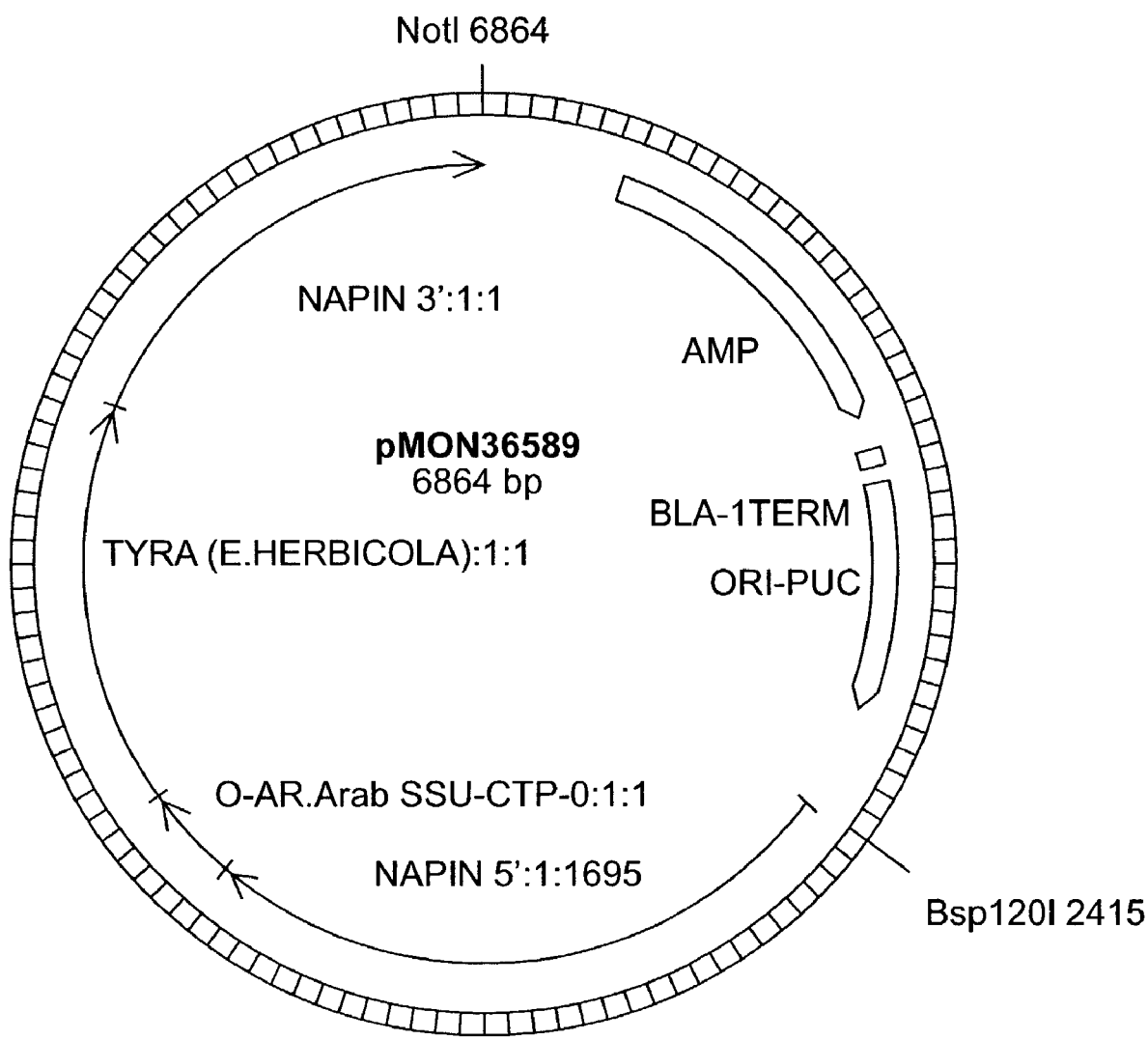
FIG. 69 is a schematic of construct pMON36589.
Figure 70:
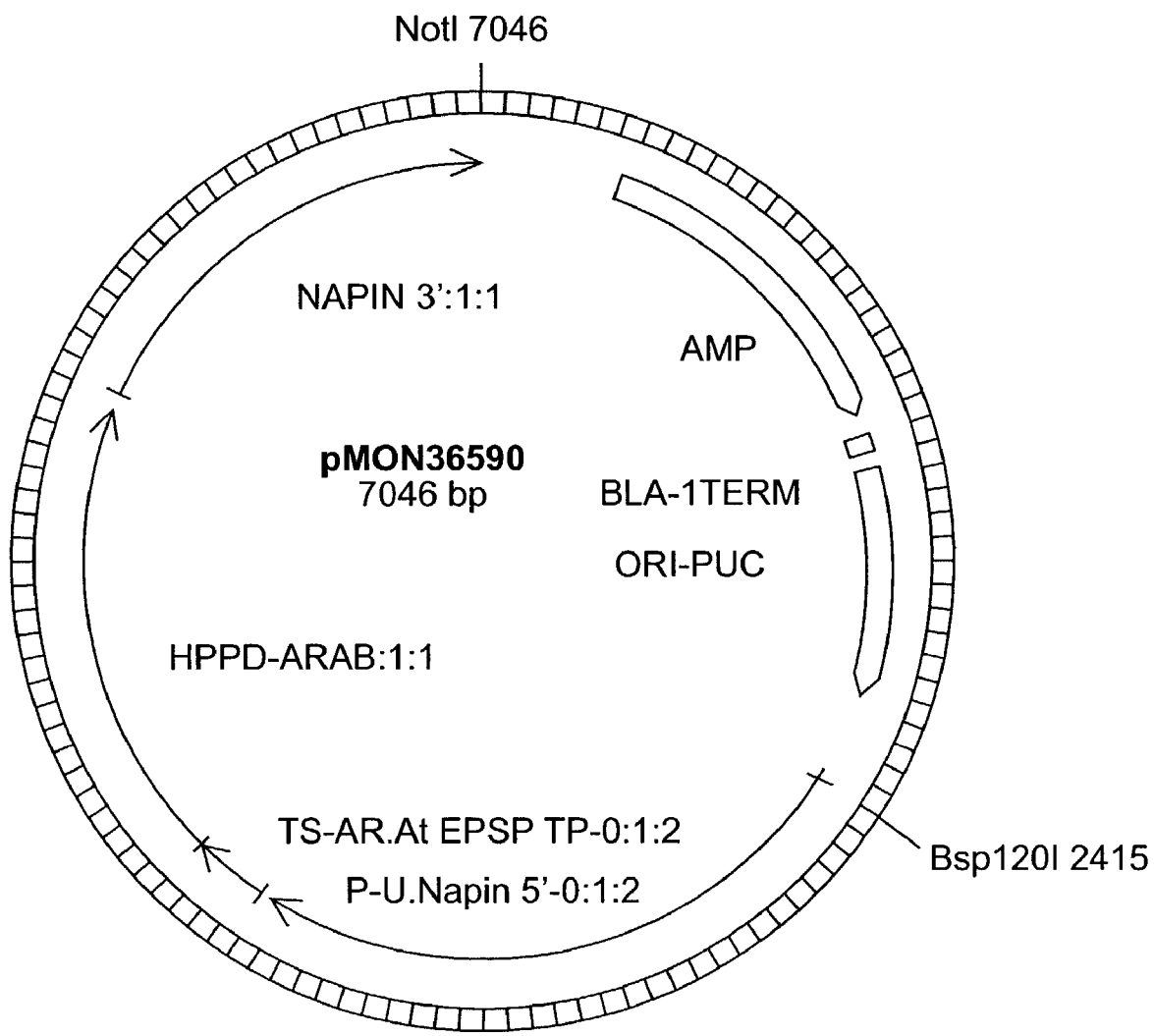
FIG. 70 is a schematic of construct pMON36590.

The shuttle vector pMON36593 (FIG. 68) (containing tyrA and HPPD expression cassettes) is prepared by ligating a Bsp120I/Not I digested gel purified tyrA expression cassette from pMON36589 (FIG. 69) into NotI digested and alkaline phosphatase treated pMON36590 (FIG. 70).

Figure 71:
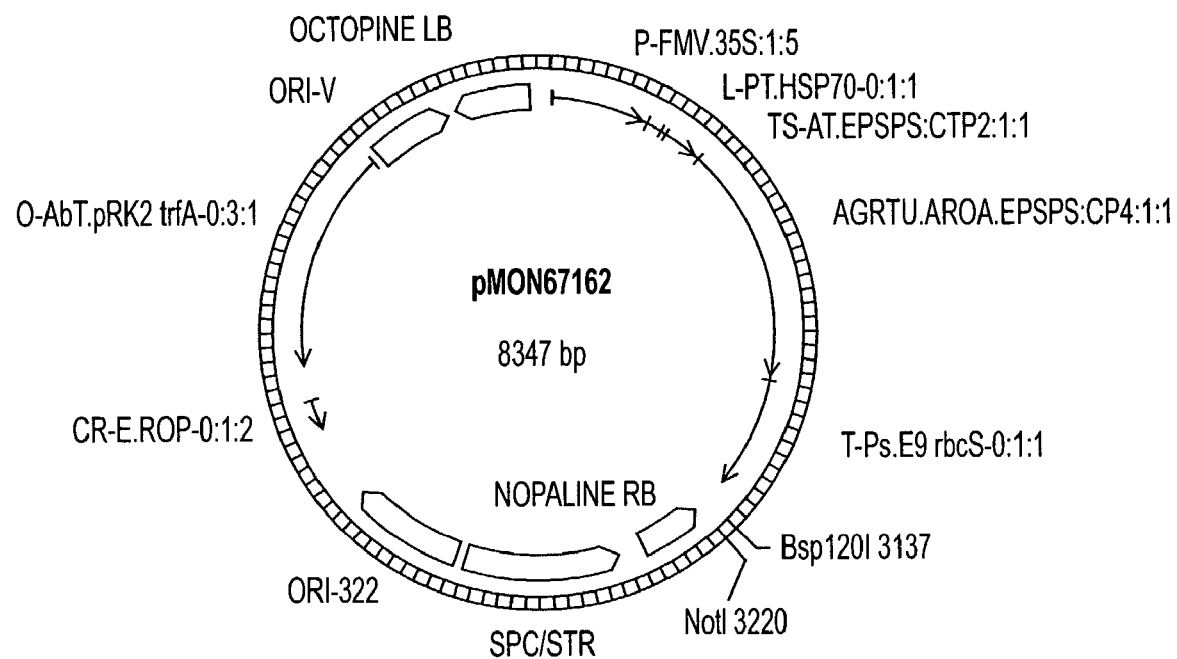
FIG. 71 is a schematic of construct pMON67162.
Figure 72:
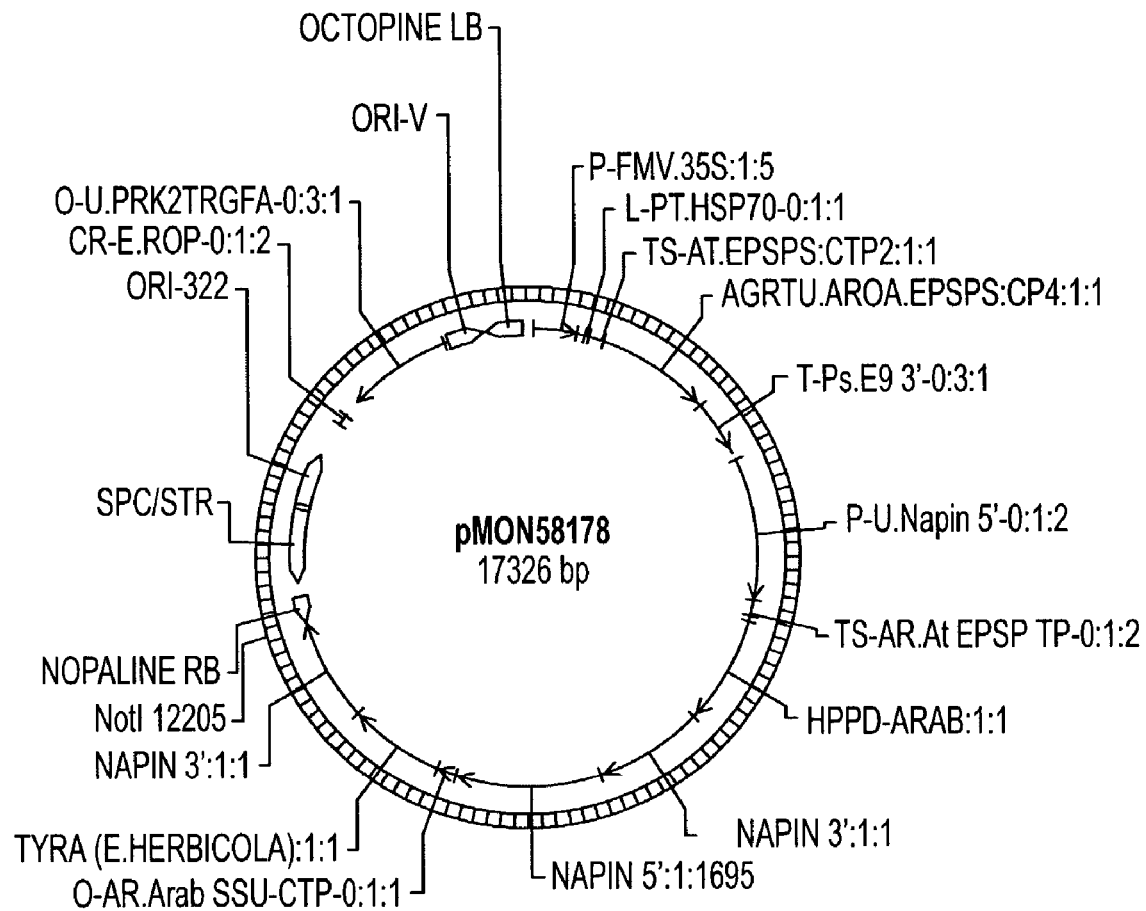
FIG. 72 is a schematic of construct pMON58178.
Figure 73:
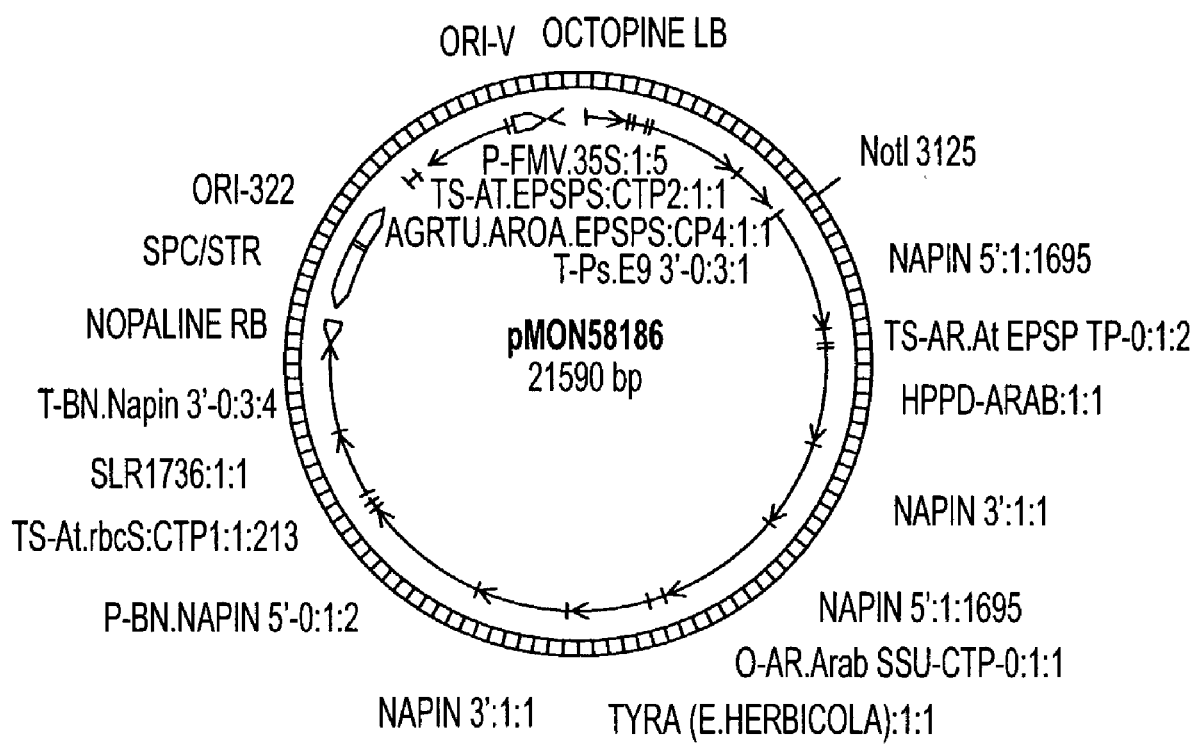
FIG. 73 is a schematic of construct pMON58186.
Figure 74:
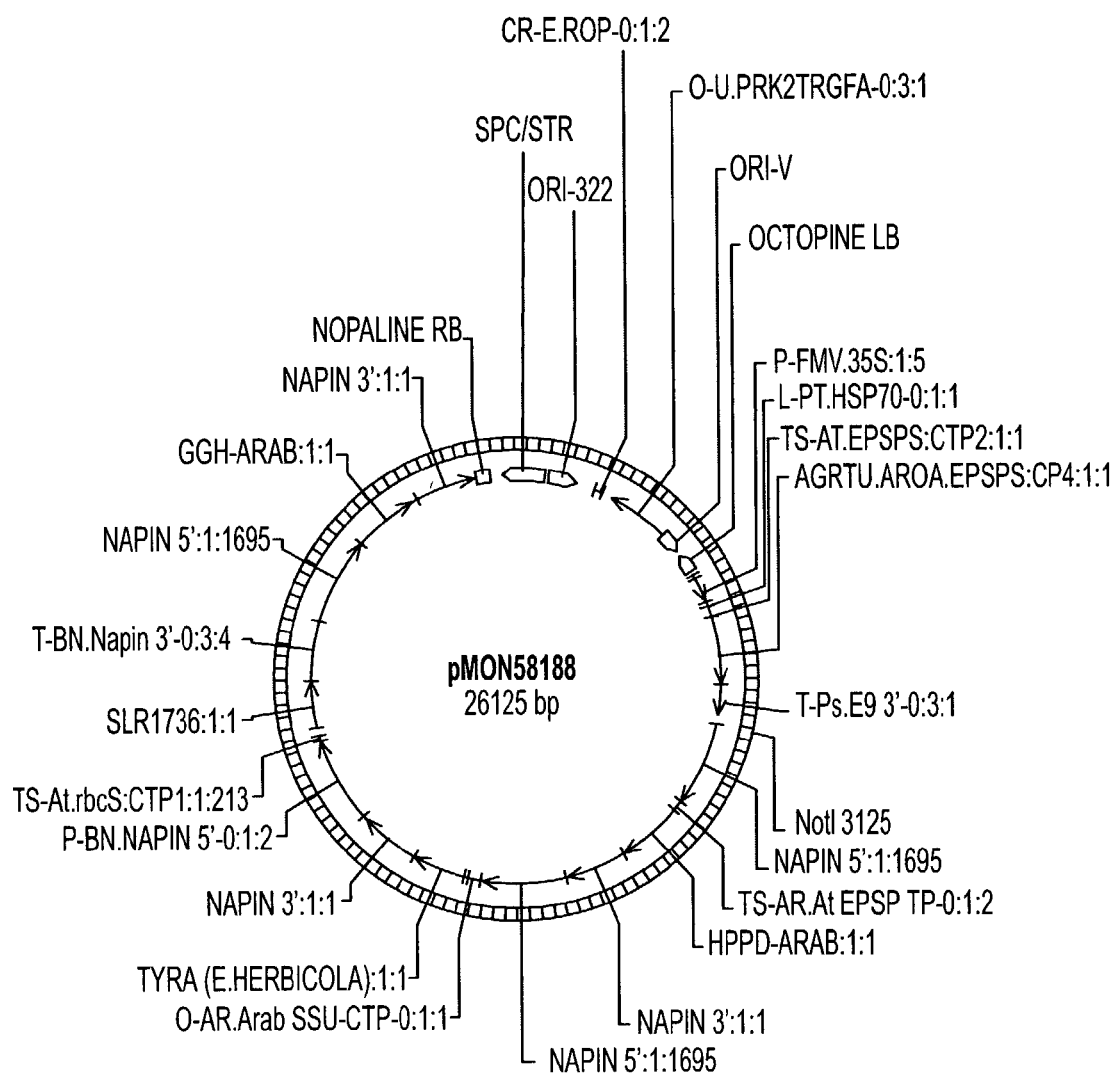
FIG. 74 is a schematic of construct pMON58188.

The combined gene expression cassettes are excised by Bsp120I/Not I digest from pMON36593 (HPPD/tyrA), pMON58183 (HPPD/tyrA/slr1736), and pMON58185 (HPPD, tyrA, slr1736, GGH). These combined gene expression cassettes are gel purified, and ligated into Not I digested, alkaline phosphatase treated pMON67162 (FIG. 71), resulting in the formation of binary vectors pMON58178 (FIG. 72), pMON58186 (FIG. 73), and pMON58188 (FIG. 74), respectively. The latter three binary vectors are used for canola transformation.

What is claimed is:

1. A substantially purified nucleic acid molecule comprising as operably linked components: (A) a promoter region which functions in a plant cell to cause the production of an mRNA molecule; (B) a heterologous nucleic acid molecule that encodes an enzyme with chorismate mutase and prephenate dehydrogenase activities wherein the heterologous nucleic acid molecule is selected from the group consisting of a nucleic acid sequence that encodes the amino acid sequence of SEQ ID NO: 2, the nucleic acid sequence of SEQ ID NO: 1, and a nucleic acid sequence that hybridizes to the complement of SEQ ID NO:1 under conditions of 2×SSC and 65° C.

2. The nucleic acid molecule of claim 1, further comprising a 3' non-translated sequence that functions in said plant cell to cause termination of transcription and addition of polyadenylated ribonucleotides to a 3' end of the mRNA molecule.

3. The nucleic acid molecule of claim 1, wherein said heterologous nucleic acid molecule comprises the nucleic acid sequence of SEQ ID NO:1.

4. The nucleic acid molecule of claim 1, wherein said heterologous nucleic acid molecule further comprises an expression cassette which expresses phytyl prenyltransferase.

5. The nucleic acid molecule of claim 4, wherein said heterologous nucleic acid molecule further comprises an expression cassette which expresses hydroxyphenylpyruvate dehydrogenase.

6. The nucleic acid molecule of claim 1, wherein said heterologous nucleic acid molecule further comprises a nucleic acid sequence encoding HPPD and either slr 1736 or ATPT2.

7. A transformed plant comprising the substantially purified nucleic acid molecule of claim 1.

8. The transformed plant of claim 7, wherein said plant further comprises an expression cassette which expresses phytyl prenyltransferase.

9. The transformed plant of claim 8, wherein said plant further comprises an expression cassette which expresses hydroxyphenylpyruvate dehydrogenase.

10. The transformed plant of claim 7, wherein said plant further comprises a nucleic acid sequence encoding HPPD and either slr 1737 or ATPT2.

11. The transformed plant according to claim 7, wherein said plant is selected from the group consisting of canola, maize, *Arabidopsis, Brassica campestris, Brassica napus*, soybean, crambe, mustard, castor bean, peanut, sesame, cottonseed, linseed, safflower, oil palm, flax and sunflower.

12. The transformed plant according to claim 7, wherein said plant is soybean.

13. The transformed plant according to claim 7, wherein said plant is canola.

14. The transformed plant according to claim 7, wherein said plant is *Brassica napus*.

15. The transformed plant according to claim 7, wherein said plant exhibits increased tocopherol levels relative to a plant with the same genetic background but lacking said exogenous nucleic acid molecule.

16. The transformed plant according to claim 7, wherein said plant exhibits increased tocotrienol levels rejative to a plant with the same genetic background but lacking said exogenous nucleic acid molecule.

17. The transformed plant according to claim 7, wherein said plant exhibits increased a-tocopherol levels relative to a plant with the same genetic background but lacking said exogenous nucleic acid molecule.

18. The transformed plant according to claim 7, wherein said plant exhibits increased α-tocotrienol relative to a plant with the same genetic background but lacking said exogenous nucleic acid molecule.

19. The transformed plant according to claim 7, wherein said plant exhibits increased γ-tocopherol levels relative to a plant with the same genetic background but lacking said exogenous nucleic acid molecule.

20. The transformed plant according to claim 7, wherein said plant exhibits increased γ-tocotrienol levels relative to a plant with the same genetic background but lacking said exogenous nucleic acid molecule.

21. The transfonned plant of claim 7, wherein said nucleic acid molecule further comprises a plastid targeting sequence, wherein said plastid targeting sequence is operably linked to said exogenous nucleic acid molecule to cause a transcript of said exogenous nucleic acid molecule to further encode a plastid peptide target sequence operably linked to said amino acid sequence.

22. The transfonned plant of claim 7, further comprising an expression cassette which expresses phytyl prenyltransferase.

23. The transformed plant of claim 22, wherein said nucleic acid molecule further comprises said expression cassette.

24. The transformed plant of claim 7, wherein said nucleic acid molecule encodes SEQ ID NO: 2.

25. A method of producing a plant having increased tocopherol levels comprising:
(A) transforming said plant with the substantially purified nucleic acid molecule of claim 1; and
(B) growing said plant.

26. The method of claim 25, wherein said plant further comprises an expression cassette which expresses phytyl prenyltransferase.

27. The method of claim 26, wherein said plant further comprises an expression cassette which expresses hydroxyphenylpyruvate dehydrogenase.

28. The method of claim 25, wherein said plant further comprises a nucleic acid sequence encoding HPPD and either slr1736 or ATPT2.

29. The method of claim 25, wherein said substantially purified nucleic acid molecule is linked to a 3' non-translated sequence that functions in the plant to cause termination of transcription and addition of polyadenylated ribonucleotides to a 3' end of an mRNA molecule, and wherein said expression of said substantially purified nucleic acid molecule results in overexpression of said protein.

30. The method of producing a plant according to claim 25, wherein said plant is selected from the group of canola, maize, *Arabidopsis, Brassica campestris, Brassica napus*, soybean, crambe, mustard, castor bean, peanut, sesame, cottonseed, linseed, safflower, oil palm, flax and sunflower.

31. The method of producing a plant according to claim 25, wherein said plant is canola.

32. The method of producing a plant according to claim 25, wherein said plant is soybean.

33. The method of producing a plant according to claim 25, wherein said plant is *Brassica napus*.

34. The method of producing a plant according to claim 25, wherein said plant exhibits increased α-tocopherol levels relative to a plant with the same genetic background but lacking said substantially purified nucleic acid molecule.

35. The method of producing a plant according to claim 25, wherein said plant exhibits increased γ-tocopherol levels relative to a plant with the same genetic background but lacking said substantially purified nucleic acid molecule.

36. The method of producing a plant according to claim 25, wherein said plant exhibits increased tocopherol levels relative to a plant with the same genetic background but lacking said substantially purified nucleic acid molecule.

37. The method of producing a plant according to claim 25, wherein said plant exhibits increased tocotrienol levels relative to a plant with the same genetic background but lacking said substantially purified nucleic acid molecule.

38. A cell comprising the substantially purified nucleic acid molecule of claim 1.

39. The cell according to claim 38, wherein said cell is a bacterial cell.

40. The cell according to claim 38, wherein said cell is a blue green algae cell.

* * * * *

UNITED STATES PATENT AND TRADEMARK OFFICE
CERTIFICATE OF CORRECTION

PATENT NO. : 7,238,855 B2
APPLICATION NO. : 10/137310
DATED : July 3, 2007
INVENTOR(S) : Valentine et al.

It is certified that error appears in the above-identified patent and that said Letters Patent is hereby corrected as shown below:

In claim 1, column 70, line 61, please delete "2xSSC" and insert --2X SSC--.

In claim 16, column 71, line 43, please delete "rejative" and insert --relative--.

In claim 17, column 71, line 47, please delete "a-tocopherol" and insert --α-tocopherol--.

In claim 21, column 71, line 62, please delete "transfonned" and insert --transformed--.

In claim 22, column 72, line 3, please delete "transfonned" and insert --transformed--.

Signed and Sealed this

Twenty-first Day of August, 2007

JON W. DUDAS
*Director of the United States Patent and Trademark Office*

```
                       SEQUENCE LISTING

<160> NUMBER OF SEQ ID NOS: 12

<210> SEQ ID NO 1
<211> LENGTH: 1122
<212> TYPE: DNA
<213> ORGANISM: Erwinia herbicola

<400> SEQUENCE: 1
atggtggctg aactgaccgc gttacgcgat caaattgaca gtgtagataa agcgctgctg      60
gatctgctgg ctaagcgact ggaactggtg gccgaggtag gtgaggtgaa gagccgttac     120
ggcctgccta tctatgtgcc tgagcgtgag gcgtcgatgc tggcttcgcg tcgcaaagag     180
gccgaagcgc tcggcgtacc accggatctg attgaggatg tgctgcgtcg cgtgatgcgg     240
gaatcctata ccagcgagaa tgataaaggc tttaaaaccc tctgtcctga actgcgcccg     300
gtggtgattg tcggtggtaa gggccagatg ggccggctgt ttgaaaaaat gctcgggcta     360
tcaggctaca cggttaaaac gctggataaa gaggactggc tcaggctga gactctgctc      420 agcgatgccg gaatggtgat cattagcgtg ccgattcacc tgaccgagca ggtgattgcc     480
caactgccac cactgccgga agattgtatt ctggtcgatc tggcgtcagt caaaaaccgg     540
cctctgcagg caatgctggc tgcccataac gggcctgtac tgggtctgca tccgatgttt     600
ggcccggaca gcggcagcct ggcaaaacag gtggtggtct ggtgtgatgg aagacaaccg     660
gaagcgtatc agtggttcct ggagcagatt caggtctggg gtgcgcgtct gcatcgtatc     720
agcgctgttg agcatgacca gaacatggca ttcattcagg cgctgcgtca ctttgctacc     780
ttcgcttatg gtctgcattt agccgaagag aacgtcaatc tggatcagct gctggcgctc     840
tcgtcgccca tttaccggct tgaactggcg atggtggggc ggttgttcgc tcaggatccg     900
caactctatg cggatatcat catgtcttca gagagtaatc tggcgctgat aaaacgctat     960
taccagcggt ttggtgaagc gattgcgctg ctggagcagg gcgacaagca ggcgtttatc    1020
gccagcttta accgggttga acagtggttt ggcgatcacg caaaacgctt cctggtcgaa    1080
agccgaagcc tgttgcgatc ggccaatgac agccgcccat aa                      1122
```

```
<210> SEQ ID NO 2
<211> LENGTH: 373
<212> TYPE: PRT
<213> ORGANISM: Erwinia herbicola

<400> SEQUENCE: 2

Met Val Ala Glu Leu Thr Ala Leu Arg Asp Gln Ile Asp Ser Val Asp
1               5                   10                  15

Lys Ala Leu Leu Asp Leu Leu Ala Lys Arg Leu Glu Leu Val Ala Glu
            20                  25                  30

Val Gly Glu Val Lys Ser Arg Tyr Gly Leu Pro Ile Tyr Val Pro Glu
        35                  40                  45

Arg Glu Ala Ser Met Leu Ala Ser Arg Lys Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Thr Ser Glu Asn Asp Lys Gly Phe Lys Thr Leu Cys Pro
                85                  90                  95

Glu Leu Arg Pro Val Val Ile Val Gly Gly Lys Gly Gln Met Gly Arg
            100                 105                 110

Leu Phe Glu Lys Met Leu Gly Leu Ser Gly Tyr Thr Val Lys Thr Leu
        115                 120                 125

Asp Lys Glu Asp Trp Pro Gln Ala Glu Thr Leu Leu Ser Asp Ala Gly
    130                 135                 140

Met Val Ile Ile Ser Val Pro Ile His Leu Thr Glu Gln Val Ile Ala
145                 150                 155                 160

Gln Leu Pro Pro Leu Pro Glu Asp Cys Ile Leu Val Asp Leu Ala Ser
                165                 170                 175

Val Lys Asn Arg Pro Leu Gln Ala Met Leu Ala Ala His Asn Gly Pro
            180                 185                 190

Val Leu Gly Leu His Pro Met Phe Gly Pro Asp Ser Gly Ser Leu Ala
        195                 200                 205

Lys Gln Val Val Trp Cys Asp Gly Arg Gln Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Asn Leu Asp Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
    290                 295                 300

Asp Ile Ile Met Ser Ser Glu Ser Asn Leu Ala Leu Ile Lys Arg Tyr
305                 310                 315                 320

Tyr Gln Arg Phe Gly Glu Ala Ile Ala Leu Leu Glu Gln Gly Asp Lys
                325                 330                 335

Gln Ala Phe Ile Ala Ser Phe Asn Arg Val Glu Gln Trp Phe Gly Asp
            340                 345                 350

His Ala Lys Arg Phe Leu Val Glu Ser Arg Ser Leu Leu Arg Ser Ala
        355                 360                 365

Asn Asp Ser Arg Pro
    370
```

<210> SEQ ID NO 3
<211> LENGTH: 1122
<212> TYPE: DNA
<213> ORGANISM: Escherichia coli

<400> SEQUENCE: 3

```
atggttgctg aattgaccgc attacgcgat caaattgatg aagtcgataa agcgctgctg      60
aatttattag cgaagcgtct ggaactggtt gctgaagtgg gcgaggtgaa aagccgcttt     120
ggactgccta tttatgttcc ggagcgagag gcatctatgt tggcctcgcg tcgtgcagag     180
gcggaagctc tgggtgtacc gccagatctg attgaggatg ttttgcgtcg ggtgatgcgt     240
gaatcttact ccagtgaaaa cgacaaagga tttaaaacgc tttgtcctgc gttacgcccg     300
gtagttatcg ttggcggcgg cggtcagatg ggacgtctgt tcgagaagat gctgacactc     360
tcgggttatc aggtgcggat tctggagcaa catgactggg atcgagcggc tgatattgtt     420
gccgatgccg aatggtgat tgttagtgtg ccaatccacg ttactgagca agttattggc     480
aaattaccgc ctttaccgaa agattgtatt ctggttgatc tggcatcagt gaaaaatgga     540
ccattacagg ccatgctggc ggcgcacgat ggcccggtac tggggttaca cccaatgttc     600
ggtccggaca gcgtagcct ggcaaagcaa gttgtggtct ggtgtgatgg acgtaaaccg     660
gaagcatacc aatggtttct ggagcaaatt caggtctggg gcgctcggtt gcatcgtatt     720
agcgccgtcg agcacgatca gaatatggcg tttattcagg cactgcgcca ctttgctact     780
tttgcttacg ggctgcacct ggcagaagaa atgttcagc ttgagcaact tctggcgctc     840
tcttcgccga tttaccgcct tgagctggca tggtcgggc gactgttcgc tcaggatccg     900
cagctttatg ccgacattat tatgtcgtca gagcgtaatc tggcgttaat caaacgttac     960
tataagcgtt tcggcgaggc gattgagttg ctggagcagg gcgataagca ggcgtttatt    1020
gacagtttcc gcaaggtgga gcactggttc ggcgattacg cacagcgttt tcagagtgaa    1080
agccgcgtgt tattgcgtca ggcgaatgac aatcgccagt aa                       1122
```

<210> SEQ ID NO 4
<211> LENGTH: 373
<212> TYPE: PRT
<213> ORGANISM: Escherichia coli

<400> SEQUENCE: 4

```
Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ala Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125
```

```
Glu Gln His Asp Trp Asp Arg Ala Ala Asp Ile Val Ala Asp Ala Gly
            130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Ala Ala His Asp Gly Pro
            180                 185                 190

Val Leu Gly Leu His Pro Met Phe Gly Pro Asp Ser Gly Ser Leu Ala
        195                 200                 205

Lys Gln Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Asp
            340                 345                 350

Tyr Ala Gln Arg Phe Gln Ser Glu Ser Arg Val Leu Leu Arg Gln Ala
        355                 360                 365

Asn Asp Asn Arg Gln
    370
```

<210> SEQ ID NO 5
<211> LENGTH: 25
<212> TYPE: DNA
<213> ORGANISM: artificial sequence
<220> FEATURE:
<223> OTHER INFORMATION: synthetic primer

<400> SEQUENCE: 5
actgccatgg tggctgaact gaccg                                    25

<210> SEQ ID NO 6
<211> LENGTH: 32
<212> TYPE: DNA
<213> ORGANISM: artificial sequence
<220> FEATURE:
<223> OTHER INFORMATION: synthetic primer

<400> SEQUENCE: 6
actggaattc ttattatggg cggctgtcat tg                            32

<210> SEQ ID NO 7
<211> LENGTH: 25
<212> TYPE: DNA
<213> ORGANISM: artificial sequence
<220> FEATURE:
<223> OTHER INFORMATION: synthetic primer

```
<400> SEQUENCE: 7
actgccatgg ttgctgaatt gaccg                                    25

<210> SEQ ID NO 8
<211> LENGTH: 26
<212> TYPE: DNA
<213> ORGANISM: artificial sequence
<220> FEATURE:
<223> OTHER INFORMATION: synthetic primer

<400> SEQUENCE: 8
actggaattc ttattactgg cgattg                                   26

<210> SEQ ID NO 9
<211> LENGTH: 59
<212> TYPE: DNA
<213> ORGANISM: artificial sequence
<220> FEATURE:
<223> OTHER INFORMATION: synthetic primer

<400> SEQUENCE: 9
gatctcccgg gaagggcccc ggccgtctag agaattcgcg gccgcggcgc gccaccggt     59

<210> SEQ ID NO 10
<211> LENGTH: 59
<212> TYPE: DNA
<213> ORGANISM: artificial sequence
<220> FEATURE:
<223> OTHER INFORMATION: synthetic primer

<400> SEQUENCE: 10
tcgaaccggt ggcgcgccgc ggccgcgaat tctctagacg gccggggccc ttcccggga     59

<210> SEQ ID NO 11
<211> LENGTH: 37
<212> TYPE: DNA
<213> ORGANISM: artificial sequence
<220> FEATURE:
<223> OTHER INFORMATION: synthetic primer

<400> SEQUENCE: 11
ggatccgcgg ccgcaccatg gttgatcaag ttcagca                       37

<210> SEQ ID NO 12
<211> LENGTH: 39
<212> TYPE: DNA
<213> ORGANISM: artificial sequence
<220> FEATURE:
<223> OTHER INFORMATION: synthetic primer

<400> SEQUENCE: 12
gagctcctgc aggaagcttt taggcacctc ctgatccgt                     39
```